United States Patent
Lopez et al.

(10) Patent No.: US 8,822,444 B2
(45) Date of Patent: Sep. 2, 2014

(54) HEPATITIS C VIRUS INHIBITORS

(75) Inventors: Omar D. Lopez, Wallingford, CT (US); Qi Chen, Stamford, CT (US); Makonen Belema, North Havan, CT (US); Lawrence G. Hamann, North Grafton, MA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 13/548,298

(22) Filed: Jul. 13, 2012

(65) Prior Publication Data

US 2012/0277266 A1      Nov. 1, 2012

Related U.S. Application Data

(63) Continuation of application No. 12/731,935, filed on Mar. 25, 2010, now abandoned.

(60) Provisional application No. 61/164,579, filed on Mar. 30, 2009.

(51) Int. Cl.
*A01N 43/00* (2006.01)
*A61K 31/33* (2006.01)

(52) U.S. Cl.
USPC ........... 514/183; 514/326; 514/374; 514/397; 546/210; 548/312.1; 548/313.1; 548/236

(58) Field of Classification Search
None
See application file for complete search history.

(56) References Cited

FOREIGN PATENT DOCUMENTS

WO    WO 2008021936 A2 *   2/2008
WO    WO 2010065681 A1 *   6/2010

* cited by examiner

*Primary Examiner* — Wu-Cheng Winston Shen
*Assistant Examiner* — Jean Cornet
(74) *Attorney, Agent, or Firm* — Pamela A. Mingo

(57) ABSTRACT

This disclosure concerns novel compounds of Formula (I) as defined in the specification and compositions comprising such novel compounds. These compounds are useful antiviral agents, especially in inhibiting the function of the NS5A protein encoded by Hepatitis C virus (HCV). Thus, the disclosure also concerns a method of treating HCV related diseases or conditions by use of these novel compounds or a composition comprising such novel compounds.

20 Claims, No Drawings

HEPATITIS C VIRUS INHIBITORS

CROSS-REFERENCE TO RELATED APPLICATIONS

This application is a continuation of U.S. Non-Provisional application Ser. No. 12/731,935 filed Mar. 25, 2010 which claims the benefit of U.S. Provisional Application Ser. No. 61/164,579 filed Mar. 30, 2009.

FIELD OF THE INVENTION

The present disclosure is generally directed to antiviral compounds, and more specifically directed to compounds which can inhibit the function of the NS5A protein encoded by Hepatitis C virus (HCV), compositions comprising such compounds, and methods for inhibiting the function of the NS5A protein.

BACKGROUND OF THE INVENTION

HCV is a major human pathogen, infecting an estimated 170 million persons worldwide—roughly five times the number infected by human immunodeficiency virus type 1. A substantial fraction of these HCV infected individuals develop serious progressive liver disease, including cirrhosis and hepatocellular carcinoma.

The current standard of care for HCV, which employs a combination of pegylated-interferon and ribavirin, has a non-optimal success rate in achieving sustained viral response and causes numerous side effects. Thus, there is a clear and long-felt need to develop effective therapies to address this under-met medical need.

HCV is a positive-stranded RNA virus. Based on a comparison of the deduced amino acid sequence and the extensive similarity in the 5' untranslated region, HCV has been classified as a separate genus in the Flaviviridae family. All members of the Flaviviridae family have enveloped virions that contain a positive stranded RNA genome encoding all known virus-specific proteins via translation of a single, uninterrupted, open reading frame.

Considerable heterogeneity is found within the nucleotide and encoded amino acid sequence throughout the HCV genome due to the high error rate of the encoded RNA dependent RNA polymerase which lacks a proof-reading capability. At least six major genotypes have been characterized, and more than 50 subtypes have been described with distribution worldwide. The clinical significance of the genetic heterogeneity of HCV has demonstrated a propensity for mutations to arise during monotherapy treatment, thus additional treatment options for use are desired. The possible modulator effect of genotypes on pathogenesis and therapy remains elusive.

The single strand HCV RNA genome is approximately 9500 nucleotides in length and has a single open reading frame (ORF) encoding a single large polyprotein of about 3000 amino acids. In infected cells, this polyprotein is cleaved at multiple sites by cellular and viral proteases to produce the structural and non-structural (NS) proteins. In the case of HCV, the generation of mature non-structural proteins (NS2, NS3, NS4A, NS4B, NS5A, and NS5B) is effected by two viral proteases. The first one is believed to be a metalloprotease and cleaves at the NS2-NS3 junction; the second one is a serine protease contained within the N-terminal region of NS3 (also referred to herein as NS3 protease) and mediates all the subsequent cleavages downstream of NS3, both in cis, at the NS3-NS4A cleavage site, and in trans, for the remaining NS4A-NS4B, NS4B-NS5A, NS5A-NS5B sites. The NS4A protein appears to serve multiple functions by both acting as a cofactor for the NS3 protease and assisting in the membrane localization of NS3 and other viral replicase components. The formation of a NS3-NS4A complex is necessary for proper protease activity resulting in increased proteolytic efficiency of the cleavage events. The NS3 protein also exhibits nucleoside triphosphatase and RNA helicase activities. NS5B (also referred to herein as HCV polymerase) is a RNA-dependent RNA polymerase that is involved in the replication of HCV with other HCV proteins, including NS5A, in a replicase complex.

Compounds useful for treating HCV-infected patients are desired which selectively inhibit HCV viral replication. In particular, compounds which are effective to inhibit the function of the NS5A protein are desired. The HCV NS5A protein is described, for example, in the following references: S. L. Tan, et al., *Virology*, 284:1-12 (2001); K.-J. Park, et al., *J. Biol. Chem.*, 30711-30718 (2003); T. L. Tellinghuisen, et al., *Nature*, 435, 374 (2005); R. A. Love, et al., *J. Virol*, 83, 4395 (2009); N. Appel, et al., *J. Biol. Chem.*, 281, 9833 (2006); L. Huang, *J. Biol. Chem.*, 280, 36417 (2005); C. Rice, et al., WO2006093867.

SUMMARY OF THE INVENTION

The present invention provides compounds which selectively inhibit HCV viral replication, as characterized by Formula (I):

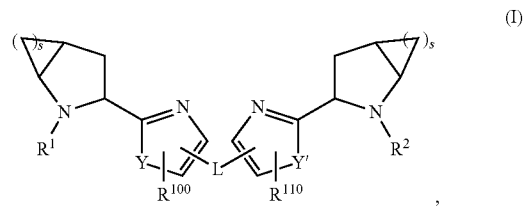

or a pharmaceutically acceptable salt thereof, wherein:

s is 0 or 1;

L is -$L^1$-$L^2$-, wherein $L^1$ and $L^2$ are independently selected from:

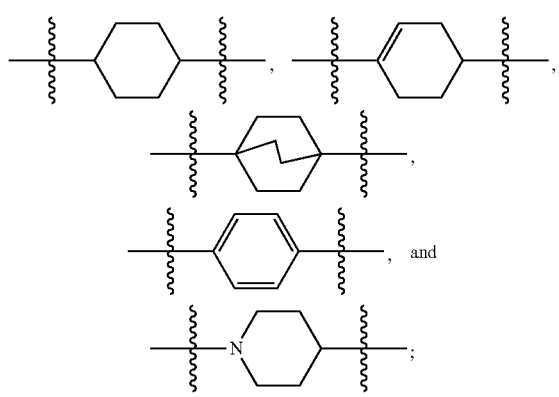

provided that at least one of $L^1$ and $L^2$ is other than

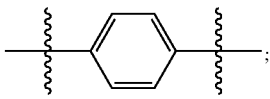

Y and Y' are independently oxygen (O) or NH;
$R^1$ is hydrogen or —C(O)$R^x$;
$R^2$ is hydrogen or —C(O)$R^y$;
$R^x$ and $R^y$ are independently selected from cycloalkyl, heteroaryl, heterocyclyl, alkoxy, and alkyl substituted with one or more substituents independently selected from aryl, alkenyl, cycloalkyl, heterocyclyl, heteroaryl, —O$R^3$,
—C(O)O$R^4$, —N$R^a R^b$, and —C(O)N$R^c R^d$,
wherein aryl and heteroaryl may optionally be substituted with one or more substituents independently selected from alkyl, haloalkyl, arylalkyl, heterocyclyl, heterocyclylalkyl, halogen, cyano, nitro, —C(O)O$R^4$, O$R^5$, —N$R^a R^b$, (N$R^a R^b$)alkyl, and (MeO)(HO)P(O)O—, and
wherein cycloalkyl and heterocyclyl may optionally be fused onto an aromatic ring and may optionally be substituted with one or more substituents independently selected from alkyl, hydroxyl, halogen, aryl, —N$R^a R^b$, oxo, and —C(O)O$R^4$;
$R^3$ is hydrogen, alkyl, or arylalkyl;
$R^4$ is alkyl or arylalkyl;
$R^5$ is hydrogen, alkyl, or arylalkyl;
$R^a$ and $R^b$ are independently selected from hydrogen, alkyl, cycloalkyl, arylalkyl, heteroaryl, —C(O)$R^6$, —C(O)O$R^7$, —C(O)N$R^c R^d$, and (N$R^c R^d$)alkyl, or alternatively, $R^a$ and $R^b$, together with the nitrogen atom to which they are attached, form a five- or six-membered ring or bridged bicyclic ring structure, wherein said five- or six-membered ring or bridged bicyclic ring structure optionally may contain one or two additional heteroatoms independently selected from nitrogen, oxygen, and sulfur and may contain one, two, or three substituents independently selected from $C_1$ to $C_6$ alkyl, $C_1$ to $C_4$ haloalkyl, aryl, hydroxyl, $C_1$ to $C_6$ alkoxy, $C_1$ to $C_4$ haloalkoxy, and halogen;
$R^6$ is alkyl;
$R^7$ is alkyl, arylalkyl, cycloalkyl, or haloalkyl;
$R^{100}$ and $R^{110}$ are independently selected from hydrogen, alkyl, cyanoalkyl, and halo;
$R^c$ and $R^d$ are independently selected from hydrogen, alkyl, arylalkyl, and cycloalkyl.

The compounds of the present disclosure can be effective to inhibit the function of the HCV NS5A protein. In particular, the compounds of the present disclosure can be effective to inhibit the HCV 1b genotype or multiple genotypes of HCV. Therefore, this invention also encompasses: (1) compositions comprising a compound of Formula (I), or a pharmaceutically acceptable salt thereof, and a pharmaceutically acceptable carrier; and (2) a method of treating an HCV infection in a patient, comprising administering to the patient a therapeutically effective amount of a compound of Formula (I), or a pharmaceutically acceptable salt thereof.

DETAILED DESCRIPTION OF THE INVENTION

In a first aspect of the present disclosure compounds of Formula (I) are provided:

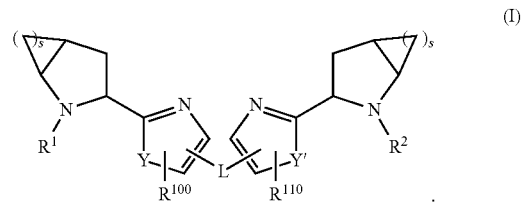

In a first embodiment of the first aspect, the present disclosure provides a compound of Formula (I), or a pharmaceutically acceptable salt or solvate thereof, wherein:
s is 0 or 1;
L is -$L^1$-$L^2$-, wherein $L^1$ and $L^2$ are independently selected from:

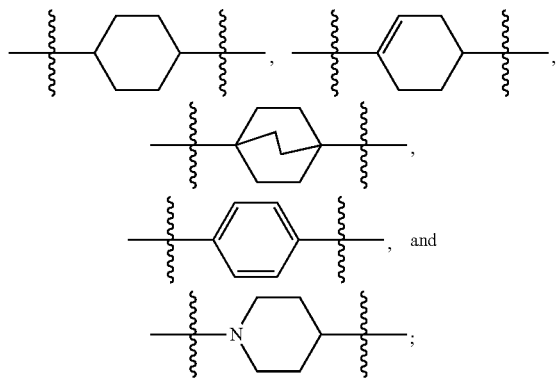

provided that at least one of $L^1$ and $L^2$ is other than

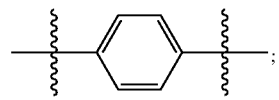 [SMILES: *c1ccc(*)cc1]

Y and Y' are independently oxygen (O) or NH;
$R^1$ is hydrogen or —C(O)$R^x$;
$R^2$ is hydrogen or —C(O)$R^y$;
$R^x$ and $R^y$ are independently selected from cycloalkyl, heteroaryl, heterocyclyl, alkoxy, and alkyl substituted with one or more substituents independently selected from aryl, alkenyl, cycloalkyl, heterocyclyl, heteroaryl, —O$R^3$,
—C(O)O$R^4$, —N$R^a R^b$, and —C(O)N$R^c R^d$,
wherein aryl and heteroaryl may optionally be substituted with one or more substituents independently selected from alkyl, haloalkyl, arylalkyl, heterocyclyl, heterocyclylalkyl, halogen, cyano, nitro, —C(O)O$R^4$, O$R^5$, —N$R^a R^b$, (N$R^a R^b$)alkyl, and (MeO)(HO)P(O)O—, and
wherein cycloalkyl and heterocyclyl may optionally be fused onto an aromatic ring and may optionally be substituted with one or more substituents independently selected from alkyl, hydroxyl, halogen, aryl, —N$R^a R^b$, oxo, and —C(O)O$R^4$;
$R^3$ is hydrogen, alkyl, or arylalkyl;
$R^4$ is alkyl or arylalkyl;
$R^5$ is hydrogen, alkyl, or arylalkyl;
$R^a$ and $R^b$ are independently selected from hydrogen, alkyl, cycloalkyl, arylalkyl, heteroaryl, —C(O)$R^6$, —C(O)

OR$^7$, —C(O)NR$^c$R$^d$, and (NR$^c$R$^d$)alkyl, or alternatively, R$^a$ and R$^b$, together with the nitrogen atom to which they are attached, form a five- or six-membered ring or bridged bicyclic ring structure, wherein said five- or six-membered ring or bridged bicyclic ring structure optionally may contain one or two additional heteroatoms independently selected from nitrogen, oxygen, and sulfur and may contain one, two, or three substituents independently selected from C$_1$ to C$_6$ alkyl, C$_1$ to C$_4$ haloalkyl, aryl, hydroxyl, C$_1$ to C$_6$ alkoxy, C$_1$ to C$_4$ haloalkoxy, and halogen;

R$^6$ is alkyl;

R$^7$ is alkyl, arylalkyl, or haloalkyl;

R$^{100}$ and R$^{110}$ are independently selected from hydrogen, alkyl, cyanoalkyl, and halo;

R$^c$ and R$^d$ are independently selected from hydrogen, alkyl, arylalkyl, and cycloalkyl.

In a first class of compounds of the first embodiment, the present disclosure provides a compound of Formula (I), or a pharmaceutically acceptable salt or solvate thereof, wherein s is 0.

In a second class of compounds of the first embodiment, the present disclosure provides a compound of Formula (I), or a pharmaceutically acceptable salt or solvate thereof, wherein s is 1.

In a second embodiment of the first aspect, the present disclosure provides a compound of Formula (I), or a pharmaceutically acceptable salt or solvate thereof, wherein:

s is 0 or 1;

L is selected from:

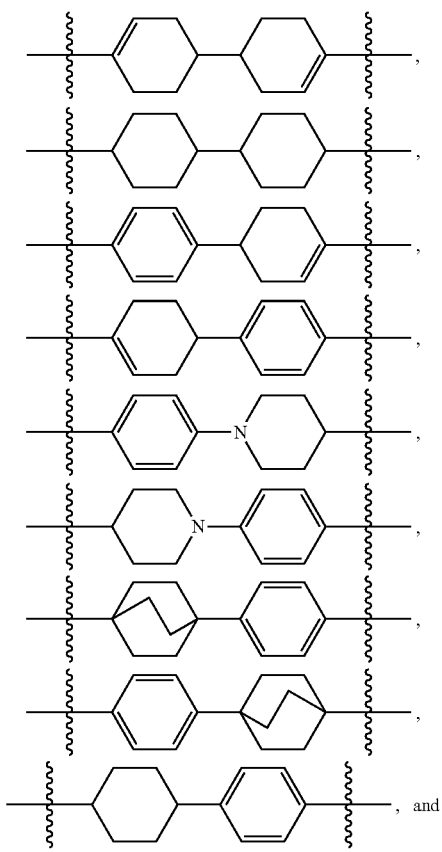, and

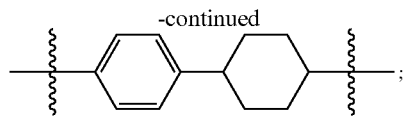

Y and Y' are independently oxygen (O) or NH;

R$^1$ is hydrogen or —C(O)R$^x$;

R$^2$ is hydrogen or —C(O)R$^y$;

R$^x$ and R$^y$ are independently selected from cycloalkyl, heteroaryl, heterocyclyl, alkoxy, and alkyl substituted with one or more substituents independently selected from aryl, alkenyl, cycloalkyl, heterocyclyl, heteroaryl, —OR$^3$, —C(O)OR$^4$, —NR$^a$R$^b$, and —C(O)NR$^c$R$^d$, wherein aryl and heteroaryl may optionally be substituted with one or more substituents independently selected from alkyl, haloalkyl, arylalkyl, heterocyclyl, heterocyclylalkyl, halogen, cyano, nitro, —C(O)OR$^4$, OR$^5$, —NR$^a$R$^b$, (NR$^a$R$^b$)alkyl, and (MeO)(HO)P(O)O—, and wherein cycloalkyl and heterocyclyl may optionally be fused onto an aromatic ring and may optionally be substituted with one or more substituents independently selected from alkyl, hydroxyl, halogen, aryl, —NR$^a$R$^b$, oxo, and —C(O)OR$^4$;

R$^3$ is hydrogen, alkyl, or arylalkyl;

R$^4$ is alkyl or arylalkyl;

R$^5$ is hydrogen, alkyl, or arylalkyl;

R$^a$ and R$^b$ are independently selected from hydrogen, alkyl, cycloalkyl, arylalkyl, heteroaryl, —C(O)R$^6$, —C(O)OR$^7$, —C(O)NR$^c$R$^d$, and (NR$^c$R$^d$)alkyl, or alternatively, R$^a$ and R$^b$, together with the nitrogen atom to which they are attached, form a five- or six-membered ring or bridged bicyclic ring structure, wherein said five- or six-membered ring or bridged bicyclic ring structure optionally may contain one or two additional heteroatoms independently selected from nitrogen, oxygen, and sulfur and may contain one, two, or three substituents independently selected from C$_1$ to C$_6$ alkyl, C$_1$ to C$_4$ haloalkyl, aryl, hydroxyl, C$_1$ to C$_6$ alkoxy, C$_1$ to C$_4$ haloalkoxy, and halogen;

R$^6$ is alkyl;

R$^7$ is alkyl, arylalkyl, or haloalkyl;

R$^{100}$ and R$^{110}$ are independently selected from hydrogen, alkyl, cyanoalkyl, and halo;

R$^c$ and R$^d$ are independently selected from hydrogen, alkyl, arylalkyl, and cycloalkyl.

In a first class of compounds in the second embodiment, the present disclosure provides a compound of Formula (I), or a pharmaceutically acceptable salt or solvate thereof, wherein L is

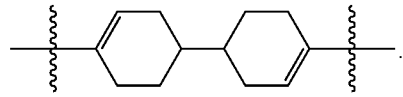 [SMILES: *C1=CCC(C2CC=C(*)CC2)CC1]

In a second class of compounds of the second embodiment, the present disclosure provides a compound of Formula (I), or a pharmaceutically acceptable salt or solvate thereof, wherein L is

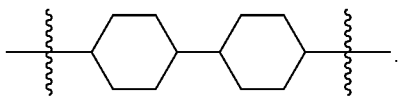

In a third class of compounds of the second embodiment, the present disclosure provides a compound of Formula (I), or a pharmaceutically acceptable salt or solvate thereof, wherein L is

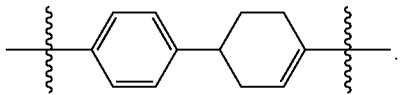

In a fourth class of compounds of the second embodiment, the present disclosure provides a compound of Formula (I), or a pharmaceutically acceptable salt or solvate thereof, wherein L is

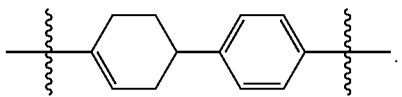

In a fifth class of compounds of the second embodiment, the present disclosure provides a compound of Formula (I), or a pharmaceutically acceptable salt or solvate thereof, wherein L is

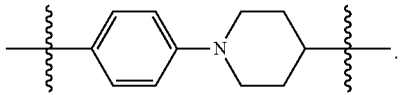

In a sixth class of compounds of the second embodiment, the present disclosure provides a compound of Formula (I), or a pharmaceutically acceptable salt or solvate thereof, wherein L is

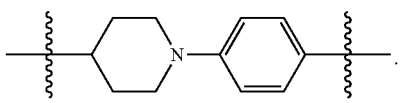

In a seventh class of compounds of the second embodiment, the present disclosure provides a compound of Formula (I), or a pharmaceutically acceptable salt or solvate thereof, wherein L is

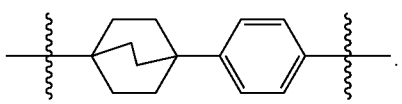

In an eighth class of compounds of the second embodiment, the present disclosure provides a compound of Formula (I), or a pharmaceutically acceptable salt or solvate thereof, wherein L is

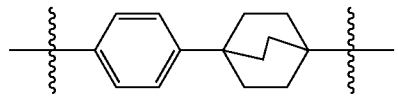

In a ninth class of compounds of the second embodiment, the present disclosure provides a compound of Formula (I), or a pharmaceutically acceptable salt or solvate thereof, wherein L is

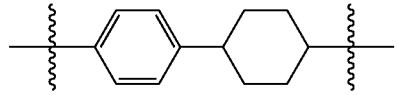

In a third embodiment of the first aspect, the present disclosure provides a compound of Formula (I), or a pharmaceutically acceptable salt or solvate thereof, wherein:
  s is 0 or 1;
  L is -$L^1$-$L^2$-, wherein $L^1$ and $L^2$ are independently selected from:

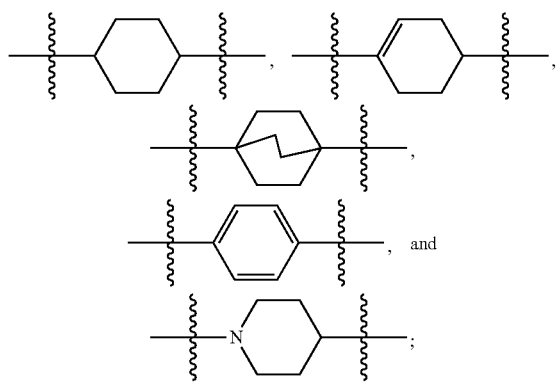

provided that at least one of $L^1$ and $L^2$ is other than

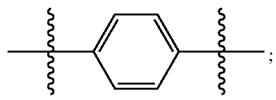 [SMILES: *c1ccc(*)cc1]

Y and Y' are each NH;
$R^1$ is hydrogen or —C(O)$R^x$;
$R^2$ is hydrogen or —C(O)$R^y$;
$R^x$ and $R^y$ are independently selected from cycloalkyl, heteroaryl, heterocyclyl, alkoxy, and alkyl substituted with one or more substituents independently selected from aryl, alkenyl, cycloalkyl, heterocyclyl, heteroaryl, —O$R^3$, —C(O)O$R^4$, —N$R^a R^b$, and —C(O)N$R^c R^d$,
  wherein aryl and heteroaryl may optionally be substituted with one or more substituents independently selected from alkyl, haloalkyl, arylalkyl, heterocyclyl, heterocyclylalkyl, halogen, cyano, nitro, —C(O)O$R^4$, O$R^5$, —N$R^a R^b$, (N$R^a R^b$)alkyl, and (MeO)(HO)P(O)O—, and
  wherein cycloalkyl and heterocyclyl may optionally be fused onto an aromatic ring and may optionally be substituted with one or more substituents independently selected from alkyl, hydroxyl, halogen, aryl, —N$R^a R^b$, oxo, and —C(O)O$R^4$;

$R^3$ is hydrogen, alkyl, or arylalkyl;

$R^4$ is alkyl or arylalkyl;

$R^5$ is hydrogen, alkyl, or arylalkyl;

$R^a$ and $R^b$ are independently selected from hydrogen, alkyl, cycloalkyl, arylalkyl, heteroaryl, —C(O)$R^6$, —C(O)O$R^7$, —C(O)N$R^c R^d$, and (N$R^c R^d$)alkyl, or alternatively, $R^a$ and $R^b$, together with the nitrogen atom to which they are attached, form a five- or six-membered ring or bridged bicyclic ring structure, wherein said five- or six-membered ring or bridged bicyclic ring structure optionally may contain one or two additional heteroatoms independently selected from nitrogen, oxygen, and sulfur and may contain one, two, or three substituents independently selected from $C_1$ to $C_6$ alkyl, $C_1$ to $C_4$ haloalkyl, aryl, hydroxyl, $C_1$ to $C_6$ alkoxy, $C_1$ to $C_4$ haloalkoxy, and halogen;

$R^6$ is alkyl;

$R^7$ is alkyl, arylalkyl, or haloalkyl;

$R^{100}$ and $R^{110}$ are independently selected from hydrogen, alkyl, cyanoalkyl, and halo;

$R^c$ and $R^d$ are independently selected from hydrogen, alkyl, arylalkyl, and cycloalkyl.

In a fourth embodiment of the first aspect, the present disclosure provides a compound of Formula (I), or a pharmaceutically acceptable salt or solvate thereof, wherein:

s is 0 or 1;

L is -$L^1$-$L^2$-, wherein $L^1$ and $L^2$ are independently selected from:

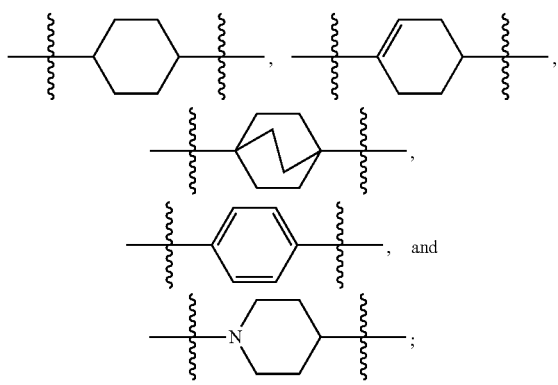

provided that at least one of $L^1$ and $L^2$ is other than

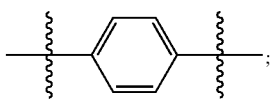

Y is oxygen (O), and Y' is NH;

$R^1$ is hydrogen or —C(O)$R^x$;

$R^2$ is hydrogen or —C(O)$R^y$;

$R^x$ and $R^y$ are independently selected from cycloalkyl, heteroaryl, heterocyclyl, alkoxy, and alkyl substituted with one or more substituents independently selected from aryl, alkenyl, cycloalkyl, heterocyclyl, heteroaryl, —O$R^3$, —C(O)O$R^4$, —N$R^a R^b$, and —C(O)N$R^c R^d$, wherein aryl and heteroaryl may optionally be substituted with one or more substituents independently selected from alkyl, haloalkyl, arylalkyl, heterocyclyl, heterocyclylalkyl, halogen, cyano, nitro, —C(O)O$R^4$, O$R^5$, —N$R^a R^b$, (N$R^a R^b$)alkyl, and (MeO)(HO)P(O)O—, and wherein cycloalkyl and heterocyclyl may optionally be fused onto an aromatic ring and may optionally be substituted with one or more substituents independently selected from alkyl, hydroxyl, halogen, aryl, —N$R^a R^b$, oxo, and —C(O)O$R^4$;

$R^3$ is hydrogen, alkyl, or arylalkyl;

$R^4$ is alkyl or arylalkyl;

$R^5$ is hydrogen, alkyl, or arylalkyl;

$R^a$ and $R^b$ are independently selected from hydrogen, alkyl, cycloalkyl, arylalkyl, heteroaryl, —C(O)$R^6$, —C(O)O$R^7$, —C(O)N$R^c R^d$, and (N$R^c R^d$)alkyl, or alternatively, $R^a$ and $R^b$, together with the nitrogen atom to which they are attached, form a five- or six-membered ring or bridged bicyclic ring structure, wherein said five- or six-membered ring or bridged bicyclic ring structure optionally may contain one or two additional heteroatoms independently selected from nitrogen, oxygen, and sulfur and may contain one, two, or three substituents independently selected from $C_1$ to $C_6$ alkyl, $C_1$ to $C_4$ haloalkyl, aryl, hydroxyl, $C_1$ to $C_6$ alkoxy, $C_1$ to $C_4$ haloalkoxy, and halogen;

$R^6$ is alkyl;

$R^7$ is alkyl, arylalkyl, or haloalkyl;

$R^{100}$ and $R^{110}$ are independently selected from hydrogen, alkyl, cyanoalkyl, and halo;

$R^c$ and $R^d$ are independently selected from hydrogen, alkyl, arylalkyl, and cycloalkyl.

In a fifth embodiment of the first aspect, the present disclosure provides a compound of Formula (I), or a pharmaceutically acceptable salt or solvate thereof, wherein:

s is 0 or 1;

L is -$L^1$-$L^2$-, wherein $L^1$ and $L^2$ are independently selected from:

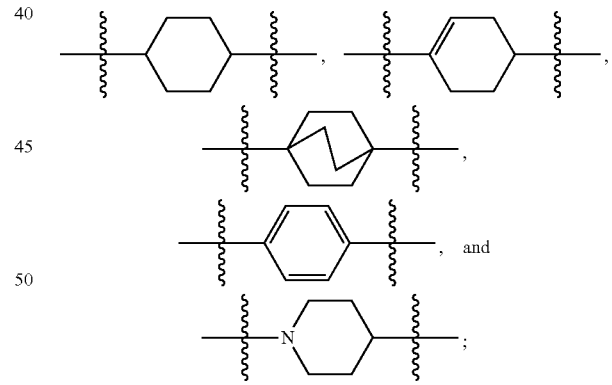

provided that at least one of $L^1$ and $L^2$ is other than

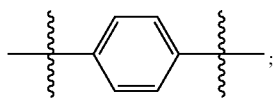

$R^1$ is —C(O)$R^x$;

$R^2$ is —C(O)$R^y$;

$R^x$ and $R^y$ are independently alkyl substituted by at least one —N$R^a R^b$, characterized by Formula (A):

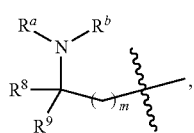
(A)

wherein:
m is 0 or 1;
$R^8$ is hydrogen or alkyl;
$R^9$ is selected from hydrogen, cycloalkyl, aryl, heteroaryl, heterocyclyl, and alkyl optionally substituted with a substituent selected from aryl, alkenyl, cycloalkyl, heterocyclyl, heteroaryl, heterobicyclyl, —$OR^3$, —$C(O)OR^4$, —$NR^aR^b$, and —$C(O)NR^cR^d$,
wherein aryl and heteroaryl may optionally be substituted with one or more substituents independently selected from alkyl, haloalkyl, arylalkyl, heterocyclyl, heterocyclylalkyl, halogen, cyano, nitro, —$C(O)OR^4$, $OR^5$, —$NR^aR^b$, ($NR^aR^b$)alkyl, and (MeO)(HO)P(O)O—, and
wherein cycloalkyl and heterocyclyl may optionally be fused onto an aromatic ring and may optionally be substituted with one or more substituents independently selected from alkyl, hydroxyl, halogen, aryl, —$NR^aR^b$, oxo, and —$C(O)OR^4$;
$R^{100}$ and $R^{110}$ are independently selected from hydrogen and halo;
$R^3$ is hydrogen, alkyl, or arylalkyl;
$R^4$ is alkyl or arylalkyl;
$R^5$ is hydrogen, alkyl, or arylalkyl;
$R^a$ and $R^b$ are independently selected from hydrogen, alkyl, cycloalkyl, arylalkyl, heteroaryl, —$C(O)R^6$, —$C(O)OR^7$, —$C(O)NR^cR^d$, and ($NR^cR^d$)alkyl, or alternatively, $R^a$ and $R^b$, together with the nitrogen atom to which they are attached, form a five- or six-membered ring or bridged bicyclic ring structure, wherein said five- or six-membered ring or bridged bicyclic ring structure optionally may contain one or two additional heteroatoms independently selected from nitrogen, oxygen, and sulfur and may contain one, two, or three substituents independently selected from $C_1$ to $C_6$ alkyl, $C_1$ to $C_4$ haloalkyl, aryl, hydroxyl, $C_1$ to $C_6$ alkoxy, $C_1$ to $C_4$ haloalkoxy, and halogen;
$R^6$ is alkyl;
$R^2$ is alkyl, arylalkyl, or haloalkyl;
$R^{100}$ and $R^{110}$ are independently selected from hydrogen, alkyl, cyanoalkyl, and halo; and
$R^c$ and $R^d$ are independently selected from hydrogen, alkyl, arylalkyl, and cycloalkyl.

In a sixth embodiment of the first aspect, the present disclosure provides a compound of Formula (I), or a pharmaceutically acceptable salt or solvate thereof, wherein:
s is 0 or 1;
L is -$L^1$-$L^2$-, wherein $L^1$ and $L^2$ are independently selected from:

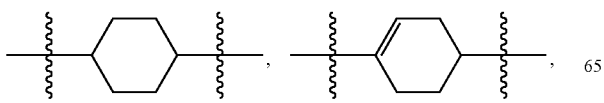

-continued

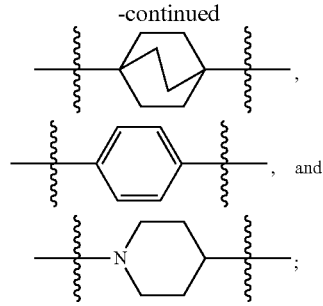
, and provided that at least one of $L^1$ and $L^2$ is other than

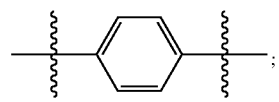
;

$R^1$ is —$C(O)R^x$;
$R^2$ is —$C(O)R^y$;
$R^x$ and $R^y$ are independently alkyl substituted by at least one —$NR^aR^b$, characterized by Formula (A):

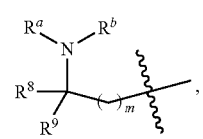
(A)

wherein:
m is 0;
$R^8$ is hydrogen or $C_1$ to $C_4$ alkyl;
$R^9$ is selected from hydrogen, $C_1$ to $C_6$ alkyl optionally substituted with —$OR^{12}$, $C_3$ to $C_6$ cycloalkyl, allyl, —$CH_2C(O)NR^cR^d$, ($NR^cR^d$)alkyl,

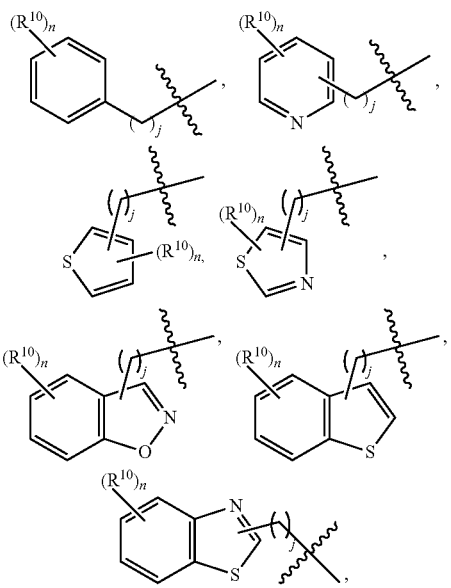

-continued

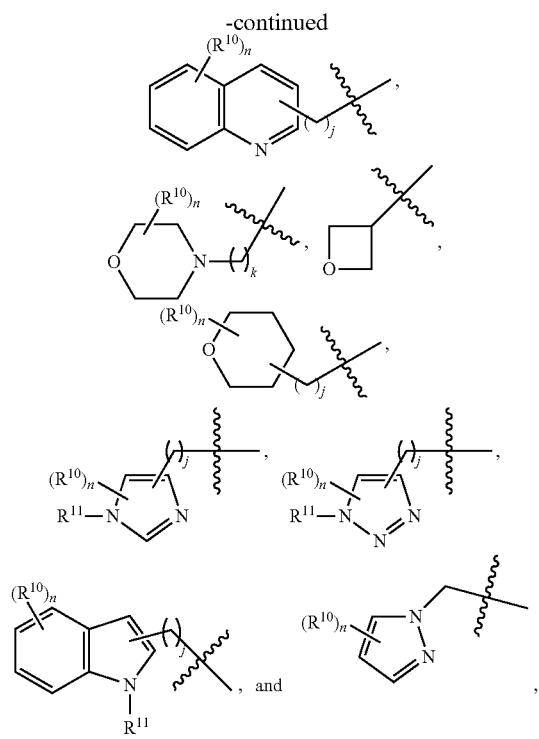

wherein j is 0 or 1;
k is 1, 2, or 3;
n is 0 or an integer selected from 1 through 4;
each $R^{10}$ is independently hydrogen, $C_1$ to $C_4$ alkyl, $C_1$ to $C_4$ haloalkyl, halogen, nitro, —OBn, or (MeO)(OH)P(O)O—;
$R^{11}$ is hydrogen, $C_1$ to $C_4$ alkyl, or benzyl;
$R^{12}$ is hydrogen, $C_1$ to $C_4$ alkyl, or benzyl;
$R^a$ is hydrogen or $C_1$ to $C_4$ alkyl;
$R^b$ is $C_1$ to $C_4$ alkyl, $C_3$ to $C_6$ cycloalkyl, benzyl, 3-pyridyl, pyrimidin-5-yl, acetyl, —C(O)OR$^7$, or —C(O)NR$^c$R$^d$;
$R^7$ is $C_1$ to $C_4$ alkyl or $C_1$ to $C_4$ haloalkyl;
$R^{100}$ and $R^{110}$ are independently selected from hydrogen and halo; and
$R^c$ is hydrogen or $C_1$ to $C_4$ alkyl; and
$R^d$ is hydrogen, $C_1$ to $C_4$ alkyl, or $C_3$ to $C_6$ cycloalkyl.

In a seventh embodiment of the first aspect, the present disclosure provides a compound of Formula (I), or a pharmaceutically acceptable salt or solvate thereof, wherein:
s is 0 or 1;
L is -$L^1$-$L^2$-, wherein $L^1$ and $L^2$ are independently selected from:

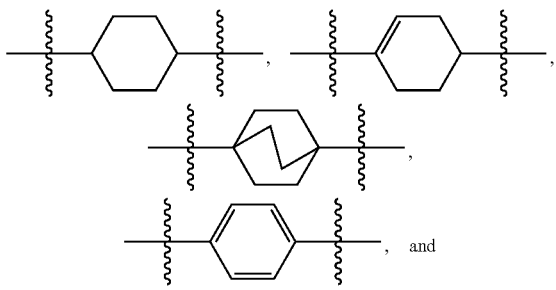

-continued

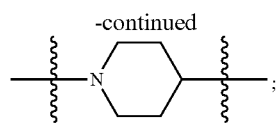

provided that at least one of $L^1$ and $L^2$ is other than

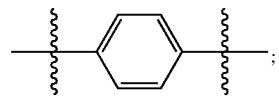

$R^1$ is —C(O)R$^x$;
$R^2$ is —C(O)R$^y$;
$R^x$ and $R^y$ are independently alkyl substituted by at least one —NR$^a$R$^b$, characterized by Formula (A):

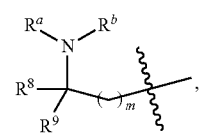

wherein:
m is 0;
$R^8$ is hydrogen;
$R^9$ is phenyl optionally substituted with one up to five substituents independently selected from $C_1$ to $C_6$ alkyl, $C_1$ to $C_4$ haloalkyl, halogen, $C_1$ to $C_6$ alkoxy, hydroxyl, cyano, and nitro; and
NR$^a$R$^b$ is a heterocyclyl or heterobicyclyl group selected from:

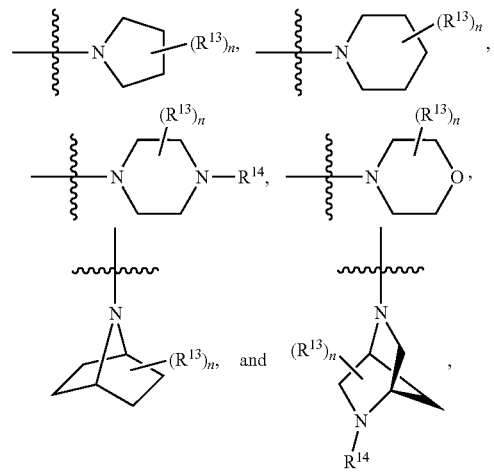

wherein n is 0, 1, or 2;
each $R^{13}$ is independently selected from $C_1$ to $C_6$ alkyl, phenyl, trifluoromethyl, halogen, hydroxyl, methoxy, and oxo;
$R^{14}$ is $C_1$ to $C_6$ alkyl, phenyl, benzyl, or C(O)OR$^{15}$ group, wherein $R^{15}$ is $C_1$ to $C_4$ alkyl, phenyl, or benzyl; and
$R^{100}$ and $R^{110}$ are independently selected from hydrogen and halo.

In an eighth embodiment of the first aspect, the present disclosure provides a compound of Formula (I), or a pharmaceutically acceptable salt or solvate thereof, wherein:

s is 0 or 1;
L is -L$^1$-L$^2$-, wherein L$^1$ and L$^2$ are independently selected from:

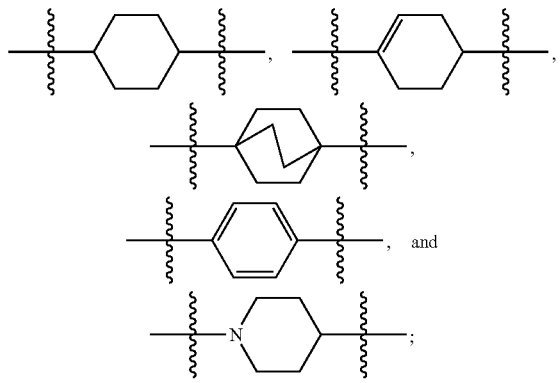

provided that at least one of L$^1$ and L$^2$ is other than

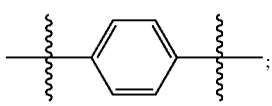 [SMILES: *c1ccc(*)cc1]

R$^1$ is —C(O)R$^x$;
R$^2$ is —C(O)R$^y$;
R$^x$ and R$^y$ are independently alkyl substituted by at least one —NR$^a$R$^b$, characterized by Formula (A):

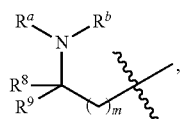
(A)

wherein:
  m is 1;
  R$^8$ is hydrogen;
  R$^9$ is C$_1$ to C$_6$ alkyl, arylalkyl, or heteroarylalkyl;
  R$^{100}$ and R$^{110}$ are independently selected from hydrogen and halo;
  R$^a$ is hydrogen; and
  R$^b$ is —C(O)OR$^7$, wherein R$^7$ is C$_1$ to C$_6$ alkyl.

In a ninth embodiment of the first aspect, the present disclosure provides a compound of Formula (I), or a pharmaceutically acceptable salt or solvate thereof, wherein:
  s is 0 or 1;
  L is -L$^1$-L$^2$-, wherein L$^1$ and L$^2$ are independently selected from:

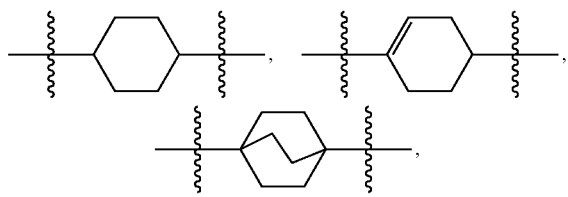

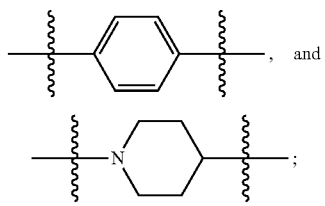

provided that at least one of L$^1$ and L$^2$ is other than

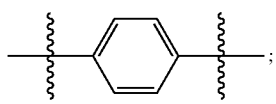 [SMILES: *c1ccc(*)cc1]

R$^1$ is —C(O)R$^x$;
R$^2$ is —C(O)R$^y$;
R$^x$ and R$^y$ are heteroaryl or heterocyclyl independently selected from:

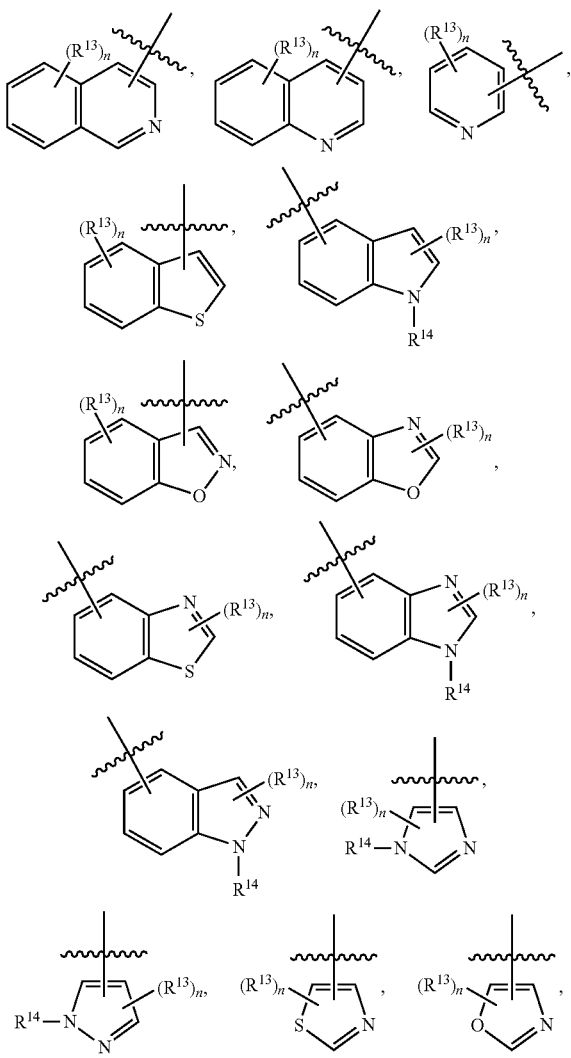

-continued

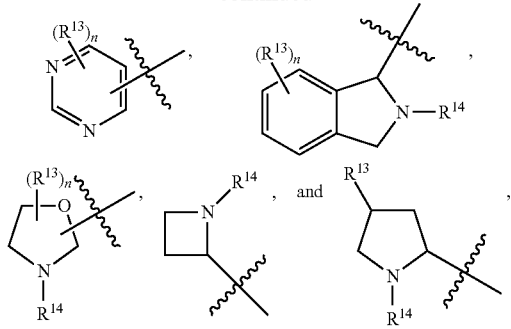

wherein n is 0 or an integer selected from 1 through 4;
each $R^{13}$ is independently selected from hydrogen, $C_1$ to $C_6$ alkyl, $C_1$ to $C_4$ haloalkyl, phenyl, benzyl, $C_1$ to $C_6$ alkoxy, $C_1$ to $C_4$ haloalkoxy, heterocyclyl, halogen, $—NR^cR^d$, hydroxyl, cyano, and oxo, where $R^c$ and $R^d$ are independently hydrogen or $C_1$ to $C_4$ alkyl; and
$R^{14}$ is hydrogen (H), $C_1$ to $C_6$ alkyl, benzyl, or $—C(O)OR^4$, wherein $R^4$ is $C_1$ to $C_6$ alkyl.

In a tenth embodiment of the first aspect, the present disclosure provides a compound of Formula (I), or a pharmaceutically acceptable salt or solvate thereof, wherein:
s is 0 or 1;
L is $-L^1-L^2-$, wherein $L^1$ and $L^2$ are independently selected from:

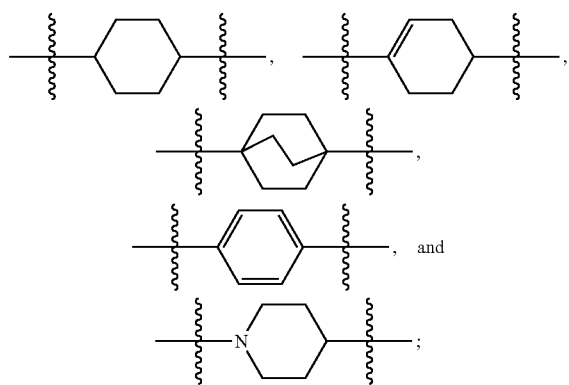

provided that at least one of $L^1$ and $L^2$ is other than

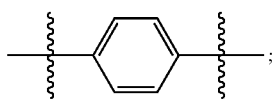 [SMILES: *c1ccc(*)cc1]

$R^1$ is $—C(O)R^x$;
$R^2$ is $—C(O)R^y$;
$R^x$ and $R^y$ are cycloalkyl independently selected from:

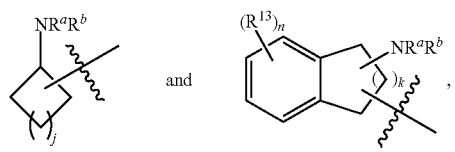

wherein j is 0, 1, 2, or 3;
k is 0, 1, or 2;
n is 0 or an integer selected from 1 through 4;
each $R^{13}$ is independently selected from hydrogen, $C_1$ to $C_6$ alkyl, $C_1$ to $C_4$ haloalkyl, $C_1$ to $C_6$ alkoxy, halogen, hydroxyl, cyano, and nitro; and
$R^a$ and $R^b$ are each independently hydrogen, $C_1$ to $C_6$ alkyl, or $C(O)OR^7$,
wherein $R^7$ is $C_1$ to $C_6$ alkyl.

In an eleventh embodiment of the first aspect, the present disclosure provides a compound of Formula (I), or a pharmaceutically acceptable salt or solvate thereof, wherein:
s is 0 or 1;
L is $-L^1-L^2-$, wherein $L^1$ and $L^2$ are independently selected from:

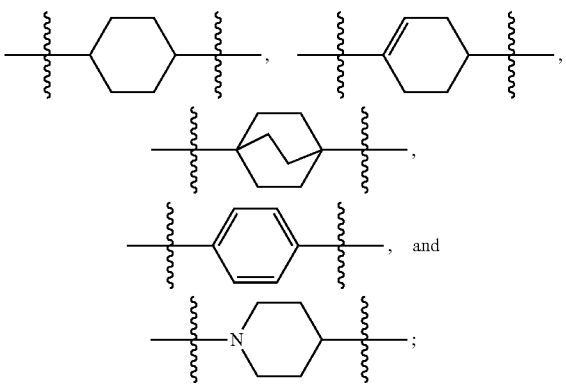

provided that at least one of $L^1$ and $L^2$ is other than

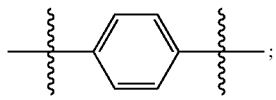

$R^1$ is $—C(O)R^x$;
$R^2$ is $—C(O)R^y$;
$R^x$ and $R^y$ are independently arylalkyl, wherein aryl part of said arylalkyl may optionally be substituted with $(NR^aR^b)$alkyl; and
$R^a$ and $R^b$ are independently hydrogen, $C_1$ to $C_6$ alkyl, or benzyl, or alternatively, $R^a$ and $R^b$, together with the nitrogen atom to which they are attached, form a five- or six-membered ring selected from

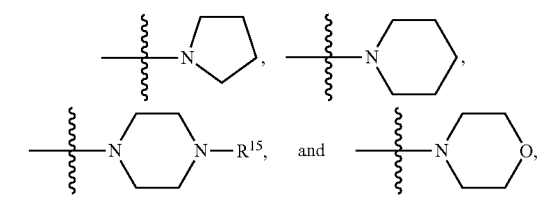

wherein $R^{15}$ is hydrogen,
$C_1$ to $C_6$ alkyl, or benzyl.

In a twelfth embodiment of the first aspect, the present disclosure provides a compound of Formula (I), or a pharmaceutically acceptable salt or solvate thereof, wherein:

s is 0 or 1;

L is -L$^1$-L$^2$-, wherein L$^1$ and L$^2$ are independently selected from:

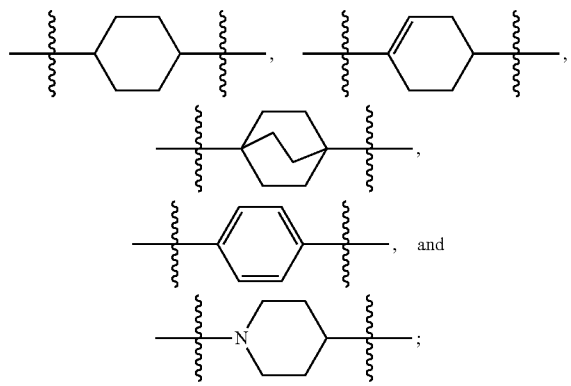

provided that at least one of L$^1$ and L$^2$ is other than

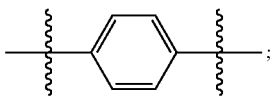

R$^1$ is —C(O)R$^x$;

R$^2$ is —C(O)R$^y$; and

R$^x$ and R$^y$ are the same and are selected from the group consisting of:

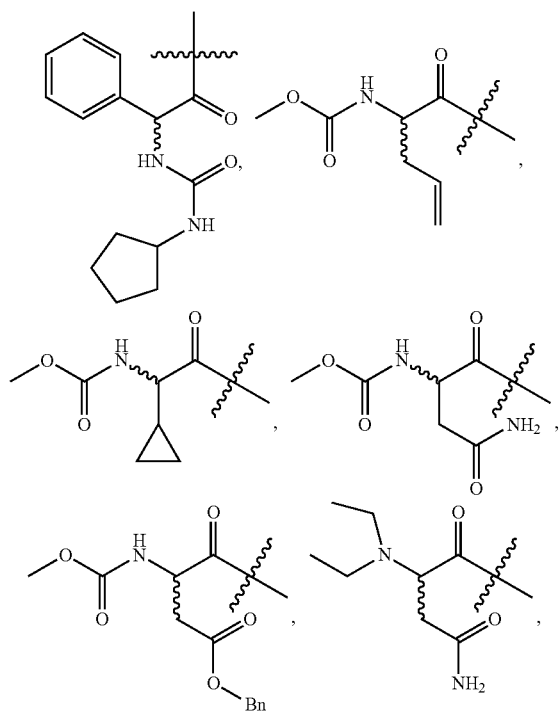

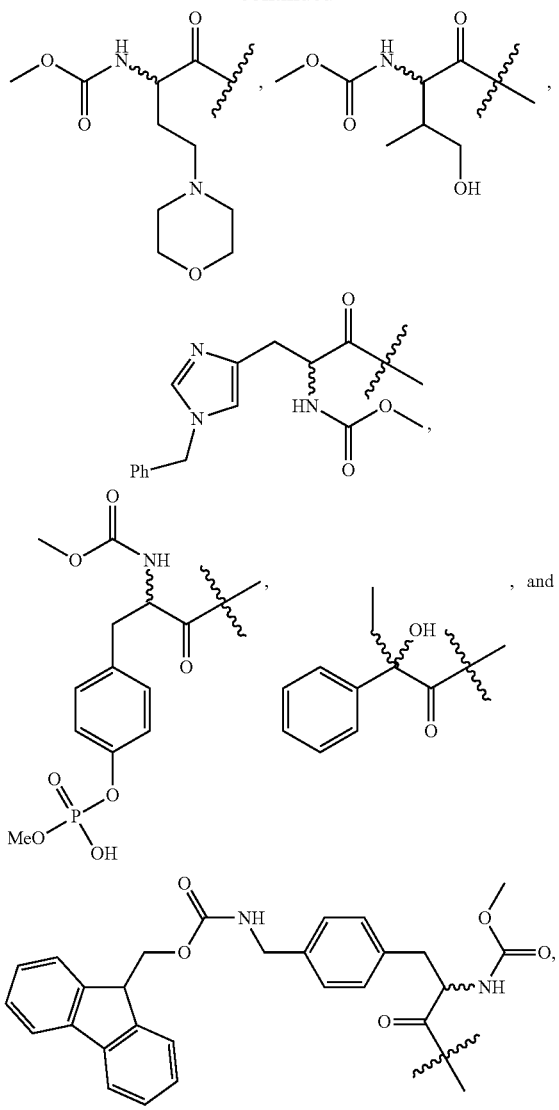

wherein a squiggle bond (⌇) in the structure indicates that a stereogenic center to which the bond is attached can take either (R)- or (S)-configuration so long as chemical bonding principles are not violated.

In a thirteenth embodiment of the first aspect, the present disclosure provides a compound of Formula (I), or a pharmaceutically acceptable salt or solvate thereof, wherein:

S is 0 or 1;

R$^1$ is —C(O)R$^x$;

R$^2$ is —C(O)R$^y$; and

R$^x$ and R$^y$ are both t-butoxy.

In a fourteenth embodiment of the first aspect, the present disclosure provides a compound of Formula (I), or a pharmaceutically acceptable salt or solvate thereof, wherein:

s is 0 or 1; and

R$^1$ and R$^2$ are both hydrogen.

In a fiftheenth embodiment of the first aspect, the present disclosure provides a compound of Formula (II):

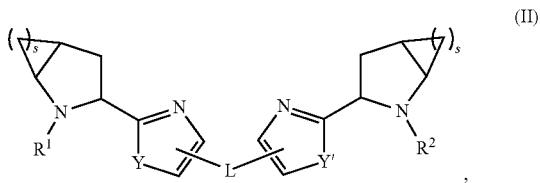

(II)

or a pharmaceutically acceptable salt thereof, wherein:
s is 0 or 1;
L is -L$^1$-L$^2$-, wherein L$^1$ and L$^2$ are independently selected from:

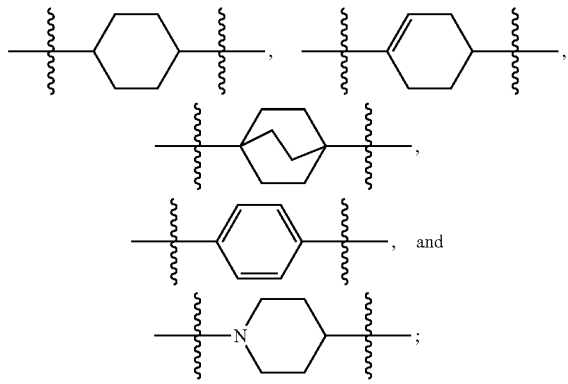

provided that at least one of L$^1$ and L$^2$ is other than

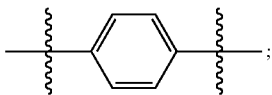

Y and Y' are independently oxygen (O) or NH;
R$^1$ is hydrogen or —C(O)R$^x$;
R$^2$ is hydrogen or —C(O)R$^y$;
R$^x$ and R$^y$ are independently selected from cycloalkyl, heteroaryl, heterocyclyl, alkoxy, and alkyl substituted with one or more substituents independently selected from aryl, alkenyl, cycloalkyl, heterocyclyl, heteroaryl, —OR$^3$, —C(O)OR$^4$, —NR$^a$R$^b$, and —C(O)NR$^c$R$^d$,
wherein aryl and heteroaryl may optionally be substituted with one or more substituents independently selected from alkyl, haloalkyl, arylalkyl, heterocyclyl, heterocyclylalkyl, halogen, cyano, nitro, —C(O)OR$^4$, OR$^5$, —NR$^a$R$^b$, (NR$^a$R$^b$)alkyl, and (MeO)(HO)P(O)O—, and
wherein cycloalkyl and heterocyclyl may optionally be fused onto an aromatic ring and may optionally be substituted with one or more substituents independently selected from alkyl, hydroxyl, halogen, aryl, —NR$^a$R$^b$, oxo, and —C(O)OR$^4$;
R$^3$ is hydrogen, alkyl, or arylalkyl;
R$^4$ is alkyl or arylalkyl;
R$^5$ is hydrogen, alkyl, or arylalkyl;
R$^a$ and R$^b$ are independently selected from hydrogen, alkyl, cycloalkyl, arylalkyl, heteroaryl, —C(O)R$^6$, —C(O)OR$^7$, —C(O)NR$^c$R$^d$, and (NR$^c$R$^d$)alkyl, or alternatively, R$^a$ and R$^b$, together with the nitrogen atom to which they are attached, form a five- or six-membered ring or bridged bicyclic ring structure, wherein said five- or six-membered ring or bridged bicyclic ring structure optionally may contain one or two additional heteroatoms independently selected from nitrogen, oxygen, and sulfur and may contain one, two, or three substituents independently selected from C$_1$ to C$_6$ alkyl, C$_1$ to C$_4$ haloalkyl, aryl, hydroxyl, C$_1$ to C$_6$ alkoxy, C$_1$ to C$_4$ haloalkoxy, and halogen;
R$^6$ is alkyl;
R$^7$ is alkyl, arylalkyl, or haloalkyl; and
R$^c$ and R$^d$ are independently selected from hydrogen, alkyl, arylalkyl, and cycloalkyl.

In a sixteenth embodiment of the first aspect, the present disclosure provides a compound, or a pharmaceutically acceptable salt or solvate thereof, selected from the group consisting of:

(1R)-2-((2S)-2-(4-(4-(4-(2-((2S)-1-((2R)-2-(dimethylamino)-2-phenylacetyl)-2-pyrrolidinyl)-1H-imidazol-5-yl)phenoxy)phenyl)-1H-imidazol-2-yl)-1-pyrrolidinyl)-N,N-dimethyl-2-oxo-1-phenylethanamine;

(1R)-2-((2S)-2-(4-(4-(4-(2-((2S)-1-((2R)-2-hydroxy-2-phenylacetyl)-2-pyrrolidinyl)-1H-imidazol-5-yl)phenoxy)phenyl)-1H-imidazol-2-yl)-1-pyrrolidinyl)-2-oxo-1-phenylethanol;

dimethyl(oxybis(4,1-phenylene-1H-imidazole-4,2-diyl(2S)-2,1-pyrrolidinediyl((1R)-2-oxo-1-phenyl-2,1-ethanediyl)))biscarbamate;

(1R)-2-((2S)-2-(4-(3-(4-(2-((2S)-1-((2R)-2-(dimethylamino)-2-phenylacetyl)-2-pyrrolidinyl)-1H-imidazol-4-yl)phenoxy)phenyl)-1H-imidazol-2-yl)-1-pyrrolidinyl)-N,N-dimethyl-2-oxo-1-phenylethanamine;

(1R)-2-((2S)-2-(4-(3-(4-(2-((2S)-1-((2R)-2-hydroxy-2-phenylacetyl)-2-pyrrolidinyl)-1H-imidazol-4-yl)phenoxy)phenyl)-1H-imidazol-2-yl)-1-pyrrolidinyl)-2-oxo-1-phenylethanol;

methyl((1R)-2-((2S)-2-(4-(3-(4-(2-((2S)-1-((2R)-2-((methoxycarbonyl)amino)-2-phenylacetyl)-2-pyrrolidinyl)-1H-imidazol-4-yl)phenoxy)phenyl)-1H-imidazol-2-yl)-1-pyrrolidinyl)-2-oxo-1-phenylethyl)carbamate;

(1R)-2-((2S)-2-(4-(4-((4-(2-((2S)-1-((2R)-2-(dimethylamino)-2-phenylacetyl)-2-pyrrolidinyl)-1H-imidazol-4-yl)benzyl)oxy)phenyl)-1H-imidazol-2-yl)-1-pyrrolidinyl)-N,N-dimethyl-2-oxo-1-phenylethanamine;

methyl((1R)-2-((2S)-2-(4-(4-((4-(2-((2S)-1-((2R)-2-((methoxycarbonyl)amino)-2-phenylacetyl)-2-pyrrolidinyl)-1H-imidazol-4-yl)benzyl)oxy)phenyl)-1H-imidazol-2-yl)-1-pyrrolidinyl)-2-oxo-1-phenylethyl)carbamate;

(1R)-2-((2S)-2-(4-(4-(2-(4-(2-((2S)-1-((2R)-2-(dimethylamino)-2-phenylacetyl)-2-pyrrolidinyl)-1H-imidazol-5-yl)phenyl)ethyl)phenyl)-1H-imidazol-2-yl)-1-pyrrolidinyl)-N,N-dimethyl-2-oxo-1-phenylethanamine;

(1R,1'R)-2,2'-(1,2-ethanediylbis(4,1-phenylene-1H-imidazole-4,2-diyl(2S)-2,1-pyrrolidinediyl))bis(2-oxo-1-phenylethanol);

dimethyl (1,2-ethanediylbis(4,1-phenylene-1H-imidazole-4,2-diyl(2S)-2,1-pyrrolidinediyl((1R)-2-oxo-1-phenyl-2,1-ethanediyl)))biscarbamate;

N',N'''-(1,2-ethanediylbis(4,1-phenylene-1H-imidazole-4,2-diyl(2S)-2,1-pyrrolidinediyl((1R)-2-oxo-1-phenyl-2,1-ethanediyl)))bis(1-ethylurea);

1-cyclopentyl-3-((1R)-2-((2S)-2-(4-(4-(2-(4-(2-((2S)-1-((2R)-2-((cyclopentylcarbamoyl)amino)-2-phenylacetyl)-2-pyrrolidinyl)-1H-imidazol-5-yl)phenyl)ethyl)phenyl)-1H-imidazol-2-yl)-1-pyrrolidinyl)-2-oxo-1-phenylethyl)urea;

(1R)-2-((2S)-2-(4-(4-(((4-(2-((2S)-1-((2R)-2-(dimethylamino)-2-phenylacetyl)-2-pyrrolidinyl)-1H-imidazol-5-yl)benzyl)oxy)methyl)phenyl)-1H-imidazol-2-yl)-1-pyrrolidinyl)-N,N-dimethyl-2-oxo-1-phenylethanamine;
(1R)-2-((2S)-2-(4-(4-(((4-(2-((2S)-1-((2R)-2-hydroxy-2-phenylacetyl)-2-pyrrolidinyl)-1H-imidazol-5-yl)benzyl)oxy)methyl)phenyl)-1H-imidazol-2-yl)-1-pyrrolidinyl)-2-oxo-1-phenylethanol;
dimethyl(oxybis(methylene-4,1-phenylene-1H-imidazole-4,2-diyl(2S)-2,1-pyrrolidinediyl((1R)-2-oxo-1-phenyl-2,1-ethanediyl)))biscarbamate;
1-methyl-3-((1R)-2-((2S)-2-(4-(4-(((4-(2-((2S)-1-((2R)-2-((methylcarbamoyl)amino)-2-phenylacetyl)-2-pyrrolidinyl)-1H-imidazol-5-yl)benzyl)oxy)methyl)phenyl)-1H-imidazol-2-yl)-1-pyrrolidinyl)-2-oxo-1-phenylethyl)urea;
1-ethyl-3-((1R)-2-((2S)-2-(4-(4-(((4-(2-((2S)-1-((2R)-2-((ethylcarbamoyl)amino)-2-phenylacetyl)-2-pyrrolidinyl)-1H-imidazol-5-yl)benzyl)oxy)methyl)phenyl)-1H-imidazol-2-yl)-1-pyrrolidinyl)-2-oxo-1-phenylethyl)urea;
1-cyclopentyl-3-((1R)-2-((2S)-2-(4-(4-(((4-(2-((2S)-1-((2R)-2-((cyclopentylcarbamoyl)amino)-2-phenylacetyl)-2-pyrrolidinyl)-1H-imidazol-5-yl)benzyl)oxy)methyl)phenyl)-1H-imidazol-2-yl)-1-pyrrolidinyl)-2-oxo-1-phenylethyl)urea;
(1R)-2-((2S)-2-(4-(3-(((4-(2-((2S)-1-((2R)-2-(dimethylamino)-2-phenylacetyl)-2-pyrrolidinyl)-1H-imidazol-4-yl)benzyl)oxy)methyl)phenyl)-1H-imidazol-2-yl)-1-pyrrolidinyl)-N,N-dimethyl-2-oxo-1-phenylethanamine;
(1R)-2-((2S)-2-(4-(3-(((4-(2-((2S)-1-((2R)-2-hydroxy-2-phenylacetyl)-2-pyrrolidinyl)-1H-imidazol-4-yl)benzyl)oxy)methyl)phenyl)-1H-imidazol-2-yl)-1-pyrrolidinyl)-2-oxo-1-phenylethanol;
(methyl((1R)-2-((2S)-2-(4-(3-(((4-(2-((2S)-1-((2R)-2-((methoxycarbonyl)amino)-2-phenylacetyl)-2-pyrrolidinyl)-1H-imidazol-4-yl)benzyl)oxy)methyl)phenyl)-1H-imidazol-2-yl)-1-pyrrolidinyl)-2-oxo-1-phenylethyl) carbamate;
1-methyl-3-((1R)-2-((2S)-2-(4-(3-(((4-(2-((2S)-1-((2R)-2-((methylcarbamoyl)amino)-2-phenylacetyl)-2-pyrrolidinyl)-1H-imidazol-4-yl)benzyl)oxy)methyl)phenyl)-1H-imidazol-2-yl)-1-pyrrolidinyl)-2-oxo-1-phenylethyl)urea;
1-ethyl-3-((1R)-2-((2S)-2-(4-(3-(((4-(2-((2S)-1-((2R)-2-((ethylcarbamoyl)amino)-2-phenylacetyl)-2-pyrrolidinyl)-1H-imidazol-4-yl)benzyl)oxy)methyl)phenyl)-1H-imidazol-2-yl)-1-pyrrolidinyl)-2-oxo-1-phenylethyl)urea;
1-cyclopentyl-3-((1R)-2-((2S)-2-(4-(3-(((4-(2-((2S)-1-((2R)-2-((cyclopentylcarbamoyl)amino)-2-phenylacetyl)-2-pyrrolidinyl)-1H-imidazol-4-yl)benzyl)oxy)methyl)phenyl)-1H-imidazol-2-yl)-1-pyrrolidinyl)-2-oxo-1-phenylethyl)urea;
dimethyl (1,1':4',1''-terphenyl-4,4''-diylbis(1H-imidazole-4,2-diyl(2S)-2,1-pyrrolidinediyl((1R)-2-oxo-1-phenyl-2,1-ethanediyl)))biscarbamate;
(1R)-2-((2S)-2-(4-(4''-(2-((2S)-1-((2R)-2-(dimethylamino)-2-phenylacetyl)-2-pyrrolidinyl)-1H-imidazol-5-yl)-1,1':4',1''-terphenyl-4-yl)-1H-imidazol-2-yl)-1-pyrrolidinyl)-N,N-dimethyl-2-oxo-1-phenylethanamine;
methyl((1S)-1-(((2S)-2-(4-(4-(4-(2-((2S)-1-((2S)-2-((methoxycarbonyl)amino)-3-methylbutanoyl)pyrrolidin-2-yl)-1H-imidazol-4-yl)phenyl)cyclohexyl)-1H-imidazol-2-yl)pyrrolidin-1-yl)carbonyl)-2-methylpropyl)carbamate;
methyl((1S)-1-(1R,3S,5R)-3-(4-chloro-5-(4-(4-(4-chloro-2-((1R,3S,5R)-2-((2S)-2-((methoxycarbonyl)amino)-3-methylbutanoyl)-2-azabicyclo[3.1.0]hex-3-yl)-1H-imidazol-5-yl)bicyclo[2.2.2]oct-1-yl)phenyl)-1H-imidazol-2-yl)-2-azabicyclo[3.1.0]hex-2-yl)carbonyl)-2-methylpropyl) carbamate; and
corresponding stereoisomers thereof.

In a second aspect the present disclosure provides a composition comprising a compound of Formula (I), or a pharmaceutically acceptable salt thereof, and a pharmaceutically acceptable carrier, wherein:

s is 0 or 1;

L is -L$^1$-L$^2$-, wherein L$^1$ and L$^2$ are independently selected from:

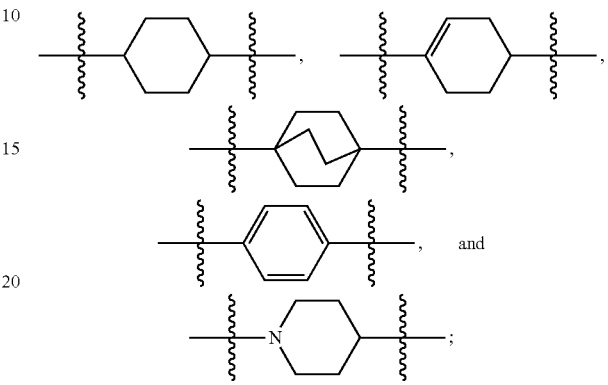

Y and Y' are independently oxygen (O) or NH;

R$^1$ is hydrogen or —C(O)R$^x$;

R$^2$ is hydrogen or —C(O)R$^y$;

R$^x$ and R$^y$ are independently selected from cycloalkyl, heteroaryl, heterocyclyl, alkoxy, and alkyl substituted with one or more substituents independently selected from aryl, alkenyl, cycloalkyl, heterocyclyl, heteroaryl, —OR$^3$, —C(O)OR$^4$, —NR$^a$R$^b$, and —C(O)NR$^c$R$^d$, wherein aryl and heteroaryl may optionally be substituted with one or more substituents independently selected from alkyl, haloalkyl, arylalkyl, heterocyclyl, heterocyclylalkyl, halogen, cyano, nitro, —C(O)OR$^4$, OR$^5$, —NR$^a$R$^b$, (NR$^a$R$^b$)alkyl, and (MeO)(HO)P(O)O—, and wherein cycloalkyl and heterocyclyl may optionally be fused onto an aromatic ring and may optionally be substituted with one or more substituents independently selected from alkyl, hydroxyl, halogen, aryl, —NR$^a$R$^b$, oxo, and —C(O)OR$^4$;

R$^3$ is hydrogen, alkyl, or arylalkyl;

R$^4$ is alkyl or arylalkyl;

R$^5$ is hydrogen, alkyl, or arylalkyl;

R$^a$ and R$^b$ are independently selected from hydrogen, alkyl, cycloalkyl, arylalkyl, heteroaryl, —C(O)R$^6$, —C(O)OR$^7$, —C(O)NR$^c$R$^d$, and (NR$^c$R$^d$)alkyl, or alternatively, R$^a$ and R$^b$, together with the nitrogen atom to which they are attached, form a five- or six-membered ring or bridged bicyclic ring structure, wherein said five- or six-membered ring or bridged bicyclic ring structure optionally may contain one or two additional heteroatoms independently selected from nitrogen, oxygen, and sulfur and may contain one, two, or three substituents independently selected from C$_1$ to C$_6$ alkyl, C$_1$ to C$_4$ haloalkyl, aryl, hydroxyl, C$_1$ to C$_6$ alkoxy, C$_1$ to C$_4$ haloalkoxy, and halogen;

R$^6$ is alkyl;

R$^7$ is alkyl, arylalkyl, or haloalkyl;

R$^{100}$ and R$^{110}$ are independently selected from hydrogen and halo; and $R^c$ and $R^d$ are independently selected from hydrogen, alkyl, arylalkyl, and cycloalkyl.

In a first embodiment of the second aspect the composition further comprises at least one additional compound having anti-HCV activity.

In a second embodiment of the second aspect at least one of the additional compounds is an interferon or a ribavirin.

In a third embodiment of the second aspect the interferon is selected from interferon alpha 2B, pegylated interferon alpha, consensus interferon, interferon alpha 2A, and lymphoblastoid interferon tau.

In a fourth embodiment of the second aspect the present disclosure provides a composition comprising a compound of Formula (I), or a pharmaceutically acceptable salt thereof, a pharmaceutically acceptable carrier, and at least one additional compound having anti-HCV activity, wherein at least one of the additional compounds is selected from interleukin 2, interleukin 6, interleukin 12, a compound that enhances the development of a type 1 helper T cell response, interfering RNA, anti-sense RNA, Imiqimod, ribavirin, an inosine 5'-monophospate dehydrogenase inhibitor, amantadine, and rimantadine.

In a fifth embodiment of the second aspect the present disclosure provides a composition comprising a compound of Formula (I), or a pharmaceutically acceptable salt thereof, a pharmaceutically acceptable carrier, and at least one additional compound having anti-HCV activity, wherein at least one of the additional compounds is effective to inhibit the function of a target selected from HCV metalloprotease, HCV serine protease, HCV polymerase, HCV helicase, HCV NS4B protein, HCV entry, HCV assembly, HCV egress, HCV NS5A protein, and IMPDH for the treatment of an HCV infection.

In a third aspect the present disclosure provides a method of treating an HCV infection in a patient, comprising administering to the patient a therapeutically effective amount of a compound of Formula (I), or a pharmaceutically acceptable salt thereof, wherein:

s is 0 or 1;

L is -$L^1$-$L^2$-, wherein $L^1$ and $L^2$ are independently selected from:

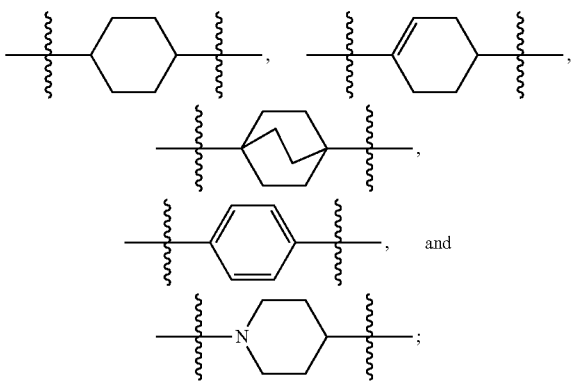

Y and Y' are independently oxygen (O) or NH;
$R^1$ is hydrogen or —C(O)$R^x$;
$R^2$ is hydrogen or —C(O)$R^y$;
$R^x$ and $R^y$ are independently selected from cycloalkyl, heteroaryl, heterocyclyl, alkoxy, and alkyl substituted with one or more substituents independently selected from aryl, alkenyl, cycloalkyl, heterocyclyl, heteroaryl, —O$R^3$,
—C(O)O$R^4$, —N$R^a R^b$, and —C(O)N$R^c R^d$,
  wherein aryl and heteroaryl may optionally be substituted with one or more substituents independently selected from alkyl, haloalkyl, arylalkyl, heterocyclyl, heterocyclylalkyl, halogen, cyano, nitro, —C(O)O$R^4$, O$R^5$, —N$R^a R^b$, (N$R^a R^b$)alkyl, and (MeO)(HO)P(O)O—, and
  wherein cycloalkyl and heterocyclyl may optionally be fused onto an aromatic ring and may optionally be substituted with one or more substituents independently selected from alkyl, hydroxyl, halogen, aryl, —N$R^a R^b$, oxo, and —C(O)O$R^4$;
$R^3$ is hydrogen, alkyl, or arylalkyl;
$R^4$ is alkyl or arylalkyl;
$R^5$ is hydrogen, alkyl, or arylalkyl;
$R^a$ and $R^b$ are independently selected from hydrogen, alkyl, cycloalkyl, arylalkyl, heteroaryl, —C(O)$R^6$, —C(O)O$R^7$, —C(O)N$R^c R^d$, and (N$R^c R^d$)alkyl, or alternatively, $R^a$ and $R^b$, together with the nitrogen atom to which they are attached, form a five- or six-membered ring or bridged bicyclic ring structure, wherein said five- or six-membered ring or bridged bicyclic ring structure optionally may contain one or two additional heteroatoms independently selected from nitrogen, oxygen, and sulfur and may contain one, two, or three substituents independently selected from $C_1$ to $C_6$ alkyl, $C_1$ to $C_4$ haloalkyl, aryl, hydroxyl, $C_1$ to $C_6$ alkoxy, $C_1$ to $C_4$ haloalkoxy, and halogen;
$R^6$ is alkyl;
$R^7$ is alkyl, arylalkyl, or haloalkyl; and
$R^c$ and $R^d$ are independently selected from hydrogen, alkyl, arylalkyl, and cycloalkyl.

In a first embodiment of the third aspect the method further comprises administering at least one additional compound having anti-HCV activity prior to, after or simultaneously with the compound of Formula (I), or a pharmaceutically acceptable salt thereof.

In a second embodiment of the third aspect at least one of the additional compounds is an interferon or a ribavirin.

In a third embodiment of the third aspect the interferon is selected from interferon alpha 2B, pegylated interferon alpha, consensus interferon, interferon alpha 2A, and lymphoblastoid interferon tau.

In a fourth embodiment of the third aspect the present disclosure provides a method of treating an HCV infection in a patient, comprising administering to the patient a therapeutically effective amount of a compound of Formula (I), or a pharmaceutically acceptable salt thereof, and at least one additional compound having anti-HCV activity prior to, after or simultaneously with the compound of Formula (I), or a pharmaceutically acceptable salt thereof, wherein at least one of the additional compounds is selected from interleukin 2, interleukin 6, interleukin 12, a compound that enhances the development of a type 1 helper T cell response, interfering RNA, anti-sense RNA, Imiqimod, ribavirin, an inosine 5'-monophospate dehydrogenase inhibitor, amantadine, and rimantadine.

In a fifth embodiment of the third aspect the present disclosure provides a method of treating an HCV infection in a patient, comprising administering to the patient a therapeutically effective amount of a compound of Formula (I), or a pharmaceutically acceptable salt thereof, and at least one additional compound having anti-HCV activity prior to, after or simultaneously with the compound of Formula (I), or a pharmaceutically acceptable salt thereof, wherein at least one of the additional compounds is effective to inhibit the function of a target selected from HCV metalloprotease, HCV serine protease, HCV polymerase, HCV helicase, HCV NS4B protein, HCV entry, HCV assembly, HCV egress, HCV NS5A protein, and IMPDH for the treatment of an HCV infection.

Other aspects of the present disclosure may include suitable combinations of embodiments disclosed herein.

Yet other aspects and embodiments may be found in the description provided herein.

The description of the present disclosure herein should be construed in congruity with the laws and principals of chemical bonding. In some instances it may be necessary to remove a hydrogen atom in order to accommodate a substituent at any given location.

Certain features of the structure of Formula (I) are further illustrated below:

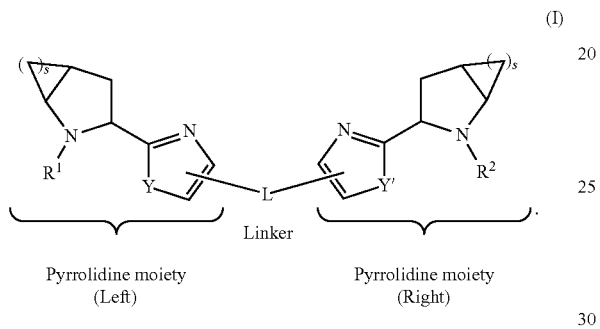

(I)

In Formula (I), as depicted above, the "pyrrolidine moiety" on the left side of the "linker" is independent from the "pyrrolidine moiety" on the right side in respect to, e.g., (1) tautomer form of imidazole ring when Y or Y' is NH, (2) absolute configuration of the stereogenic centers on the pyrrolidine ring, and (3) substituents on the pyrrolidine nitrogen, i.e., $R^1$ and $R^2$ are independent from each other, although in some circumstances they are preferably the same.

As for connection between the linker "L" and the pyrrolidine moieties, Formula (I) encompasses all the following possible combinations:

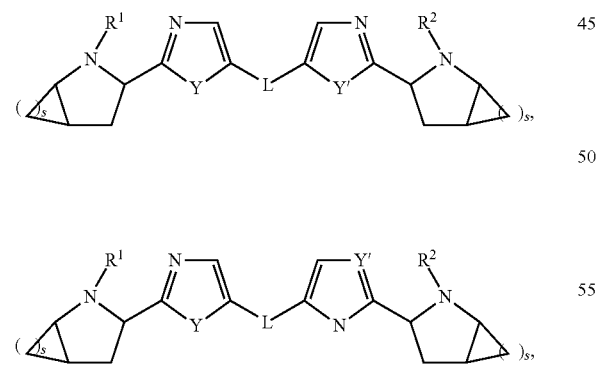

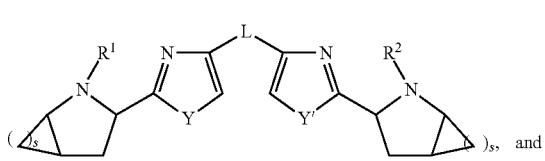
and

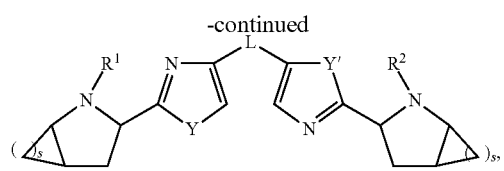

wherein Y and Y' are independently oxygen (O) or NH.

In a pyrrolidine ring, the stereogenic carbon center to which a five-membered heterocycle is attached can take either (R)- or (S)-configuration as depicted below:

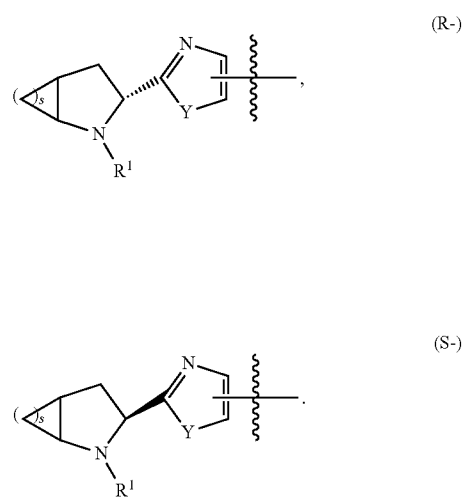

When a cyclopropyl ring is fused onto a pyrrolidine ring, i.e., when s is 1, the $CH_2$ group of the fused cyclopropyl ring can take either α- or β-position relative to the pyrrolidine ring, as depicted below:

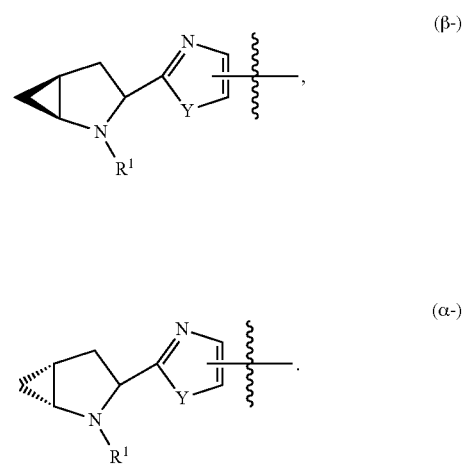

In Formula (I), when either Y or Y' is NH, the linkage between the linker "L" and the resultant imidazole ring can take place in either the C-4 or the C-5 position (see below) of the imidazole ring. As a person of ordinary skill in the art would understand, due to tautomerization of the imidazole ring, a bonding of the linker "L" to the C-4 position may be equivalent to a bonding of the linker to the C-5 position, as shown in the following equation:

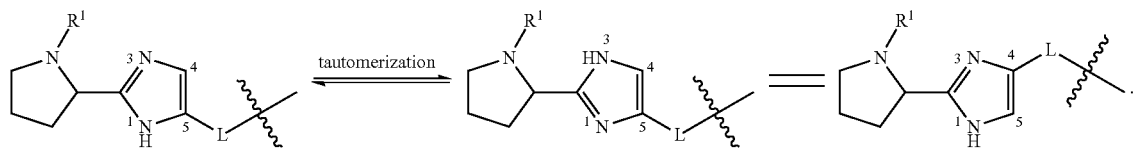

Thus, this disclosure is intended to cover both possible linkages even when a structure depicts only one of them.
In this disclosure, a floating bond (e.g.,

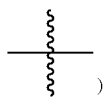
)

or a floating substituent (e.g., —$R^{13}$) on a structure indicates that the bond or substituent can attach to any available position of the structure by removal of a hydrogen from the available position. It should be understood that in a bicyclic or polycyclic ring structure, unless specifically defined otherwise, the position of a floating bond or a floating substituent does not limit the position of such bond or substituent to a specific ring. Thus, the following two substituent groups should be construed to be equivalent:

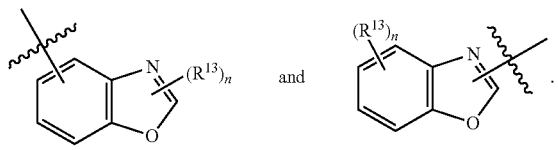

It should be understood that the compounds encompassed by the present disclosure are those that are suitably stable for use as pharmaceutical agent.
It is intended that the definition of any substituent or variable at a particular location in a molecule be independent of its definitions elsewhere in that molecule. For example, for substituent $(R^{10})_n$, when n is 2, each of the two $R^{10}$ groups may be the same or different.

All patents, patent applications, and literature references cited in the specification are herein incorporated by reference in their entirety. In the case of inconsistencies, the present disclosure, including definitions, will prevail.

DEFINITIONS

Definitions have been provided above for each of the groups defined. In addition, the following definitions shall be used.

As used herein, the singular forms "a", "an", and "the" include plural reference unless the context clearly dictates otherwise.

Unless stated otherwise, all aryl, cycloalkyl, heteroaryl, and heterocyclyl groups of the present disclosure may be substituted as described in each of their respective definitions. For example, the aryl part of an arylalkyl group may be substituted as described in the definition of the term "aryl."

The term "acetyl," as used herein, refers to —C(O)CH$_3$.

The term "alkenyl," as used herein, refers to a monovalent, straight or branched hydrocarbon chain having one or more double bonds therein. The double bond of an alkenyl group can be unconjugated or conjugated to another unsaturated group. Suitable alkenyl groups include, but are not limited to, $C_2$ to $C_{10}$ alkenyl groups, such as vinyl, allyl, butenyl, pentenyl, hexenyl, butadienyl, pentadienyl, hexadienyl, 2-ethylhexenyl, 2-propyl-2-butenyl, 4-(2-methyl-3-butene)-pentenyl. An alkenyl group can be unsubstituted or substituted with one or two suitable substituents.

The term "alkoxy," as used herein, refers to an alkyl group attached to the parent molecular moiety through an oxygen atom. Representative examples of alkoxy group include, but are not limited to, methoxy (CH$_3$O—), ethoxy (CH$_3$CH$_2$O—), and t-butoxy ((CH$_3$)$_3$CO—).

The term "alkyl," as used herein, refers to a group derived from a straight or branched chain saturated hydrocarbon by removal of a hydrogen from one of the saturated carbons. The alkyl group preferably contains from one to ten carbon atoms. Representative examples of alkyl group include, but are not limited to, methyl, ethyl, isopropyl, and tert-butyl.

The term "alkylcarbonyl," as used herein, refers to an alkyl group attached to the parent molecular moiety through a carbonyl group. Representative examples of alkylcarbonyl group include, but are not limited to, acetyl (—C(O)CH$_3$), propanoyl (—C(O)CH$_2$CH$_3$), n-butyryl (—C(O)CH$_2$CH$_2$CH$_3$), and 2,2-dimethylpropanoyl or pivaloyl (—C(O)C(CH$_3$)$_3$).

The term "allyl," as used herein, refers to the —CH$_2$CH=CH$_2$ group.

The term "aryl," as used herein, refers to a group derived from an aromatic carbocycle by removal of a hydrogen atom from an aromatic ring. The aryl group can be monocyclic, bicyclic or polycyclic, wherein in bicyclic or polycyclic aryl group, the aromatic carbocycle can be fused onto another four- to six-membered aromatic or non-aromatic carbocycle. Representative examples of aryl groups include, but are not limited to, phenyl, indanyl, indenyl, naphthyl, and 1,2,3,4-tetrahydronaphth-5-yl.

The term "arylalkyl," as used herein, refers to an alkyl group substituted with one, two, or three aryl groups, wherein aryl part of the arylalkyl group may optionally be substituted by one to five substituents independently selected from $C_1$ to $C_6$ alkyl, $C_1$ to $C_4$ haloalkyl, $C_1$ to $C_6$ alkoxy, halogen, cyano, and nitro groups. Represented examples of arylalkyl include, but are not limited to, benzyl, 2-phenyl-1-ethyl (PhCH$_2$CH$_2$—), (naphth-1-yl)methyl, and (naphth-2-yl)methyl.

The term "benzyl," as used herein, refers to a methyl group on which one of the hydrogen atoms is replaced by a phenyl group, wherein said phenyl group may optionally be substituted by one to five substituents independently selected from methyl, trifluoromethyl (—CF$_3$), methoxy (—OCH$_3$), halogen, and nitro (—NO$_2$). Representative examples of benzyl group include, but are not limited to, PhCH$_2$—, 4-MeO—C$_6$H$_4$CH$_2$—, and 2,4,6-tri-methyl-C$_6$H$_4$CH$_2$—.

The terms "Cap" and "cap," as used herein, refer to the group which is placed on the nitrogen atom of the pyrrolidine ring in the compounds of formula (I). It should be understood that "Cap" or "cap" can also refer to the reagent which is a precursor to the final "cap" in compounds of formula (I) and is used as one of the starting materials in the reaction to append a group on the pyrrolidine nitrogen that results in the final product, a compound which contains the functionalized pyrrolidine that will be present in the compound of formula (I).

The term "carbonyl," as used herein, refers to —C(O)—.

The term "carboxyl," as used herein, refers to —CO$_2$H.

The term "cyano," as used herein, refers to —CN.

The term "cycloalkyl," as used herein, refers to a group derived from a saturated carbocycle, having preferably three to eight carbon atoms, by removal of a hydrogen atom from the saturated carbocycle, wherein the saturated carbocycle can optionally be fused onto one or two other aromatic or nonaromatic carbocycles. Representative examples of cycloalkyl groups include, but are not limited to, cyclopropyl, cyclopentyl, cyclohexyl, and 1,2,3,4-tetrahydronaphth-1-yl.

The term "formyl," as used herein, refers to —CHO.

The terms "halo" and "halogen," as used herein, refer to F, Cl, Br, or I.

The term "haloalkoxy," as used herein, refers to a haloalkyl group attached to the parent molecular moiety through an oxygen atom.

The term "haloalkyl," as used herein, refers to an alkyl group substituted by at least one halogen atom. The haloalkyl group can be an alkyl group of which all hydrogen atoms are substituted by halogens. Representative examples of haloalkyl include, but are not limited to, trifluoromethyl (CF$_3$—), 1-chloroethyl (ClCH$_2$CH$_2$—), and 2,2,2-trifluoroethyl (CF$_3$CH$_2$—).

The term "heteroaryl," as used herein, refers to group derived from a monocyclic, bicyclic, or polycyclic compound comprising at least one aromatic ring comprising one or more heteroatoms, preferably, one to three heteroatoms, independently selected from nitrogen, oxygen, and sulfur, by removal of a hydrogen atom from an aromatic ring thereof. As is well known to those skilled in the art, heteroaryl rings have less aromatic character than their all-carbon counterparts. Thus, for the purposes of the invention, a heteroaryl group need only have some degree of aromatic character. Illustrative examples of heteroaryl groups include, but are not limited to, pyridyl, pyridazinyl, pyrimidyl, pyrazyl, triazinyl, pyrrolyl, pyrazolyl, imidazolyl, (1,2,3,)- and (1,2,4)-triazolyl, pyrazinyl, pyrimidinyl, tetrazolyl, furyl, thienyl, isoxazolyl, thiazolyl, isoxazolyl, oxazolyl, indolyl, quinolinyl, isoquinolinyl, benzisoxazolyl, benzothiazolyl, benzothienyl, and pyrrolopyridinyl.

The term "heteroarylalkyl," as used herein, refers to an alkyl group substituted with one, two, or three heteroaryl groups.

The term "heterobicyclyl," as used herein, refers to a ring structure comprising two fused or bridged rings that include carbon and one or more heteroatoms independently selected from nitrogen, oxygen, and sulfur as the ring atom(s). The heterobicyclic ring structure is a subset of heterocyclic ring and can be saturated or unsaturated. Examples of heterobicyclic ring structures include tropane, quinuclidine, and 7-azabicyclo[2.2.1]heptane.

The term "heterocyclyl," as used herein, refers to a group derived from a monocyclic, bicyclic, or polycyclic compound comprising at least one nonaromatic ring comprising one or more heteroatoms, preferably, one to three heteroatoms, independently selected from nitrogen, oxygen, and sulfur, by removal of a hydrogen atom from the nonaromatic ring. The heterocyclyl group encompasses the heterobicyclyl group. The heterocyclyl groups of the present disclosure can be attached to the parent molecular moiety through a carbon atom or a nitrogen atom in the group. Examples of heterocyclyl groups include, but are not limited to, morpholinyl, oxazolidinyl, piperazinyl, piperidinyl, pyrrolidinyl, tetrahydrofuryl, thiomorpholinyl, and indolinyl.

The term "heterocyclylalkyl," as used herein, refers to an alkyl group substituted with one, two, or three heterocyclyl groups.

The terms "hydroxy" or "hydroxyl," as used herein, refer to —OH.

The term "nitro," as used herein, refers to —NO$_2$.

The term "—NR$^a$R$^b$," as used herein, refers to two groups, R$^a$ and R$^b$, which are attached to the parent molecular moiety through a nitrogen atom, or alternatively R$^a$ and R$^b$, together with the nitrogen atom to which they are attached, form a 5- or 6-membered ring or a fused- or bridged-bicyclic ring structure optionally containing one, two, or three additional heteroatom independently selected from nitrogen, oxygen, and sulfur. The term "—NR$^c$R$^d$" is defined similarly.

The term "(NR$^a$R$^b$)alkyl," as used herein, refers to an alkyl group substituted with one, two, or three —NR$^a$R$^b$ groups. The term "(NR$^c$R$^d$)alkyl" is defined similarly.

The term "oxo," as used herein, refers to =O.

The term "sulfonyl," as used herein, refers to —SO$_2$—.

In the compounds of the present disclosure, it should be understood that when is 0, the compound of formula (Z) shown below is the result:

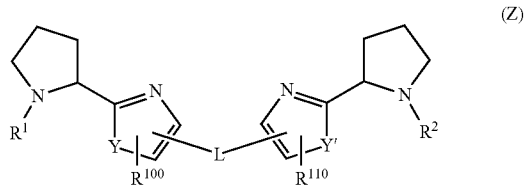

Asymmetric centers exist in the compounds of the present disclosure. These centers are designated by the symbols "R" or "S", depending on the configuration of substituents around the chiral carbon atom. It should be understood that the disclosure encompasses all stereochemical isomeric forms, or mixtures thereof, which possess the ability to inhibit NS5A. Individual stereoisomers of compounds can be prepared synthetically from commercially available starting materials which contain chiral centers or by preparation of mixtures of enantiomeric products followed by separation such as conversion to a mixture of diastereomers followed by separation or recrystallization, chromatographic techniques, or direct separation of enantiomers on chiral chromatographic columns. Starting compounds of particular stereochemistry are either commercially available or can be made and resolved by techniques known in the art.

Certain compounds of the present disclosure may also exist in different stable conformational forms which may be separable. Torsional asymmetry due to restricted rotation about an asymmetric single bond, for example because of steric hindrance or ring strain, may permit separation of different conformers. The present disclosure includes each conformational isomer of these compounds and mixtures thereof.

The term "compounds of the present disclosure", and equivalent expressions, are meant to embrace compounds of Formula (I), and pharmaceutically acceptable enantiomers, diastereomers, and salts thereof. Similarly, references to intermediates are meant to embrace their salts where the context so permits.

The present disclosure is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds may have a variety of potential uses, for example as standards and reagents in determining biological activity. In the case of stable isotopes, such compounds may have the potential to favorably modify biological, pharmacological, or pharmacokinetic properties.

The compounds of the present disclosure can exist as pharmaceutically acceptable salts. The term "pharmaceutically acceptable salt," as used herein, represents salts or zwitterionic forms of the compounds of the present disclosure which are water or oil-soluble or dispersible, which are, within the scope of sound medical judgment, suitable for use in contact with the tissues of patients without excessive toxicity, irritation, allergic response, or other problem or complication commensurate with a reasonable benefit/risk ratio, and are effective for their intended use The salts can be prepared during the final isolation and purification of the compounds or separately by reacting a suitable nitrogen atom with a suitable acid. Representative acid addition salts include acetate, adipate, alginate, citrate, aspartate, benzoate, benzenesulfonate, bisulfate, butyrate, camphorate, camphorsulfonate; digluconate, glycerophosphate, hemisulfate, heptanoate, hexanoate, formate, fumarate, hydrochloride, hydrobromide, hydroiodide, 2-hydroxyethanesulfonate, lactate, maleate, mesitylenesulfonate, methanesulfonate, naphthylenesulfonate, nicotinate, 2-naphthalenesulfonate, oxalate, palmoate, pectinate, persulfate, 3-phenylproprionate, picrate, pivalate, propionate, succinate, tartrate, trichloroacetate, trifluoroacetate, phosphate, glutamate, bicarbonate, para-toluenesulfonate, and undecanoate. Examples of acids which can be employed to form pharmaceutically acceptable addition salts include inorganic acids such as hydrochloric, hydrobromic, sulfuric, and phosphoric, and organic acids such as oxalic, maleic, succinic, and citric.

Basic addition salts can be prepared during the final isolation and purification of the compounds by reacting a carboxy group with a suitable base such as the hydroxide, carbonate, or bicarbonate of a metal cation or with ammonia or an organic primary, secondary, or tertiary amine. The cations of pharmaceutically acceptable salts include lithium, sodium, potassium, calcium, magnesium, and aluminum, as well as nontoxic quaternary amine cations such as ammonium, tetramethylammonium, tetraethylammonium, methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, and N,N'-dibenzylethylenediamine. Other representative organic amines useful for the formation of base addition salts include ethylenediamine, ethanolamine, diethanolamine, piperidine, and piperazine.

When it is possible that, for use in therapy, therapeutically effective amounts of a compound of Formula (I), as well as pharmaceutically acceptable salts thereof, may be administered as the raw chemical, it is possible to present the active ingredient as a pharmaceutical composition. Accordingly, the disclosure further provides pharmaceutical compositions, which include therapeutically effective amounts of compounds of Formula (I) or pharmaceutically acceptable salts thereof, and one or more pharmaceutically acceptable carriers, diluents, or excipients. The term "therapeutically effective amount," as used herein, refers to the total amount of each active component that is sufficient to show a meaningful patient benefit, e.g., a sustained reduction in viral load. When applied to an individual active ingredient, administered alone, the term refers to that ingredient alone. When applied to a combination, the term refers to combined amounts of the active ingredients that result in the therapeutic effect, whether administered in combination, serially, or simultaneously. The compounds of Formula (I) and pharmaceutically acceptable salts thereof, are as described above. The carrier(s), diluent (s), or excipient(s) must be acceptable in the sense of being compatible with the other ingredients of the formulation and not deleterious to the recipient thereof. In accordance with another aspect of the present disclosure there is also provided a process for the preparation of a pharmaceutical formulation including admixing a compound of Formula (I), or a pharmaceutically acceptable salt thereof, with one or more pharmaceutically acceptable carriers, diluents, or excipients. The term "pharmaceutically acceptable," as used herein, refers to those compounds, materials, compositions, and/or dosage forms which are, within the scope of sound medical judgment, suitable for use in contact with the tissues of patients without excessive toxicity, irritation, allergic response, or other problem or complication commensurate with a reasonable benefit/risk ratio, and are effective for their intended use.

Pharmaceutical formulations may be presented in unit dose forms containing a predetermined amount of active ingredient per unit dose. Dosage levels of between about 0.01 and about 250 milligram per kilogram ("mg/kg") body weight per day, preferably between about 0.05 and about 100 mg/kg body weight per day of the compounds of the present disclosure are typical in a monotherapy for the prevention and treatment of HCV mediated disease. Typically, the pharmaceutical compositions of this disclosure will be administered from about 1 to about 5 times per day or alternatively, as a continuous infusion. Such administration can be used as a chronic or acute therapy. The amount of active ingredient that may be combined with the carrier materials to produce a single dosage form will vary depending on the condition being treated, the severity of the condition, the time of administration, the route of administration, the rate of excretion of the compound employed, the duration of treatment, and the age, gender, weight, and condition of the patient. Preferred unit dosage formulations are those containing a daily dose or sub-dose, as herein above recited, or an appropriate fraction thereof, of an active ingredient. Generally, treatment is initiated with small dosages substantially less than the optimum dose of the compound. Thereafter, the dosage is increased by small increments until the optimum effect under the circumstances is reached. In general, the compound is most desirably administered at a concentration level that will generally afford antivirally effective results without causing any harmful or deleterious side effects.

When the compositions of this disclosure comprise a combination of a compound of the present disclosure and one or more additional therapeutic or prophylactic agent, both the compound and the additional agent are usually present at dosage levels of between about 10 to 150%, and more preferably between about 10 and 80% of the dosage normally administered in a monotherapy regimen.

Pharmaceutical formulations may be adapted for administration by any appropriate route, for example by the oral (including buccal or sublingual), rectal, nasal, topical (including buccal, sublingual, or transdermal), vaginal, or parenteral (including subcutaneous, intracutaneous, intramuscular, intra-articular, intrasynovial, intrasternal, intrathecal, intralesional, intravenous, or intradermal injections or infusions) route. Such formulations may be prepared by any method known in the art of pharmacy, for example by bringing into association the active ingredient with the carrier(s) or excipient(s). Oral administration or administration by injection are preferred.

Pharmaceutical formulations adapted for oral administration may be presented as discrete units such as capsules or tablets; powders or granules; solutions or suspensions in aqueous or non-aqueous liquids; edible foams or whips; or oil-in-water liquid emulsions or water-in-oil emulsions.

For instance, for oral administration in the form of a tablet or capsule, the active drug component can be combined with an oral, non-toxic pharmaceutically acceptable inert carrier such as ethanol, glycerol, water, and the like. Powders are prepared by comminuting the compound to a suitable fine size and mixing with a similarly comminuted pharmaceutical carrier such as an edible carbohydrate, as, for example, starch or mannitol. Flavoring, preservative, dispersing, and coloring agent can also be present.

Capsules are made by preparing a powder mixture, as described above, and filling formed gelatin sheaths. Glidants and lubricants such as colloidal silica, talc, magnesium stearate, calcium stearate, or solid polyethylene glycol can be added to the powder mixture before the filling operation. A disintegrating or solubilizing agent such as agar-agar, calcium carbonate, or sodium carbonate can also be added to improve the availability of the medicament when the capsule is ingested.

Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, and the like. Lubricants used in these dosage forms include sodium oleate, sodium chloride, and the like. Disintegrators include, without limitation, starch, methyl cellulose, agar, betonite, xanthan gum, and the like. Tablets are formulated, for example, by preparing a powder mixture, granulating or slugging, adding a lubricant and disintegrant, and pressing into tablets. A powder mixture is prepared by mixing the compound, suitable comminuted, with a diluent or base as described above, and optionally, with a binder such as carboxymethylcellulose, an aliginate, gelating, or polyvinyl pyrrolidone, a solution retardant such as paraffin, a resorption accelerator such as a quaternary salt and/or and absorption agent such as betonite, kaolin, or dicalcium phosphate. The powder mixture can be granulated by wetting with a binder such as syrup, starch paste, acadia mucilage, or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc, or mineral oil. The lubricated mixture is then compressed into tablets. The compounds of the present disclosure can also be combined with a free flowing inert carrier and compressed into tablets directly without going through the granulating or slugging steps. A clear or opaque protective coating consisting of a sealing coat of shellac, a coating of sugar or polymeric material, and a polish coating of wax can be provided. Dyestuffs can be added to these coatings to distinguish different unit dosages.

Oral fluids such as solution, syrups, and elixirs can be prepared in dosage unit form so that a given quantity contains a predetermined amount of the compound. Syrups can be prepared by dissolving the compound in a suitably flavored aqueous solution, while elixirs are prepared through the use of a non-toxic vehicle. Solubilizers and emulsifiers such as ethoxylated isostearyl alcohols and polyoxyethylene sorbitol ethers, preservatives, flavor additive such as peppermint oil or natural sweeteners, or saccharin or other artificial sweeteners, and the like can also be added.

Where appropriate, dosage unit formulations for oral administration can be microencapsulated. The formulation can also be prepared to prolong or sustain the release as for example by coating or embedding particulate material in polymers, wax, or the like.

The compounds of Formula (I), and pharmaceutically acceptable salts thereof, can also be administered in the form of liposome delivery systems, such as small unilamellar vesicles, large unilamellar vesicles, and multilamellar vesicles. Liposomes can be formed from a variety of phospholipids, such as cholesterol, stearylamine, or phophatidylcholines.

The compounds of Formula (I) and pharmaceutically acceptable salts thereof may also be delivered by the use of monoclonal antibodies as individual carriers to which the compound molecules are coupled. The compounds may also be coupled with soluble polymers as targetable drug carriers. Such polymers can include polyvinylpyrrolidone, pyran copolymer, polyhydroxypropylmethacrylamidephenol, polyhydroxyethylaspartamidephenol, or polyethyleneoxidepolylysine substituted with palitoyl residues. Furthermore, the compounds may be coupled to a class of biodegradable polymers useful in achieving controlled release of a drug, for example, polylactic acid, polepsilon caprolactone, polyhydroxy butyric acid, polyorthoesters, polyacetals, polydihydropyrans, polycyanoacrylates, and cross-linked or amphipathic block copolymers of hydrogels.

Pharmaceutical formulations adapted for transdermal administration may be presented as discrete patches intended to remain in intimate contact with the epidermis of the recipient for a prolonged period of time. For example, the active ingredient may be delivered from the patch by iontophoresis as generally described in *Pharm. Res.,* 3(6):318 (1986).

Pharmaceutical formulations adapted for topical administration may be formulated as ointments, creams, suspensions, lotions, powders, solutions, pastes, gels, sprays, aerosols, or oils.

For treatments of the eye or other external tissues, for example mouth and skin, the formulations are preferably applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in oil base.

Pharmaceutical formulations adapted for topical administrations to the eye include eye drops wherein the active ingredient is dissolved or suspended in a suitable carrier, especially an aqueous solvent.

Pharmaceutical formulations adapted for topical administration in the mouth include lozenges, pastilles, and mouth washes.

Pharmaceutical formulations adapted for rectal administration may be presented as suppositories or as enemas.

Pharmaceutical formulations adapted for nasal administration wherein the carrier is a solid include a course powder having a particle size for example in the range 20 to 500 microns which is administered in the manner in which snuff is taken, i.e., by rapid inhalation through the nasal passage from a container of the powder held close up to the nose. Suitable formulations wherein the carrier is a liquid, for administration as a nasal spray or nasal drops, include aqueous or oil solutions of the active ingredient.

Pharmaceutical formulations adapted for administration by inhalation include fine particle dusts or mists, which may be generated by means of various types of metered, dose pressurized aerosols, nebulizers, or insufflators.

Pharmaceutical formulations adapted for vaginal administration may be presented as pessaries, tampons, creams, gels, pastes, foams, or spray formulations.

Pharmaceutical formulations adapted for parenteral administration include aqueous and non-aqueous sterile injection solutions which may contain anti-oxidants, buffers, bacteriostats, and soutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules, and tablets.

It should be understood that in addition to the ingredients particularly mentioned above, the formulations may include other agents conventional in the art having regard to the type of formulation in question, for example those suitable for oral administration may include flavoring agents.

The term "patient" includes both human and other mammals.

The term "treating" refers to: (i) preventing a disease, disorder or condition from occurring in a patient that may be predisposed to the disease, disorder, and/or condition but has not yet been diagnosed as having it; (ii) inhibiting the disease, disorder, or condition, i.e., arresting its development; and (iii) relieving the disease, disorder, or condition, i.e., causing regression of the disease, disorder, and/or condition.

The compounds of the present disclosure can also be administered with a cyclosporin, for example, cyclosporin A. Cyclosporin A has been shown to be active against HCV in clinical trials (*Hepatology*, 38:1282 (2003); *Biochem. Biophys. Res. Commun.*, 313:42 (2004); *J. Gastroenterol.*, 38:567 (2003)).

Table 1 below lists some illustrative examples of compounds that can be administered with the compounds of this disclosure. The compounds of the disclosure can be administered with other anti-HCV activity compounds in combination therapy, either jointly or separately, or by combining the compounds into a composition.

TABLE 1

| Brand Name | Physiological Class | Type of Inhibitor or Target | Source Company |
|---|---|---|---|
| NIM811 | | Cyclophilin Inhibitor | Novartis |
| Zadaxin | | Immuno-modulator | Sciclone |
| Suvus | | Methylene blue | Bioenvision |
| Actilon (CPG10101) | | TLR9 agonist | Coley |
| Batabulin (T67) | Anticancer | β-Tubulin inhibitor | Tularik Inc., South San Francisco, CA |
| ISIS 14803 | Antiviral | Antisense | ISIS Pharmaceuticals Inc, Carlsbad, CA/Elan Phamaceuticals Inc., New York, NY |
| Summetrel | Antiviral | Antiviral | Endo Pharmaceuticals Holdings Inc., Chadds Ford, PA |
| GS-9132 (ACH-806) | Antiviral | HCV inhibitor | Achillion/Gilead |
| Pyrazolopyrimidine compounds and salts From WO2005/047288 26 May 2005 | Antiviral | HCV inhibitors | Arrow Therapeutics Ltd. |
| Levovirin | Antiviral | IMPDH inhibitor | Ribapharm Inc., Costa Mesa, CA |
| Merimepodib (VX-497) | Antiviral | IMPDH inhibitor | Vertex Pharmaceuticals Inc., Cambridge, MA |
| XTL-6865 (XTL-002) | Antiviral | Monoclonal antibody | XTL Biopharmaceuticals Ltd., Rehovot, Israel |
| Telaprevir (VX-950, LY-570310) | Antiviral | NS3 serine protease inhibitor | Vertex Pharmaceuticals Inc., Cambridge, MA/Eli Lilly and Co. Inc., Indianapolis, IN |
| HCV-796 | Antiviral | NS5B replicase inhibitor | Wyeth/Viropharma |
| NM-283 | Antiviral | NS5B replicase inhibitor | Idenix/Novartis |
| GL-59728 | Antiviral | NS5B replicase inhibitor | Gene Labs/Novartis |
| GL-60667 | Antiviral | NS5B replicase inhibitor | Gene Labs/Novartis |
| 2'C MeA | Antiviral | NS5B replicase inhibitor | Gilead |

TABLE 1-continued

| Brand Name | Physiological Class | Type of Inhibitor or Target | Source Company |
|---|---|---|---|
| PSI 6130 | Antiviral | NS5B replicase inhibitor | Roche |
| R1626 | Antiviral | NS5B replicase inhibitor | Roche |
| 2'C Methyl adenosine | Antiviral | NS5B replicase inhibitor | Merck |
| JTK-003 | Antiviral | RdRp inhibitor | Japan Tobacco Inc., Tokyo, Japan |
| Levovirin | Antiviral | Ribavirin | ICN Pharmaceuticals, Costa Mesa, CA |
| Ribavirin | Antiviral | Ribavirin | Schering-Plough Corporation, Kenilworth, NJ |
| Viramidine | Antiviral | Ribavirin prodrug | Ribapharm Inc., Costa Mesa, CA |
| Heptazyme | Antiviral | Ribozyme | Ribozyme Pharmaceuticals Inc., Boulder, CO |
| BILN-2061 | Antiviral | Serine protease inhibitor | Boehringer Ingelheim Pharma KG, Ingelheim, Germany |
| SCH 503034 | Antiviral | Serine protease inhibitor | Schering Plough |
| Zadazim | Immune modulator | Immune modulator | SciClone Pharmaceuticals Inc., San Mateo, CA |
| Ceplene | Immunomodulator | Immune modulator | Maxim Pharmaceuticals Inc., San Diego, CA |
| CellCept | Immunosuppressant | HCV IgG immuno-suppressant | F. Hoffmann-La Roche LTD, Basel, Switzerland |
| Civacir | Immunosuppressant | HCV IgG immuno-suppressant | Nabi Biopharmaceuticals Inc., Boca Raton, FL |
| Albuferon - α | Interferon | Albumin IFN-α2b | Human Genome Sciences Inc., Rockville, MD |
| Infergen A | Interferon | IFN alfacon-1 | InterMune Pharmaceuticals Inc., Brisbane, CA |
| Omega IFN | Interferon | IFN-ω | Intarcia Therapeutics |
| IFN-β and EMZ701 | Interferon | IFN-β and EMZ701 | Transition Therapeutics Inc., Ontario, Canada |
| Rebif | Interferon | IFN-β1a | Serono, Geneva, Switzerland |
| Roferon A | Interferon | IFN-α2a | F. Hoffmann-La Roche LTD, Basel, Switzerland |
| Intron A | Interferon | IFN-α2b | Schering-Plough Corporation, Kenilworth, NJ |
| Intron A and Zadaxin | Interferon | IFN-α2b/α1-thymosin | RegeneRx Biopharma. Inc., Bethesda, MD/ SciClone Pharmaceuticals Inc, San Mateo, CA |
| Rebetron | Interferon | IFN-α2b/ribavirin | Schering-Plough Corporation, Kenilworth, NJ |
| Actimmune | Interferon | INF-γ | InterMune Inc., Brisbane, CA |
| Interferon-β | Interferon | Interferon-β-1a | Serono |
| Multiferon | Interferon | Long lasting IFN | Viragen/Valentis |
| Wellferon | Interferon | Lymphoblastoid IFN-αn1 | GlaxoSmithKline plc, Uxbridge, UK |
| Omniferon | Interferon | natural IFN-α | Viragen Inc., Plantation, FL |
| Pegasys | Interferon | PEGylated IFN-α2a | F. Hoffmann-La Roche LTD, Basel, Switzerland |
| Pegasys and Ceplene | Interferon | PEGylated IFN-α2a/ immune modulator | Maxim Pharmaceuticals Inc., San Diego, CA |

TABLE 1-continued

| Brand Name | Physiological Class | Type of Inhibitor or Target | Source Company |
|---|---|---|---|
| Pegasys and Ribavirin | Interferon | PEGylated IFN-α2a/ribavirin | F. Hoffmann-La Roche LTD, Basel, Switzerland |
| PEG-Intron | Interferon | PEGylated IFN-α2b | Schering-Plough Corporation, Kenilworth, NJ |
| PEG-Intron/ Ribavirin | Interferon | PEGylated IFN-α2b/ribavirin | Schering-Plough Corporation, Kenilworth, NJ |
| IP-501 | Liver protection | Antifibrotic | Indevus Pharmaceuticals Inc., Lexington, MA |
| IDN-6556 | Liver protection | Caspase inhibitor | Idun Pharmaceuticals Inc., San Diego, CA |
| ITMN-191 (R-7227) | Antiviral | Serine protease inhibitor | InterMune Pharmaceuticals Inc., Brisbane, CA |
| GL-59728 | Antiviral | NS5B replicase inhibitor | Genelabs |
| ANA-971 | Antiviral | TLR-7 agonist | Anadys |
| Boceprevir | Antiviral | Serine protease inhibitor | Schering Plough |
| TMS-435 | Antiviral | Serine protease inhibitor | Tibotec BVBA, Mechelen, Belgium |
| BI-201335 | Antiviral | Serine protease inhibitor | Boehringer Ingelheim Pharma KG, Ingelheim, Germany |
| MK-7009 | Antiviral | Serine protease inhibitor | Merck |
| PF-00868554 | Antiviral | Replicase inhibitor | Pfizer |
| ANA598 | Antiviral | Non-Nucleoside NS5B polymerase inhibitor | Anadys Pharmaceuticals, Inc., San Diego, CA, USA |
| IDX375 | Antiviral | Non-Nucleoside replicase inhibitor | Idenix Pharmaceuticals, Cambridge, MA, USA |
| BILB 1941 | Antiviral | NS5B polymerase inhibitor | Boehringer Ingelheim Canada Ltd R&D, Laval, QC, Canada |
| PSI-7851 | Antiviral | Nucleoside polymerase inhibitor | Pharmasset, Princeton, NJ, USA |
| VCH-759 | Antiviral | NS5B polymerase inhibitor | ViroChem Pharma |
| VCH-916 | Antiviral | NS5B polymerase inhibitor | ViroChem Pharma |
| GS-9190 | Antiviral | NS5B polymerase inhibitor | Gilead |
| Peg-interferon lamda | Antiviral | Interferon | ZymoGenetics/ Bristol-Myers Squibb |

The compounds of the present disclosure may also be used as laboratory reagents. Compounds may be instrumental in providing research tools for designing of viral replication assays, validation of animal assay systems and structural biology studies to further enhance knowledge of the HCV disease mechanisms. Further, the compounds of the present disclosure are useful in establishing or determining the binding site of other antiviral compounds, for example, by competitive inhibition.

The compounds of this disclosure may also be used to treat or prevent viral contamination of materials and therefore reduce the risk of viral infection of laboratory or medical personnel or patients who come in contact with such materials, e.g., blood, tissue, surgical instruments and garments, laboratory instruments and garments, and blood collection or transfusion apparatuses and materials.

This disclosure is intended to encompass compounds having Formula (I) when prepared by synthetic processes or by metabolic processes including those occurring in the human or animal body (in vivo) or processes occurring in vitro.

The abbreviations used in the present application, including particularly in the illustrative examples which follow, are well-known to those skilled in the art. Some of the abbreviations used are as follows:
Et ethyl;
t-Bu tert-butyl;
iPr isopropyl;
min minutes;
rt or RT room temperature or retention time (context will dictate);
TFA trifluoroacetic acid;
h or hr hours;
DMSO dimethylsulfoxide;
DME dimethyl ether;
LDA lithium diisopropylamide;
NBS N-bromosuccinimide;
SEM-Cl 2-(trimethylsilyl)ethoxymethyl chloride;
TBAF tetrabutylammonium fluoride;
HATU O-(7-azabenzotriazol-1-yl)-N,N,N',N'-tetramethyluronium hexafluorophosphate;

iPr₂EtN diisopropylethylamine;
DIEA diisopropylethylamine;
DIPEA diisopropylethylamine;
Hunig's diisopropylethylamine;
Boc or BOC tert-butoxycarbonyl;
DMAP 4-dimethylaminopyridine;
HCl hydrochloric acid;
Na₂SO₄ sodium sulfate;
MgSO₄ magnesium sulfate,
PdCl₂(PPh₃)₂ bis(triphenylphosphine)palladium(II)dichloride; MCX cartridge Waters OASIS® MCX LP extraction cartridge.

The compounds and processes of the present disclosure will be better understood in connection with the following synthetic schemes which illustrate the methods by which the compounds of the present disclosure may be prepared. Starting materials can be obtained from commercial sources or prepared by well-established literature methods known to those of ordinary skill in the art. It will be readily apparent to one of ordinary skill in the art that the compounds defined above can be synthesized by substitution of the appropriate reactants and agents in the syntheses shown below. It will also be readily apparent to one skilled in the art that the selective protection and deprotection steps, as well as the order of the steps themselves, can be carried out in varying order, depending on the nature of the variables to successfully complete the syntheses below. The variables are as defined above unless otherwise noted below.

Scheme 1: Substituted Phenylglycine Derivatives

Substituted phenylglycine derivatives can be prepared by a number of methods shown below. Phenylglycine t-butyl ester can be reductively alkylated (pathway A) with an appropriate aldehyde and a reductant such as sodium cyanoborohydride in acidic medium. Hydrolysis of the t-butyl ester can be accomplished with strong acid such as HCl or trifluoroacetic acid. Alternatively, phenylglycine can be alkylated with an alkyl halide such as ethyl iodide and a base such as sodium bicarbonate or potassium carbonate (pathway B). Pathway C illustrates reductive alkylation of phenylglycine as in pathway A followed by a second reductive alkylation with an alternate aldehyde such as formaldehyde in the presence of a reducing agent and acid. Pathway D illustrates the synthesis of substituted phenylglycines via the corresponding mandelic acid analogs. Conversion of the secondary alcohol to a competent leaving group can be accomplished with p-toluensulfonyl chloride. Displacement of the tosylate group with an appropriate amine followed by reductive removal of the benzyl ester can provide substituted phenylglycine derivatives. In pathway E a racemic substituted phenylglycine derivative is resolved by esterification with an enantiomerically pure chiral auxiliary such as but not limited to (+)-1-phenylethanol, (−)-1-phenylethanol, an Evan's oxazolidinone, or enantiomerically pure pantolactone. Separation of the diastereomers is accomplished via chromatography (silica gel, HPLC, crystallization, etc) followed by removal of the chiral auxiliary providing enantiomerically pure phenylglycine derivatives. Pathway H illustrates a synthetic sequence which intersects with pathway E wherein the aforementioned chiral auxiliary is installed prior to amine addition. Alternatively, an ester of an arylacetic acid can be brominated with a source of bromonium ion such as bromine, N-bromosuccinimide, or CBr₄. The resultant benzylic bromide can be displaced with a variety of mono- or disubstituted amines in the presence of a tertiary amine base such as triethylamine or Hunig's base. Hydrolysis of the methyl ester via treatment with lithium hydroxide at low temperature or 6N HCl at elevated temperature provides the substituted phenylglycine derivatives. Another method is shown in pathway G. Glycine analogs can be derivatized with a variety of aryl halides in the presence of a source of palladium (0) such as palladium bis(tributylphosphine) and base such as potassium phosphate. The resultant ester can then be hydrolyzed by treatment with base or acid. It should be understood that other well known methods to prepare phenylglycine derivatives exist in the art and can be amended to provide the desired compounds in this description. It should also be understood that the final phenylglycine derivatives can be purified to enantiomeric purity greater than 98% ee via preparative HPLC.

Scheme 2: Acylated Amino Acid Derivatives

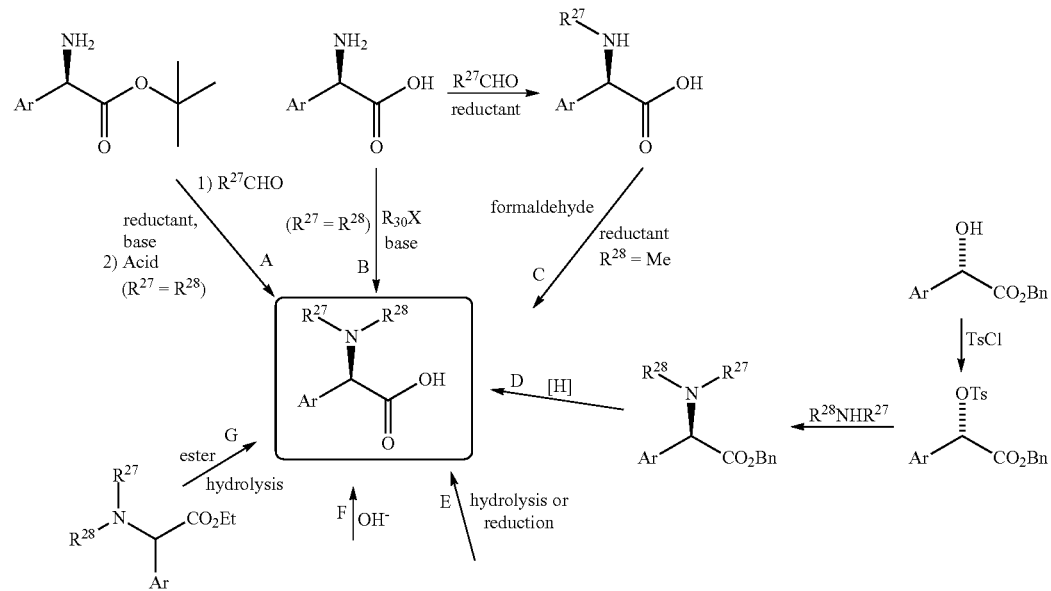

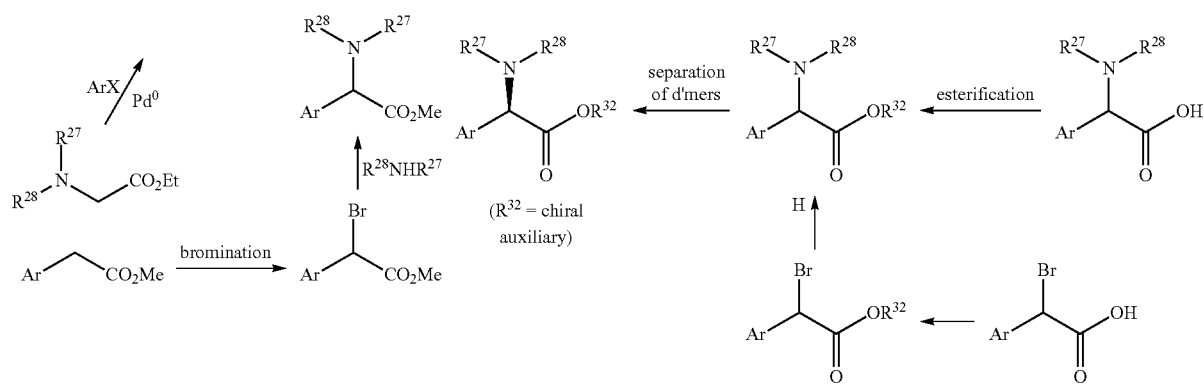

In another embodiment of the present disclosure, acylated phenylglycine derivatives may be prepared as illustrated below. Phenylglycine derivatives wherein the carboxylic acid is protected as an easily removed ester, may be acylated with an acid chloride in the presence of a base such as triethylamine to provide the corresponding amides (pathway A). Pathway B illustrates the acylation of the starting phenylglycine derivative with an appropriate chloroformate while pathway C shows reaction with an appropriate isocyanate or carbamoyl chloride. Each of the three intermediates shown in pathways A-C may be deprotected by methods known by those skilled in the art (ie; treatment of the t-butyl ester with strong base such as HCl or trifluoroacetic acid).

Scheme 3

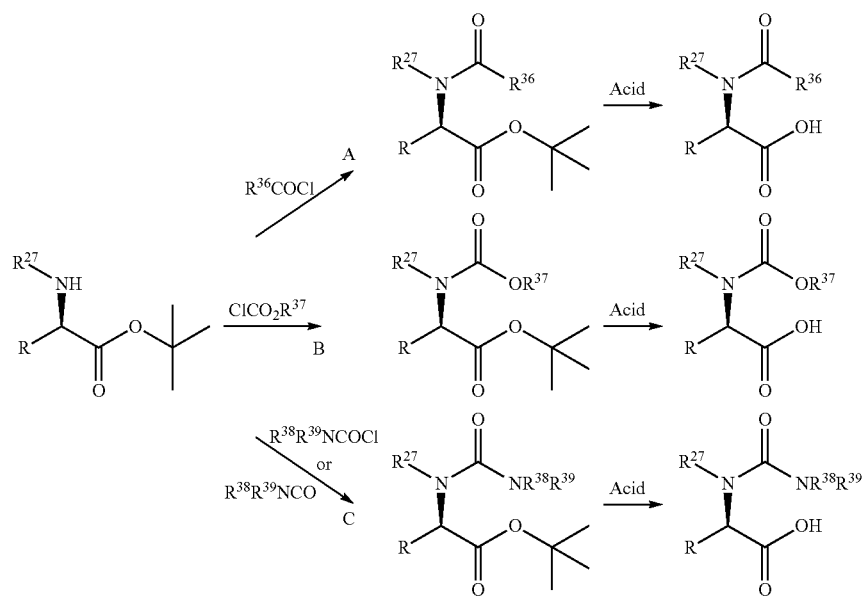

$R^{27}$ = H, alkyl

Amino-substituted phenylacetic acids may be prepared by treatment of a chloromethylphenylacetic acid with an excess of an amine

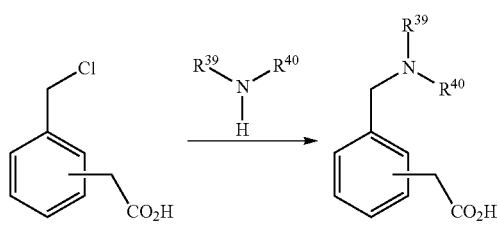

Synthesis of Common Caps

Compound Analysis Conditions:

Purity assessment and low resolution mass analysis were conducted on a Shimadzu LC system coupled with Waters Micromass ZQ MS system. It should be noted that retention times may vary slightly between machines. Additional LC conditions applicable to the current section, unless noted otherwise.

Cond.-MS-W1

| | |
|---|---|
| Column = | XTERRA 3.0 × 50 mm S7 |
| Start % B = | 0 |
| Final % B = | 100 |
| Gradient time = | 2 min |
| Stop time = | 3 min |
| Flow Rate = | 5 mL/min |
| Wavelength = | 220 nm |
| Solvent A = | 0.1% TFA in 10% methanol/90% $H_2O$ |
| Solvent B = | 0.1% TFA in 90% methanol/10% $H_2O$ |

Cond.-MS-W2

| | |
|---|---|
| Column = | XTERRA 3.0 × 50 mm S7 |
| Start % B = | 0 |
| Final % B = | 100 |
| Gradient time = | 3 min |
| Stop time = | 4 min |
| Flow Rate = | 4 mL/min |
| Wavelength = | 220 nm |
| Solvent A = | 0.1% TFA in 10% methanol/90% $H_2O$ |
| Solvent B = | 0.1% TFA in 90% methanol/10% $H_2O$ |

Cond.-MS-W5

| | |
|---|---|
| Column = | XTERRA 3.0 × 50 mm S7 |
| Start % B = | 0 |
| Final % B = | 30 |
| Gradient time = | 2 min |
| Stop time = | 3 min |
| Flow Rate = | 5 mL/min |
| Wavelength = | 220 nm |
| Solvent A = | 0.1% TFA in 10% methanol/90% $H_2O$ |
| Solvent B = | 0.1% TFA in 90% methanol/10% $H_2O$ |

Cond.-D1

| | |
|---|---|
| Column = | XTERRA C18 3.0 × 50 mm S7 |
| Start % B = | 0 |
| Final % B = | 100 |
| Gradient time = | 3 min |
| Stop time = | 4 min |
| Flow Rate = | 4 mL/min |
| Wavelength = | 220 nm |
| Solvent A = | 0.1% TFA in 10% methanol/90% $H_2O$ |
| Solvent B = | 0.1% TFA in 90% methanol/10% $H_2O$ |

Cond.-D2

| | |
|---|---|
| Column = | Phenomenex-Luna 4.6 × 50 mm S10 |
| Start % B = | 0 |
| Final % B = | 100 |
| Gradient time = | 3 min |
| Stop time = | 4 min |
| Flow Rate = | 4 mL/min |
| Wavelength = | 220 nm |
| Solvent A = | 0.1% TFA in 10% methanol/90% $H_2O$ |
| Solvent B = | 0.1% TFA in 90% methanol/10% $H_2O$ |

Cond.-MD1

| | |
|---|---|
| Column = | XTERRA 4.6 × 50 mm S5 |
| Start % B = | 0 |
| Final % B = | 100 |
| Gradient time = | 3 min |
| Stop time = | 4 min |
| Flow Rate = | 4 mL/min |
| Wavelength = | 220 nm |
| Solvent A = | 0.1% TFA in 10% methanol/90% $H_2O$ |
| Solvent B = | 0.1% TFA in 90% methanol/10% $H_2O$ |

Cond.-M3

| | |
|---|---|
| Column = | XTERRA C18 3.0 × 50 mm S7 |
| Start % B = | 0 |
| Final % B = | 40 |
| Gradient time = | 2 min |
| Stop time = | 3 min |
| Flow Rate = | 5 mL/min |
| Wavelength = | 220 nm |
| Solvent A = | 0.1% TFA in 10% methanol/90% $H_2O$ |
| Solvent B = | 0.1% TFA in 90% methanol/10% $H_2O$ |

Condition OL1

| | |
|---|---|
| Column = | Phenomenex-Luna 3.0 × 50 mm S10 |
| Start % B = | 0 |
| Final % B = | 100 |
| Gradient time = | 4 min |
| Stop time = | 5 min |
| Flow Rate = | 4 mL/min |
| Wavelength = | 220 nm |
| Solvent A = | 0.1% TFA in 10% methanol/90% $H_2O$ |
| Solvent B = | 0.1% TFA in 90% methanol/10% $H_2O$ |

Condition OL2

| | |
|---|---|
| Column = | Phenomenex-Luna 50 × 2 mm 3 u |
| Start % B = | 0 |
| Final % B = | 100 |
| Gradient time = | 4 min |
| Stop time = | 5 min |
| Flow Rate = | 0.8 mL/min |
| Oven Temp = | 40° C. |
| Wavelength = | 220 nm |
| Solvent A = | 0.1% TFA in 10% Acetonitrile/90% $H_2O$ |
| Solvent B = | 0.1% TFA in 90% Acetonitrile/10% $H_2O$ |

Condition I

| | |
|---|---|
| Column = | Phenomenex-Luna 3.0 × 50 mm S10 |
| Start % B = | 0 |
| Final % B = | 100 |
| Gradient time = | 2 min |
| Stop time = | 3 min |

-continued

| | |
|---|---|
| Flow Rate = | 4 mL/min |
| Wavelength = | 220 nm |
| Solvent A = | 0.1% TFA in 10% methanol/90% H$_2$O |
| Solvent B = | 0.1% TFA in 90% methanol/10% H$_2$O |

Condition II

| | |
|---|---|
| Column = | Phenomenex-Luna 4.6 × 50 mm S10 |
| Start % B = | 0 |
| Final % B = | 100 |
| Gradient time = | 2 min |
| Stop time = | 3 min |
| Flow Rate = | 5 mL/min |
| Wavelength = | 220 nm |
| Solvent A = | 0.1% TFA in 10% methanol/90% H$_2$O |
| Solvent B = | 0.1% TFA in 90% methanol/10% H$_2$O |

Condition III

| | |
|---|---|
| Column = | XTERRA C18 3.0 × 50 mm S7 |
| Start % B = | 0 |
| Final % B = | 100 |
| Gradient time = | 3 min |
| Stop time = | 4 min |
| Flow Rate = | 4 mL/min |
| Wavelength = | 220 nm |
| Solvent A = | 0.1% TFA in 10% methanol/90% H$_2$O |
| Solvent B = | 0.1% TFA in 90% methanol/10% H$_2$O |

Cap-1

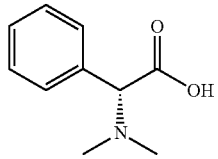

A suspension of 10% Pd/C (2.0 g) in methanol (10 mL) was added to a mixture of (R)-2-phenylglycine (10 g, 66.2 mmol), formaldehyde (33 mL of 37% wt. in water), 1N HCl (30 mL) and methanol (30 mL), and exposed to H$_2$ (60 psi) for 3 hours. The reaction mixture was filtered through diatomaceous earth (Celite®), and the filtrate was concentrated in vacuo. The resulting crude material was recrystallized from isopropanol to provide the HCl salt of Cap-1 as a white needle (4.0 g). Optical rotation: −117.1° [c=9.95 mg/mL in H$_2$O; λ=589 nm]. $^1$H NMR (DMSO-d$_6$, δ=2.5 ppm, 500 MHz): δ 7.43-7.34 (m, 5H), 4.14 (s, 1H), 2.43 (s, 6H); LC (Cond. I): RT=0.25; LC/MS: Anal. Calcd. for [M+H]$^+$ C$_{10}$H$_{14}$NO$_2$ 180.10. found 180.17; HRMS: Anal. Calcd. for [M+H]$^+$ C$_{10}$H$_{14}$NO$_2$ 180.1025. found 180.1017.

Cap-2

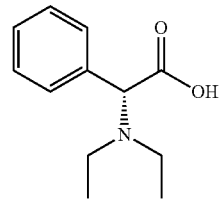

NaBH$_3$CN (6.22 g, 94 mmol) was added in portions over a few minutes to a cooled (ice/water) mixture of (R)-2-Phenylglycine (6.02 g, 39.8 mmol) and methanol (100 mL), and stirred for 5 minutes. Acetaldehyde (10 mL) was added dropwise over 10 minutes and stirring was continued at the same cooled temperature for 45 minutes and at ambient temperature for ~6.5 hours. The reaction mixture was cooled back with ice-water bath, treated with water (3 mL) and then quenched with a dropwise addition of concentrated HCl over ~45 minutes until the pH of the mixture was ~1.5-2.0. The cooling bath was removed and the stirring was continued while adding concentrated HCl in order to maintain the pH of the mixture around 1.5-2.0. The reaction mixture was stirred overnight, filtered to remove the white suspension, and the filtrate was concentrated in vacuo. The crude material was recrystallized from ethanol to afford the HCl salt of Cap-2 as a shining white solid in two crops (crop-1: 4.16 g; crop-2: 2.19 g). $^1$H NMR (DMSO-d$_6$, δ=2.5 ppm, 400 MHz): 10.44 (1.00, br s, 1H), 7.66 (m, 2H), 7.51 (m, 3H), 5.30 (s, 1H), 3.15 (br m, 2H), 2.98 (br m, 2H), 1.20 (app br s, 6H). Crop-1: [α]$^{25}$ −102.21° (c=0.357, H$_2$O); crop-2: [α]$^{25}$ −99.7° (c=0.357, H$_2$O). LC (Cond. I): RT=0.43 min; LC/MS: Anal. Calcd. for [M+H]$^+$ C$_{12}$H$_{18}$NO$_2$: 208.13. found 208.26.

Cap-3

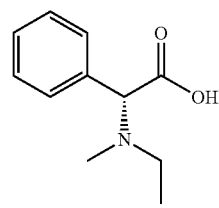

Acetaldehyde (5.0 mL, 89.1 mmol) and a suspension of 10% Pd/C (720 mg) in methanol/H$_2$O (4 mL/1 mL) was sequentially added to a cooled (~15° C.) mixture of (R)-2-phenylglycine (3.096 g, 20.48 mmol), 1N HCl (30 mL) and methanol (40 mL). The cooling bath was removed and the reaction mixture was stirred under a balloon of H$_2$ for 17 hours. An additional acetaldehyde (10 mL, 178.2 mmol) was added and stirring continued under H$_2$ atmosphere for 24 hours [Note: the supply of H$_2$ was replenished as needed throughout the reaction]. The reaction mixture was filtered through diatomaceous earth (Celite®), and the filtrate was concentrated in vacuo. The resulting crude material was recrystallized from isopropanol to provide the HCl salt of (R)-2-(ethylamino)-2-phenylacetic acid as a shining white solid (2.846 g). ¹H NMR (DMSO-d₆, δ=2.5 ppm, 400 MHz): δ 14.15 (br s, 1H), 9.55 (br s, 2H), 7.55-7.48 (m, 5H), 2.88 (br m, 1H), 2.73 (br m, 1H), 1.20 (app t, J=7.2, 3H). LC (Cond. I): RT=0.39 min; >95% homogeneity index; LC/MS: Anal. Calcd. for [M+H]⁺ C₁₀H₁₄NO₂: 180.10. found 180.18.

A suspension of 10% Pd/C (536 mg) in methanol/H₂O (3 mL/1 mL) was added to a mixture of (R)-2-(ethylamino)-2-phenylacetic acid/HCl (1.492 g, 6.918 mmol), formaldehyde (20 mL of 37% wt. in water), 1N HCl (20 mL) and methanol (23 mL). The reaction mixture was stirred under a balloon of H₂ for ~72 hours, where the H₂ supply was replenished as needed. The reaction mixture was filtered through diatomaceous earth (Celite®) and the filtrate was concentrated in vacuo. The resulting crude material was recrystallized from isopropanol (50 mL) to provide the HCl salt of Cap-3 as a white solid (985 mg). ¹H NMR (DMSO-d₆, δ=2.5 ppm, 400 MHz): δ 10.48 (br s, 1H), 7.59-7.51 (m, 5H), 5.26 (s, 1H), 3.08 (app br s, 2H), 2.65 (br s, 3H), 1.24 (br m, 3H). LC (Cond. I): RT=0.39 min; >95% homogeneity index; LC/MS: Anal. Calcd. for [M+H]⁺ C₁₁H₁₆NO₂: 194.12. found 194.18; HRMS: Anal. Calcd. for [M+H]⁺ C₁₁H₁₆NO₂: 194.1180. found 194.1181.

Cap-4

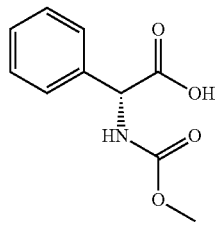

ClCO₂Me (3.2 mL, 41.4 mmol) was added dropwise to a cooled (ice/water) THF (410 mL) semi-solution of (R)-tert-butyl 2-amino-2-phenylacetate/HCl (9.877 g, 40.52 mmol) and diisopropylethylamine (14.2 mL, 81.52 mmol) over 6 min, and stirred at similar temperature for 5.5 hours. The volatile component was removed in vacuo, and the residue was partitioned between water (100 mL) and ethyl acetate (200 mL). The organic layer was washed with 1N HCl (25 mL) and saturated NaHCO₃ solution (30 mL), dried (MgSO₄), filtered, and concentrated in vacuo. The resultant colorless oil was triturated from hexanes, filtered and washed with hexanes (100 mL) to provide (R)-tert-butyl 2-(methoxycarbonylamino)-2-phenylacetate as a white solid (7.7 g). ¹H NMR (DMSO-d₆, δ=2.5 ppm, 400 MHz): 7.98 (d, J=8.0, 1H), 7.37-7.29 (m, 5H), 5.09 (d, J=8, 1H), 3.56 (s, 3H), 1.33 (s, 9H). LC (Cond. I): RT=1.53 min; ~90% homogeneity index; LC/MS: Anal. Calcd. for [M+Na]⁺ C₁₄H₁₉NNaO₄: 288.12. found 288.15.

TFA (16 mL) was added dropwise to a cooled (ice/water) CH₂Cl₂ (160 mL) solution of the above product over 7 minutes, and the cooling bath was removed and the reaction mixture was stirred for 20 hours. Since the deprotection was still not complete, an additional TFA (1.0 mL) was added and stirring continued for an additional 2 hours. The volatile component was removed in vacuo, and the resulting oil residue was treated with diethyl ether (15 mL) and hexanes (12 mL) to provide a precipitate. The precipitate was filtered and washed with diethyl ether/hexanes (~1:3 ratio; 30 mL) and dried in vacuo to provide Cap-4 as a fluffy white solid (5.57 g). Optical rotation: −176.9° [c=3.7 mg/mL in H₂O; λ=589 nm]. ¹H NMR (DMSO-d₆, δ=2.5 ppm, 400 MHz): δ 12.84 (br s, 1H), 7.96 (d, J=8.3, 1H), 7.41-7.29 (m, 5H), 5.14 (d, J=8.3, 1H), 3.55 (s, 3H). LC (Cond. I): RT=1.01 min; >95% homogeneity index; LC/MS: Anal. Calcd. for [M+H]⁺ C₁₀H₁₂NO₄ 210.08. found 210.17; HRMS: Anal. Calcd. for [M+H]⁺ C₁₀H₁₂NO₄ 210.0766. found 210.0756.

Cap-5

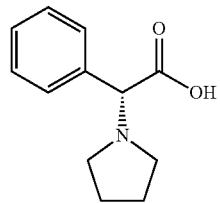 [SMILES: O=C(O)[C@@H](c1ccccc1)N1CCCC1]

A mixture of (R)-2-phenylglycine (1.0 g, 6.62 mmol), 1,4-dibromobutane (1.57 g, 7.27 mmol) and Na₂CO₃ (2.10 g, 19.8 mmol) in ethanol (40 mL) was heated at 100° C. for 21 hours. The reaction mixture was cooled to ambient temperature and filtered, and the filtrate was concentrated in vacuo. The residue was dissolved in ethanol and acidified with 1N HCl to pH 3-4, and the volatile component was removed in vacuo. The resulting crude material was purified by a reverse phase HPLC (water/methanol/TFA) to provide the TFA salt of Cap-5 as a semi-viscous white foam (1.0 g). ¹H NMR (DMSO-d₆, δ=2.5, 500 MHz) δ 10.68 (br s, 1H), 7.51 (m, 5H), 5.23 (s, 1H), 3.34 (app br s, 2H), 3.05 (app br s, 2H), 1.95 (app br s, 4H); RT=0.30 minutes (Cond. I); >98% homogeneity index; LC/MS: Anal. Calcd. for [M+H]⁺ C₁₂H₁₆NO₂: 206.12. found 206.25.

Cap-6

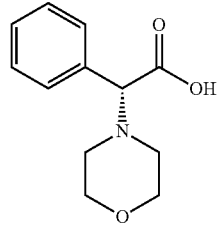 [SMILES: O=C(O)[C@@H](c1ccccc1)N1CCOCC1]

The TFA salt of Cap-6 was synthesized from (R)-2-phenylglycine and 1-bromo-2-(2-bromoethoxy)ethane by using the method of preparation of Cap-5. ¹H NMR (DMSO-d₆, δ=2.5, 500 MHz) δ 12.20 (br s, 1H), 7.50 (m, 5H), 4.92 (s, 1H), 3.78 (app br s, 4H), 3.08 (app br s, 2H), 2.81 (app br s, 2H); RT=0.32 minutes (Cond. I); >98%; LC/MS: Anal.

Calcd. for [M+H]+ $C_{12}H_{16}NO_3$: 222.11. found 222.20; HRMS: Anal. Calcd. for [M+H]+ $C_{12}H_{16}NO_3$: 222.1130. found 222.1121.

Cap-7

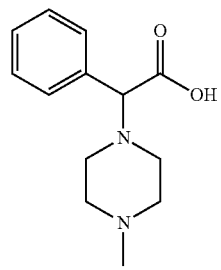

Cap-7a: enantiomer-1
Cap-7b: enantiomer-2

A $CH_2Cl_2$ (200 mL) solution of p-toluenesulfonyl chloride (8.65 g, 45.4 mmol) was added dropwise to a cooled (−5° C.) $CH_2Cl_2$ (200 mL) solution of (S)-benzyl 2-hydroxy-2-phenylacetate (10.0 g, 41.3 mmol), triethylamine (5.75 mL, 41.3 mmol) and 4-dimethylaminopyridine (0.504 g, 4.13 mmol), while maintaining the temperature between −5° C. and 0° C. The reaction was stirred at 0° C. for 9 hours, and then stored in a freezer (−25° C.) for 14 hours. It was allowed to thaw to ambient temperature and washed with water (200 mL), 1N HCl (100 mL) and brine (100 mL), dried ($MgSO_4$), filtered, and concentrated in vacuo to provide benzyl 2-phenyl-2-(tosyloxy)acetate as a viscous oil which solidified upon standing (16.5 g). The chiral integrity of the product was not checked and that product was used for the next step without further purification. $^1$H NMR (DMSO-$d_6$, δ=2.5, 500 MHz) δ 7.78 (d, J=8.6, 2H), 7.43-7.29 (m, 10H), 7.20 (m, 2H), 6.12 (s, 1H), 5.16 (d, J=12.5, 1H), 5.10 (d, J=12.5, 1H), 2.39 (s, 3H). RT=3.00 (Cond. III); >90% homogeneity index; LC/MS: Anal. Calcd. for [M+H]+ $C_{22}H_{20}NaO_5S$: 419.09. found 419.04.

A THF (75 mL) solution of benzyl 2-phenyl-2-(tosyloxy)acetate (6.0 g, 15.1 mmol), 1-methylpiperazine (3.36 mL, 30.3 mmol) and N,N-diisopropylethylamine (13.2 mL, 75.8 mmol) was heated at 65° C. for 7 hours. The reaction was allowed to cool to ambient temperature and the volatile component was removed in vacuo. The residue was partitioned between ethylacetate and water, and the organic layer was washed with water and brine, dried ($MgSO_4$), filtered, and concentrated in vacuo. The resulting crude material was purified by flash chromatography (silica gel, ethyl acetate) to provide benzyl 2-(4-methylpiperazin-1-yl)-2-phenylacetate as an orangish-brown viscous oil (4.56 g). Chiral HPLC analysis (Chiralcel OD-H) indicated that the sample is a mixture of enantiomers in a 38.2 to 58.7 ratio. The separation of the enantiomers were effected as follow: the product was dissolved in 120 mL of ethanol/heptane (1:1) and injected (5 mL/injection) on chiral HPLC column (Chiracel OJ, 5 cm ID×50 cm L, 20 µm) eluting with 85:15 Heptane/ethanol at 75 mL/min, and monitored at 220 nm. Enantiomer-1 (1.474 g) and enantiomer-2 (2.2149 g) were retrieved as viscous oil. $^1$H NMR (CDCl$_3$, δ=7.26, 500 MHz) 7.44-7.40 (m, 2H), 7.33-7.24 (m, 6H), 7.21-7.16 (m, 2H), 5.13 (d, J=12.5, 1H), 5.08 (d, J=12.5, 1H), 4.02 (s, 1H), 2.65-2.38 (app br s, 8H), 2.25 (s, 3H). RT=2.10 (Cond. III); >98% homogeneity index; LC/MS: Anal. Calcd. for [M+H]+ $C_{20}H_{25}N_2O_2$: 325.19. found 325.20.

A methanol (10 mL) solution of either enantiomer of benzyl 2-(4-methylpiperazin-1-yl)-2-phenylacetate (1.0 g, 3.1 mmol) was added to a suspension of 10% Pd/C (120 mg) in methanol (5.0 mL). The reaction mixture was exposed to a balloon of hydrogen, under a careful monitoring, for <50 minutes. Immediately after the completion of the reaction, the catalyst was filtered through diatomaceous earth (Celite®) and the filtrate was concentrated in vacuo to provide Cap-7, contaminated with phenylacetic acid as a tan foam (867.6 mg; mass is above the theoretical yield). The product was used for the next step without further purification. $^1$H NMR (DMSO-$d_6$, δ=2.5, 500 MHz) δ 7.44-7.37 (m, 2H), 7.37-7.24 (m, 3H), 3.92 (s, 1H), 2.63-2.48 (app. br s, 2H), 2.48-2.32 (m, 6H), 2.19 (s, 3H); RT=0.31 (Cond. II); >90% homogeneity index; LC/MS: Anal. Calcd. for [M+H]+ $C_{13}H_{19}N_2O_2$: 235.14. found 235.15; HRMS: Anal. Calcd. for [M+H]+ $C_{13}H_{19}N_2O_2$: 235.1447. found 235.1440.

The synthesis of Cap-8 and Cap-9 was conducted according to the synthesis of Cap-7 by using appropriate amines for the $SN_2$ displacement step (i.e., 4-hydroxypiperidine for Cap-8 and (S)-3-fluoropyrrolidine for Cap-9) and modified conditions for the separation of the respective stereoisomeric intermedites, as described below.

Cap-8

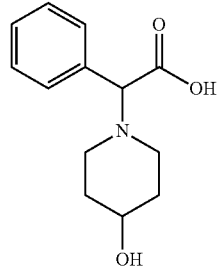

8a: enantiomer-1
8b: enantiomer-2

The enantiomeric separation of the intermediate benzyl 2-(4-hydroxypiperidin-1-yl)-2-phenyl acetate was effected by employing the following conditions: the compound (500 mg) was dissolved in ethanol/heptane (5 mL/45 mL). The resulting solution was injected (5 mL/injection) on a chiral HPLC column (Chiracel OJ, 2 cm ID×25 cm L, 10 µm) eluting with 80:20 heptane/ethanol at 10 mL/min, monitored at 220 nm, to provide 186.3 mg of enantiomer-1 and 209.1 mg of enantiomer-2 as light-yellow viscous oils. These benzyl ester was hydrogenolysed according to the preparation of Cap-7 to provide Cap-8: $^1$H NMR (DMSO-$d_6$, δ=2.5, 500 MHz) 7.40 (d, J=7, 2H), 7.28-7.20 (m, 3H), 3.78 (s 1H), 3.46 (m, 1H), 2.93 (m, 1H), 2.62 (m, 1H), 2.20 (m, 1H), 1.70 (m, 2H), 1.42 (m, 2H). RT=0.28 (Cond. II); >98% homogeneity index; LC/MS: Anal. Calcd. for [M+H]+ $C_{13}H_{18}NO_3$:

236.13. found 236.07; HRMS: Calcd. for [M+H]+ $C_{13}H_{18}NO_3$: 236.1287. found 236.1283.

Cap-9

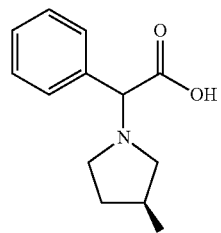

9a: diastereomer-1
9b: diastereomer-2

The diastereomeric separation of the intermediate benzyl 2-((S)-3-fluoropyrrolidin-1-yl)-2-phenylacetate was effected by employing the following conditions: the ester (220 mg) was separated on a chiral HPLC column (Chiracel OJ-H, 0.46 cm ID×25 cm L, 5 μm) eluting with 95% $CO_2$/5% methanol with 0.1% TFA, at 10 bar pressure, 70 mL/min flow rate, and a temperature of 35° C. The HPLC elute for the respective stereoisomers was concentrated, and the residue was dissolved in $CH_2Cl_2$ (20 mL) and washed with an aqueous medium (10 mL water+1 mL saturated $NaHCO_3$ solution). The organic phase was dried ($MgSO_4$), filtered, and concentrated in vacuo to provide 92.5 mg of fraction-1 and 59.6 mg of fraction-2. These benzyl esters were hydrogenolysed according to the preparation of Cap-7 to prepare Caps 9a and 9b. Cap-9a (diastereomer-1; the sample is a TFA salt as a result of purification on a reverse phase HPLC using $H_2O$/methanol/TFA solvent): $^1$H NMR (DMSO-$d_6$, δ=2.5, 400 MHz) 7.55-7.48 (m, 5H), 5.38 (d of m, J=53.7, 1H), 5.09 (br s, 1H), 3.84-2.82 (br m, 4H), 2.31-2.09 (m, 2H). RT=0.42 (Cond. I); >95% homogeneity index; LC/MS: Anal. Calcd. for [M+H]+ $C_{12}H_{15}FNO_2$: 224.11. found 224.14; Cap-9b (diastereomer-2): $^1$H NMR (DMSO-$d_6$, δ=2.5, 400 MHz) 7.43-7.21 (m, 5H), 5.19 (d of m, J=55.9, 1H), 3.97 (s, 1H), 2.95-2.43 (m, 4H), 2.19-1.78 (m, 2H). RT=0.44 (Cond. I); LC/MS: Anal. Calcd. for [M+H]+ $C_{12}H_{15}FNO_2$: 224.11. found 224.14.

Cap-10

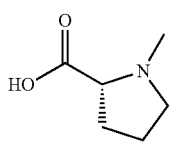

To a solution of D-proline (2.0 g, 17 mmol) and formaldehyde (2.0 mL of 37% wt. in $H_2O$) in methanol (15 mL) was added a suspension of 10% Pd/C (500 mg) in methanol (5 mL). The mixture was stirred under a balloon of hydrogen for 23 hours. The reaction mixture was filtered through diatomaceous earth (Celite®) and concentrated in vacuo to provide Cap-10 as an off-white solid (2.15 g). $^1$H NMR (DMSO-$d_6$, δ=2.5, 500 MHz) 3.42 (m, 1H), 3.37 (dd, J=9.4, 6.1, 1H), 2.85-2.78 (m, 1H), 2.66 (s, 3H), 2.21-2.13 (m, 1H), 1.93-1.84 (m, 2H), 1.75-1.66 (m, 1H). RT=0.28 (Cond. II); >98% homogeneity index; LC/MS: Anal. Calcd. for [M+H]+ $C_6H_{12}NO_2$: 130.09. found 129.96.

Cap-11

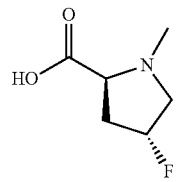

A mixture of (2S,4R)-4-fluoropyrrolidine-2-carboxylic acid (0.50 g, 3.8 mmol), formaldehyde (0.5 mL of 37% wt. in $H_2O$), 12 N HCl (0.25 mL) and 10% Pd/C (50 mg) in methanol (20 mL) was stirred under a balloon of hydrogen for 19 hours. The reaction mixture was filtered through diatomaceous earth (Celite®) and the filtrate was concentrated in vacuo. The residue was recrystallized from isopropanol to provide the HCl salt of Cap-11 as a white solid (337.7 mg). $^1$H NMR (DMSO-$d_6$, δ=2.5, 500 MHz) 5.39 (d m, J=53.7, 1H), 4.30 (m, 1H), 3.90 (ddd, J=31.5, 13.5, 4.5, 1H), 3.33 (dd, J=25.6, 13.4, 1H), 2.85 (s, 3H), 2.60-2.51 (m, 1H), 2.39-2.26 (m, 1H). RT=0.28 (Cond. II); >98% homogeneity index; LC/MS: Anal. Calcd. for [M+H]+ $C_6H_{11}FNO_2$: 148.08. found 148.06.

Cap-12 (Same as Cap 52)

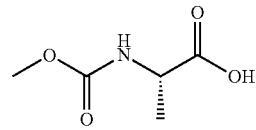

L-Alanine (2.0 g, 22.5 mmol) was dissolved in 10% aqueous sodium carbonate solution (50 mL), and a THF (50 mL) solution of methyl chloroformate (4.0 mL) was added to it. The reaction mixture was stirred under ambient conditions for 4.5 hours and concentrated in vacuo. The resulting white solid was dissolved in water and acidified with 1N HCl to a pH ~2-3. The resulting solutions was extracted with ethyl acetate (3×100 mL), and the combined organic phase was dried ($Na_2SO_4$), filtered, and concentrated in vacuo to provide a colorless oil (2.58 g). 500 mg of this material was purified by a reverse phase HPLC($H_2O$/methanol/TFA) to provide 150 mg of Cap-12 as a colorless oil. $^1$H NMR (DMSO-$d_6$, δ=2.5, 500 MHz) 7.44 (d, J=7.3, 0.8H), 7.10 (br s, 0.2H), 3.97 (m, 1H), 3.53 (s, 3H), 1.25 (d, J=7.3, 3H).

Cap-13

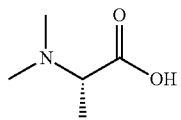

A mixture of L-alanine (2.5 g, 28 mmol), formaldehyde (8.4 g, 37 wt. %), 1N HCl (30 mL) and 10% Pd/C (500 mg) in methanol (30 mL) was stirred under a hydrogen atmosphere (50 psi) for 5 hours. The reaction mixture was filtered through diatomaceous earth (Celite®) and the filtrate was concentrated in vacuo to provide the HCl salt of Cap-13 as an oil which solidified upon standing under vacuum (4.4 g; the mass is above theoretical yield). The product was used without further purification. $^1$H NMR (DMSO-d$_6$, δ=2.5, 500 MHz) δ 12.1 (br s, 1H), 4.06 (q, J=7.4, 1H), 2.76 (s, 6H), 1.46 (d, J=7.3, 3H).

Cap-14

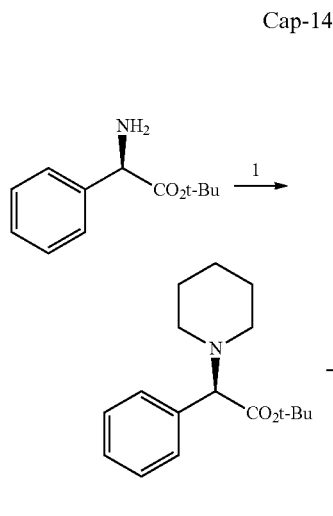

Cap-14

Step 1

A mixture of (R)-(−)-D-phenylglycine tert-butyl ester (3.00 g, 12.3 mmol), NaBH$_3$CN (0.773 g, 12.3 mmol), KOH (0.690 g, 12.3 mmol) and acetic acid (0.352 mL, 6.15 mmol) were stirred in methanol at 0° C. To this mixture was added glutaric dialdehyde (2.23 mL, 12.3 mmol) dropwise over 5 minutes. The reaction mixture was stirred as it was allowed to warm to ambient temperature and stirring was continued at the same temperature for 16 hours. The solvent was subsequently removed and the residue was partitioned with 10% aqueous NaOH and ethyl acetate. The organic phase was separated, dried (MgSO$_4$), filtered and concentrated to dryness to provide a clear oil. This material was purified by reverse-phase preparative HPLC (Primesphere C-18, 30×100 mm; CH$_3$CN—H$_2$O-0.1% TFA) to give the intermediate ester (2.70 g, 56%) as a clear oil. $^1$H NMR (400 MHz, CDCl$_3$) δ 7.53-7.44 (m, 3H), 7.40-7.37 (m, 2H), 3.87 (d, J=10.9 Hz, 1H), 3.59 (d, J=10.9 Hz, 1H), 2.99 (t, J=11.2 Hz, 1H), 2.59 (t, J=11.4 Hz, 1H), 2.07-2.02 (m, 2H), 1.82 (d, J=1.82 Hz, 3H), 1.40 (s, 9H). LC/MS: Anal. Calcd. for C$_{17}$H$_{25}$NO$_2$: 275. found: 276 (M+H)$^+$.

Step 2

To a stirred solution of the intermediate ester (1.12 g, 2.88 mmol) in dichloromethane (10 mL) was added TFA (3 mL). The reaction mixture was stirred at ambient temperature for 4 hours and then it was concentrated to dryness to give a light yellow oil. The oil was purified using reverse-phase preparative HPLC (Primesphere C-18, 30×100 mm; CH$_3$CN—H$_2$O-0.1% TFA). The appropriate fractions were combined and concentrated to dryness in vacuo. The residue was then dissolved in a minimum amount of methanol and applied to applied to MCX LP extraction cartridges (2×6 g). The cartridges were rinsed with methanol (40 mL) and then the desired compound was eluted using 2M ammonia in methanol (50 mL). Product-containing fractions were combined and concentrated and the residue was taken up in water. Lyophilization of this solution provided the title compound (0.492 g, 78%) as a light yellow solid. $^1$H NMR (DMSO-d$_6$) δ 7.50 (s, 5H), 5.13 (s, 1H), 3.09 (br s, 2H), 2.92-2.89 (m, 2H), 1.74 (m, 4H), 1.48 (br s, 2H). LC/MS: Anal. Calcd. for C$_{13}$H$_{12}$NO$_2$: 219. found: 220 (M+H)$^+$.

Cap-15

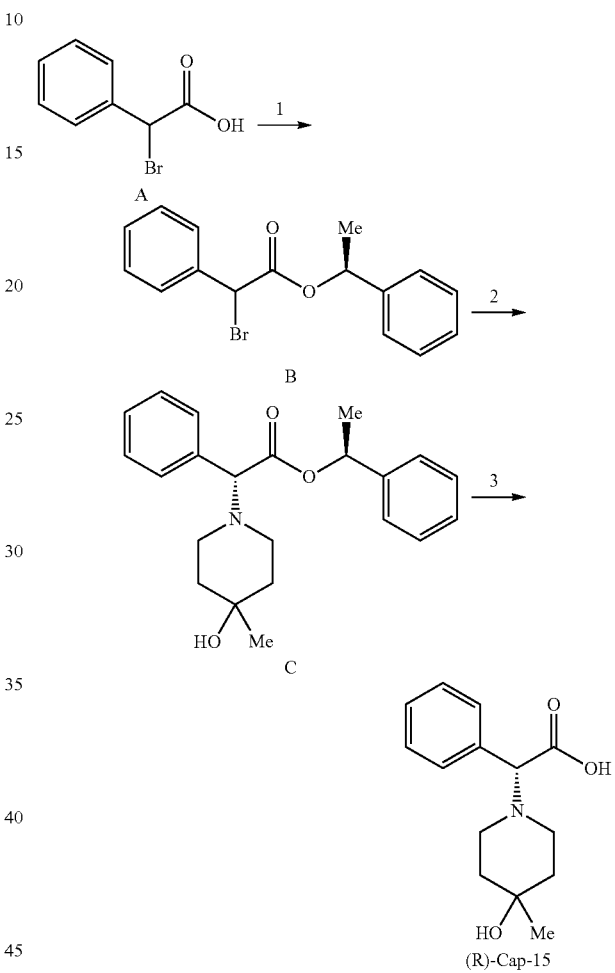

(R)-Cap-15

Step 1

(S)-1-Phenylethyl 2-bromo-2-phenylacetate: To a mixture of α-bromophenylacetic acid (10.75 g, 0.050 mol), (S)-(−)-1-phenylethanol (7.94 g, 0.065 mol) and DMAP (0.61 g, 5.0 mmol) in dry dichloromethane (100 mL) was added solid EDCI (12.46 g, 0.065 mol) all at once. The resulting solution was stirred at room temperature under Ar for 18 hours and then it was diluted with ethyl acetate, washed (H$_2$O×2, brine), dried (Na$_2$SO$_4$), filtered, and concentrated to give a pale yellow oil. Flash chromatography (SiO$_2$/hexane-ethyl acetate, 4:1) of this oil provided the title compound (11.64 g, 73%) as a white solid. $^1$H NMR (400 MHz, CDCl$_3$) δ 7.53-7.17 (m, 10H), 5.95 (q, J=6.6 Hz, 0.5H), 5.94 (q, J=6.6 Hz, 0.5H), 5.41 (s, 0.5H), 5.39 (s, 0.5H), 1.58 (d, J=6.6 Hz, 1.5H), 1.51 (d, J=6.6 Hz, 1.5H).

Step 2

(S)-1-Phenylethyl(R)-2-(4-hydroxy-4-methylpiperidin-1-yl)-2-phenylacetate: To a solution of (S)-1-phenylethyl 2-bromo-2-phenylacetate (0.464 g, 1.45 mmol) in THF (8 mL) was added triethylamine (0.61 mL, 4.35 mmol), followed by tetrabutylammonium iodide (0.215 g, 0.58 mmol). The reaction mixture was stirred at room temperature for 5 minutes and then a solution of 4-methyl-4-hydroxypiperidine (0.251 g, 2.18 mmol) in THF (2 mL) was added. The mixture was stirred for 1 hour at room temperature and then it was heated at 55-60° C. (oil bath temperature) for 4 hours. The cooled reaction mixture was then diluted with ethyl acetate (30 mL), washed (H$_2$O×2, brine), dried (MgSO$_4$), filtered and concentrated. The residue was purified by silica gel chromatography (0-60% ethyl acetate-hexane) to provide first the (S,R)-isomer of the title compound (0.306 g, 60%) as a white solid and then the corresponding (S,S)-isomer (0.120 g, 23%), also as a white solid. (S,R)-isomer: $^1$H NMR (CD$_3$OD) δ 7.51-7.45 (m, 2H), 7.41-7.25 (m, 8H), 5.85 (q, J=6.6 Hz, 1H), 4.05 (s, 1H), 2.56-2.45 (m, 2H), 2.41-2.29 (m, 2H), 1.71-1.49 (m, 4H), 1.38 (d, J=6.6 Hz, 3H), 1.18 (s, 3H). LCMS: Anal. Calcd. for C$_{22}$H$_{27}$NO$_3$: 353. found: 354 (M+H)$^+$. (S,S)-isomer: $^1$H NMR (CD$_3$OD) δ 7.41-7.30 (m, 5H), 7.20-7.14 (m, 3H), 7.06-7.00 (m, 2H), 5.85 (q, J=6.6 Hz, 1H), 4.06 (s, 1H), 2.70-2.60 (m, 1H), 2.51 (dt, J=6.6, 3.3 Hz, 1H), 2.44-2.31 (m, 2H), 1.75-1.65 (m, 1H), 1.65-1.54 (m, 3H), 1.50 (d, J=6.8 Hz, 3H), 1.20 (s, 3H). LCMS: Anal. Calcd. for C$_{22}$H$_{27}$NO$_3$: 353. found: 354 (M+H)$^+$.

Step 3

(R)-2-(4-Hydroxy-4-methylpiperidin-1-yl)-2-phenylacetic acid: To a solution of (S)-1-phenylethyl(R)-2-(4-hydroxy-4-methylpiperidin-1-yl)-2-phenylacetate (0.185 g, 0.52 mmol) in dichloromethane (3 mL) was added trifluoroacetic acid (1 mL) and the mixture was stirred at room temperature for 2 hours. The volatiles were subsequently removed in vacuo and the residue was purified by reverse-phase preparative HPLC (Primesphere C-18, 20×100 mm; CH$_3$CN—H$_2$O-0.1% TFA) to give the title compound (as TFA salt) as a pale bluish solid (0.128 g, 98%). LCMS: Anal. Calcd. for C$_{14}$H$_{19}$NO$_3$: 249. found: 250 (M+H)$^+$.

Cap-16

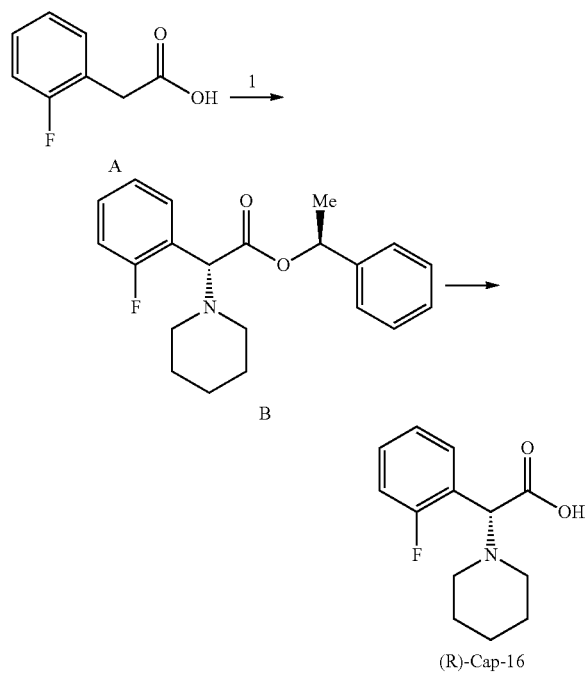

Step 1

(S)-1-Phenylethyl 2-(2-fluorophenyl)acetate: A mixture of 2-fluorophenylacetic acid (5.45 g, 35.4 mmol), (S)-1-phenylethanol (5.62 g, 46.0 mmol), EDCI (8.82 g, 46.0 mmol) and DMAP (0.561 g, 4.60 mmol) in CH$_2$Cl$_2$ (100 mL) was stirred at room temperature for 12 hours. The solvent was then concentrated and the residue partitioned with H$_2$O-ethyl acetate. The phases were separated and the aqueous layer back-extracted with ethyl acetate (2×). The combined organic phases were washed (H$_2$O, brine), dried (Na$_2$SO$_4$), filtered, and concentrated in vacuo. The residue was purified by silica gel chromatography (Biotage/0-20% ethyl acetate-hexane) to provide the title compound as a colorless oil (8.38 g, 92%). $^1$H NMR (400 MHz, CD$_3$OD) δ 7.32-7.23 (m, 7H), 7.10-7.04 (m, 2), 5.85 (q, J=6.5 Hz, 1H), 3.71 (s, 2H), 1.48 (d, J=6.5 Hz, 3H).

Step 2

(R)—((S)-1-Phenylethyl) 2-(2-fluorophenyl)-2-(piperidin-1-yl)acetate: To a solution of (S)-1-phenylethyl 2-(2-fluorophenyl)acetate (5.00 g, 19.4 mmol) in THF (1200 mL) at 0° C. was added DBU (6.19 g, 40.7 mmol) and the solution was allowed to warm to room temperature while stirring for 30 minutes. The solution was then cooled to −78° C. and a solution of CBr$_4$ (13.5 g, 40.7 mmol) in THF (100 mL) was added and the mixture was allowed to warm to −10° C. and stirred at this temperature for 2 hours. The reaction mixture was quenched with saturated aq. NH$_4$Cl and the layers were separated. The aqueous layer was back-extracted with ethyl acetate (2×) and the combined organic phases were washed (H$_2$O, brine), dried (Na$_2$SO$_4$), filtered, and concentrated in vacuo. To the residue was added piperidine (5.73 mL, 58.1 mmol) and the solution was stirred at room temperature for 24 hours. The volatiles were then concentrated in vacuo and the residue was purified by silica gel chromatography (Biotage/0-30% diethyl ether-hexane) to provide a pure mixture of diastereomers (2:1 ratio by $^1$H NMR) as a yellow oil (2.07 g, 31%), along with unreacted starting material (2.53 g, 51%). Further chromatography of the diastereomeric mixture (Biotage/0-10% diethyl ether-toluene) provided the title compound as a colorless oil (0.737 g, 11%). $^1$H NMR (400 MHz, CD$_3$OD) δ 7.52 (ddd, J=9.4, 7.6, 1.8 Hz, 1H), 7.33-7.40 (m, 1), 7.23-7.23 (m, 4H), 7.02-7.23 (m, 4H), 5.86 (q, J=6.6 Hz, 1H), 4.45 (s, 1H), 2.39-2.45 (m, 4H), 1.52-1.58 (m, 4H), 1.40-1.42 (m, 1H), 1.38 (d, J=6.6 Hz, 3H). LCMS: Anal. Calcd. for C$_{21}$H$_{24}$FNO$_2$: 341. found: 342 (M+H)$^+$.

Step 3

(R)-2-(2-fluorophenyl)-2-(piperidin-1-yl)acetic acid: A mixture of (R)—((S)-1-phenylethyl) 2-(2-fluorophenyl)-2-(piperidin-1-yl)acetate (0.737 g, 2.16 mmol) and 20% Pd(OH)$_2$/C (0.070 g) in ethanol (30 mL) was hydrogenated at room temperature and atmospheric pressure (H$_2$ balloon) for 2 hours. The solution was then purged with Ar, filtered through diatomaceous earth (Celite®), and concentrated in vacuo. This provided the title compound as a colorless solid (0.503 g, 98%). $^1$H NMR (400 MHz, CD$_3$OD) δ 7.65 (ddd, J=9.1, 7.6, 1.5 Hz, 1H), 7.47-7.53 (m, 1H), 7.21-7.30 (m, 2H), 3.07-3.13 (m, 4H), 1.84 (br s, 4H), 1.62 (br s, 2H). LCMS: Anal. Calcd. for C$_{13}$H$_{16}$FNO$_2$: 237. found: 238 (M+H)$^+$.

Cap-17

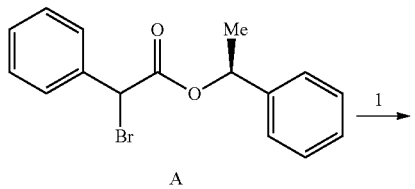

A

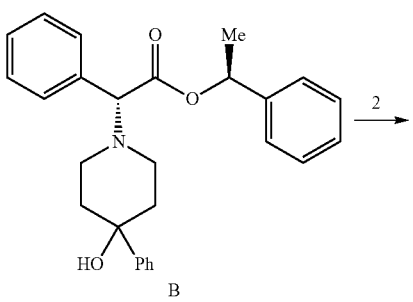

B

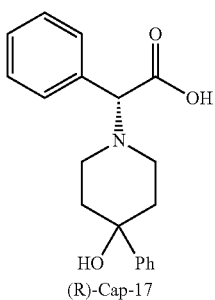

(R)-Cap-17

Step 1

(S)-1-Phenylethyl(R)-2-(4-hydroxy-4-phenylpiperidin-1-yl)-2-phenylacetate: To a solution of (S)-1-phenylethyl 2-bromo-2-phenylacetate (1.50 g, 4.70 mmol) in THF (25 mL) was added triethylamine (1.31 mL, 9.42 mmol), followed by tetrabutylammonium iodide (0.347 g, 0.94 mmol). The reaction mixture was stirred at room temperature for 5 minutes and then a solution of 4-phenyl-4-hydroxypiperidine (1.00 g, 5.64 mmol) in THF (5 mL) was added. The mixture was stirred for 16 hours and then it was diluted with ethyl acetate (100 mL), washed ($H_2O \times 2$, brine), dried ($MgSO_4$), filtered and concentrated. The residue was purified on a silica gel column (0-60% ethyl acetate-hexane) to provide an approximately 2:1 mixture of diastereomers, as judged by $^1$H NMR. Separation of these isomers was performed using supercritical fluid chromatography (Chiralcel OJ-H, 30×250 mm; 20% ethanol in $CO_2$ at 35° C.), to give first the (R)-isomer of the title compound (0.534 g, 27%) as a yellow oil and then the corresponding (S)-isomer (0.271 g, 14%), also as a yellow oil. (S,R)-isomer: $^1$H NMR (400 MHz, $CD_3OD$) δ 7.55-7.47 (m, 4H), 7.44-7.25 (m, 10H), 7.25-7.17 (m, 1H), 5.88 (q, J=6.6 Hz, 1H), 4.12 (s, 1H), 2.82-2.72 (m, 1H), 2.64 (dt, J=11.1, 2.5 Hz, 1H), 2.58-2.52 (m, 1H), 2.40 (dt, J=11.1, 2.5 Hz, 1H), 2.20 (dt, J=12.1, 4.6 Hz, 1H), 2.10 (dt, J=12.1, 4.6 Hz, 1H), 1.72-1.57 (m, 2H), 1.53 (d, J=6.5 Hz, 3H). LCMS: Anal. Calcd. for $C_{27}H_{29}NO_3$: 415. found: 416 $(M+H)^+$; (S,S)-isomer: $H^1$NMR (400 MHz, $CD_3OD$) δ 7.55-7.48 (m, 2H), 7.45-7.39 (m, 2H), 7.38-7.30 (m, 5H), 7.25-7.13 (m, 4H), 7.08-7.00 (m, 2H), 5.88 (q, J=6.6 Hz, 1H), 4.12 (s, 1H), 2.95-2.85 (m, 1H), 2.68 (dt, J=11.1, 2.5 Hz, 1H), 2.57-2.52 (m, 1H), 2.42 (dt, J=11.1, 2.5 Hz, 1H), 2.25 (dt, J=12.1, 4.6 Hz, 1H), 2.12 (dt, J=12.1, 4.6 Hz, 1H), 1.73 (dd, J=13.6, 3.0 Hz, 1H), 1.64 (dd, J=13.6, 3.0 Hz, 1H), 1.40 (d, J=6.6 Hz, 3H). LCMS: Anal. Calcd. for $C_{27}H_{29}NO_3$: 415. found: 416 $(M+H)^+$.

The following esters were prepared in similar fashion:

| Intermediate-17a | | |
|---|---|---|
| 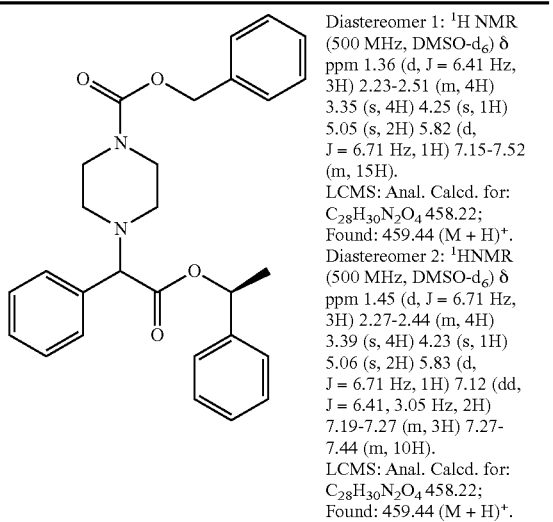 | Diastereomer 1: $^1$H NMR (500 MHz, DMSO-$d_6$) δ ppm 1.36 (d, J = 6.41 Hz, 3H) 2.23-2.51 (m, 4H) 3.35 (s, 4H) 4.25 (s, 1H) 5.05 (s, 2H) 5.82 (d, J = 6.71 Hz, 1H) 7.15-7.52 (m, 15H). LCMS: Anal. Calcd. for: $C_{28}H_{30}N_2O_4$ 458.22; Found: 459.44 $(M + H)^+$. Diastereomer 2: $^1$HNMR (500 MHz, DMSO-$d_6$) δ ppm 1.45 (d, J = 6.71 Hz, 3H) 2.27-2.44 (m, 4H) 3.39 (s, 4H) 4.23 (s, 1H) 5.06 (s, 2H) 5.83 (d, J = 6.71 Hz, 1H) 7.12 (dd, J = 6.41, 3.05 Hz, 2H) 7.19-7.27 (m, 3H) 7.27-7.44 (m, 10H). LCMS: Anal. Calcd. for: $C_{28}H_{30}N_2O_4$ 458.22; Found: 459.44 $(M + H)^+$. | |

| | | |
|---|---|---|
| Intermediate-17b | 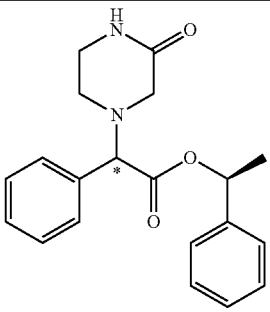 | Diasteromer 1: RT = 11.76 minutes (Cond'n II); LCMS: Anal. Calcd. for: $C_{20}H_{22}N_2O_3$ 338.16 Found: 339.39 $(M + H)^+$; Diastercomer 2: RT =10.05 minutes (Cond'n II); LCMS: Anal. Calcd. for: $C_{20}H_{22}N_2O_3$ 338.16; Found: 339.39 $(M + H)^+$. |
| Intermediate-17c | 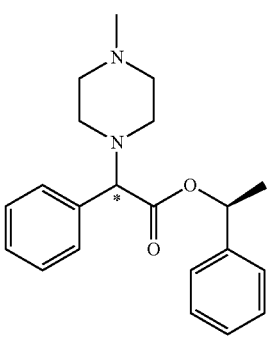 [SMILES: C[C@H](OC(=O)C(c1ccccc1)N1CCN(C)CC1)c1ccccc1] | Diastereomer 1: $T_R$ = 4.55 minutes (Cond'n I); LCMS: Anal. Calcd. for: $C_{21}H_{26}N_2O_2$ 338.20 Found: 339.45 $(M + H)^+$; Diastereomer 2: $T_R$ = 6.00 minutes (Cond'n I); LCMS: Anal. Calcd. for: $C_{21}H_{26}N_2O_2$ 338.20 Found: 339.45 $(M + H)^+$. |
| Intermediate-17d | 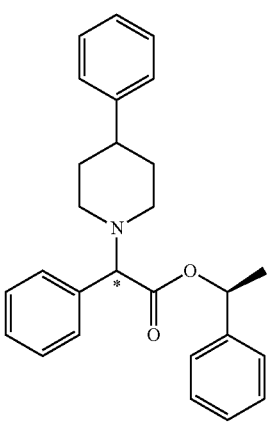 [SMILES: C[C@H](OC(=O)C(c1ccccc1)N1CCC(c2ccccc2)CC1)c1ccccc1] | Diastercomer 1: RT = 7.19 minutes (Cond'n I); LCMS: Anal. Calcd. for: $C_{27}H_{29}NO_2$ 399.22 Found: 400.48 $(M + H)^+$; Diastercomer 2: RT = 9.76 minutes (Cond'n I); LCMS: Anal. Calcd. for: $C_{27}H_{29}NO_2$ 399.22 Found: 400.48 $(M + H)^+$. |

Chiral SFC Conditions for determining retention time
Condition I
Column: Chiralpak AD-H Column, 4.62×50 mm, 5 μm
Solvents: 90% CO2-10% methanol with 0.1% DEA
Temp: 35° C.
Pressure: 150 bar
Flow rate: 2.0 mL/min.
UV monitored @ 220 nm
Injection: 1.0 mg/3 mL methanol
Condition II
Column: Chiralcel OD-H Column, 4.62×50 mm, 5 μm
Solvents: 90% CO2-10% methanol with 0.1% DEA
Temp: 35° C.
Pressure: 150 bar
Flow rate: 2.0 mL/min.
UV monitored @ 220 nm
Injection: 1.0 mg/mL methanol Cap 17, Step 2; (R)-2-(4-Hydroxy-4-phenylpiperidin-1-yl)-2-phenylacetic acid: To a solution of (S)-1-phenylethyl (R)-2-(4-hydroxy-4-phenylpiperidin-1-yl)-2-phenylacetate (0.350 g, 0.84 mmol) in dichloromethane (5 mL) was added trifluoroacetic acid (1 mL) and the mixture was stirred at room temperature for 2 hours. The volatiles were subsequently removed in vacuo and the residue was purified by reverse-phase preparative HPLC (Primesphere C-18, 20×100 mm; $CH_3CN$—$H_2O$-0.1% TFA) to give the title compound (as TFA salt) as a white solid (0.230 g, 88%). LCMS: Anal. Calcd. for $C_{19}H_{21}NO_3$: 311.15. found: 312 (M+H)$^+$.

The following carboxylic acids were prepared in optically pure form in a similar fashion:

| | | |
|---|---|---|
| Cap-17a | 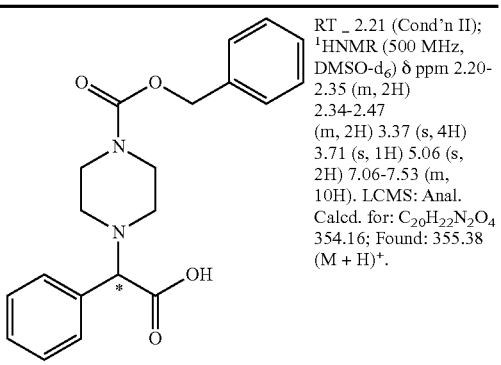 | RT_2.21 (Cond'n II); ¹HNMR (500 MHz, DMSO-d₆) δ ppm 2.20-2.35 (m, 2H) 2.34-2.47 (m, 2H) 3.37 (s, 4H) 3.71 (s, 1H) 5.06 (s, 2H) 7.06-7.53 (m, 10H). LCMS: Anal. Calcd. for: $C_{20}H_{22}N_2O_4$ 354.16; Found: 355.38 (M + H)⁺. |
| Cap-17b | 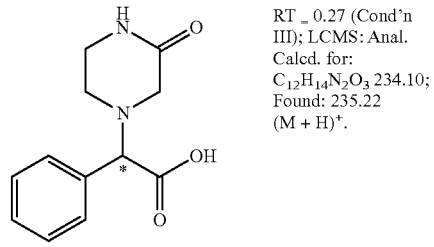 | RT_0.27 (Cond'n III); LCMS: Anal. Calcd. for: $C_{12}H_{14}N_2O_3$ 234.10; Found: 235.22 (M + H)⁺. |
| Cap-17c | 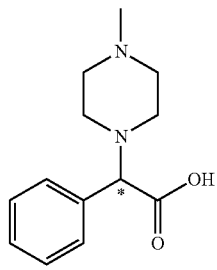 [SMILES: CN1CCN(C(C(=O)O)c2ccccc2)CC1] | RT_0.48 (Cond'n II); LCMS: Anal. Calcd. for: $C_{13}H_{18}N_2O_2$ 234.14; Found: 235.31 (M + H)⁺. |
| Cap-17d | 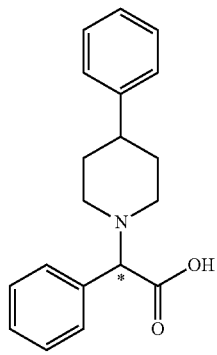 [SMILES: O=C(O)C(c1ccccc1)N1CCC(c2ccccc2)CC1] | RT_2.21 (Cond'n I); LCMS: Anal. Calcd. for: $C_{19}H_{21}NO_2$ 295.16; Found: 296.33 (M + H)⁺. |

LCMS Conditions for Determining Retention Time
Condition I
Column: Phenomenex-Luna 4.6×50 mm S10
Start % B=0
Fianl % B=100
Gradient Time=4 min
Flow Rate=4 mL/min
Wavelength=220
Solvent A=10% methanol-90% $H_2O$-0.1% TFA
Solvent B=90% methanol-10% $H_2O$-0.1% TFA
Condition II
Column: Waters-Sunfire 4.6×50 mm S5
Start % B=0
Fianl % B=100
Gradient Time=2 min
Flow Rate=4 mL/min
Wavelength=220
Solvent A=10% methanol-90% $H_2O$-0.1% TFA
Solvent B=90% methanol-10% $H_2O$-0.1% TFA
Condition III
Column: Phenomenex 10μ 3.0×50 mm
Start % B=0
Fianl % B=100
Gradient Time=2 min
Flow Rate=4 mL/min
Wavelength=220
Solvent A=10% methanol-90% $H_2O$-0.1% TFA
Solvent B=90% methanol-10% $H_2O$-0.1% TFA Cap-18

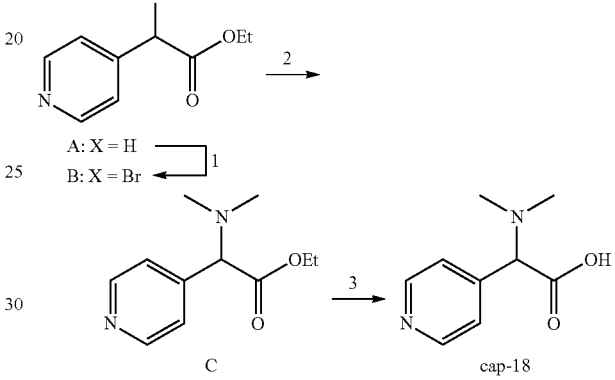

Step 1

(R,S)-Ethyl 2-(4-pyridyl)-2-bromoacetate: To a solution of ethyl 4-pyridylacetate (1.00 g, 6.05 mmol) in dry THF (150 mL) at 0° C. under argon was added DBU (0.99 mL, 6.66 mmol). The reaction mixture was allowed to warm to room temperature over 30 minutes and then it was cooled to −78° C. To this mixture was added $CBr_4$ (2.21 g, 6.66 mmol) and stirring was continued at −78° C. for 2 hours. The reaction mixture was then quenched with sat. aq. $NH_4Cl$ and the phases were separated. The organic phase was washed (brine), dried ($Na_2SO_4$), filtered, and concentrated in vacuo. The resulting yellow oil was immediately purified by flash chromatography ($SiO_2$/hexane-ethyl acetate, 1:1) to provide the title compound (1.40 g, 95%) as a somewhat unstable yellow oil. ¹H NMR (400 MHz, $CDCl_3$) δ 8.62 (dd, J=4.6, 1.8 Hz, 2H), 7.45 (dd, J=4.6, 1.8 Hz, 2H), 5.24 (s, 1H), 4.21-4.29 (m, 2H), 1.28 (t, J=7.1 Hz, 3H). LCMS: Anal. Calcd. for $C_9H_{10}BrNO_2$: 242, 244. found: 243, 245 (M+H)⁺.

Step 2

(R,S)-Ethyl 2-(4-pyridyl)-2-(N,N-dimethylamino)acetate: To a solution of (R,S)-ethyl 2-(4-pyridyl)-2-bromoacetate (1.40 g, 8.48 mmol) in DMF (10 mL) at room temperature was added dimethylamine (2M in THF, 8.5 mL, 17.0 mmol). After completion of the reaction (as judged by thin layer chromatography) the volatiles were removed in vacuo and the residue was purified by flash chromatography (Biotage, 40+M $SiO_2$ column; 50%-100% ethyl acetate-hexane) to provide the title compound (0.539 g, 31%) as a light yellow oil. ¹H NMR (400 MHz, $CDCl_3$) δ 8.58 (d, J=6.0 Hz, 2H), 7.36 (d, J=6.0 Hz, 2H), 4.17 (m, 2H), 3.92 (s, 1H), 2.27 (s, 6H), 1.22 (t, J=7.0 Hz). LCMS: Anal. Calcd. for $C_{11}H_{16}N_2O_2$: 208. found: 209 (M+H)⁺.

Step 3

(R,S)-2-(4-Pyridyl)-2-(N,N-dimethylamino)acetic acid: To a solution of (R,S)-ethyl 2-(4-pyridyl)-2-(N,N-dimethylamino)acetate (0.200 g, 0.960 mmol) in a mixture of THF-methanol-$H_2O$ (1:1:1, 6 mL) was added powdered LiOH (0.120 g, 4.99 mmol) at room temperature. The solution was stirred for 3 hours and then it was acidified to pH 6 using 1N HCl. The aqueous phase was washed with ethyl acetate and then it was lyophilized to give the dihydrochloride of the title compound as a yellow solid (containing LiCl). The product was used as such in subsequent steps. $^1$H NMR (400 MHz, DMSO-$d_6$) δ 8.49 (d, J=5.7 Hz, 2H), 7.34 (d, J=5.7 Hz, 2H), 3.56 (s, 1H), 2.21 (s, 6H).

The following examples were prepared in similar fashion using the method described above;

| | Structure | Data |
|---|---|---|
| Cap-19 | 3-pyridyl-CH(NMe$_2$)-CO$_2$H | LCMS: Anal. Calcd. for $C_9H_{12}N_2O_2$: 180; found: 181 (M + H)$^+$. |
| Cap-20 | 2-pyridyl-CH(NMe$_2$)-CO$_2$H | LCMS: no ionization. $^1$H NMR (400 MHz, CD$_3$OD) δ 8.55 (d, J = 4.3 Hz, 1H), 7.84 (app t, J = 5.3 Hz, 1H), 7.61 (d, J = 7.8 Hz, 1H), 7.37 (app t, J = 5.3 Hz, 1H), 4.35 (s, 1H), 2.60 (s, 6H). |
| Cap-21 | 6-chloro-3-pyridyl-CH(NMe$_2$)-CO$_2$H | LCMS: Anal. Calcd. for $C_9H_{11}ClN_2O_2$: 214, 216; found: 215, 217 (M + H)$^+$. |
| Cap-22 | 4-nitrophenyl-CH(NMe$_2$)-CO$_2$H | LCMS: Anal. Calcd. for $C_{10}H_{12}N_2O_4$: 224; found: 225 (M + H)$^+$. |
| Cap-23 | 1-naphthyl-CH(NMe$_2$)-CO$_2$H | LCMS: Anal. Calcd. for $C_{14}H_{15}NO_2$: 229; found: 230 (M + H)$^+$. |
| Cap-24 | 3-CF$_3$-phenyl-CH(NMe$_2$)-CO$_2$H | LCMS: Anal. Calcd. for $C_{11}H_{12}F_3NO_2$: 247; found: 248 (M + H)$^+$. |
| Cap-25 | 2-CF$_3$-phenyl-CH(NMe$_2$)-CO$_2$H | LCMS: Anal. Calcd. for $C_{11}H_{12}F_3NO_2$: 247; found: 248 (M + H)$^+$. |
| Cap-26 | 2-F-phenyl-CH(NMe$_2$)-CO$_2$H | LCMS: Anal. Calcd. for $C_{10}H_{12}FNO_2$: 197; found: 198 (M + H)$^+$. |
| Cap-27 | 3-F-phenyl-CH(NMe$_2$)-CO$_2$H | LCMS: Anal. Calcd. for $C_{10}H_{12}FNO_2$: 247; found: 248 (M + H)$^+$. |
| Cap-28 | 3-Cl-phenyl-CH(NMe$_2$)-CO$_2$H | LCMS: Anal. Calcd. for $C_{10}H_{12}ClNO_2$: 213; found: 214 (M + H)$^+$. |
| Cap-29 | 2-Cl-phenyl-CH(NMe$_2$)-CO$_2$H | LCMS: Anal. Calcd. for $C_{10}H_{12}ClNO_2$: 213; found: 214 (M + H)$^+$. |
| Cap-30 | 4-Cl-phenyl-CH(NMe$_2$)-CO$_2$H | LCMS: Anal. Calcd. for $C_{10}H_{12}ClNO_2$: 213; found: 214 (M + H)$^+$. |
| Cap-31 | 2-methylthiazol-4-yl-CH(NMe$_2$)-CO$_2$H | LCMS: Anal. Calcd. for $C_8H_{12}N_2O_2S$: 200; found: 201 (M + H)$^+$. |
| Cap-32 | thiophen-2-yl-CH(NMe$_2$)-CO$_2$H | LCMS: Anal. Calcd. for $C_8H_{11}NO_2S$: 185; found: 186 (M + H)$^+$. |
| Cap-33 | thiophen-3-yl-CH(NMe$_2$)-CO$_2$H | LCMS: Anal. Calcd. for $C_8H_{11}NO_2S$: 185; found: 186 (M + H)$^+$. |
| Cap-34 | benzo[d]isoxazol-3-yl-CH(NMe$_2$)-CO$_2$H | LCMS: Anal. Calcd. for $C_{11}H_{12}N_2O_3$: 220; found: 221 (M + H)$^+$. |
| Cap-35 | benzo[b]thiophen-3-yl-CH(NMe$_2$)-CO$_2$H | LCMS: Anal. Calcd. for $C_{12}H_{13}NO_2S$: 235; found: 236 (M + H)$^+$. |

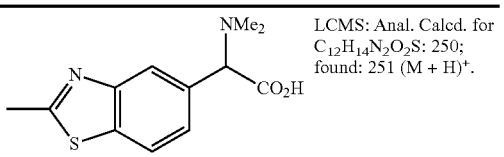

Cap-36  LCMS: Anal. Calcd. for $C_{12}H_{14}N_2O_2S$: 250; found: 251 (M + H)⁺.

Cap-37

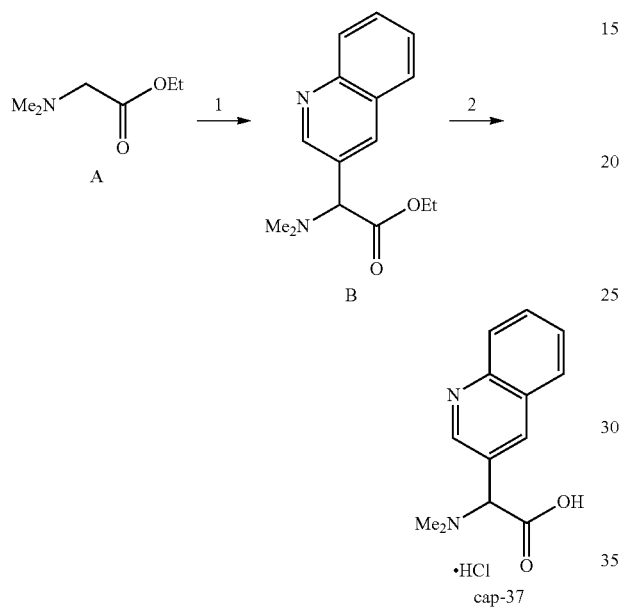

cap-37

Step 1

(R,S)-Ethyl 2-(quinolin-3-yl)-2-(N,N-dimethylamino)-acetate: A mixture of ethyl N,N-dimethylaminoacetate (0.462 g, 3.54 mmol), $K_3PO_4$ (1.90 g, 8.95 mmol), $Pd(t-Bu_3P)_2$ (0.090 g, 0.176 mmol) and toluene (10 mL) was degassed with a stream of Ar bubbles for 15 minutes. The reaction mixture was then heated at 100° C. for 12 hours, after which it was cooled to room temperature and poured into $H_2O$. The mixture was extracted with ethyl acetate (2×) and the combined organic phases were washed ($H_2O$, brine), dried ($Na_2SO_4$), filtered, and concentrated in vacuo. The residue was purified first by reverse-phase preparative HPLC (Primesphere C-18, 30×100 mm; $CH_3CN$—$H_2O$-5 mM $NH_4OAc$) and then by flash chromatography ($SiO_2$/hexane-ethyl acetate, 1:1) to provide the title compound (0.128 g, 17%) as an orange oil. $^1H$ NMR (400 MHz, $CDCl_3$) δ 8.90 (d, J=2.0 Hz, 1H), 8.32 (d, J=2.0 Hz, 1H), 8.03-8.01 (m, 2H), 7.77 (ddd, J=8.3, 6.8, 1.5 Hz, 1H), 7.62 (ddd, J=8.3, 6.8, 1.5 Hz, 1H), 4.35 (s, 1H), 4.13 (m, 2H), 2.22 (s, 6H), 1.15 (t, J=7.0 Hz, 3H). LCMS: Anal. Calcd. for $C_{15}H_{18}N_2O_2$: 258. found: 259 (M+H)⁺.

Step 2

(R,S) 2-(Quinolin-3-yl)-2-(N,N-dimethylamino)acetic acid: A mixture of (R,S)-ethyl 2-(quinolin-3-yl)-2-(N,N-dimethylamino)acetate (0.122 g, 0.472 mmol) and 6M HCl (3 mL) was heated at 100° C. for 12 hours. The solvent was removed in vacuo to provide the dihydrochloride of the title compound (0.169 g, >100%) as a light yellow foam. The unpurified material was used in subsequent steps without further purification. LCMS: Anal. Calcd. for $C_{13}H_{14}N_2O_2$: 230. found: 231 (M+H)⁺.

Cap-38

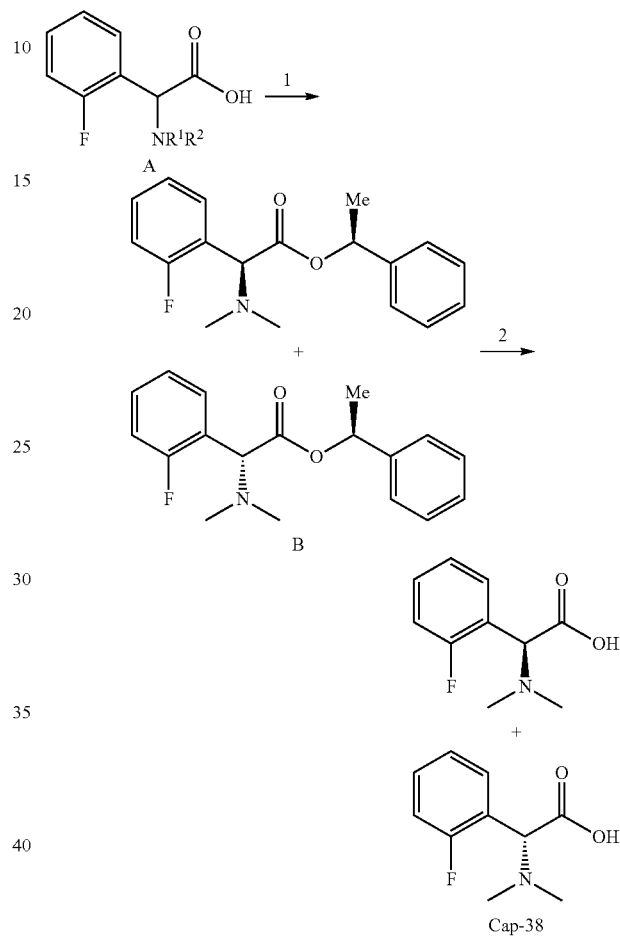

Cap-38

Step 1

(R)—((S)-1-phenylethyl) 2-(dimethylamino)-2-(2-fluorophenyl)acetate and (S)—((S)-1-phenylethyl) 2-(dimethylamino)-2-(2-fluorophenyl)acetate: To a mixture of (RS)-2-(dimethylamino)-2-(2-fluorophenyl)acetic acid (2.60 g, 13.19 mmol), DMAP (0.209 g, 1.71 mmol) and (S)-1-phenylethanol (2.09 g, 17.15 mmol) in $CH_2Cl_2$ (40 mL) was added EDCI (3.29 g, 17.15 mmol) and the mixture was allowed to stir at room temperature for 12 hours. The solvent was then removed in vacuo and the residue partitioned with ethyl acetate-$H_2O$. The layers were separated, the aqueous layer was back-extracted with ethyl acetate (2×) and the combined organic phases were washed ($H_2O$, brine), dried ($Na_2SO_4$), filtered, and concentrated in vacuo. The residue was purified by silica gel chromatography (Biotage/0-50% diethyl ether-hexane). The resulting pure diastereomeric mixture was then separated by reverse-phase preparative HPLC (Primesphere C-18, 30×100 mm; $CH_3CN$—$H_2O$-0.1% TFA) to give first (S)-1-phenethyl(R)-2-(dimethylamino)-2-(2-fluorophenyl)acetate (0.501 g, 13%) and then (S)-1-phenethyl(S)-2-(dimethylamino)-2-(2-fluorophenyl)-acetate (0.727 g, 18%), both as their TFA salts. (S,R)-isomer: $^1H$ NMR (400 MHz, CD$_3$OD) δ 7.65-7.70 (m, 1H), 7.55-7.60 (ddd, J=9.4, 8.1, 1.5 Hz, 1H), 7.36-7.41 (m, 2H), 7.28-7.34 (m, 5H), 6.04 (q, J=6.5 Hz, 1H), 5.60 (s, 1H), 2.84 (s, 6H), 1.43 (d, J=6.5 Hz, 3H). LCMS: Anal. Calcd. for C$_{18}$H$_{20}$FNO$_2$: 301. found: 302 (M+H)$^+$; (S,S)-isomer: $^1$H NMR (400 MHz, CD$_3$OD) δ 7.58-7.63 (m, 1H), 7.18-7.31 (m, 6H), 7.00 (dd, J=8.5, 1.5 Hz, 2H), 6.02 (q, J=6.5 Hz, 1H), 5.60 (s, 1H), 2.88 (s, 6H), 1.54 (d, J=6.5 Hz, 3H). LCMS: Anal. Calcd. for C$_{18}$H$_{20}$FNO$_2$: 301. found: 302 (M+H)$^+$.

Step 2

(R)-2-(dimethylamino)-2-(2-fluorophenyl)acetic acid: A mixture of (R)—((S)-1-phenylethyl) 2-(dimethylamino)-2-(2-fluorophenyl)acetate TFA salt (1.25 g, 3.01 mmol) and 20% Pd(OH)$_2$/C (0.125 g) in ethanol (30 mL) was hydrogenated at room temperature and atmospheric pressure (H$_2$ balloon) for 4 hours. The solution was then purged with Ar, filtered through diatomaceous earth (Celite®), and concentrated in vacuo. This gave the title compound as a colorless solid (0.503 g, 98%). $^1$H NMR (400 MHz, CD$_3$OD) δ 7.53-7.63 (m, 2H), 7.33-7.38 (m, 2H), 5.36 (s, 1H), 2.86 (s, 6H). LCMS: Anal. Calcd. for C$_{10}$H$_{12}$FNO$_2$: 197. found: 198 (M+H)$^+$.

The S-isomer could be obtained from (S)—((S)-1-phenylethyl) 2-(dimethylamino)-2-(2-fluorophenyl)acetate TFA salt in similar fashion.

Cap-39

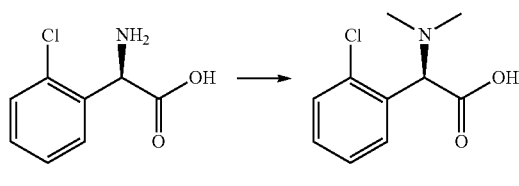

cap-39

A mixture of (R)-(2-chlorophenyl)glycine (0.300 g, 1.62 mmol), formaldehyde (35% aqueous solution, 0.80 mL, 3.23 mmol) and 20% Pd(OH)$_2$/C (0.050 g) was hydrogenated at room temperature and atmospheric pressure (H$_2$ balloon) for 4 hours. The solution was then purged with Ar, filtered through diatomaceous earth (Celite®) and concentrated in vacuo. The residue was purified by reverse-phase preparative HPLC (Primesphere C-18, 30×100 mm; CH$_3$CN—H$_2$O-0.1% TFA) to give theTFA salt of the title compound (R)-2-(dimethylamino)-2-(2-chlorophenyl)acetic acid as a colorless oil (0.290 g, 55%). $^1$H NMR (400 MHz, CD$_3$OD) δ 7.59-7.65 (m, 2H), 7.45-7.53 (m, 2H), 5.40 (s, 1H), 2.87 (s, 6H). LCMS: Anal. Calcd. for C$_{10}$H$_{12}$ClNO$_2$: 213. found: 214 (M+H)$^+$.

Cap-40

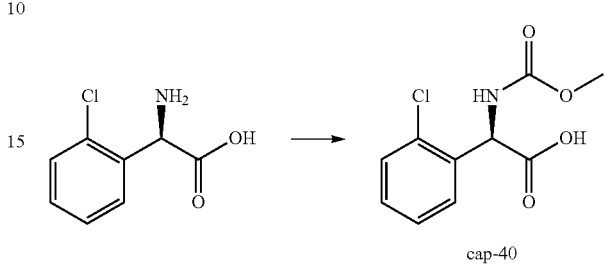

cap-40

To an ice-cold solution of (R)-(2-chlorophenyl)glycine (1.00 g, 5.38 mmol) and NaOH (0.862 g, 21.6 mmol) in H$_2$O (5.5 mL) was added methyl chloroformate (1.00 mL, 13.5 mmol) dropwise. The mixture was allowed to stir at 0° C. for 1 hour and then it was acidified by the addition of conc. HCl (2.5 mL). The mixture was extracted with ethyl acetate (2×) and the combined organic phase was washed (H$_2$O, brine), dried (Na$_2$SO$_4$), filtered, and concentrated in vacuo to give the title compound (R)-2-(methoxycarbonylamino)-2-(2-chlorophenyl)acetic acid as a yellow-orange foam (1.31 g, 96%). $^1$H NMR (400 MHz, CD$_3$OD) δ 7.39-7.43 (m, 2H), 7.29-7.31 (m, 2H), 5.69 (s, 1H), 3.65 (s, 3H). LCMS: Anal. Calcd. for C$_{10}$H$_{10}$ClNO$_4$: 243. found: 244 (M+H)$^+$.

Cap-41

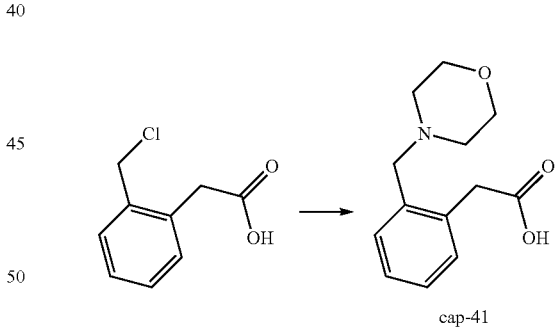

cap-41

To a suspension of 2-(2-(chloromethyl)phenyl)acetic acid (2.00 g, 10.8 mmol) in THF (20 mL) was added morpholine (1.89 g, 21.7 mmol) and the solution was stirred at room temperature for 3 hours. The reaction mixture was then diluted with ethyl acetate and extracted with H$_2$O (2×). The aqueous phase was lyophilized and the residue was purified by silica gel chromatography (Biotage/0-10% methanol-CH$_2$Cl$_2$) to give the title compound 2-(2-(Morpholinomethyl)phenyl)acetic acid as a colorless solid (2.22 g, 87%). $^1$H NMR (400 MHz, CD$_3$OD) δ 7.37-7.44 (m, 3H), 7.29-7.33 (m, 1H), 4.24 (s, 2H), 3.83 (br s, 4H), 3.68 (s, 2H), 3.14 (br s, 4H). LCMS: Anal. Calcd. for C$_{13}$H$_{17}$NO$_3$: 235. found: 236 (M+H)$^+$.

The following examples were similarly prepared using the method described for Cap-41:

| | | |
|---|---|---|
| Cap-42 | 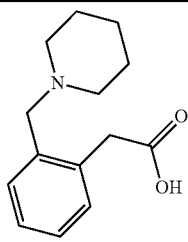 | LCMS: Anal. Calcd. for C$_{14}$H$_{19}$NO$_2$: 233; found: 234 (M + H)$^+$. |
| Cap-43 | 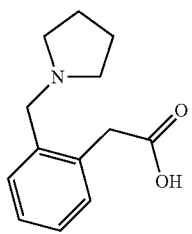 [SMILES: O=C(O)Cc1ccccc1CN1CCCC1] | LCMS: Anal. Calcd. for C$_{13}$H$_{17}$NO$_2$: 219; found: 220 (M + H)$^+$. |
| Cap-44 | 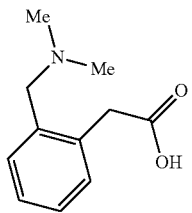 [SMILES: CN(C)Cc1ccccc1CC(=O)O] | LCMS: Anal. Calcd. for C$_{11}$H$_{15}$NO$_2$: 193; found: 194 (M + H)$^+$. |
| Cap-45 | 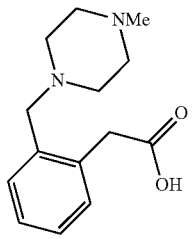 [SMILES: CN1CCN(Cc2ccccc2CC(=O)O)CC1] | LCMS: Anal. Calcd. for C$_{14}$H$_{20}$N$_2$O$_2$: 248; found: 249 (M + H)$^+$. |

Cap-45a

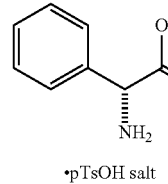

Cap-45a

HMDS (1.85 mL, 8.77 mmol) was added to a suspension of (R)-2-amino-2-phenylacetic acid p-toluenesulfonate (2.83 g, 8.77 mmol) in CH$_2$Cl$_2$ (10 mL) and the mixture was stirred at room temperature for 30 minutes. Methyl isocyanate (0.5 g, 8.77 mmol) was added in one portion stirring continued for 30 minutes. The reaction was quenched by addition of H$_2$O (5 mL) and the resulting precipitate was filtered, washed with H$_2$O and n-hexanes, and dried under vacuum. (R)-2-(3-methylureido)-2-phenylacetic acid (1.5 g; 82%) was recovered as a white solid and it was used without further purification. $^1$H NMR (500 MHz, DMSO-d$_6$) δ ppm 2.54 (d, J=4.88 Hz, 3H) 5.17 (d, J=7.93 Hz, 1H) 5.95 (q, J=4.48 Hz, 1H) 6.66 (d, J=7.93 Hz, 1H) 7.26-7.38 (m, 5H) 12.67 (s, 1H). LCMS: Anal. Calcd. for C$_{10}$H$_{12}$N$_2$O$_3$ 208.08. found 209.121 (M+H)$^+$. HPLC Phenomenex C-18 3.0×46 mm, 0 to 100% B over 2 minutes, 1 minute hold time, A=90% water, 10% methanol, 0.1% TFA, B=10% water, 90% methanol, 0.1% TFA, RT=1.38 min, 90% homogeneity index.

Cap-46

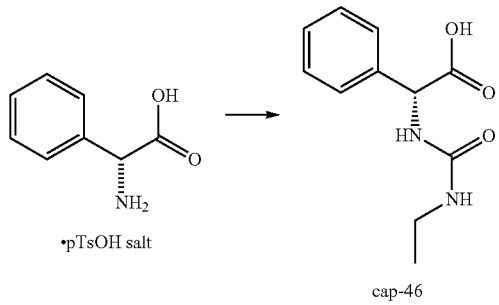 [SMILES: N[C@@H](C(=O)O)c1ccccc1 ; CCNC(=O)N[C@@H](C(=O)O)c1ccccc1]

cap-46

The desired product was prepared according to the method described for Cap-45a. $^1$H NMR (500 MHz, DMSO-d$_6$) δ ppm 0.96 (t, J=7.17 Hz, 3H) 2.94-3.05 (m, 2H) 5.17 (d, J=7.93 Hz, 1H) 6.05 (t, J=5.19 Hz, 1H) 6.60 (d, J=7.63 Hz, 1H) 7.26-7.38 (m, 5H) 12.68 (s, 1H). LCMS: Anal. Calcd. for C$_{11}$H$_{14}$N$_2$O$_3$ 222.10 found 223.15 (M+H)$^+$. HPLC XTERRA C-18 3.0×506 mm, 0 to 100% B over 2 minutes, 1 minute hold time, A=90% water, 10% methanol, 0.2% H$_3$PO$_4$, B=10% water, 90% methanol, 0.2% H$_3$PO$_4$, RT=0.87 min, 90% homogeneity index.

Cap-47

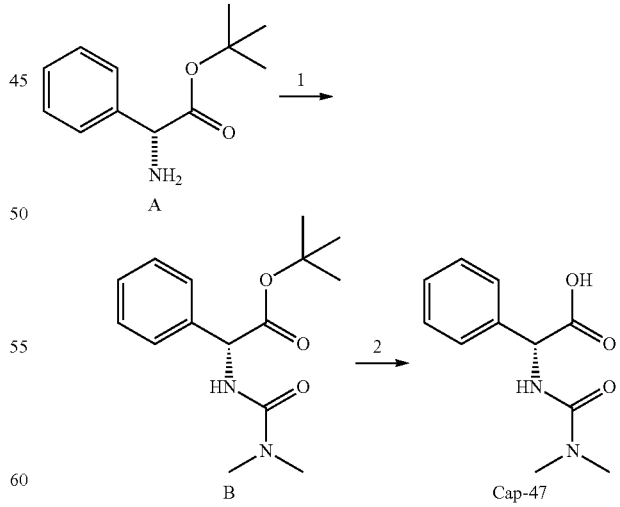

Step 1

(R)-tert-butyl 2-(3,3-dimethylureido)-2-phenylacetate: To a stirred solution of (R)-tert-butyl-2-amino-2-phenylacetate (1.0 g, 4.10 mmol) and Hunig's base (1.79 mL, 10.25 mmol) in DMF (40 mL) was added dimethylcarbamoyl chloride (0.38 mL, 4.18 mmol) dropwise over 10 minutes. After stirring at room temperature for 3 hours, the reaction was concentrated under reduced pressure and the resulting residue was dissolved in ethyl acetate. The organic layer was washed with $H_2O$, 1N aq. HCl and brine, dried ($MgSO_4$), filtered and concentrated under reduced pressure. (R)-tert-butyl 2-(3,3-dimethylureido)-2-phenylacetate was obtained as a white solid (0.86 g, 75%) and used without further purification. $^1$H NMR (500 MHz, DMSO-$d_6$) δ ppm 1.33 (s, 9H) 2.82 (s, 6H) 5.17 (d, J=7.63 Hz, 1H) 6.55 (d, J=7.32 Hz, 1H) 7.24-7.41 (m, 5H). LCMS: Anal. Calcd. for $C_{15}H_{22}N_2O_3$ 278.16 found 279.23 (M+H)$^+$; HPLC Phenomenex LUNA C-18 4.6×50 mm, 0 to 100% B over 4 minutes, 1 minute hold time, A=90% water, 10% methanol, 0.1% TFA, B=10% water, 90% methanol, 0.1% TFA, RT=2.26 min, 97% homogeneity index.

Step 2

(R)-2-(3,3-dimethylureido)-2-phenylacetic acid: To a stirred solution of ((R)-tert-butyl 2-(3,3-dimethylureido)-2-phenylacetate (0.86 g, 3.10 mmol) in $CH_2Cl_2$ (250 mL) was added TFA (15 mL) dropwise and the resulting solution was stirred at rt for 3 hours. The desired compound was then precipitated out of solution with a mixture of EtOAC:Hexanes (5:20), filtered off and dried under reduced pressure. (R)-2-(3,3-dimethylureido)-2-phenylacetic acid was isolated as a white solid (0.59 g, 86%) and used without further purification. $^1$H NMR (500 MHz, DMSO-$d_6$) δ ppm 2.82 (s, 6H) 5.22 (d, J=7.32 Hz, 1H) 6.58 (d, J=7.32 Hz, 1H) 7.28 (t, J=7.17 Hz, 1H) 7.33 (t, J=7.32 Hz, 2H) 7.38-7.43 (m, 2H) 12.65 (s, 1H). LCMS: Anal. Calcd. for $C_{11}H_{14}N_2O_3$: 222.24. found: 223.21 (M+H)$^+$. HPLC XTERRA C-18 3.0×50 mm, 0 to 100% B over 2 minutes, 1 minute hold time, A=90% water, 10% methanol, 0.2% $H_3PO_4$, B=10% water, 90% methanol, 0.2% $H_3PO_4$, RT=0.75 min, 93% homogeneity index.

Cap-48

After stirring at room temperature for 3 hours, the reaction was concentrated under reduced pressure and the resulting residue was traken up in ethyl acetate. The organic layer was washed with $H_2O$ and brine, dried ($MgSO_4$), filtered, and concentrated under reduced pressure. (R)-tert-butyl 2-(3-cyclopentylureido)-2-phenylacetate was obtained as an opaque oil (1.32 g; 100%) and used without further purification. $^1$H NMR (500 MHz, $CD_3Cl$-D) δ ppm 1.50-1.57 (m, 2H) 1.58-1.66 (m, 2H) 1.87-1.97 (m, 2H) 3.89-3.98 (m, 1H) 5.37 (s, 1H) 7.26-7.38 (m, 5H). LCMS: Anal. Calcd. for $C_{18}H_{26}N_2O_3$ 318.19 found 319.21 (M+H)$^+$; HPLC XTERRA C-18 3.0×50 mm, 0 to 100% B over 4 minutes, 1 minute hold time, A=90% water, 10% methanol, 0.1% TFA, B=10% water, 90% methanol, 0.1% TFA, RT=2.82 min, 96% homogeneity index.

Step 2

(R)-2-(3-cyclopentylureido)-2-phenylacetic acid: To a stirred solution of (R)-tert-butyl 2-(3-cyclopentylureido)-2-phenylacetate (1.31 g, 4.10 mmol) in $CH_2Cl_2$ (25 mL) was added TFA (4 mL) and trietheylsilane (1.64 mL; 10.3 mmol) dropwise, and the resulting solution was stirred at room temperature for 6 hours. The volatile components were removed under reduced pressure and the crude product was recrystallized in ethyl acetate/pentanes to yield (R)-2-(3-cyclopentylureido)-2-phenylacetic acid as a white solid (0.69 g, 64%). $^1$H NMR (500 MHz, DMSO-$d_6$) δ ppm 1.17-1.35 (m, 2H) 1.42-1.52 (m, 2H) 1.53-1.64 (m, 2H) 1.67-1.80 (m, 2H) 3.75-3.89 (m, 1H) 5.17 (d, J=7.93 Hz, 1H) 6.12 (d, J=7.32 Hz, 1H) 6.48 (d, J=7.93 Hz, 1H) 7.24-7.40 (m, 5H) 12.73 (s, 1H). LCMS: Anal. Calcd. for $C_{14}H_{18}N_2O_3$: 262.31. found: 263.15 (M+H)$^+$. HPLC XTERRA C-18 3.0×50 mm, 0 to 100% B over 2 minutes, 1 minute hold time, A=90% water, 10% methanol, 0.2% $H_3PO_4$, B=10% water, 90% methanol, 0.2% $H_3PO_4$, RT=1.24 min, 100% homogeneity index.

Cap-49

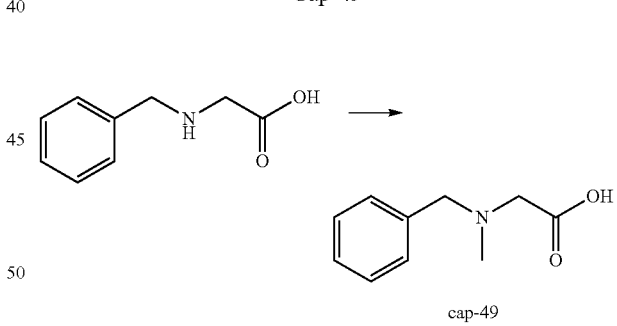

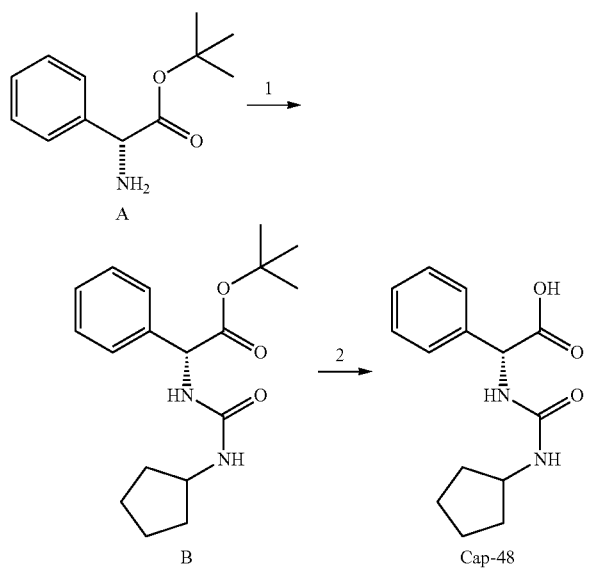

Step 1

(R)-tert-butyl 2-(3-cyclopentylureido)-2-phenylacetate: To a stirred solution of (R)-2-amino-2-phenylacetic acid hydrochloride (1.0 g, 4.10 mmol) and Hunig's base (1.0 mL, 6.15 mmol) in DMF (15 mL) was added cyclopentyl isocyanate (0.46 mL, 4.10 mmol) dropwise and over 10 minutes.

To a stirred solution of 2-(benzylamino)acetic acid (2.0 g, 12.1 mmol) in formic acid (91 mL) was added formaldehyde (6.94 mL, 93.2 mmol). After five hours at 70° C., the reaction mixture was concentrated under reduced pressure to 20 mL and a white solid precipitated. Following filtration, the mother liquors were collected and further concentrated under reduced pressure providing the crude product. Purification by reverse-phase preparative HPLC (Xterra 30×100 mm, detection at 220 nm, flow rate 35 mL/min, 0 to 35% B over 8 min; A=90% water, 10% methanol, 0.1% TFA, B=10% water, 90% methanol, 0.1% TFA) provided the title compound 2-(benzyl (methyl)-amino)acetic acid as its TFA salt (723 mg, 33%) as a colorless wax. $^1$H NMR (300 MHz, DMSO-$d_6$) δ ppm 2.75

(s, 3H) 4.04 (s, 2H) 4.34 (s, 2H) 7.29-7.68 (m, 5H). LCMS: Anal. Calcd. for: $C_{10}H_{13}NO_2$ 179.09. Found: 180.20 $(M+H)^+$.

Cap-50

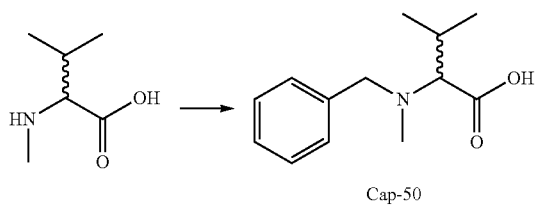

Cap-50

To a stirred solution of 3-methyl-2-(methylamino)butanoic acid (0.50 g, 3.81 mmol) in water (30 mL) was added $K_2CO_3$ (2.63 g, 19.1 mmol) and benzyl chloride (1.32 g, 11.4 mmol). The reaction mixture was stirred at ambient temperature for 18 hours. The reaction mixture was extracted with ethyl acetate (30 mL×2) and the aqueous layer was concentrated under reduced pressure providing the crude product which was purified by reverse-phase preparative HPLC (Xterra 30×100 mm, detection at 220 nm, flow rate 40 mL/min, 20 to 80% B over 6 min; A=90% water, 10% methanol, 0.1% TFA, B=10% water, 90% methanol, 0.1% TFA) to provide 2-(benzyl(methyl)amino)-3-methylbutanoic acid, TFA salt (126 mg, 19%) as a colorless wax. $^1H$ NMR (500 MHz, DMSO-$d_6$) δ ppm 0.98 (d, 3H) 1.07 (d, 3H) 2.33-2.48 (m, 1H) 2.54-2.78 (m, 3H) 3.69 (s, 1H) 4.24 (s, 2H) 7.29-7.65 (m, 5H). LCMS: Anal. Calcd. for: $C_{13}H_{19}NO_2$ 221.14. Found: 222.28 $(M+H)^+$.

Cap-51

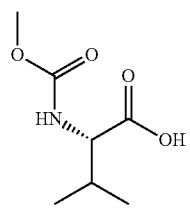

$Na_2CO_3$ (1.83 g, 17.2 mmol) was added to NaOH (33 mL of 1M/$H_2O$, 33 mmol) solution of L-valine (3.9 g, 33.29 mmol) and the resulting solution was cooled with ice-water bath. Methyl chloroformate (2.8 mL, 36.1 mmol) was added dropwise over 15 min, the cooling bath was removed and the reaction mixture was stirred at ambient temperature for 3.25 hr. The reaction mixture was washed with ether (50 mL, 3×), and the aqueous phase was cooled with ice-water bath and acidified with concentrated HCl to a pH region of 1-2, and extracted with $CH_2Cl_2$ (50 mL, 3×). The organic phase was dried (MgSO$_4$) and evaporated in vacuo to afford Cap-51 as a white solid (6 g). $^1H$ NMR for the dominant rotamer (DMSO-$d_6$, δ=2.5 ppm, 500 MHz): 12.54 (s, 1H), 7.33 (d, J=8.6, 1H), 3.84 (dd, J=8.4, 6.0, 1H), 3.54 (s, 3H), 2.03 (m, 1H), 0.87 (m, 6H). HRMS: Anal. Calcd. for $[M+H]^+$ $C_2H_{14}NO_4$: 176.0923. found 176.0922.

Cap 51 (Alternate Route)

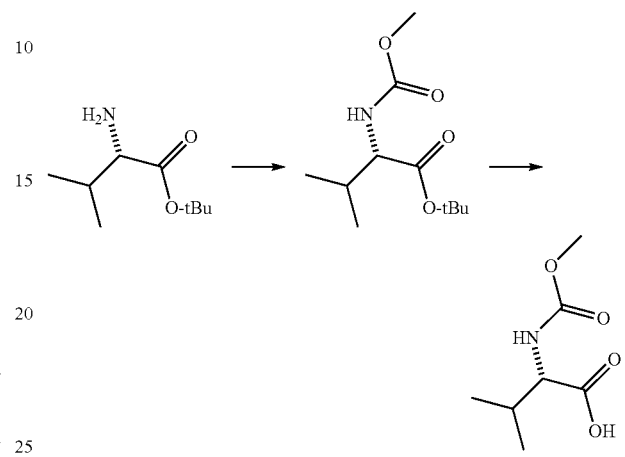

DIEA (137.5 mL, 0.766 mol) was added to a suspension of (S)-tert-butyl 2-amino-3-methylbutanoate hydrochloride (75.0 g, 0.357 mol) in THF (900 mL), and the mixture was cooled to 0° C. (ice/water bath). Methyl chloroformate (29.0 mL, 0.375 mol) was added dropwise over 45 min, the cooling bath was removed and the heterogeneous mixture was stirred at ambient temperature for 3 h. The solvent was removed under diminished pressure and the residue partitioned between EtOAc and water (1 L each). The organic layer was washed with $H_2O$ (1 L) and brine (1 L), dried (MgSO$_4$), filtered and concentrated under diminished pressure. The crude material was passed through a plug of silica gel (1 kg), eluting with hexanes (4 L) and 15:85 EtOAc/hexanes (4 L) to afford (S)-tert-butyl 2-(methoxycarbonylamino)-3-methylbutanoate as a clear oil (82.0 g, 99% yield). $^1H$-NMR (500 MHz, DMSO-$d_6$, δ=2.5 ppm) 7.34 (d, J=8.6, 1H), 3.77 (dd, J=8.6, 6.1, 1H), 3.53 (s, 3H), 1.94-2.05 (m, 1H), 1.39 (s, 9H), 0.83-0.92 (m, 6H). $^{13}C$-NMR (126 MHz, DMSO-$d_6$, δ=39.2 ppm) 170.92, 156.84, 80.38, 60.00, 51.34, 29.76, 27.62, 18.92, 17.95. LC/MS: $[M+Na]^+$ 254.17.

Trifluoroacetic acid (343 mL, 4.62 mol) and $Et_3SiH$ (142 mL, 0.887 mol) were added sequentially to a solution of (S)-tert-butyl 2-(methoxycarbonylamino)-3-methylbutanoate (82.0 g, 0.355 mol) in $CH_2Cl_2$ (675 mL), and the mixture was stirred at ambient temperature for 4 h. The volatile component was removed under diminished pressure and the resultant oil triturated with petroleum ether (600 mL) to afford a white solid, which was filtered and washed with hexanes (500 mL) and petroleum ether (500 mL). Recrystallization from EtOAc/petroleum ether afforded Cap-51 as white flaky crystals (54.8 g, 88% yield). MP=108.5-109.5° C. $^1H$ NMR (500 MHz, DMSO-$d_6$, δ=2.5 ppm) 12.52 (s, 1H), 7.31 (d, J=8.6, 1H), 3.83 (dd, J=8.6, 6.1, 1H), 3.53 (s, 3 H), 1.94-2.07 (m, 1H), 0.86 (dd, J=8.9, 7.0, 6H). $^{13}C$ NMR (126 MHz, DMSO-$d_6$, δ=39.2 ppm) 173.30, 156.94, 59.48, 51.37, 29.52, 19.15, 17.98. LC/MS: $[M+H]^+$=176.11. Anal. Calcd. for $C_7H_{13}NO_4$: C, 47.99; H, 7.48; N, 7.99. Found: C, 48.17; H, 7.55; N, 7.99. Optical Rotation: $[\alpha]_D$=−4.16 (12.02 mg/mL; MeOH). Optical purity: >99.5% ee. Note: the optical purity assessment was made on the methyl ester derivative of Cap-51, which was prepared under a standard TMSCHN$_2$ (benzene/MeOH) esterification protocol. HPLC analytical conditions: column, ChiralPak AD-H (4.6×250 mm, 5 μm); solvent, 95% heptane/5% IPA (isocratic); flow rate, 1 mL/min; temperature, 35° C.; UV monitored at 205 nm. [Note: Cap 51 could also be purchased from Flamm.]

Cap-52 (Same as Cap-12)

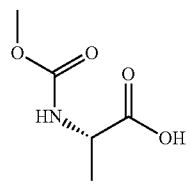

Cap-52 was synthesized from L-alanine according to the procedure described for the synthesis of Cap-51. For characterization purposes, a portion of the crude material was purified by a reverse phase HPLC(H$_2$O/methanol/TFA) to afford Cap-52 as a colorless viscous oil. $^1$H NMR (DMSO-d$_6$, δ=2.5 ppm, 500 MHz): 12.49 (br s, 1H), 7.43 (d, J=7.3, 0.88H), 7.09 (app br s, 0.12H), 3.97 (m, 1H), 3.53 (s, 3H), 1.25 (d, J=7.3, 3H).

Cap-53 to -64 were prepared from appropriate starting materials according to the procedure described for the synthesis of Cap-51, with noted modifications if any.

| Cap | Structure | Data |
|---|---|---|
| Cap-53a: (R) Cap-53b: (S) | 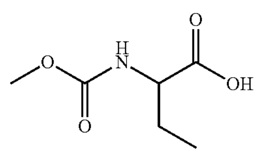 | $^1$H NMR (DMSO-d$_6$, δ = 2.5 ppm, 500 MHz): δ 12.51 (br s, 1H), 7.4 (d, J = 7.9, 0.9H), 7.06 (app s, 0.1H), 3.86-3.82 (m, 1H), 3.53 (s,3H), 1.75-1.67 (m, 1H), 1.62-1.54 (m, 1H), 0.88 (d, J = 7.3, 3H). RT = 0.77 minutes (Cond. 2); LC/MS: Anal. Calcd. for [M + Na]$^+$ C$_6$H$_{11}$NNaO$_4$: 184.06; found 184.07. HRMS Calcd. for [M + Na]$^+$ C$_6$H$_{11}$NNaO$_4$: 184.0586; found 184.0592. |
| Cap-54a: (R) Cap-54b: (S) | 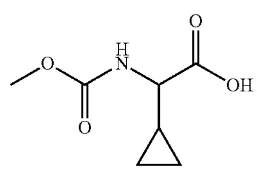 | $^1$H NMR (DMSO-d$_6$, δ = 2.5 ppm. 500 MHz): δ 12.48 (s, 1H), 7.58 (d, J = 7.6, 0.9H), 7.25 (app s, 0.1H), 3.52 (s, 3H), 3.36-3.33 (m, 1H), 1.10-1.01 (m, 1H), 0.54-0.49 (m, 1H), 0.46-0.40 (m, 1H), 0.39-0.35 (m, 1H), 0.31-0.21 (m, 1H). HRMS Calcd. for [M + H]$^+$ C$_7$H$_{12}$NO$_4$: 174.0766; found 174.0771 |
| Cap-55: | 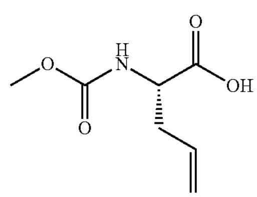 | $^1$H NMR (DMSO-d$_6$, δ = 2.5 ppm, 500 MHz): δ 12.62 (s, 1H), 7.42 (d, J = 8.2, 0.9H), 7.07 (app s, 0.1H), 5.80-5.72 (m, 1H), 5.10 (d, J = 17.1, 1H), 5.04 (d, J = 10.4, 1H), 4.01-3.96 (m, 1H), 3.53 (s, 3H), 2.47-2.42 (m, 1H), 2.35-2.29 (m, 1H). |
| Cap-56: | 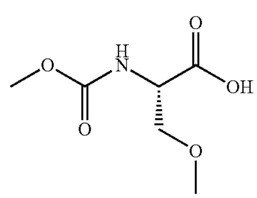 | $^1$H NMR (DMSO-d$_6$, δ = 2.5 ppm, 500 MHz): δ 12.75 (s, 1H), 7.38 (d, J = 8.3, 0.9H), 6.96 (app s, 0.1H), 4.20-4.16 (m, 1H), 3.60-3.55 (m, 2H), 3.54 (s, 3H), 3.24 (s, 3H). |
| Cap-57: | 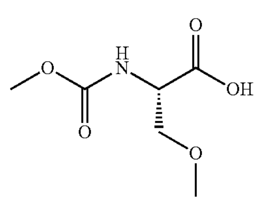 | $^1$H NMR (DMSO-d$_6$, δ = 2.5 ppm, 500 MHz): δ 12.50 (s, 1H), 8.02 (d, J = 7.7, 0.08H), 7.40 (d, J = 7.9, 0.76H), 7.19 (d, J = 8.2, 0.07H), 7.07 (d, J = 6.7, 0.09H), 4.21-4.12 (m, 0.08H), 4.06-3.97 (m, 0.07H), 3.96-3.80 (m, 0.85H), 3.53 (s, 3H), 1.69-1.51 (m, 2H), 1.39-1.26 (m, 2H), 0.85 (t, J = 7.4, 3H). LC (Cond. 2): RT = 1.39 LC/MS: Anal. Calcd. for [M + H]$^+$ C$_7$H$_{14}$NO$_4$: 176.09; found 176.06. |

| Cap | Structure | Data |
|---|---|---|
| Cap-58: | 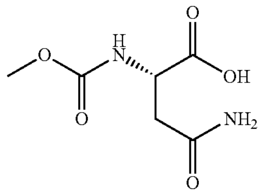 | $^1$H NMR (DMSO-d$_6$, δ = 2.5 ppm, 500 MHz): δ 12.63 (brs, 1H), 7.35 (s, 1H), 7.31 (d, J = 8.2, 1H), 6.92 (s, 1H), 4.33-4.29 (m, 1H), 3.54 (s,3H), 2.54 (dd, J = 15.5, 5.4, 1H), 2.43 (dd, J = 15.6, 8.0, 1H). RT = 0.16 min (Cond. 2); LC/MS: Anal. Calcd. for [M + H]$^+$ C$_6$H$_{11}$N$_2$O$_5$: 191.07; found 191.14. |
| Cap-59a: (R) Cap-59b: (S) | 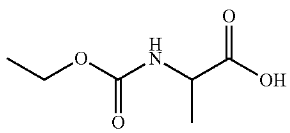 | $^1$H NMR (DMSO-d$_6$, δ = 2.5 ppm, 400 MHz): δ 12.49 (br s, 1H), 7.40 (d, J = 7.3, 0.89H), 7.04 (br s, 0.11H), 4.00-3.95 (m, 3H), 1.24 (d, J = 7.3, 3H), 1.15 (t, J = 7.2, 3H). HRMS: Anal. Calcd. for [M + H]$^+$ C$_6$H$_{12}$NO$_4$: 162.0766; found 162.0771. |
| Cap-60: | 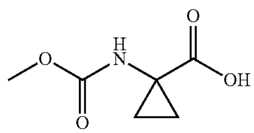 | The crude material was purified with a reverse phase HPLC (H$_2$O/MeOH/TFA) to afford a colorless viscous oil that crystallized to a white solid upon exposure to high vacuum. $^1$H NMR (DMSO-d$_6$, δ = 2.5 ppm, 400 MHz): δ 12.38 (br s, 1H), 7.74 (s, 0.82H), 7.48 (s, 0.18H), 3.54/3.51 (two s, 3H), 1.30 (m, 2H), 0.98 (m, 2H). HRMS: Anal. Calcd. for [M + H]$^+$ C$_6$H$_{10}$NO$_4$: 160.0610; found 160.0604. |
| Cap-61: | 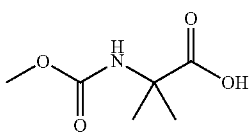 | $^1$H NMR (DMSO-d$_6$, δ = 2.5 ppm, 400 MHz): δ 12.27 (brs, 1H), 7.40 (brs, 1H), 3.50 (s, 3H), 1.32 (s, 6H). HRMS: Anal. Calcd. for [M + H]$^+$ C$_6$H$_{12}$NO$_4$: 162.0766; found 162.0765. |
| Cap-62: | 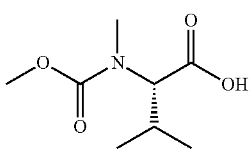 | $^1$H NMR (DMSO-d$_6$, δ = 2.5 ppm, 400 MHz): δ 12.74 (br s, 1H), 4.21 (d, J = 10.3, 0.6H), 4.05 (d, J = 10.0, 0.4H), 3.62/3.60 (two singlets, 3H), 3.0 (s, 3H), 2.14-2.05 (m, 1H), 0.95 (d, J = 6.3, 3H), 0.81 (d, J = 6.6, 3H). LC/MS: Anal. Calcd. for [M − H]$^−$ C$_8$H$_{14}$NO$_4$: 188.09; found 188.05. |
| Cap-63: | 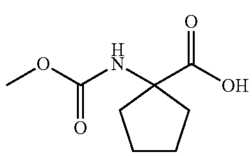 | [Note: the reaction was allowed to run for longer than what was noted for the general procedure.] $^1$H NMR (DMSO-d$_6$, δ = 2.5 ppm, 400 MHz): 12.21 (brs, 1H), 7.42 (br s, 1H), 3.50 (s, 3H), 2.02-1.85 (m, 4H), 1.66-1.58 (m,4H). LC/MS: Anal. Calcd. for [M + H]$^+$ C$_8$H$_{14}$NO$_4$: 188.09; found 188.19. |
| Cap-64: | 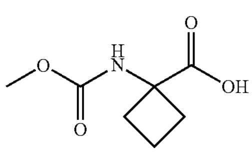 | [Note: the reaction was allowed to run for longer than what was noted for the general procedure.] $^1$H NMR (DMSO-d$_6$, δ = 2.5 ppm, 400 MHz): 12.35 (br s, 1H), 7.77 (s, 0.82H), 7.56/7.52 (overlapping br s, 0.18H), 3.50 (s, 3H), 2.47-2.40 (m, 2H), 2.14-2.07 (m, 2H), 1.93-1.82 (m, 2H). |

Cap-65

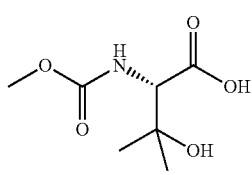

Methyl chloroformate (0.65 mL, 8.39 mmol) was added dropwise over 5 min to a cooled (ice-water) mixture of Na$_2$CO$_3$ (0.449 g, 4.23 mmol), NaOH (8.2 mL of 1M/H$_2$O, 8.2 mmol) and (S)-2-amino-3-hydroxy-3-methylbutanoic acid (1.04 g, 7.81 mmol). The reaction mixture was stirred for 45 min, and then the cooling bath was removed and stirring was continued for an additional 3.75 hr. The reaction mixture was washed with CH$_2$Cl$_2$, and the aqueous phase was cooled with ice-water bath and acidified with concentrated HCl to a pH region of 1-2. The volatile component was removed in vacuo and the residue was taken up in a 2:1 mixture of MeOH/CH$_2$Cl$_2$ (15 mL) and filtered, and the filtrate was rotervaped to afford Cap-65 as a white semi-viscous foam (1.236 g). $^1$H NMR (DMSO-d$_6$, δ=2.5 ppm, 400 MHz): δ 6.94 (d, J=8.5, 0.9H), 6.53 (br s, 0.1H), 3.89 (d, J=8.8, 1H), 2.94 (s, 3H), 1.15 (s, 3H), 1.13 (s, 3H).

Cap-66 and -67 were prepared from appropriate commercially available starting materials by employing the procedure described for the synthesis of Cap-65.

Cap-66

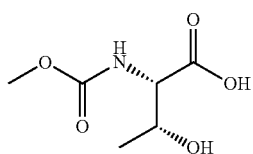

¹H NMR (DMSO-d₆, δ=2.5 ppm, 400 MHz): δ 12.58 (br s, 1H), 7.07 (d, J=8.3, 0.13H), 6.81 (d, J=8.8, 0.67H), 4.10-4.02 (m, 1.15H), 3.91 (dd, J=9.1, 3.5, 0.85H), 3.56 (s, 3H), 1.09 (d, J=6.2, 3H). [Note: only the dominant signals of NH were noted].

Cap-67

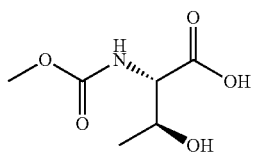

¹H NMR (DMSO-d₆, δ=2.5 ppm, 400 MHz): 12.51 (br s, 1H), 7.25 (d, J=8.4, 0.75H), 7.12 (br d, J=0.4, 0.05H), 6.86 (br s, 0.08H), 3.95-3.85 (m, 2H), 3.54 (s, 3H), 1.08 (d, J=6.3, 3H). [Note: only the dominant signals of NH were noted].

Cap-68

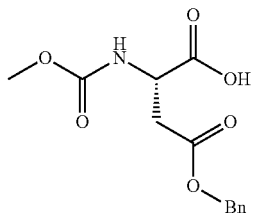 [SMILES: COC(=O)N[C@@H](CC(=O)OCc1ccccc1)C(=O)O]

Methyl chloroformate (0.38 ml, 4.9 mmol) was added drop-wise to a mixture of 1N NaOH (aq) (9.0 ml, 9.0 mmol), 1M NaHCO₃ (aq) (9.0 ml, 9.0 mol), L-aspartic acid β-benzyl ester (1.0 g, 4.5 mmol) and Dioxane (9 ml). The reaction mixture was stirred at ambient conditions for 3 hr, and then washed with Ethyl acetate (50 ml, 3×). The aqueous layer was acidified with 12N HCl to a pH ~1-2, and extracted with ethyl acetate (3×50 ml). The combined organic layers were washed with brine, dried (Na₂SO₄), filtered, and concentrated in vacuo to afford Cap-68 as a light yellow oil (1.37 g; mass is above theoretical yield, and the product was used without further purification). ¹H NMR (DMSO-d₆, δ=2.5 ppm, 500 MHz): δ 12.88 (br s, 1H), 7.55 (d, J=8.5, 1H), 7.40-7.32 (m, 5H), 5.13 (d, J=12.8, 1H), 5.10 (d, J=12.9, 1H), 4.42-4.38 (m, 1H), 3.55 (s, 3H), 2.87 (dd, J=16.2, 5.5, 1H), 2.71 (dd, J=16.2, 8.3, 1H). LC (Cond. 2): RT=1.90 min; LC/MS: Anal. Calcd. For [M+H]⁺ C₁₃H₁₆NO₆: 282.10. found 282.12.

Cap-69a and -69b

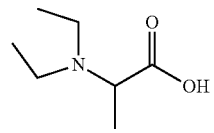

Cap-69a: (R)-enantiomer
Cap-69b: (S)-enantiomer

NaCNBH₃ (2.416 g, 36.5 mmol) was added in batches to a chilled (~15° C.) water (17 mL)/MeOH (10 mL) solution of alanine (1.338 g, 15.0 mmol). A few minutes later acetaldehyde (4.0 mL, 71.3 mmol) was added drop-wise over 4 min, the cooling bath was removed, and the reaction mixture was stirred at ambient condition for 6 hr. An additional acetaldehyde (4.0 mL) was added and the reaction was stirred for 2 hr. Concentrated HCl was added slowly to the reaction mixture until the pH reached ~1.5, and the resulting mixture was heated for 1 hr at 40° C. Most of the volatile component was removed in vacuo and the residue was purified with a Dowex® 50WX8-100 ion-exchange resin (column was washed with water, and the compound was eluted with dilute NH₄OH, prepared by mixing 18 ml of NH₄OH and 282 ml of water) to afford Cap-69 (2.0 g) as an off-white soft hygroscopic solid. ¹H NMR (DMSO-d₆, δ=2.5 ppm, 400 MHz): δ 3.44 (q, J=7.1, 1H), 2.99-2.90 (m, 2H), 2.89-2.80 (m, 2H), 1.23 (d, J=7.1, 3H), 1.13 (t, J=7.3, 6H).

Cap-70 to -74x were prepared according to the procedure described for the synthesis of Cap-69 by employing appropriate starting materials.

| | | |
|---|---|---|
| Cap-70a: (R) Cap-70b: (S) | 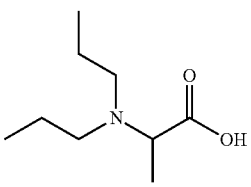 | 1H NMR (DMSO-d₆, δ = 2.5 ppm, 400 MHz): δ 3.42 (q, J = 7.1, 1H), 2.68-2.60 (m, 4H), 1.53-1.44 (m, 4H), 1.19 (d, J = 7.3, 3H), 0.85 (t, J = 7.5, 6H). LC/MS: Anal. Calcd. for [M + H]⁺ C₉H₂₀NO₂: 174.15; found 174.13. |
| Cap-71a: (R) Cap-71b: (S) | 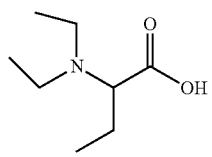 | ¹H NMR (DMSO-d₆, δ = 2.5 ppm, 500 MHz): δ 3.18-3.14 (m, 1H), 2.84-2.77 (m, 2H), 2.76-2.68 (m, 2H), 1.69-1.54 (m, 2H), 1.05 (t, J = 7.2, 6H), 0.91 (t, J = 7.3, 3H). LC/MS: Anal. Calcd. for [M + H]⁺ C₈H₁₈NO₂: 160.13; found 160.06. |

-continued

Cap-72: 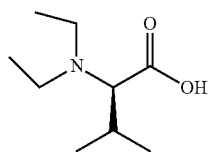

¹H NMR (DMSO-d$_6$, δ = 2.5 ppm, 400 MHz): δ 2.77-2.66 (m, 3H), 2.39-2.31 (m, 2H), 1.94-1.85 (m, 1H), 0.98 (t, J = 7.1, 6H), 0.91 (d, J = 6.5, 3H), 0.85 (d, J = 6.5, 3H). LC/MS: Anal. Calcd. for [M + H]$^+$ C$_9$H$_{20}$NO$_2$: 174.15; found 174.15.

Cap-73: 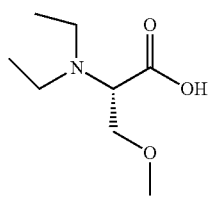

¹H NMR (DMSO-d$_6$, δ = 2.5 ppm, 500 MHz): δ 9.5 (br s, 1H). 3.77 (dd, J = 10.8, 4.1, 1H), 3.69-3.61 (m, 2H), 3.26 (s, 3H), 2.99-2.88 (m, 4H), 1.13 (t, J = 7.2, 6H).

Cap-74: 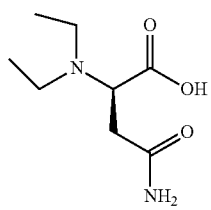

¹H NMR (DMSO-d$_6$, δ = 2.5 ppm, 500 MHz): δ 7.54 (s, 1H), 6.89 (s, 1H), 3.81 (t, J = 6.6, k, 1H), 2.82-2.71 (m, 4H), 2.63 (dd, J = 15.6, 7.0, 1H), 2.36 (dd, J = 15.4,6.3, 1H), 1.09 (t, J = 7.2, 6H). RT = 0.125 minutes (Cond. 2); LC/MS: Anal. Calcd. for [M + H]$^+$ C$_8$H$_{17}$N$_2$O$_3$: 189.12; found 189.13.

Cap-74x: 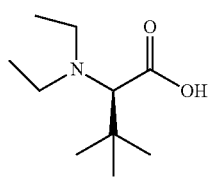

LC/MS: Anal. Calcd. for [M + H]$^+$ C$_{10}$H$_{22}$NO$_2$: 188.17; found 188.21

Cap-75

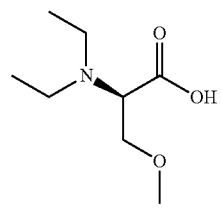

Cap-75, step a

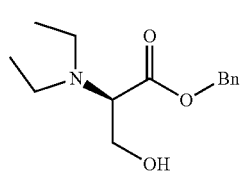 [SMILES: CCN(CC)[C@H](CO)C(=O)OCc1ccccc1]

NaBH$_3$CN (1.6 g, 25.5 mmol) was added to a cooled (ice/water bath) water (25 ml)/methanol (15 ml) solution of H-D-Ser-OBzl HCl (2.0 g, 8.6 mmol). Acetaldehyde (1.5 ml, 12.5 mmol) was added drop-wise over 5 min, the cooling bath was removed, and the reaction mixture was stirred at ambient condition for 2 hr. The reaction was carefully quenched with 12N HCl and concentrated in vacuo. The residue was dissolved in water and purified with a reverse phase HPLC (MeOH/H$_2$O/TFA) to afford the TFA salt of (R)-benzyl 2-(diethylamino)-3-hydroxypropanoate as a colorless viscous oil (1.9 g). ¹H NMR (DMSO-d$_6$, δ=2.5 ppm, 500 MHz): δ 9.73 (br s, 1H), 7.52-7.36 (m, 5H), 5.32 (d, J=12.2, 1H), 5.27 (d, J=12.5, 1H), 4.54-4.32 (m, 1H), 4.05-3.97 (m, 2H), 3.43-3.21 (m, 4H), 1.23 (t, J=7.2, 6H). LC/MS (Cond. 2): RT=1.38 min; LC/MS: Anal. Calcd. for [M+H]$^+$ C$_{14}$H$_{22}$NO$_3$: 252.16. found 252.19.

Cap-75

NaH (0.0727 g, 1.82 mmol, 60%) was added to a cooled (ice-water) THF (3.0 mL) solution of the TFA salt (R)-benzyl 2-(diethylamino)-3-hydroxypropanoate (0.3019 g, 0.8264 mmol) prepared above, and the mixture was stirred for 15 min. Methyl iodide (56 µL, 0.90 mmol) was added and stirring was continued for 18 hr while allowing the bath to thaw to ambient condition. The reaction was quenched with water and loaded onto a MeOH pre-conditioned MCX (6 g) cartridge, and washed with methanol followed by elution with 2N NH$_3$/Methanol. Removal of the volatile component in vacuo afforded Cap-75, contaminated with (R)-2-

(diethylamino)-3-hydroxypropanoic acid, as a yellow semi-solid (100 mg). The product was used as is without further purification.

Cap-76

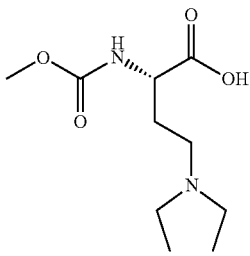 [SMILES: CCN(CC)CC[C@H](NC(=O)OC)C(=O)O]

NaCNBH$_3$ (1.60 g, 24.2 mmol) was added in batches to a chilled (~15° C.) water/MeOH (12 mL each) solution of (S)-4-amino-2-(tert-butoxycarbonylamino) butanoic acid (2.17 g, 9.94 mmol). A few minutes later acetaldehyde (2.7 mL, 48.1 mmol) was added drop-wise over 2 min, the cooling bath was removed, and the reaction mixture was stirred at ambient condition for 3.5 hr. An additional acetaldehyde (2.7 mL, 48.1 mmol) was added and the reaction was stirred for 20.5 hr. Most of the MeOH component was removed in vacuo, and the remaining mixture was treated with concentrated HCl until its pH reached ~1.0 and then heated for 2 hr at 40° C. The volatile component was removed in vacuo, and the residue was treated with 4 M HCl/dioxane (20 mL) and stirred at ambient condition for 7.5 hr. The volatile component was removed in vacuo and the residue was purified with Dowex® 50WX8-100 ion-exchange resin (column was washed with water and the compound was eluted with dilute NH$_4$OH, prepared from 18 ml of NH$_4$OH and 282 ml of water) to afford intermediate (S)-2-amino-4-(diethylamino) butanoic acid as an off-white solid (1.73 g).

Methyl chloroformate (0.36 mL, 4.65 mmol) was added drop-wise over 11 min to a cooled (ice-water) mixture of Na$_2$CO$_3$ (0.243 g, 2.29 mmol), NaOH (4.6 mL of 1M/H$_2$O, 4.6 mmol) and the above product (802.4 mg). The reaction mixture was stirred for 55 min, and then the cooling bath was removed and stirring was continued for an additional 5.25 hr. The reaction mixture was diluted with equal volume of water and washed with CH$_2$Cl$_2$ (30 mL, 2×), and the aqueous phase was cooled with ice-water bath and acidified with concentrated HCl to a pH region of 2. The volatile component was then removed in vacuo and the crude material was free-based with MCX resin (6.0 g; column was washed with water, and sample was eluted with 2.0 M NH$_3$/MeOH) to afford impure Cap-76 as an off-white solid (704 mg). $^1$H NMR (MeOH-d$_4$, δ=3.29 ppm, 400 MHz): δ 3.99 (dd, J=7.5, 4.7, 1H), 3.62 (s, 3H), 3.25-3.06 (m, 6H), 2.18-2.09 (m, 1H), 2.04-1.96 (m, 1H), 1.28 (t, J=7.3, 6H). LC/MS: Anal. Calcd. for [M+H]$^+$ C$_{10}$H$_{21}$N$_2$O$_4$: 233.15. found 233.24.

Cap-77a and -77b

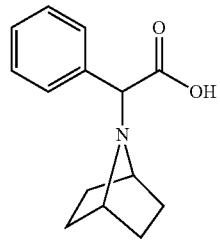

Cap-77a: enantiomer-1
Cap-77b: enantiomer-2

The synthesis of Cap-77 was conducted according to the procedure described for Cap-7 by using 7-azabicyclo[2.2.1] heptane for the SN$_2$ displacement step, and by effecting the enantiomeric separation of the intermediate benzyl 2-(7-azabicyclo[2.2.1]heptan-7-yl)-2-phenylacetate using the following condition: the intermediate (303.7 mg) was dissolved in ethanol, and the resulting solution was injected on a chiral HPLC column (Chiracel AD-H column, 30×250 mm, 5 um) eluting with 90% CO$_2$-10% EtOH at 70 mL/min, and a temperature of 35° C. to provide 124.5 mg of enantiomer-1 and 133.8 mg of enantiomer-2. These benzyl esters were hydrogenolysed according to the preparation of Cap-7 to provide Cap-77: $^1$H NMR (DMSO-d$_6$, δ=2.5 ppm, 400 MHz): δ 7.55 (m, 2H), 7.38-7.30 (m, 3H), 4.16 (s, 1H), 3.54 (app br s, 2H), 2.08-1.88 (m, 4H), 1.57-1.46 (m, 4H). LC (Cond. 1): RT=0.67 min; LC/MS: Anal. Calcd. for [M+H]$^+$ C$_{14}$H$_{18}$NO$_2$: 232.13. found 232.18. HRMS: Anal. Calcd. for [M+H]$^+$ C$_{14}$H$_{18}$NO$_2$: 232.1338. found 232.1340.

Cap-78

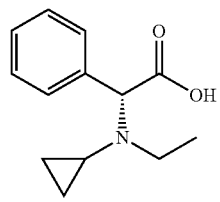 [SMILES: CCN(C1CC1)[C@@H](C(=O)O)c1ccccc1]

NaCNBH$_3$ (0.5828 g, 9.27 mmol) was added to a mixture of the HCl salt of (R)-2-(ethylamino)-2-phenylacetic acid (an intermediate in the synthesis of Cap-3; 0.9923 mg, 4.60 mmol) and (1-ethoxycyclopropoxy)trimethylsilane (1.640 g, 9.40 mmol) in MeOH (10 mL), and the semi-heterogeneous mixture was heated at 50° C. with an oil bath for 20 hr. More (1-ethoxycyclopropoxy)trimethylsilane (150 mg, 0.86 mmol) and NaCNBH$_3$ (52 mg, 0.827 mmol) were added and the reaction mixture was heated for an additional 3.5 hr. It was then allowed to cool to ambient temperature and acidified to a ~pH region of 2 with concentrated HCl, and the mixture was filtered and the filtrate was rotervaped. The resulting crude material was taken up in i-PrOH (6 mL) and heated to effect dissolution, and the non-dissolved part was filtered off and the filtrate concentrated in vacuo. About ⅓ of the resultant crude material was purified with a reverse phase HPLC(H$_2$O/MeOH/TFA) to afford the TFA salt of Cap-78 as a colorless viscous oil (353 mg). $^1$H NMR (DMSO-d$_6$, δ=2.5 ppm, 400 MHz; after D$_2$O exchange): δ 7.56-7.49 (m, 5H), 5.35 (S, 1H), 3.35 (m, 1H), 3.06 (app br s, 1H), 2.66 (m, 1H), 1.26 (t, J=7.3, 3H), 0.92 (m, 1H), 0.83-0.44 (m, 3H). LC (Cond. 1): RT=0.64 min; LC/MS: Anal. Calcd. for [M+H]$^+$ C$_{13}$H$_{18}$NO$_2$: 220.13. found 220.21. HRMS: Anal. Calcd. for [M+H]$^+$ C$_{13}$H$_{18}$NO$_2$: 220.1338. found 220.1343.

Cap-79

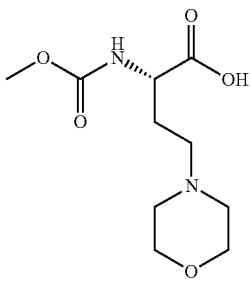 [SMILES: COC(=O)N[C@@H](CCN1CCOCC1)C(=O)O]

Ozone was bubbled through a cooled (–78° C.) CH$_2$Cl$_2$ (5.0 mL) solution Cap-55 (369 mg, 2.13 mmol) for about 50 min until the reaction mixture attained a tint of blue color. Me$_2$S (10 pipet drops) was added, and the reaction mixture was stirred for 35 min. The –78° C. bath was replaced with a –10° C. bath and stirring continued for an additional 30 min, and then the volatile component was removed in vacuo to afford a colorless viscous oil.

NaBH$_3$CN (149 mg, 2.25 mmol) was added to a MeOH (5.0 mL) solution of the above crude material and morpholine (500 µL, 5.72 mmol) and the mixture was stirred at ambient condition for 4 hr. It was cooled to ice-water temperature and treated with concentrated HCl to bring its pH to ~2.0, and then stirred for 2.5 hr. The volatile component was removed in vacuo, and the residue was purified with a combination of MCX resin (MeOH wash; 2.0 N NH$_3$/MeOH elution) and a reverse phase HPLC(H$_2$O/MeOH/TFA) to afford Cap-79 containing unknown amount of morpholine.

In order to consume the morpholine contaminant, the above material was dissolved in CH$_2$Cl$_2$ (1.5 mL) and treated with Et$_3$N (0.27 mL, 1.94 mmol) followed by acetic anhydride (0.10 mL, 1.06 mmol) and stirred at ambient condition for 18 hr. THF (1.0 mL) and H$_2$O (0.5 mL) were added and stirring continued for 1.5 hr. The volatile component was removed in vacuo, and the resultant residue was passed through MCX resin (MeOH wash; 2.0 N NH$_3$/MeOH elution) to afford impure Cap-79 as a brown viscous oil, which was used for the next step without further purification.

Cap-80a and -80b

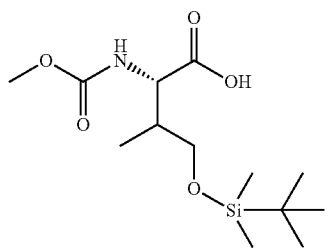

Cap-80a: S/S-diastereomer
Cap-80b: S/R-diastereomer

SOCl$_2$ (6.60 mL, 90.5 mmol) was added drop-wise over 15 min to a cooled (ice-water) mixture of (S)-3-amino-4-(benzyloxy)-4-oxobutanoic acid (10.04 g, 44.98 mmol) and MeOH (300 mL), the cooling bath was removed and the reaction mixture was stirred at ambient condition for 29 hr. Most of the volatile component was removed in vacuo and the residue was carefully partitioned between EtOAc (150 mL) and saturated NaHCO$_3$ solution. The aqueous phase was extracted with EtOAc (150 mL, 2×), and the combined organic phase was dried (MgSO$_4$), filtered, and concentrated in vacuo to afford (S)-1-benzyl 4-methyl 2-aminosuccinate as a colorless oil (9.706 g). $^1$H NMR (DMSO-d$_6$, δ=2.5 ppm, 400 MHz): δ 7.40-7.32 (m, 5H), 5.11 (s, 2H), 3.72 (app t, J=6.6, 1H), 3.55 (s, 3H), 2.68 (dd, J=15.9, 6.3, 1H), 2.58 (dd, J=15.9, 6.8, 1H), 1.96 (s, 2H). LC (Cond. 1): RT=0.90 min; LC/MS: Anal. Calcd. for [M+H]$^+$ C$_{12}$H$_{16}$NO$_4$: 238.11. found 238.22.

Pb(NO$_3$)$_2$ (6.06 g, 18.3 mmol) was added over 1 min to a CH$_2$Cl$_2$ (80 mL) solution of (S)-1-benzyl 4-methyl 2-aminosuccinate (4.50 g, 19.0 mmol), 9-bromo-9-phenyl-9H-fluorene (6.44 g, 20.0 mmol) and Et$_3$N (3.0 mL, 21.5 mmol), and the heterogeneous mixture was stirred at ambient condition for 48 hr. The mixture was filtered and the filtrate was treated with MgSO$_4$ and filtered again, and the final filtrate was concentrated. The resulting crude material was submitted to a Biotage purification (350 g silica gel, CH$_2$Cl$_2$ elution) to afford (S)-1-benzyl 4-methyl 2-(9-phenyl-9H-fluoren-9-ylamino)succinate as highly viscous colorless oil (7.93 g). $^1$H NMR (DMSO-d$_6$, δ=2.5 ppm, 400 MHz): δ 7.82 (m, 2H), 7.39-7.13 (m, 16H), 4.71 (d, J=12.4, 1H), 4.51 (d, J=12.6, 1H), 3.78 (d, J=9.1, NH), 3.50 (s, 3H), 2.99 (m, 1H), 2.50-2.41 (m, 2H, partially overlapped with solvent). LC (Cond. 1): RT=2.16 min; LC/MS: Anal. Calcd. for [M+H]$^+$ C$_{31}$H$_{28}$NO$_4$: 478.20. found 478.19.

LiHMDS (9.2 mL of 1.0 M/THF, 9.2 mmol) was added drop-wise over 10 min to a cooled (–78° C.) THF (50 mL) solution of (S)-1-benzyl 4-methyl 2-(9-phenyl-9H-fluoren-9-ylamino)succinate (3.907 g, 8.18 mmol) and stirred for ~1 hr. MeI (0.57 mL, 9.2 mmol) was added drop-wise over 8 min to the mixture, and stirring was continued for 16.5 hr while allowing the cooling bath to thaw to room temperature. After quenching with saturated NH$_4$Cl solution (5 mL), most of the organic component was removed in vacuo and the residue was partitioned between CH$_2$Cl$_2$ (100 mL) and water (40 mL). The organic layer was dried (MgSO$_4$), filtered, and concentrated in vacuo, and the resulting crude material was purified with a Biotage (350 g silica gel; 25% EtOAc/hexanes) to afford 3.65 g of a 2S/3S and 2S/3R diastereomeric mixtures of 1-benzyl 4-methyl 3-methyl-2-(9-phenyl-9H-fluoren-9-ylamino)succinate in ~1.0:0.65 ratio ($^1$H NMR). The stereochemistry of the dominant isomer was not determined at this juncture, and the mixture was submitted to the next step without separation. Partial $^1$H NMR data (DMSO-$d_6$, δ=2.5 ppm, 400 MHz): major diastereomer, δ 4.39 (d, J=12.3, 1H of $CH_2$), 3.33 (s, 3H, overlapped with $H_2O$ signal), 3.50 (d, J=10.9, NH), 1.13 (d, J=7.1, 3H); minor diastereomer, δ 4.27 (d, J=12.3, 1H of $CH_2$), 3.76 (d, J=10.9, NH), 3.64 (s, 3H), 0.77 (d, J=7.0, 3H). LC (Cond. 1): RT=2.19 min; LC/MS: Anal. Calcd. for [M+H]$^+$ $C_{32}H_{30}NO_4$: 492.22. found 492.15.

Diisobutylaluminum hydride (20.57 ml of 1.0 M in hexanes, 20.57 mmol) was added drop-wise over 10 min to a cooled (−78° C.) THF (120 mL) solution of (2S)-1-benzyl 4-methyl 3-methyl-2-(9-phenyl-9H-fluoren-9-ylamino)succinate (3.37 g, 6.86 mmol) prepared above, and stirred at −78° C. for 20 hr. The reaction mixture was removed from the cooling bath and rapidly poured into ~1M $H_3PO_4/H_2O$ (250 mL) with stirring, and the mixture was extracted with ether (100 mL, 2×). The combined organic phase was washed with brine, dried ($MgSO_4$), filtered and concentrated in vacuo. A silica gel mesh of the crude material was prepared and submitted to chromatography (25% EtOAc/hexanes; gravity elution) to afford 1.1 g of (2S,3S)-benzyl 4-hydroxy-3-methyl-2-(9-phenyl-9H-fluoren-9-ylamino)butanoate, contaminated with benzyl alcohol, as a colorless viscous oil and (2S,3R)-benzyl 4-hydroxy-3-methyl-2-(9-phenyl-9H-fluoren-9-ylamino)butanoate containing the (2S,3R) stereoisomer as an impurity. The later sample was resubmitted to the same column chromatography purification conditions to afford 750 mg of purified material as a white foam. [Note: the (2S,3S) isomer elutes before the (2S,3R) isomer under the above condition]. (2S,3S) isomer: $^1$H NMR (DMSO-$d_6$, δ=2.5 ppm, 400 MHz): 7.81 (m, 2H), 7.39-7.08 (m, 16H), 4.67 (d, J=12.3, 1H), 4.43 (d, J=12.4, 1H), 4.21 (app t, J=5.2, OH), 3.22 (d, J=10.1, NH), 3.17 (m, 1H), 3.08 (m, 1H), ~2.5 (m, 1H, overlapped with the solvent signal), 1.58 (m, 1H), 0.88 (d, J=6.8, 3H). LC (Cond. 1): RT=2.00 min; LC/MS: Anal. Calcd. for [M+H]$^+$ $C_{31}H_{30}NO_3$: 464.45. found 464.22. (2S,3R) isomer: $^1$H NMR (DMSO-$d_6$, δ=2.5 ppm, 400 MHz): 7.81 (d, J=7.5, 2H), 7.39-7.10 (m, 16H), 4.63 (d, J=12.1, 1H), 4.50 (app t, J=4.9, 1H), 4.32 (d, J=12.1, 1H), 3.59-3.53 (m, 2H), 3.23 (m, 1H), 2.44 (dd, J=9.0, 8.3, 1H), 1.70 (m, 1H), 0.57 (d, J=6.8, 3H). LC (Cond. 1): RT=1.92 min; LC/MS: Anal. Calcd. for [M+H]$^+$ $C_{31}H_{30}NO_3$: 464.45. found 464.52.

The relative stereochemical assignments of the DIBAL-reduction products were made based on NOE studies conducted on lactone derivatives prepared from each isomer by employing the following protocol: LiHMDS (50 µL of 1.0 M/THF, 0.05 mmol) was added to a cooled (ice-water) THF (2.0 mL) solution of (2S,3S)-benzyl 4-hydroxy-3-methyl-2-(9-phenyl-9H-fluoren-9-ylamino)butanoate (62.7 mg, 0.135 mmol), and the reaction mixture was stirred at similar temperature for ~2 hr. The volatile component was removed in vacuo and the residue was partitioned between $CH_2Cl_2$ (30 mL), water (20 mL) and saturated aqueous $NH_4Cl$ solution (1 mL). The organic layer was dried ($MgSO_4$), filtered, and concentrated in vacuo, and the resulting crude material was submitted to a Biotage purification (40 g silica gel; 10-15% EtOAc/hexanes) to afford (3S,4S)-4-methyl-3-(9-phenyl-9H-fluoren-9-ylamino)dihydrofuran-2(3H)-one as a colorless film of solid (28.1 mg). (2S,3R)-benzyl 4-hydroxy-3-methyl-2-(9-phenyl-9H-fluoren-9-ylamino)butanoate was elaborated similarly to (3S,4R)-4-methyl-3-(9-phenyl-9H-fluoren-9-ylamino)dihydrofuran-2(3H)-one. (3S,4S)-lactone isomer: $^1$H NMR (DMSO-$d_6$, δ=2.5 ppm, 400 MHz), 7.83 (d, J=7.5, 2H), 7.46-7.17 (m, 11H), 4.14 (app t, J=8.3, 1H), 3.60 (d, J=5.8, NH), 3.45 (app t, J=9.2, 1H), ~2.47 (m, 1H, partially overlapped with solvent signal), 2.16 (m, 1H), 0.27 (d, J=6.6, 3H). LC (Cond. 1): RT=1.98 min; LC/MS: Anal. Calcd. for [M+Na]$^+$ $C_{24}H_{21}NNaO_2$: 378.15. found 378.42. (3S,4R)-lactone isomer: $^1$H NMR (DMSO-$d_6$, δ=2.5 ppm, 400 MHz), 7.89 (d, J=7.6, 1H), 7.85 (d, J=7.3, 1H), 7.46-7.20 (m, 11H), 3.95 (dd, J=9.1, 4.8, 1H), 3.76 (d, J=8.8, 1H), 2.96 (d, J=3.0, NH), 2.92 (dd, J=6.8, 3, NCH), 1.55 (m, 1H), 0.97 (d, J=7.0, 3H). LC (Cond. 1): RT=2.03 min; LC/MS: Anal. Calcd. for [M+Na]$^+$ $C_{24}H_{21}NNaO_2$: 378.15. found 378.49.

TBDMS-Cl (48 mg, 0.312 mmol) followed by imidazole (28.8 mg, 0.423 mmol) were added to a $CH_2Cl_2$ (3 ml) solution of (2S,3S)-benzyl 4-hydroxy-3-methyl-2-(9-phenyl-9H-fluoren-9-ylamino)butanoate (119.5 mg, 0.258 mmol), and the mixture was stirred at ambient condition for 14.25 hr. The reaction mixture was then diluted with $CH_2Cl_2$ (30 mL) and washed with water (15 mL), and the organic layer was dried ($MgSO_4$), filtered, and concentrated in vacuo. The resultant crude material was purified with a Biotage (40 g silica gel; 5% EtOAc/hexanes) to afford (2S,3S)-benzyl 4-(tert-butyldimethylsilyloxy)-3-methyl-2-(9-phenyl-9H-fluoren-9-ylamino)butanoate, contaminated with TBDMS based impurities, as a colorless viscous oil (124.4 mg). (2S,3R)-benzyl 4-hydroxy-3-methyl-2-(9-phenyl-9H-fluoren-9-ylamino)butanoate was elaborated similarly to (2S,3R)-benzyl 4-(tert-butyldimethylsilyloxy)-3-methyl-2-(9-phenyl-9H-fluoren-9-ylamino)butanoate. (2S,3S)-silyl ether isomer: $^1$H NMR (DMSO-$d_6$, δ=2.5 ppm, 400 MHz), 7.82 (d, J=4.1, 1H), 7.80 (d, J=4.0, 1H), 7.38-7.07 (m, 16H), 4.70 (d, J=12.4, 1H), 4.42 (d, J=12.3, 1H), 3.28-3.19 (m, 3H), 2.56 (dd, J=10.1, 5.5, 1H), 1.61 (m, 1H), 0.90 (d, J=6.8, 3H), 0.70 (s, 9H), −0.13 (s, 3H), −0.16 (s, 3H). LC (Cond. 1, where the run time was extended to 4 min): RT=3.26 min; LC/MS: Anal. Calcd. for [M+H]$^+$ $C_{37}H_{44}NO_3Si$: 578.31. found 578.40. (2S,3R)-silyl ether isomer: $^1$H NMR (DMSO-$d_6$, δ=2.5 ppm, 400 MHz), 7.82 (d, J=3.0, 1H), 7.80 (d, J=3.1, 1H), 7.39-7.10 (m, 16H), 4.66 (d, J=12.4, 1H), 4.39 (d, J=12.4, 1H), 3.61 (dd, J=9.9, 5.6, 1H), 3.45 (d, J=9.5, 1H), 3.41 (dd, J=10, 6.2, 1H), 2.55 (dd, J=9.5, 7.3, 1H), 1.74 (m, 1H), 0.77 (s, 9H), 0.61 (d, J=7.1, 3H), −0.06 (s, 3H), −0.08 (s, 3H).

A balloon of hydrogen was attached to a mixture of (2S, 3S)-benzyl 4-(tert-butyldimethylsilyloxy)-3-methyl-2-(9-phenyl-9H-fluoren-9-ylamino)butanoate (836 mg, 1.447 mmol) and 10% Pd/C (213 mg) in EtOAc (16 mL) and the mixture was stirred at room temperature for ~21 hr, where the balloon was recharged with $H_2$ as necessary. The reaction mixture was diluted with $CH_2Cl_2$ and filtered through a pad of diatomaceous earth (Celite-545®), and the pad was washed with EtOAc (200 mL), EtOAc/MeOH (1:1 mixture, 200 mL) and MeOH (750 mL). The combined organic phase was concentrated, and a silica gel mesh was prepared from the resulting crude material and submitted to a flash chromatography (8:2:1 mixture of EtOAc/i-PrOH/$H_2O$) to afford (2S,3S)-2-amino-4-(tert-butyldimethylsilyloxy)-3-methylbutanoic acid as a white fluffy solid (325 mg). (2S,3R)-benzyl 4-(tert-butyldimethylsilyloxy)-3-methyl-2-(9-phenyl-9H-fluoren-9-ylamino)butanoate was similarly elaborated to (2S,3R)-2-amino-4-(tert-butyldimethylsilyloxy)-3-methylbutanoic acid. (2S,3S)-amino acid isomer: $^1$H NMR (Methanol-$d_4$, δ=3.29 ppm, 400 MHz), 3.76 (dd, J=10.5, 5.2, 1H), 3.73 (d, J=3.0, 1H), 3.67 (dd, J=10.5, 7.0, 1H), 2.37 (m, 1H), 0.97 (d, J=7.0, 3H), 0.92 (s, 9H), 0.10 (s, 6H). LC/MS: Anal. Calcd. for [M+H]$^+$ $C_{11}H_{26}NO_3Si$: 248.17. found 248.44. (2S,3R)-amino acid isomer: $^1$H NMR (Methanol-$d_4$, δ=3.29 ppm, 400 MHz), 3.76-3.75 (m, 2H), 3.60 (d, J=4.1, 1H), 2.16 (m, 1H), 1.06 (d, J=7.3, 3H), 0.91 (s, 9H), 0.09 (s, 6H). Anal. Calcd. for [M+H]⁺ $C_{11}H_{26}NO_3Si$: 248.17. found 248.44.

Water (1 mL) and NaOH (0.18 mL of 1.0 M/H₂O, 0.18 mmol) were added to a mixture of (2S,3S)-2-amino-4-(tert-butyldimethylsilyloxy)-3-methylbutanoic acid (41.9 mg, 0.169 mmol) and Na₂CO₃ (11.9 mg, 0.112 mmol), and sonicated for about 1 min to effect dissolution of reactants. The mixture was then cooled with an ice-water bath, methyl chloroformate (0.02 mL, 0.259 mmol) was added over 30 s, and vigorous stirring was continued at similar temperature for 40 min and then at ambient temperature for 2.7 hr. The reaction mixture was diluted with water (5 mL), cooled with ice-water bath and treated drop-wise with 1.0 N HCl aqueous solution (~0.23 mL). The mixture was further diluted with water (10 mL) and extracted with CH₂Cl₂ (15 mL, 2×). The combined organic phase was dried (MgSO₄), filtered, and concentrated in vacuo to afford Cap-80a as an off-white solid. (2S,3R)-2-amino-4-(tert-butyldimethylsilyloxy)-3-methylbutanoic acid was similarly elaborated to Cap-80b. Cap-80a: ¹H NMR (DMSO-d₆, δ=2.5 ppm, 400 MHz), 12.57 (br s, 1H), 7.64 (d, J=8.3, 0.3H), 7.19 (d, J=8.8, 0.7H), 4.44 (dd, J=8.1, 4.6, 0.3H), 4.23 (dd, J=8.7, 4.4, 0.7H), 3.56/3.53 (two singlets, 3H), 3.48-3.40 (m, 2H), 2.22-2.10 (m, 1H), 0.85 (s, 9H), ~0.84 (d, 0.9H, overlapped with t-Bu signal), 0.79 (d, J=7, 2.1H), 0.02/0.01/0.00 (three overlapping singlets, 6H). LC/MS: Anal. Calcd. for [M+Na]⁺ $C_{13}H_{27}NNaO_5Si$: 328.16. found 328.46. Cap-80b: ¹H NMR (CDCl₃, δ=7.24 ppm, 400 MHz), 6.00 (br d, J=6.8, 1H), 4.36 (dd, J=7.1, 3.1, 1H), 3.87 (dd, J=10.5, 3.0, 1H), 3.67 (s, 3H), 3.58 (dd, J=10.6, 4.8, 1H), 2.35 (m, 1H), 1.03 (d, J=7.1, 3H), 0.90 (s, 9H), 0.08 (s, 6H). LC/MS: Anal. Calcd. for [M+Na]⁺ $C_{13}H_{27}NNaO_5Si$: 328.16. found 328.53. The crude products were utilized without further purification.

Cap-81

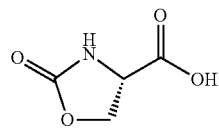

Prepared according to the protocol described by Falb et al. *Synthetic Communications* 1993, 23, 2839.

Cap-82 to Cap-85

Cap-82 to Cap-85 were synthesized from appropriate starting materials according to the procedure described for Cap-51 or Cap-13. The samples exhibited similar spectral profiles as that of their enantiomers (i.e., Cap-4, Cap-13, Cap-51 and Cap-52, respectively).

Cap-82

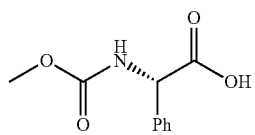

Cap-83

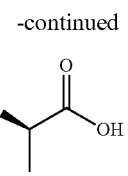

Cap-84

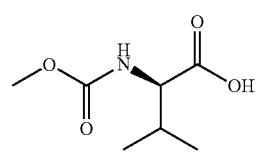

Cap-85

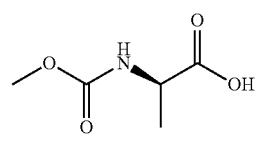

Cap-86

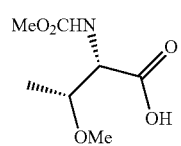

To a mixture of O-methyl-L-threonine (3.0 g, 22.55 mmol), NaOH (0.902 g, 22.55 mmol) in H₂O (15 mL) was added ClCO₂Me (1.74 mL, 22.55 mmol) dropwise at 0° C. The mixture was allowed to stir for 12 h and acidified to pH 1 using 1N HCl. The aqueous phase was extracted with EtOAc and (2×250 mL) and 10% MeOH in CH₂Cl₂ (250 mL) and the combined organic phases were concentrated under in vacuo to afford a colorless oil (4.18 g, 97%) which was of sufficient purity for use in subsequent steps. ¹HNMR (400 MHz, CDCl₃) δ 4.19 (s, 1H), 3.92-3.97 (m, 1H), 3.66 (s, 3H), 1.17 (d, J=7.7 Hz, 3H). LCMS: Anal. Calcd. for $C_7H_{13}NO_5$: 191. found: 190 (M−H)⁻.

Cap-87

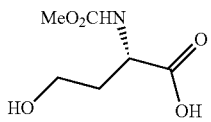

To a mixture of L-homoserine (2.0 g, 9.79 mmol), Na₂CO₃ (2.08 g, 19.59 mmol) in H₂O (15 mL) was added ClCO₂Me (0.76 mL, 9.79 mmol) dropwise at 0° C. The mixture was allowed to stir for 48 h and acidified to pH 1 using 1N HCl. The aqueous phase was extracted with EtOAc and (2×250 mL) and the combined organic phases were concentrated in vacuo to afford a colorless solid (0.719 g, 28%) which was of sufficient purity for use in subsequent steps. ¹HNMR (400 MHz, CDCl₃) δ 4.23 (dd, J=4.5, 9.1 Hz, 1H), 3.66 (s, 3H), 3.43-3.49 (m, 2H), 2.08-2.14 (m, 1H), 1.82-1.89 (m, 1H). LCMS: Anal. Calcd. for C$_7$H$_{13}$NO$_5$: 191. found: 192 (M+H)$^+$.

Cap-88

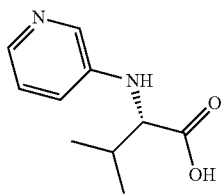

A mixture of L-valine (1.0 g, 8.54 mmol), 3-bromopyridine (1.8 mL, 18.7 mmol), K$_2$CO$_3$ (2.45 g, 17.7 mmol) and CuI (169 mg, 0.887 mmol) in DMSO (10 mL) was heated at 100° C. for 12 h. The reaction mixture was cooled to rt, poured into H$_2$O (ca. 150 mL) and washed with EtOAc (×2). The organic layers were extracted with a small amount of H$_2$O and the combined aq phases were acidified to ca. pH 2 with 6N HCl. The volume was reduced to about one-third and 20 g of cation exchange resin (Strata) was added. The slurry was allowed to stand for 20 min and loaded onto a pad of cation exchange resin (Strata) (ca. 25 g). The pad was washed with H$_2$O (200 mL), MeOH (200 mL), and then NH$_3$ (3M in MeOH, 2×200 mL). The appropriate fractions was concentrated in vacuo and the residue (ca. 1.1 g) was dissolved in H$_2$O, frozen and lyophyllized. The title compound was obtained as a foam (1.02 g, 62%). $^1$HNMR (400 MHz, DMSO-d$_6$) δ 8.00 (s, br, 1H), 7.68-7.71 (m, 1H), 7.01 (s, br, 1H), 6.88 (d, J=7.5 Hz, 1H), 5.75 (s, br, 1H), 3.54 (s, 1H), 2.04-2.06 (m, 1H), 0.95 (d, J=6.0 Hz, 3H), 0.91 (d, J=6.6 Hz, 3H). LCMS: Anal. Calcd. for C$_{10}$H$_{14}$N$_2$O$_2$: 194. found: 195 (M+H)$^+$.

Cap-89

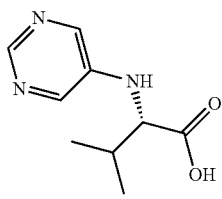

A mixture of L-valine (1.0 g, 8.54 mmol), 5-bromopyrimidine (4.03 g, 17.0 mmol), K$_2$CO$_3$ (2.40 g, 17.4 mmol) and CuI (179 mg, 0.94 mmol) in DMSO (10 mL) was heated at 100° C. for 12 h. The reaction mixture was cooled to RT, poured into H$_2$O (ca. 150 mL) and washed with EtOAc (×2). The organic layers were extracted with a small amount of H$_2$O and the combined aq phases were acidified to ca. pH 2 with 6N HCl. The volume was reduced to about one-third and 20 g of cation exchange resin (Strata) was added. The slurry was allowed to stand for 20 min and loaded onto a pad of cation exchange resin (Strata) (ca. 25 g). The pad was washed with H$_2$O (200 mL), MeOH (200 mL), and then NH$_3$ (3M in MeOH, 2×200 mL). The appropriate fractions was concentrated in vacuo and the residue (ca. 1.1 g) was dissolved in H$_2$O, frozen and lyophyllized. The title compound was obtained as a foam (1.02 g, 62%). $^1$HNMR (400 MHz, CD$_3$OD) showed the mixture to contain valine and the purity could not be estimated. The material was used as is in subsequent reactions. LCMS: Anal. Calcd. for C$_9$H$_{13}$N$_3$O$_2$: 195. found: 196 (M+H)$^+$.

Cap-90

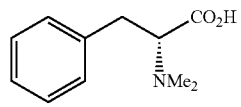 [SMILES: CN(C)[C@H](Cc1ccccc1)C(=O)O]

Cap-90 was prepared according to the method described for the preparation of Cap-1. The crude material was used as is in subsequent steps. LCMS: Anal. Calcd. for C$_{11}$H$_{15}$NO$_2$: 193. found: 192 (M−H)$^−$.

The following caps were prepared according to the method used for preparation of cap 51 unless noted otherwise:

| Cap | Structure | LCMS |
| --- | --- | --- |
| Cap-91 | NHCO$_2$Me ... CO$_2$H | LCMS: Anal. Calcd. for C$_{11}$H$_{13}$NO$_4$: 223; found: 222 (M − H)$^−$. |
| Cap-92 | NHCO$_2$Me ... CO$_2$H | LCMS: Anal. Calcd. for C$_{11}$H$_{13}$NO$_4$: 223; found: 222 (M − H)$^−$. |

-continued

| Cap | Structure | LCMS |
|---|---|---|
| Cap-93 | 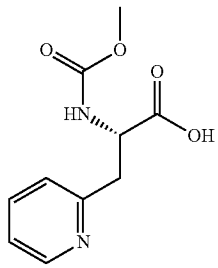 [SMILES: COC(=O)N[C@@H](Cc1ccccn1)C(=O)O] | LCMS: Anal. Calcd. for $C_{10}H_{12}N_2O_4$: 224; found: 225 $(M + H)^+$. |
| Cap-94 | 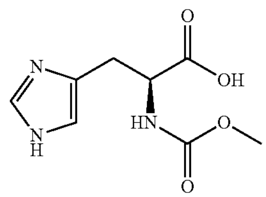 | LCMS: Anal. Calcd. for $C_8H_{11}N_3O_4$: 224; found: 214 $(M + H)^+$. |
| Cap-95 | 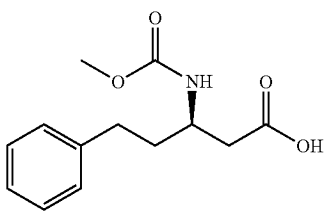 [SMILES: COC(=O)N[C@H](CCc1ccccc1)CC(=O)O] | LCMS: Anal. Calcd. for $C_{13}H_{17}NO_4$: 251; found: 250 $(M - H)^-$. |
| Cap-96 | 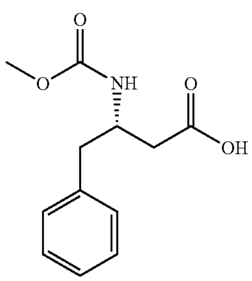 [SMILES: COC(=O)N[C@H](CC(=O)O)Cc1ccccc1] | LCMS: Anal. Calcd. for $C_{12}H_{15}NO_4$: 237; found: 236 $(M - H)^-$. |
| Cap-97 | 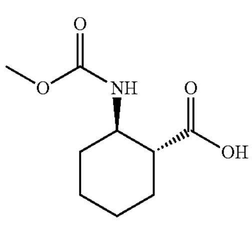 | LCMS: Anal. Calcd. for $C_9H_{15}NO_4$: 201; found: 200 $(M - H)^-$. |
| Cap-98 | 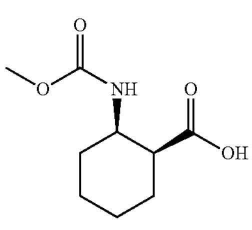 | LCMS: Anal. Calcd. for $C_9H_{15}NO_4$: 201; found: 202 $(M + H)^+$. |

-continued

| Cap | Structure | LCMS |
|---|---|---|
| Cap-99 | (methyl carbamate on cyclopentane with CO2H, stereochemistry shown) | ¹HNMR (400 MHz, CD₃OD) δ 3.88-3.94 (m, 1H), 3.60, 3.61 (s, 3H), 2.80 (m, 1H), 2.20 (m 1H), 1.82-1.94 (m, 3H), 1.45-1.71 (m, 2H). |
| Cap-99a | (methyl carbamate on cyclopentane with CO2H, opposite stereochemistry) | ¹HNMR (400 MHz, CD₃OD) δ 3.88-3.94 (m, 1H), 3.60, 3.61 (s, 3H), 2.80 (m, 1H), 2.20 (m 1H), 1.82-1.94 (m, 3H), 1.45-1.71 (m, 2H). |
| Cap-100 | (methyl carbamate derivative with 2-fluorobenzyl and CO2H) | LCMS: Anal. Calcd. for $C_{12}H_{14}NO_4F$: 255; found: 256 $(M + H)^+$. |
| Cap-101 | (N-methoxycarbonyl phenylalanine) | LCMS: Anal. Calcd. for $C_{11}H_{13}NO_4$: 223; found: 222 $(M - H)^-$. |
| Cap-102 | (N-methoxycarbonyl phenylalanine, opposite stereochemistry) | LCMS: Anal. Calcd. for C11H13NO4: 223; found: 222 $(M - H)^-$ |

-continued

| Cap | Structure | LCMS |
|---|---|---|
| Cap-103 | (structure) | LCMS: Anal. Calcd. for $C_{10}H_{12}N_2O_4$: 224; found: 225 $(M + H)^+$. |
| Cap-104 | (structure) | $^1$HNMR (400 MHz, CD$_3$OD) δ 3.60 (s, 3H), 3.50-3.53 (m, 1H), 2.66-2.69 and 2.44-2.49 (m, 1H), 1.91-2.01 (m, 2H), 1.62-1.74 (m, 4H), 1.51-1.62 (m, 2H). |
| Cap-105 | (structure) | $^1$HNMR (400 MHz, CD$_3$OD) δ 3.60 (s, 3H), 3.33-3.35 (m, 1H, partially obscured by solvent), 2.37-2.41 and 2.16-2.23 (m, 1H), 1.94-2.01 (m, 4H), 1.43-1.53 (m, 2H), 1.17-1.29 (m, 2H). |
| Cap-106 | (structure) Prepared from cis-4-aminocyclohexane carboxylic acid and acetaldehyde by employing a similar procedure described for the synthesis of Cap-2. The crude HCl salt was passed through MCX (MeOH/H$_2$O/CH$_2$Cl$_2$ wash; 2 N NH$_3$/MeOH elution) to afford an oil which was dissolved in CH$_3$CN/H$_2$O and lyophilized to afford a tan solid. | 1HNMR (400 MHz, CD$_3$OD) δ 3.16 (q, J = 7.3 Hz, 4H), 2.38-2.41 (m, 1H), 2.28-2.31 (m, 2H), 1.79-1.89 (m, 2H), 1.74 (app. ddd 7 = 3.5, 12.5, 15.9 Hz, 2H), 1.46 (app dt J = 4.0, 12.9 Hz, 2H), 1.26 (t, J = 7.3 Hz, 6H) |
| Cap-107 | (structure) | LCMS: Anal. Calcd. for $C_8H_{10}N_2O_4S$: 230; found: 231 $(M + H)^+$. |
| Cap-108 | (structure) | LCMS: Anal. Calcd. for $C_{15}H_{17}N_3O_4$: 303; found: 304 $(M + H)^+$. |

-continued

| Cap | Structure | LCMS |
|---|---|---|
| Cap-109 | 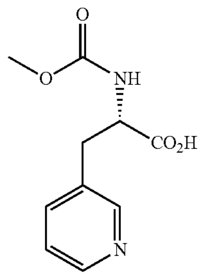 [SMILES: COC(=O)N[C@@H](Cc1cccnc1)C(=O)O] | LCMS: Anal. Calcd. for $C_{10}H_{12}N_2O_4$: 224; found: 225 (M + H)$^+$. |
| Cap-110 | 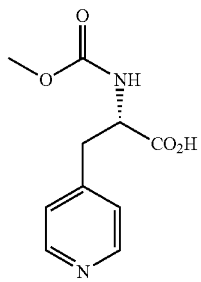 [SMILES: COC(=O)N[C@@H](Cc1ccncc1)C(=O)O] | LCMS: Anal. Calcd. for $C_{10}H_{12}N_2O_4$: 224; found: 225 (M + H)$^+$. |
| Cap-111 | 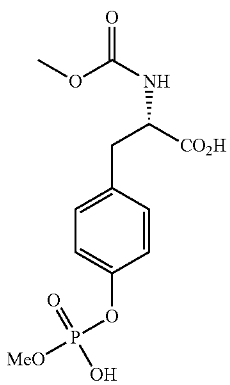 [SMILES: COC(=O)N[C@@H](Cc1ccc(OP(=O)(O)OC)cc1)C(=O)O] | LCMS: Anal. Calcd. for $C_{12}H_{16}NO_8P$: 333; found: 334 (M + H)$^+$. |
| Cap-112 | 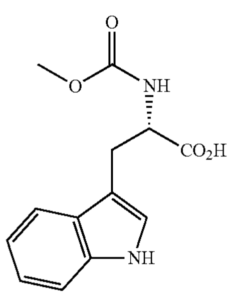 [SMILES: COC(=O)N[C@@H](Cc1c[nH]c2ccccc12)C(=O)O] | LCMS: Anal. Calcd. for $C_{13}H_{14}N_2O_4$: 262; found: 263 (M + H)$^+$. |
| Cap-113 | 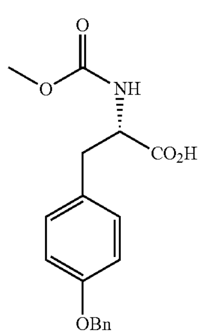 [SMILES: COC(=O)N[C@@H](Cc1ccc(OCc2ccccc2)cc1)C(=O)O] | LCMS: Anal. Calcd. for $C_{18}H_{19}NO_5$: 329; found: 330 (M + H)$^+$. |

| Cap | Structure | LCMS |
|---|---|---|
| Cap-114 | [structure: azetidine with CO₂Me on N and CO₂H substituent] | ¹HNMR (400 MHz, CDC13) δ 4.82-4.84 (m, 1H), 4.00-4.05 (m, 2H), 3.77 (s, 3H), 2.56 (s, br, 2H) |
| Cap-115 | [structure: CH₃-CH(NHCO₂Me)-CH₂-CO₂H] | ¹HNMR (400 MHz, CDCl₃) δ 5.13 (s, br, 1H), 4.13 (s, br, 1H), 3.69 (s, 3H), 2.61 (d, J = 5.0 Hz, 2H), 1.28 (d, J = 9.1 Hz, 3H). |
| Cap-116 | [structure: isopropyl-CH(NHCO₂Me)-CH₂-CO₂H] | ¹HNMR (400 MHz, CDCl₃) δ 5.10 (d, J = 8.6 Hz, 1H), 3.74-3.83 (m, 1H), 3.69 (s, 3H), 2.54-2.61 (m, 2H), 1.88 (sept, J = 7.0 Hz, 1H), 0.95 (d, J = 7.0 Hz, 6H). |

Cap-117 to Cap-123

For the preparation of Cap-117 to Cap-123 the Boc amino acids were obtained from commercially sources and were deprotected by treatment with 25% TFA in $CH_2Cl_2$. After complete reaction as judged by LCMS the solvents were removed in vacuo and the corresponding TFA salt of the amino acid was carbamoylated with methyl chloroformate according to the procedure described for Cap-51.

| Cap | Structure | LCMS |
|---|---|---|
| Cap-117 | [structure: MeO-C(O)-NH-CH(CH₂Ph)-CH₂-CO₂H] | LCMS: Anal. Calcd. for $C_{12}H_{15}NO_4$: 237; found: 238 (M + H)⁺. |
| Cap-118 | [structure: MeO-C(O)-NH-CH(CH₂-2-thienyl)-CH₂-CO₂H] | LCMS: Anal. Calcd. for $C_{10}H_{13}NO_4S$: 243; found: 244 (M + H)⁺. |
| Cap-119 | [structure: MeO-C(O)-NH-CH(CH₂-2-thienyl)-CH₂-CO₂H, opposite stereochemistry] | LCMS: Anal. Calcd. for $C_{10}H_{13}NO_4S$: 243; found: 244 (M + H)⁺. |

-continued

| Cap | Structure | LCMS |
|---|---|---|
| Cap-120 | 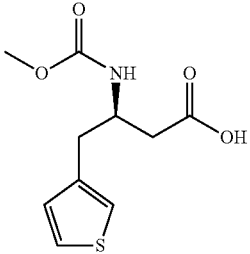 [SMILES: COC(=O)N[C@@H](CC(=O)O)Cc1ccsc1] | LCMS: Anal. Calcd. for $C_{10}H_{13}NO_4S$: 243; found: 244 $(M + H)^+$. |
| Cap-121 | 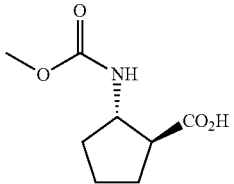 | $^1$HNMR (400 MHz, CDCl3) δ 4.06-4.16 (m, 1H), 3.63 (s, 3H), 3.43 (s, 1H), 2.82 and 2.66 (s, br, 1H), 1.86-2.10 (m, 3H), 1.64 - 1.76 (m, 2H), 1.44-1.53 (m, 1H). |
| Cap-122 | 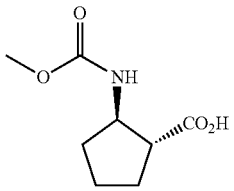 | $^1$HNMR profile is similar to that of its enantiomer, Cap-121. |
| Cap-123 | 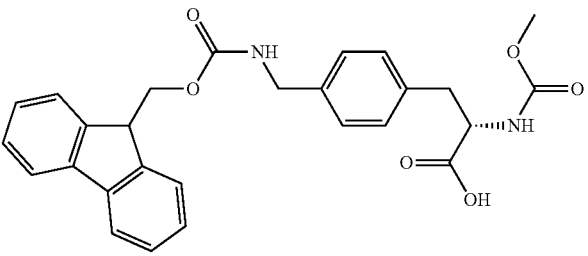 [SMILES: COC(=O)N[C@@H](Cc1ccc(CNC(=O)OCC2c3ccccc3-c3ccccc32)cc1)C(=O)O] | LCMS: Anal. Calcd. for $C_{27}H_{26}N_2O_6$: 474; found: 475 $(M + H)^+$. |

Cap-124

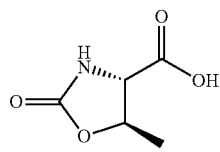

The hydrochloride salt of L-threonine tert-butyl ester was carbamoylated according to the procedure for Cap-51. The crude reaction mixture was acidified with 1N HCl to pH~1 and the mixture was extracted with EtOAc (2×50 mL). The combined organic phases were concentrated in vacuo to give a colorless oil which solidified on standing. The aqueous layer was concentrated in vacuo and the resulting mixture of product and inorganic salts was triturated with EtOAc-CH$_2$Cl$_2$-MeOH (1:1:0.1) and then the organic phase concentrated in vacuo to give a colorless oil which was shown by LCMS to be the desired product. Both crops were combined to give 0.52 g of a solid. $^1$HNMR (400 MHz, CD$_3$OD) δ 4.60 (m, 1H), 4.04 (d, J=5.0 Hz, 1H), 1.49 (d, J=6.3 Hz, 3H). LCMS: Anal. Calcd. for $C_5H_7NO_4$: 145. found: 146 (M+H)$^+$.

Cap-125

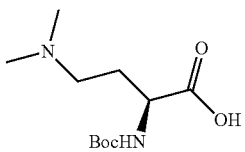 [SMILES: CN(C)CC[C@H](NC(=O)OC(C)(C)C)C(=O)O]

To a suspension of Pd(OH)$_2$, (20%, 100 mg), aqueous formaldehyde (37% wt, 4 ml), acetic acid, (0.5 mL) in methanol (15 mL) was added (S)-4-amino-2-(tert-butoxycarbonylamino)butanoic acid (1 g, 4.48 mmol). The reaction was purged several times with hydrogen and was stirred overnight with an hydrogen balloon room temp. The reaction mixture was filtered through a pad of diatomaceous earth (Celite®), and the volatile component was removed in vacuo. The result- Cap-126

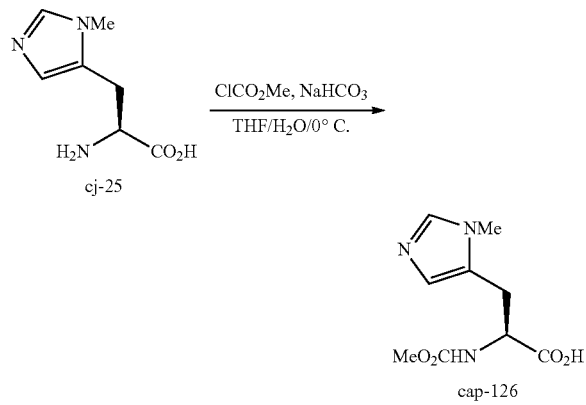

This procedure is a modification of that used to prepare Cap-51. To a suspension of 3-methyl-L-histidine (0.80 g, 4.70 mmol) in THF (10 mL) and H$_2$O (10 mL) at 0° C. was added NaHCO$_3$ (0.88 g, 10.5 mmol). The resulting mixture was treated with ClCO$_2$Me (0.40 mL, 5.20 mmol) and the mixture allowed to stir at 0° C. After stirring for ca. 2 h LCMS showed no starting material remaining. The reaction was acidified to pH 2 with 6 N HCl.

The solvents were removed in vacuo and the residue was suspended in 20 mL of 20% MeOH in CH$_2$Cl$_2$. The mixture was filtered and concentrated to give a light yellow foam (1.21 g,). LCMS and $^1$H NMR showed the material to be a 9:1 mixture of the methyl ester and the desired product. This material was taken up in THF (10 mL) and H$_2$O (10 mL), cooled to 0° C. and LiOH (249.1 mg, 10.4 mmol) was added. After stirring ca. 1 h LCMS showed no ester remaining. Therefore the mixture was acidified with 6N HCl and the solvents removed in vacuo. LCMS and $^1$H NMR confirm the absence of the ester. The title compound was obtained as its HCl salt contaminated with inorganic salts (1.91 g, >100%). The compound was used as is in subsequent steps without further purification. $^1$HNMR (400 MHz, CD$_3$OD) δ 8.84, (s, 1H), 7.35 (s, 1H), 4.52 (dd, J=5.0, 9.1 Hz, 1H), 3.89 (s, 3H), 3.62 (s, 3H), 3.35 (dd, J=4.5, 15.6 Hz, 1H, partially obscured by solvent), 3.12 (dd, J=9.0, 15.6 Hz, 1H). LCMS: Anal. Calcd. for C$_9$H$_{13}$N$_3$O$_4$: 227.09. found: 228.09 (M+H)$^+$.

Cap-127

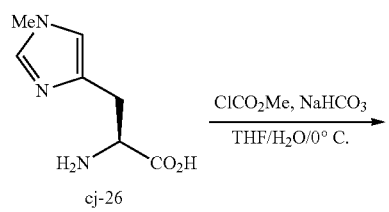

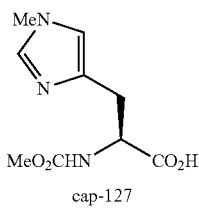

Cap-127 was prepared according to the method for Cap-126 above starting from (S)-2-amino-3-(1-methyl-1H-imidazol-4-yl)propanoic acid (1.11 g, 6.56 mmol), NaHCO$_3$ (1.21 g, 14.4 mmol) and ClCO$_2$Me (0.56 mL, 7.28 mmol). The title compound was obtained as its HCl salt (1.79 g, >100%) contaminated with inorganic salts. LCMS and $^1$H NMR showed the presence of ca. 5% of the methyl ester. The crude mixture was used as is without further purification. $^1$HNMR (400 MHz, CD$_3$OD) δ 8.90 (s, 1H), 7.35 (s, 1H), 4.48 (dd, J=5.0, 8.6 Hz, 1H), 3.89 (s, 3H), 3.62 (s, 3H), 3.35 (m, 1H), 3.08 (m, 1H); LCMS: Anal. Calcd. for C$_9$H$_{13}$N$_3$O$_4$: 227.09. found: 228 (M+H)$^+$.

Preparation of Cap-128

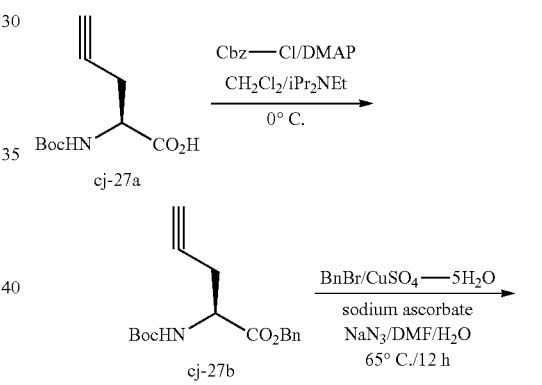

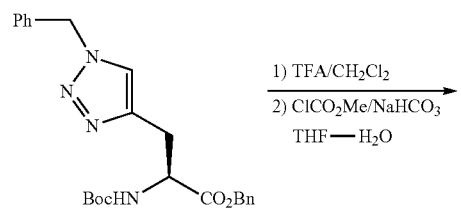

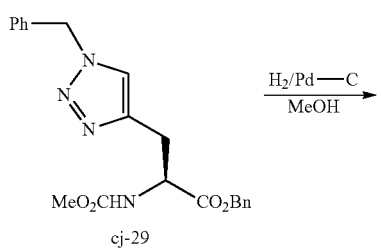

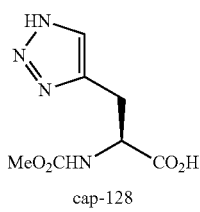

cap-128

Step 1. Preparation of (S)-benzyl 2-(tert-butoxycarbonylamino)pent-4-ynoate (cj-27b)

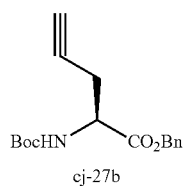 [SMILES: C#CC[C@H](NC(=O)OC(C)(C)C)C(=O)OCc1ccccc1]

cj-27b

To a solution of cj-27a (1.01 g, 4.74 mmol), DMAP (58 mg, 0.475 mmol) and iPr₂NEt (1.7 mL, 9.8 mmol) in CH₂Cl₂ (100 mL) at 0° C. was added Cbz-Cl (0.68 mL, 4.83 mmol). The solution was allowed to stir for 4 h at 0° C., washed (1N KHSO₄, brine), dried (Na₂SO₄), filtered, and concentrated in vacuo. The residue was purified by flash column chromatography (TLC 6:1 hex:EtOAc) to give the title compound (1.30 g, 91%) as a colorless oil. ¹HNMR (400 MHz, CDCl₃) δ 7.35 (s, 5H), 5.35 (d, br, J=8.1 Hz, 1H), 5.23 (d, J=12.2 Hz, 1H), 5.17 (d, J=12.2 Hz, 1H), 4.48-4.53 (m, 1H), 2.68-2.81 (m, 2H), 2.00 (t, J=2.5 Hz, 1H), 1.44 (s, 9H). LCMS: Anal. Calcd. for $C_{17}H_{21}NO_4$: 303. found: 304 (M+H)⁺.

Step 2. Preparation of (S)-benzyl 3-(1-benzyl-1H-1,2,3-triazol-4-yl)-2-(tert-butoxycarbonylamino)propanoate (cj-28)

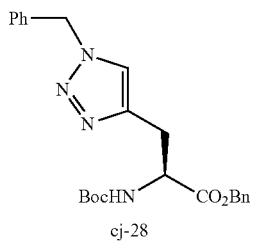 [SMILES: CC(C)(C)OC(=O)N[C@@H](Cc1cn(Cc2ccccc2)nn1)C(=O)OCc1ccccc1]

cj-28

To a mixture of (S)-benzyl 2-(tert-butoxycarbonylamino)pent-4-ynoate (0.50 g, 1.65 mmol), sodium ascorbate (0.036 g, 0.18 mmol), CuSO₄·5H₂O (0.022 g, 0.09 mmol) and NaN₃ (0.13 g, 2.1 mmol) in DMF-H₂O (5 mL, 4:1) at rt was added BnBr (0.24 mL, 2.02 mmol) and the mixture was warmed to 65° C. After 5 h LCMS indicated low conversion. A further portion of NaN₃ (100 mg) was added and heating was continued for 12 h. The reaction was poured into EtOAc and H₂O and shaken. The layers were separated and the aqueous layer extracted 3× with EtOAc and the combined organic phases washed (H₂O x3, brine), dried (Na₂SO₄), filtered, and concentrated. The residue was purified by flash (Biotage, 40+M 0-5% MeOH in CH₂Cl₂; TLC 3% MeOH in CH₂Cl₂) to afford a light yellow oil which solidified on standing (748.3 mg, 104%). The NMR was consistent with the desired product but suggests the presence of DMF. The material was used as is without further purification. ¹HNMR (400 MHz, DMSO-d₆) δ 7.84 (s, 1H), 7.27-7.32 (m, 10H), 5.54 (s, 2H), 5.07 (s, 2H), 4.25 (m, 1H), 3.16 (dd, J=1.0, 5.3 Hz, 1H), 3.06 (dd, J=5.3, 14.7 Hz), 2.96 (dd, J=9.1, 14.7 Hz, 1H), 1.31 (s, 9H). LCMS: Anal. Calcd. for $C_{24}H_{28}N_4O_4$: 436. found: 437 (M+H)⁺.

Step 3. Preparation of (S)-benzyl 3-(1-benzyl-1H-1,2,3-triazol-4-yl)-2-(methoxycarbonylamino)propanoate (cj-29)

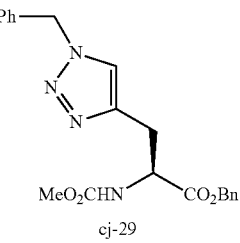

cj-29

A solution of (S)-benzyl 3-(1-benzyl-1H-1,2,3-triazol-4-yl)-2-(tert-butoxycarbonylamino)propanoate (0.52 g, 1.15 mmol) in CH₂Cl₂ was added TFA (4 mL). The mixture was allowed to stir at room temperature for 2 h. The mixture was concentrated in vacuo to give a colorless oil which solidified on standing. This material was dissolved in THF—H₂O and cooled to 0° C. Solid NaHCO₃ (0.25 g, 3.00 mmol) was added followed by ClCO₂Me (0.25 mL, 3.25 mmol). After stirring for 1.5 h the mixture was acidified to pH~2 with 6N HCl and then poured into H₂O-EtOAc. The layers were separated and the aq phase extracted 2× with EtOAc. The combined org layers were washed (H₂O, brine), dried (Na₂SO₄), filtered, and concentrated in vacuo to give a colorless oil (505.8 mg, 111%, NMR suggested the presence of an unidentified impurity) which solidified while standing on the pump. The material was used as is without further purification. ¹HNMR (400 MHz, DMSO-d₆) δ 7.87 (s, 1H), 7.70 (d, J=8.1 Hz, 1H), 7.27-7.32 (m, 10H), 5.54 (s, 2H), 5.10 (d, J=12.7 Hz, 1H), 5.06 (d, J=12.7 Hz, 1H), 4.32-4.37 (m, 1H), 3.49 (s, 3H), 3.09

(dd, J=5.6, 14.7 Hz, 1H), 2.98 (dd, J=9.6, 14.7 Hz, 1H). LCMS: Anal. Calcd. for $C_{21}H_{22}N_4O_4$: 394. found: 395 $(M+H)^+$.

Step 4. Preparation of (S)-2-(methoxycarbonylamino)-3-(1H-1,2,3-triazol-4-yl)propanoic acid (Cap-128)

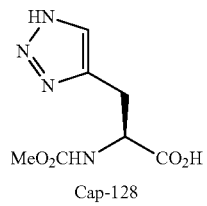

Cap-128

Cap-128

(S)-benzyl 3-(1-benzyl-1H-1,2,3-triazol-4-yl)-2-(methoxycarbonylamino)propanoate (502 mg, 1.11 mmol) was hydrogenated in the presence of Pd—C (82 mg) in MeOH (5 mL) at atmospheric pressure for 12 h. The mixture was filtered through diatomaceous earth (Celite®) and concentrated in vacuo. (S)-2-(methoxycarbonylamino)-3-(1H-1,2,3-triazol-4-yl)propanoic acid was obtained as a colorless gum (266 mg, 111%) which was contaminated with ca. 10% of the methyl ester. The material was used as is without further purification. $^1$HNMR (400 MHz, DMSO-$d_6$) δ 12.78 (s, br, 1H), 7.59 (s, 1H), 7.50 (d, J=8.0 Hz, 1H), 4.19-4.24 (m, 1H), 3.49 (s, 3H), 3.12 (dd, J=4.8 Hz, 14.9 Hz, 1H), 2.96 (dd, J=9.9, 15.0 Hz, 1H). LCMS: Anal. Calcd. for $C_2H_{10}N_4O_4$: 214. found: 215 $(M+H)^+$.

Preparation of Cap-129

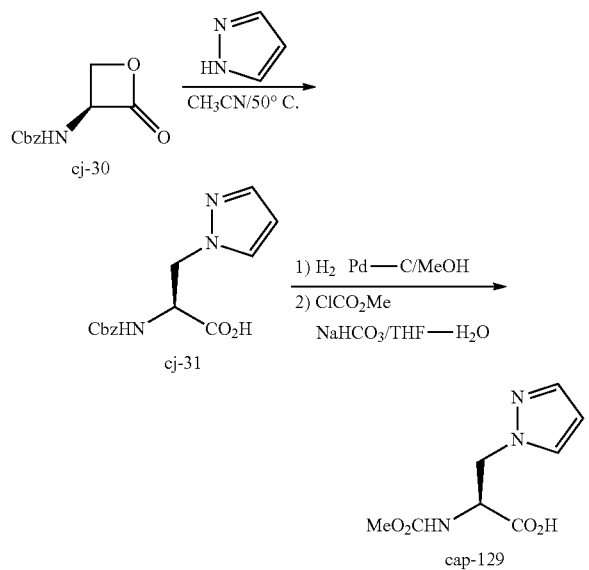

Step 1. Preparation of (S)-2-(benzyloxycarbonylamino)-3-(1H-pyrazol-1-yl)propanoic acid (cj-31)

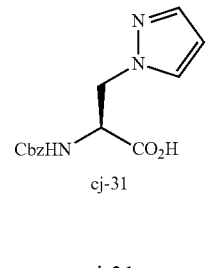

cj-31

A suspension of (S)-benzyl 2-oxooxetan-3-ylcarbamate (0.67 g, 3.03 mmol), and pyrazole (0.22 g, 3.29 mmol) in $CH_3CN$ (12 mL) was heated at 50° C. for 24 h. The mixture was cooled to rt overnight and the solid filtered to afford (S)-2-(benzyloxycarbonylamino)-3-(1H-pyrazol-1-yl)propanoic acid (330.1 mg). The filtrate was concentrated in vacuo and then triturated with a small amount of $CH_3CN$ (ca. 4 mL) to afford a second crop (43.5 mg). Total yield 370.4 mg (44%). m.p. 165.5-168° C. lit m.p. 168.5-169.5 [Vederas et al. J. Am. Chem. Soc. 1985, 107, 7105]. $^1$HNMR (400 MHz, $CD_3OD$) δ 7.51 (d, J=2.0, 1H), 7.48 (s, J=1.5 Hz, 1H), 7.24-7.34 (m, 5H), 6.23 m, 1H), 5.05 (d, 12.7H, 1H), 5.03 (d, J=12.7 Hz, 1H), 4.59-4.66 (m, 2H), 4.42-4.49 (m, 1H). LCMS: Anal. Calcd. for $C_{14}H_{15}N_3O_4$: 289. found: 290 $(M+H)^+$.

Step 2. Preparation of (S)-2-(methoxycarbonylamino)-3-(1H-pyrazol-1-yl)propanoic acid (Cap-129)

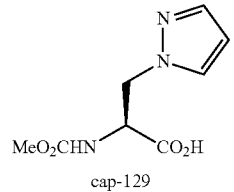

cap-129 cap-129

(S)-2-(benzyloxycarbonylamino)-3-(1H-pyrazol-1-yl)propanoic acid (0.20 g, 0.70 mmol) was hydrogenated in the presence of Pd—C (45 mg) in MeOH (5 mL) at atmospheric pressure for 2 h. The product appeared to be insoluble in MeOH, therefore the reaction mixture was diluted with 5 mL $H_2O$ and a few drops of 6NHCl. The homogeneous solution was filtered through diatomaceous earth (Celite®), and the MeOH removed in vacuo. The remaining solution was frozen and lyophyllized to give a yellow foam (188.9 mg). This material was suspended in THF—$H_2O$ (1:1, 10 mL) and then cooled to 0° C. To the cold mixture was added $NaHCO_3$ (146.0 mg, 1.74 mmol) carefully (evolution of $CO_2$). After gas evolution had ceased (ca. 15 min) $ClCO_2Me$ (0.06 mL, 0.78 mmol) was added dropwise. The mixture was allowed to stir for 2 h and was acidified to pH~2 with 6N HCl and poured into EtOAc. The layers were separated and the aqueous phase extracted with EtOAC (×5). The combined organic layers were washed (brine), dried (Na₂SO₄), filtered, and concentrated to give the title compound as a colorless solid (117.8 mg, 79%). ¹HNMR (400 MHz, DMSO-d₆) δ 13.04 (s, 1H), 7.63 (d, J=2.6 Hz, 1H), 7.48 (d, J=8.1 Hz, 1H), 7.44 (d, J=1.5 Hz, 1H), 6.19 (app t, J=2.0 Hz, 1H), 4.47 (dd, J=3.0, 12.9 Hz, 1H), 4.29-4.41 (m, 2H), 3.48 (s, 3H). LCMS: Anal. Calcd. for C₈H₁₁N₃O₄: 213. found: 214 (M+H)⁺.

Cap-130

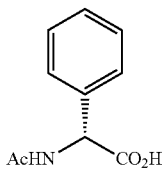

Cap-130 was prepared by acylation of commercially available (R)-phenylglycine analgous to the procedure given in: Calmes, M.; Daunis, J.; Jacquier, R.; Verducci, J. *Tetrahedron*, 1987, 43(10), 2285.

Cap-131

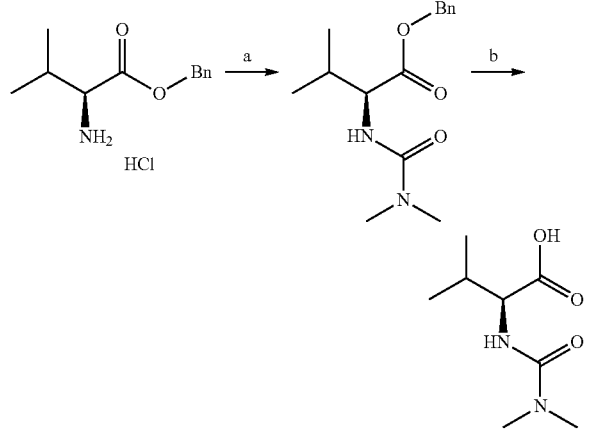

Step a

Dimethylcarbamoyl chloride (0.92 mL, 10 mmol) was added slowly to a solution of (S)-benzyl 2-amino-3-methylbutanoate hydrochloride (2.44 g; 10 mmol) and Hunig's base (3.67 mL, 21 mmol) in THF (50 mL). The resulting white suspension was stirred at room temperature overnight (16 hours) and concentrated under reduced pressure. The residue was partitioned between ethyl acetate and water. The organic layer was washed with brine, dried (MgSO₄), filtered, and concentrated under reduced pressure. The resulting yellow oil was purified by flash chromatography, eluting with ethyl acetate:hexanes (1:1). Collected fractions were concentrated under vacuum providing 2.35 g (85%) of clear oil. ¹H NMR (300 MHz, DMSO-d₆) δ ppm 0.84 (d, J=6.95 Hz, 3H), 0.89 (d, J=6.59 Hz, 3H), 1.98-2.15 (m, 1H), 2.80 (s, 6H), 5.01-5.09 (m, J=12.44 Hz, 1H), 5.13 (d, J=12.44 Hz, 1H), 6.22 (d, J=8.05 Hz, 1H), 7.26-7.42 (m, 5H). LC (Cond. 1): RT=1.76 min; MS: Anal. Calcd. for [M+H]⁺ C₁₆H₂₂N₂O₃: 279.17. found 279.03.

Step b

To a MeOH (50 mL) solution of the intermediate prepared above (2.35 g; 8.45 mmol) was added Pd/C (10%; 200 mg) and the resulting black suspension was flushed with N₂ (3×) and placed under 1 atm of H₂. The mixture was stirred at room temperature overnight and filtered though a microfiber filter to remove the catalyst. The resulting clear solution was then concentrated under reduced pressure to obtain 1.43 g (89%) of Cap-131 as a white foam, which was used without further purification. ¹H NMR (500 MHz, DMSO-d₆) δ ppm 0.87 (d, J=4.27 Hz, 3H), 0.88 (d, J=3.97 Hz, 3H), 1.93-2.11 (m, 1H), 2.80 (s, 6H), 3.90 (dd, J=8.39, 6.87 Hz, 1H), 5.93 (d, J=8.54 Hz, 1H), 12.36 (s, 1H). LC (Cond. 1): RT=0.33 min; MS: Anal. Calcd. for [M+H]⁺ C₈H₁₇N₂O₃: 189.12. found 189.04.

Cap-132

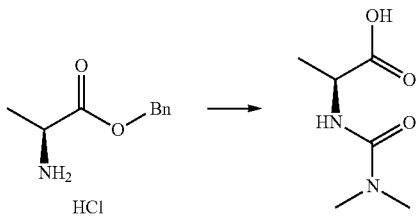

Cap-132 was prepared from (S)-benzyl 2-aminopropanoate hydrochloride according to the method described for Cap-131. ¹H NMR (500 MHz, DMSO-d₆) δ ppm 1.27 (d, J=7.32 Hz, 3H), 2.80 (s, 6H), 4.06 (qt, 1H), 6.36 (d, J=7.32 Hz, 1H), 12.27 (s, 1H). LC (Cond. 1): RT=0.15 min; MS: Anal. Calcd. for [M+H]⁺ C₆H₁₃N₂O₃: 161.09. found 161.00.

Cap-133

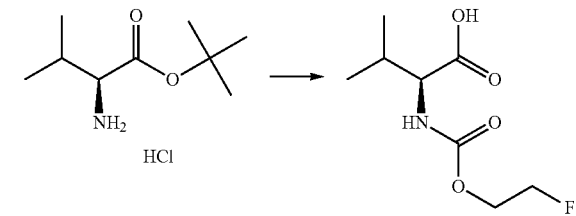

Cap-133 was prepared from (S)-tert-butyl 2-amino-3-methylbutanoate hydrochloride and 2-fluoroethyl chloroformate according to the method described for Cap-47. ¹H NMR (500 MHz, DMSO-d₆) δ ppm 0.87 (t, J=6.71 Hz, 6H), 1.97-2.10 (m, 1H), 3.83 (dd, J=8.39, 5.95 Hz, 1H), 4.14-4.18 (m, 1H), 4.20-4.25 (m, 1H), 4.50-4.54 (m, 1H), 4.59-4.65 (m, 1H), 7.51 (d, J=8.54 Hz, 1H), 12.54 (s, 1H).

Cap-134

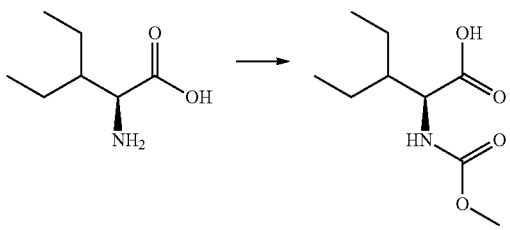

Cap-134 was prepared from (S)-diethyl alanine and methyl chloroformate according to the method described for Cap-51. $^1$H NMR (500 MHz, DMSO-$d_6$) δ ppm 0.72-0.89 (m, 6H), 1.15-1.38 (m, 4H), 1.54-1.66 (m, 1H), 3.46-3.63 (m, 3H), 4.09 (dd, J=8.85, 5.19 Hz, 1H), 7.24 (d, J=8.85 Hz, 1H), 12.55 (s, 1H). LC (Cond. 2): RT=0.66 min; LC/MS: Anal. Calcd. for $[M+H]^+$ $C_9H_{18}NO_4$: 204.12. found 204.02.

Cap-135

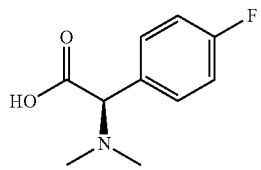

A solution of D-2-amino-(4-fluorophenyl)acetic acid (338 mg, 2.00 mmol), 1N HCl in diethylether (2.0 mL, 2.0 mmol) and formalin (37%, 1 mL) in methanol (5 mL) was subjected to balloon hydrogenation over 10% palladium on carbon (60 mg) for 16 h at 25° C. The mixture was then filtered through Celite to afford the HCl salt of Cap-135 as a white foam (316 mg, 80%). $^1$H NMR (300 MHz, MeOH-$d_4$) δ 7.59 (dd, J=8.80, 5.10 Hz, 2H), 7.29 (t, J=8.6 Hz, 2H), 5.17 (s, 1H), 3.05 (v br s, 3H), 2.63 (v br s, 3H); $R_f$=0.19 min (Cond.-MS-W5); 95% homogenity index; LRMS: Anal. Calcd. for $[M+H]^+$ $C_{10}H_{13}FNO_2$: 198.09. found: 198.10.

Cap-136

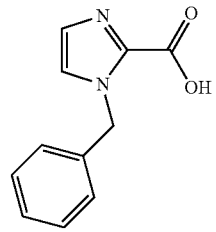 [SMILES: O=C(O)c1nccn1Cc1ccccc1]

To a cooled (−50° C.) suspension of 1-benzyl-1H-imidazole (1.58 g, 10.0 mmol) in anhydrous diethyl ether (50 mL) under nitrogen was added n-butyl lithium (2.5 M in hexanes, 4.0 mL, 10.0 mmol) dropwise. After being stirred for 20 min at −50° C., dry carbon dioxide (passed through Drierite) was bubbled into the reaction mixture for 10 min before it was allowed to warm up to 25° C. The heavy precipitate which formed on addition of carbon dioxide to the reaction mixture was filtered to yield a hygroscopic, white solid which was taken up in water (7 mL), acidified to pH=3, cooled, and induced to crystallize with scratching. Filtration of this precipitate gave a white solid which was suspended in methanol, treated with 1N HCl/diethyl ether (4 mL) and concentrated in vacuo. Lyophilization of the residue from water (5 mL) afforded the HCl salt of Cap-136 as a white solid (817 mg, 40%). $^1$H NMR (300 MHz, DMSO-$d_6$) δ 7.94 (d, J=1.5 Hz, 1H), 7.71 (d, J=1.5 Hz, 1H), 7.50-7.31 (m, 5H), 5.77 (s, 2H); $R_f$=0.51 min (Cond.-MS-W5); 95% homogenity index; LRMS: Anal. Calc. for $[M+H]^+$ $C_{11}H_{12}N_2O_2$: 203.08. found: 203.11.

Cap-137

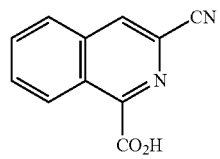 [SMILES: N#Cc1cc2ccccc2c(C(=O)O)n1]

Cap-137, step a

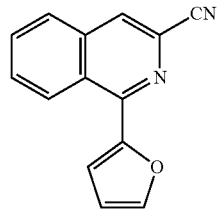 [SMILES: N#Cc1cc2ccccc2c(-c2ccco2)n1]

A suspension of 1-chloro-3-cyanoisoquinoline (188 mg, 1.00 mmol; prepared according to the procedure in WO 2003/099274) (188 mg, 1.00 mmol), cesium fluoride (303.8 mg, 2.00 mmol), bis(tri-tert-butylphosphine)palladium dichloride (10 mg, 0.02 mmol) and 2-(tributylstannyl)furan (378 µL, 1.20 mmol) in anhydrous dioxane (10 mL) under nitrogen was heated at 80° C. for 16 h before it was cooled to 25° C. and treated with saturated, aqueous potassium fluoride solution with vigorous stirring for 1 h. The mixture was partitioned between ethyl acetate and water and the organic phase was separated, washed with brine, dried over $Na_2SO_4$, filtered and concentrated. Purification of the residue on silica gel (elution with 0% to 30% ethyl acetate/hexanes) afforded Cap-137, step a (230 mg, 105%) as a white solid which was carried forward directly. $R_f$=1.95 min (Cond.-MS-W2); 90% homogeneity index; LRMS: Anal. Calc. for $[M+H]^+$ $C_{14}H_8N_2O$: 221.07. found: 221.12.

Cap-137

To a suspension of Cap 137, step a, (110 mg, 0.50 mmol) and sodium periodate (438 mg, 2.05 mmol) in carbon tetrachloride (1 mL), acetonitrile (1 mL) and water (1.5 mL) was added ruthenium trichloride hydrate (2 mg, 0.011 mmol). The mixture was stirred at 25° C. for 2 h and then partitioned between dichloromethane and water. The aqueous layer was separated, extracted twice more with dichloromethane and the combined dichloromethane extracts were dried over $Na_2SO_4$, filtered and concentrated. Trituration of the residue with hexanes afforded Cap-137 (55 mg, 55%) as a grayish-colored solid. $R_t$=1.10 min (Cond.-MS-W2); 90% homogeneity index; LCMS: Anal. Calc. for $[M+H]^+$ $C_{11}H_8N_2O_2$: 200.08. found: 200.08.

Caps 138 to 158

Synthetic Strategy. Method A.

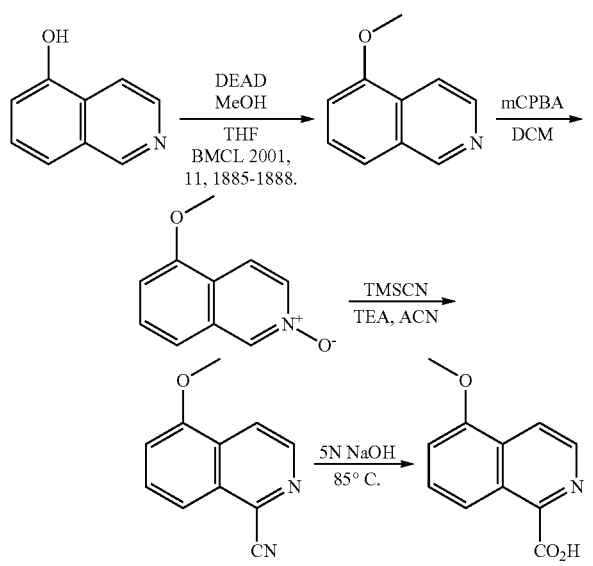

Cap-138

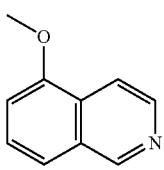

Cap-138, Step a

To a stirred suspension of 5-hydroxyisoquinoline (prepared according to the procedure in WO 2003/099274) (2.0 g, 13.8 mmol) and triphenylphosphine (4.3 g, 16.5 mmol) in dry tetrahydrofuran (20 mL) was added dry methanol (0.8 mL) and diethyl azodicarboxylate (3.0 mL, 16.5 mmol) portionwise. The mixture was stirred at room temperature for 20 h before it was diluted with ethyl acetate and washed with brine, dried over $Na_2SO_4$, filtered and concentrated. The residue was preabsorbed onto silica gel and chromatographed (elution with 40% ethyl acetate/hexanes) to afford Cap-138, step a (1.00 g, 45%) as a light yellow solid. $^1$H NMR ($CDCl_3$, 500 MHz) δ 9.19 (s, 1H), 8.51 (d, J=6.0 Hz, 1H), 7.99 (d, J=6.0 Hz, 1H), 7.52-7.50 (m, 2H), 7.00-6.99 (m, 1H), 4.01 (s, 3H); $R_t$=0.66 min (Cond.-D2); 95% homogeneity index; LCMS: Anal. Calc. for $[M+H]^+$ $C_{10}H_{10}NO$: 160.08. found 160.1.

Cap-138, Step b

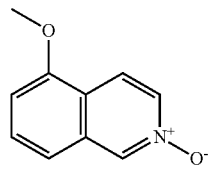

To a stirred solution of Cap 138, step a (2.34 g, 14.7 mmol) in anhydrous dichloromethane (50 mL) at room temperature was added meta-chloroperbenzoic acid (77%, 3.42 g, 19.8 mmol) in one portion. After being stirred for 20 h, powdered potassium carbonate (2.0 g) was added and the mixture was stirred for 1 h at room temperature before it was filtered and concentrated in vacuo to afford Cap-138, step b (2.15 g, 83%) as a pale, yellow solid which was sufficiently pure to carry forward directly. $^1$H NMR ($CDCl_3$, 400 MHz) δ 8.73 (d, J=1.5 Hz, 1H), 8.11 (dd, J=7.3, 1.7 Hz, 1H), 8.04 (d, J=7.1 Hz, 1H), 7.52 (t, J=8.1 Hz, 1H), 7.28 (d, J=8.3 Hz, 1H), 6.91 (d, J=7.8 Hz, 1H), 4.00 (s, 3H); $R_t$=0.92 min, (Cond.-D1); 90% homogenity index; LCMS: Anal. Calc. for $[M+H]^+$ $C_{10}H_{10}NO_2$: 176.07. found: 176.0.

Cap-138, Step c

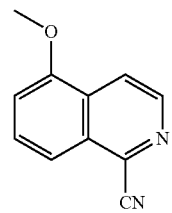

To a stirred solution of Cap 138, step b (0.70 g, 4.00 mmol) and triethylamine (1.1 mL, 8.00 mmol) in dry acetonitrile (20 mL) at room temperature under nitrogen was added trimethylsilylcyanide (1.60 mL, 12.00 mmol). The mixture was heated at 75° C. for 20 h before it was cooled to room temperature, diluted with ethyl acetate and washed with saturated sodium bicarbonate solution and brine prior to drying over $Na_2SO_4$ and solvent concentration. The residue was flash chromatographed on silica gel (gradient elution with 5% ethyl acetate in hexanes to 25% ethyl acetate in hexanes) to afford Cap-138, step c (498.7 mg, 68%) as a white, crystalline solid along with 223 mg (30%) of additional Cap-138, step c recovered from the filtrate. $^1$H NMR ($CDCl_3$, 500 MHz) δ 8.63 (d, J=5.5 Hz, 1H), 8.26 (d, J=5.5 Hz, 1H), 7.88 (d, J=8.5

Hz, 1H), 7.69 (t, J=8.0 Hz, 1H), 7.08 (d, J=7.5 Hz, 1H), 4.04 (s, 3H); $R_t$=1.75 min, (Cond.-D1); 90% homogeneity index; LCMS: Anal. Calc. for [M+H]$^+$ $C_{11}H_9N_2O$: 185.07. found: 185.10.

Cap-138

Cap-138, step c (0.45 g, 2.44 mmol) was treated with 5N sodium hydroxide solution (10 mL) and the resulting suspension was heated at 85° C. for 4 h, cooled to 25° C., diluted with dichloromethane and acidified with 1N hydrochloric acid. The organic phase was separated, washed with brine, dried over $Na_2SO_4$, concentrated to ¼ volume and filtered to afford Cap-138 (0.44 g, 88.9%) as a yellow solid. $^1$H NMR (DMSO-$d_6$, 400 MHz) δ 13.6 (br s, 1H), 8.56 (d, J=6.0 Hz, 1H), 8.16 (d, J=6.0 Hz, 1H), 8.06 (d, J=8.8 Hz, 1H), 7.71-7.67 (m, 1H), 7.30 (d, J=8.0 Hz, 1H), 4.02 (s, 3H); $R_t$=0.70 min (Cond.-D1); 95% homogenity index; LCMS: Anal. Calc. for [M+H]$^+$ $C_{11}H_{10}NO_3$: 204.07. found: 204.05.

Synthetic Strategy. Method B (derived from *Tetrahedron Letters*, 2001, 42, 6707).

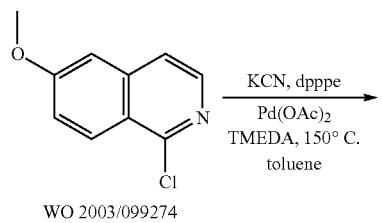

WO 2003/099274

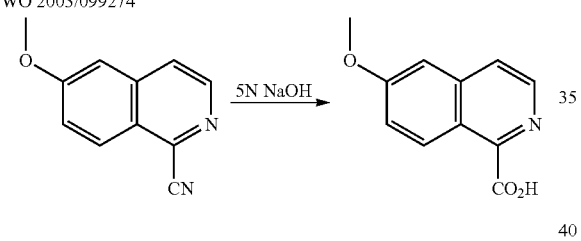

Cap-139

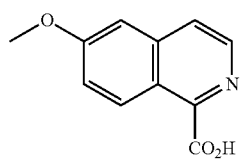

Cap-139, Step a

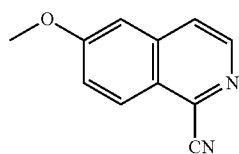

To a thick-walled, screw-top vial containing an argon-degassed suspension of 1-chloro-6-methoxyisoquinoline (1.2 g, 6.2 mmol; prepared according to the procedure in WO 2003/099274), potassium cyanide (0.40 g, 6.2 mmol), 1,5-bis(diphenylphosphino)pentane (0.27 g, 0.62 mmol) and palladium (II) acetate (70 mg, 0.31 mmol) in anhydrous toluene (6 mL) was added N,N,N',N'-tetramethylethylenediamine (0.29 mL, 2.48 mmol). The vial was sealed, heated at 150° C. for 22 h and then allowed to cool to 25° C. The reaction mixture was diluted with ethyl acetate, washed with water and brine, dried over $Na_2SO_4$, filtered and concentrated. The residue was purified on silica gel (gradient elution with 5% ethyl acetate/hexanes to 25% ethyl acetate/hexanes) to afford Cap-139, step a (669.7 mg, 59%) as a white solid. $^1$H NMR (CDCl$_3$, 500 MHz) δ 8.54 (d, J=6.0 Hz, 1H), 8.22 (d, J=9.0 Hz, 1H), 7.76 (d, J=5.5 Hz, 1H), 7.41-7.39 (m, 1H), 7.13 (d, J=2.0 Hz, 1H), 3.98 (s, 3H); $R_t$=1.66 min (Cond.-D1); 90% homogeneity index; LCMS: Anal. Calc. for [M+H]$^+$ $C_{11}H_9N_2O$: 185.07. found: 185.2.

Cap-139

Cap-139 was prepared from the basic hydrolysis of Cap-139, step a with 5N

NaOH according to the procedure described for Cap 138. $^1$H NMR (400 MHz, DMSO-$d_6$) δ 13.63 (v br s, 1H), 8.60 (d, J=9.3 Hz, 1H), 8.45 (d, J=5.6 Hz, 1H), 7.95 (d, J=5.9 Hz, 1H), 7.49 (d, J=2.2 Hz, 1H), 7.44 (dd, J=9.3, 2.5 Hz, 1H), 3.95 (s, 3H); $R_t$=0.64 min (Cond.-D1); 90% homogenity index; LCMS: Anal. Calc. for [M+H]$^+$ $C_{11}H_{10}NO_3$: 204.07. found: 204.05.

Cap-140

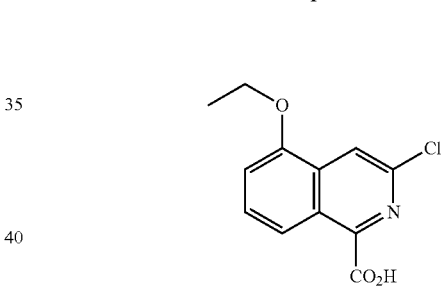

Cap-140, Step a

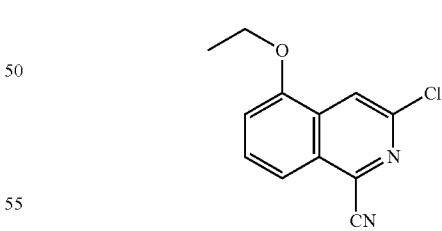

To a vigorously-stirred mixture of 1,3-dichloro-5-ethoxy-isoquinoline (482 mg, 2.00 mmol; prepared according to the procedure in WO 2005/051410), palladium (II) acetate (9 mg, 0.04 mmol), sodium carbonate (223 mg, 2.10 mmol) and 1,5-bis(diphenylphosphino)pentane (35 mg, 0.08 mmol) in dry dimethylacetamide (2 mL) at 25° C. under nitrogen was added N,N,N',N'-tetramethylethylenediamine (60 mL, 0.40 mmol). After 10 min, the mixture was heated to 150° C., and then a stock solution of acetone cyanohydrin (prepared from 457 µL of acetone cyanohydrin in 4.34 mL DMA) was added in 1 mL portions over 18 h using a syringe pump. The mixture was then partitioned between ethyl acetate and water and the organic layer was separated, washed with brine, dried over $Na_2SO_4$, filtered and concentrated. The residue was purified on silica gel (gradient elution with 10% ethyl acetate in hexanes to 40% ethyl acetate in hexanes) to afford Cap-140, step a (160 mg, 34%) as a yellow solid. $R_f$=2.46 min (Cond.-MS-W2); 90% homogenity index; LCMS: Anal. Calc. for [M+H]$^+$ $C_{12}H_9ClN_2O$: 233.05. found: 233.08.

Cap-140

Cap-140 was prepared by the acid hydrolysis of Cap-140, step a with 12N HCl as described in the procedure for the preparation of Cap 141, described below. $R_f$=2.24 min (Cond.-MS-W2); 90% homogenity index; LCMS: Anal. Calc. for [M+H]$^+$ $C_{12}H_{11}ClNO_3$: 252.04. found: 252.02.

Cap-141

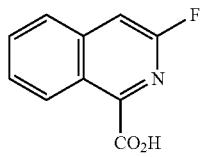 [SMILES: O=C(O)c1nc(F)cc2ccccc12]

Cap-141, Step a

Cap-141, step a was prepared from 1-bromo-3-fluoroisoquinoline (prepared from 3-amino-1-bromoisoquinoline using the procedure outlined in *J. Med. Chem.* 1970, 13, 613) as described in the procedure for the preparation of Cap-140, step a (vide supra). $^1$H NMR (500 MHz, CDCl$_3$) δ 8.35 (d, J=8.5 Hz, 1H), 7.93 (d, J=8.5 Hz, 1H), 7.83 (t, J=7.63 Hz, 1H), 7.77-7.73 (m, 1H), 7.55 (s, 1H); $R_f$=1.60 min (Cond.-D1); 90% homogenity index; LCMS: Anal. Calc. for [M+H]$^+$ $C_{10}H_6FN_2$: 173.05. found: 172.99.

Cap-141

Cap-141, step a (83 mg, 0.48 mmol) was treated with 12N HCl (3 mL) and the resulting slurry was heated at 80° C. for 16 h before it was cooled to room temperature and diluted with water (3 mL). The mixture was stirred for 10 min and then filtered to afford Cap-141 (44.1 mg, 48%) as an off-white solid. The filtrate was diluted with dichloromethane and washed with brine, dried over $Na_2SO_4$, and concentrated to afford additional Cap-141 (29.30 mg, 32%) which was sufficiently pure to be carried forward directly. $^1$H NMR (DMSO-d$_6$, 500 MHz) δ 14.0 (br s, 1H), 8.59-8.57 (m, 1H), 8.10 (d, J=8.5 Hz, 1H), 7.88-7.85 (m, 2H), 7.74-7.71 (m, 1H); $R_f$=1.33 min (Cond.-D1); 90% homogenity index; LCMS: Anal. Calc. for [M+H]$^+$ $C_{10}H_7FNO_2$: 192.05. found: 191.97.

Cap-142

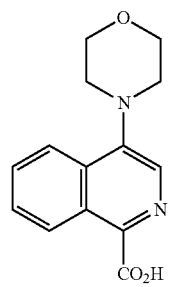 [SMILES: O=C(O)c1ncc(N2CCOCC2)c2ccccc12]

Cap-142, Step a

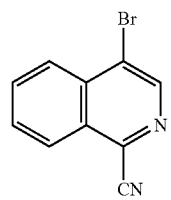 [SMILES: N#Cc1ncc(Br)c2ccccc12]

Cap-142, step a was prepared from 4-bromoisoquinoline N-oxide as described in the two-step procedure for the preparation of Cap-138, steps b and c. $R_f$=1.45 min (Cond.-MS-W1); 90% homogenity index; LCMS: Anal. Calc. for [M+H]$^+$ $C_{10}H_6BrN_2$: 232.97. found: 233.00.

Cap-142, Step b

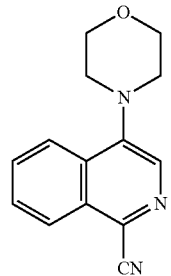 [SMILES: N#Cc1ncc(N2CCOCC2)c2ccccc12]

To an argon-degassed suspension of Cap-142, step a (116 mg, 0.50 mmol), potassium phosphate tribasic (170 mg, 0.80 mmol), palladium (II) acetate (3.4 mg, 0.015 mmol) and 2-(dicyclohexylphosphino)biphenyl (11 mg, 0.03 mmol) in anhydrous toluene (1 mL) was added morpholine (61 μL, 0.70 mmol). The mixture was heated at 100° C. for 16 h, cooled to 25° C., filtered through diatomaceous earth (Celite®) and concentrated. Purification of the residue on silica gel (gradient elution with 10% to 70% ethyl acetate in hexanes) afforded Cap-142, step b (38 mg, 32%) as a yellow solid which was carried forward directly. $R_f$=1.26 min (Cond.-MS-W1); 90% homogenity index; LCMS: Anal. Calc. for [M+H]$^+$ $C_{14}H_{14}N_3O$: 240.11. found: 240.13.

Cap-142

Cap-142 was prepared from Cap-142, step b with 5N sodium hydroxide as described in the procedure for Cap 138. $R_f$=0.72 min (Cond.-MS-W1); 90% homogeneity index; LCMS: Anal. Calc. for [M+H]$^+$ C$_{14}$H$_{15}$N$_2$O$_3$: 259.11. found: 259.08.

Cap-143

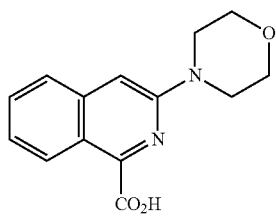 [SMILES: O=C(O)c1nc(N2CCOCC2)cc2ccccc12]

Cap-143, Step a

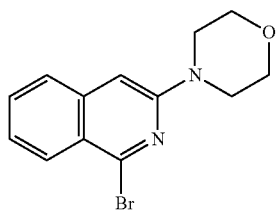 [SMILES: Brc1nc(N2CCOCC2)cc2ccccc12]

To a stirred solution of 3-amino-1-bromoisoquinoline (444 mg, 2.00 mmol) in anhydrous dimethylformamide (10 mL) was added sodium hydride (60%, unwashed, 96 mg, 2.4 mmol) in one portion. The mixture was stirred at 25° C. for 5 min before 2-bromoethyl ether (90%, 250 µL, 2.00 mmol) was added. This mixture was stirred further at 25° C. for 5 h and at 75° C. for 72 h before it was cooled to 25° C., quenched with saturated ammonium chloride solution and diluted with ethyl acetate. The organic layer was separated, washed with water and brine, dried over Na$_2$SO$_4$, filtered and concentrated. Purification of the residue on silica gel (gradient elution with 0% to 70% ethyl acetate in hexanes) afforded Cap-143, step a (180 mg, 31%) as a yellow solid. $R_f$=1.75 min (Cond.-MS-W1); 90% homogeneity index; LCMS: Anal. Calc. for [M+H]$^+$ C$_{13}$H$_{14}$BrN$_2$O: 293.03. found: 293.04.

Cap-143

To a cold (−60° C.) solution of Cap-143, step a (154 mg, 0.527 mmol) in anhydrous tetrahydrofuran (5 mL) was added a solution of n-butyllithium in hexanes (2.5 M, 0.25 mL, 0.633 mmol). After 10 min, dry carbon dioxide was bubbled into the reaction mixture for 10 min before it was quenched with 1N HCl and allowed to warm to 25° C. The mixture was then extracted with dichloromethane (3×30 mL) and the combined organic extracts were concentrated in vacuo. Purification of the residue by reverse phase HPLC (MeOH/water/TFA) afforded Cap-143 (16 mg, 12%). $R_f$=1.10 min (Cond.-MS-W1); 90% homogeneity index; LCMS: Anal. Calc. for [M+H]$^+$ C$_{14}$H$_{15}$N$_2$O$_3$: 259.11. found: 259.08.

Cap-144

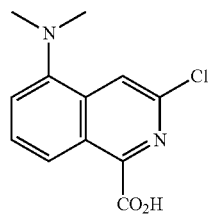 [SMILES: CN(C)c1cccc2c(C(=O)O)nc(Cl)cc12]

Cap-144, Step a

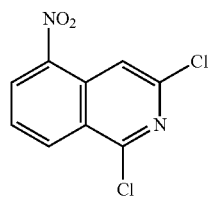 [SMILES: O=[N+]([O-])c1cccc2c(Cl)nc(Cl)cc12]

1,3-Dichloroisoquinoline (2.75 g, 13.89 mmol) was added in small portions to a cold (0° C.) solution of fuming nitric acid (10 mL) and concentrated sulfuric acid (10 mL). The mixture was stirred at 0° C. for 0.5 h before it was gradually warmed to 25° C. where it stirred for 16 h. The mixture was then poured into a beaker containing chopped ice and water and the resulting suspension was stirred for 1 h at 0° C. before it was filtered to afford Cap-144, step a (2.73 g, 81%) as a yellow solid which was used directly. $R_f$=2.01 min (Cond.-D1); 95% homogeneity index; LCMS: Anal. Calc. for [M+H]$^+$ C$_9$H$_5$Cl$_2$N$_2$O$_2$: 242.97. found: 242.92.

Cap-144, Step b

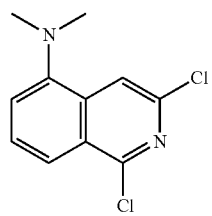

Cap-144, step a (0.30 g, 1.23 mmol) was taken up in methanol (60 mL) and treated with platinum oxide (30 mg), and the suspension was subjected to Parr hydrogenation at 7 psi H$_2$ for 1.5 h before formalin (5 mL) and additional platinum oxide (30 mg) were added. The suspension was resubjected to Parr hydrogenation at 45 psi H$_2$ for 13 h before it was suction-filtered through diatomaceous earth (Celite®) and concentrated down to ¼ volume. Suction-filtration of the ensuing precipitate afforded the title compound as a yellow solid which was flash chromatographed on silica gel (gradient elution with 5% ethyl acetate in hexanes to 25% ethyl acetate in hexanes) to afford Cap-144, step b (231 mg, 78%) as a pale, yellow solid. $R_t$=2.36 min (Cond.-D1); 95% homogenity index; $^1$H NMR (400 MHz, CDCl$_3$) δ 8.02 (s, 1H), 7.95 (d, J=8.6 Hz, 1H), 7.57-7.53 (m, 1H), 7.30 (d, J=7.3 Hz, 1H), 2.88 (s, 6H); LCMS: Anal. Calc. for [M+H]$^+$ C$_{11}$H$_{11}$Cl$_2$N$_2$: 241.03. found: 241.02. HRMS: Anal. Calc. for [M+H]$^+$ C$_{11}$H$_{11}$Cl$_2$N$_2$: 241.0299. found: 241.0296.

Cap-144, Step c

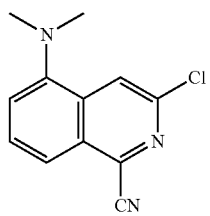 [SMILES: CN(C)c1cccc2c(C#N)nc(Cl)cc12]

Cap-144, step c was prepared from Cap-144, step b according to the procedure described for the preparation of Cap-139, step a. $R_t$=2.19 min (Cond.-D1); 95% homogenity index; LCMS: Anal. Calc. for [M+H]$^+$ C$_{12}$H$_{11}$ClN$_3$: 232.06. found: 232.03. HRMS: Anal. Calc. for [M+H]$^+$ C$_{12}$H$_{11}$ClN$_3$: 232.0642. found: 232.0631.

Cap-144

Cap-144 was prepared according to the procedure described for Cap-141. $R_t$=2.36 min (Cond.-D1); 90%; LCMS: Anal. Calc. for [M+H]$^+$ C$_{12}$H$_{12}$ClN$_2$O$_2$: 238.01. found: 238.09.

Caps-145 to -162

Caps-145 to 162 were prepared from the appropriate 1-chloroisoquinolines according to the procedure described for the preparation of Cap-138 (Method A) or Cap-139 (Method B) unless noted otherwise as outlined below.

| Cap # | Cap | Method | Hydrolysis | Rt (LC-Cond.); % homogeneity index; MS data |
|---|---|---|---|---|
| Cap-145 | (structure with Cl, CO$_2$H) Prepared from commercially available 1,3-dichloroisoquinoline | B | 12N HCl | 1.14 min (Cond.-MS-W1); 90%; LCMS: Anal. Calc. for [M + H]$^+$ C$_{10}$H$_7$ClNO$_2$: 208.02; found: 208.00. |
| Cap-146 | (structure with OMe, CO$_2$H) Prepared from commercially available 3-hydroxyisoquinoline | A | 5N NaOH | 1.40 min (Cond.-D1); 95%; LCMS: Anal. Calc. for [M + H]$^+$ C$_{11}$H$_{10}$NO$_3$: 204.07; found: 204.06. |
| Cap-147 | (structure with OMe, CO$_2$H) Prepared from commercially available 1-chloro-4-hydroxyisoquinoline | B | 5N NaOH | 0.87 min (Cond.-D1); 95%; LCMS: Anal. Calc. for [M + H]$^+$ C$_{11}$H$_{10}$NO$_3$: 204.07; found: 204.05. |

| Cap # | Cap | Method | Hydrolysis | Rt (LC-Cond.); % homogeneity index; MS data |
|---|---|---|---|---|
| Cap-148 | 7-methoxyisoquinoline-1-carboxylic acid structure; Prepared from commercially available 7-hydroxyisoquinoline | A | 5N NaOH | 0.70 min (Cond-D1); 95%; LCMS: Anal. Calc. for [M + H]$^+$ C$_{11}$H$_{10}$NO$_3$: 204.07; found: 204.05. |
| Cap-149 | 5-methoxyisoquinoline-1-carboxylic acid structure; Prepared from commercially available 5-hydroxyisoquinoline | A | 5N NaOH | 0.70 min (Cond.-D1); 95%; LCMS: Anal. Calc. for [M + H]$^+$ C$_{11}$H$_{10}$NO$_3$: 204.07; found: 204.05. |
| Cap-150 | 8-methoxyisoquinoline-1-carboxylic acid·TFA structure; Prepared from 8-methoxy-1-chloroisoquinoline, which can be synthesized following the procedure in WO 2003/099274 | A | 12N HCl | 0.26 min (Cond.-D1); 95%; LCMS: Anal. Calc. for [M + H]$^+$ C$_{11}$H$_{10}$NO$_3$: 204.07; found: 204.04. |
| Cap-151 | 3-chloro-5-methoxyisoquinoline-1-carboxylic acid structure; Prepared from 5-methoxy-1,3-dichloroisoquinoline, which can be synthesized following the procedure in WO 2005/051410. | B | 12N HCl | 1.78 min (Cond.-D1); 90%; LCMS: Anal. Calc. for [M + H]$^+$ C$_{11}$H$_9$ClNO$_3$: 238.03; found: 238.09. |
| Cap-152 | 3-chloro-6-methoxyisoquinoline-1-carboxylic acid structure; Prepared from commercially available 6-methoxy-1,3-dichloroisoquinoline | B | 12N HCl | 1.65 min (Cond.-D1); 95%; LCMS: Anal. Calc. for [M + H]$^+$ C$_{11}$H$_9$ClNO$_3$: 238.00; found: 238.09. |

-continued

| Cap # | Cap | Method | Hydrolysis | Rt (LC-Cond.); % homogeneity index; MS data |
|---|---|---|---|---|
| Cap-153 | 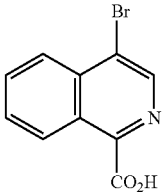 [SMILES: O=C(O)c1ncc(Br)c2ccccc12]<br>Prepared from 4-bromoisoquinoline, which can be synthesized following the procedure in WO 2003/062241 | A | 6N HCl | 1.18 min (Cond.-MS-W1); 95%; LCMS: Anal. Calc. for [M + H]$^+$ C$_{10}$H$_7$BrNO$_2$: 251.97; found: 251.95. |
| Cap-154 | 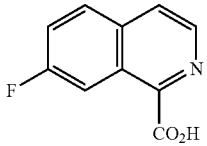 [SMILES: O=C(O)c1nccc2ccc(F)cc12]<br>Prepared from 7-fluoro-1-chloroisoquinoline, which can be synthesized following the procedure in WO 2003/099274 | B | 5N NaOH | 0.28 min (Cond.-MS-W1); 90%; LCMS: Anal. Calc. for [M + H]$^+$ C$_{10}$H$_7$FNO$_2$: 192.05; found: 192.03. |
| Cap-155 | 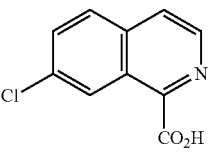 [SMILES: O=C(O)c1nccc2ccc(Cl)cc12]<br>Prepared from 1,7-dichloroisoquinoline, which can be synthesized following the procedure in WO 2003/099274 | B | 5N NaOH | 0.59 min (Cond.-MS-W1); 90%; LCMS: Anal. Calc. for [M + H]$^+$ C$_{10}$H$_7$ClNO$_2$: 208.02; found: 208.00. |
| Cap-156 | 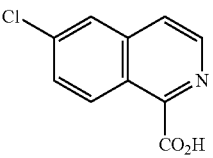 [SMILES: O=C(O)c1nccc2cc(Cl)ccc12]<br>Prepared from 1,6-dichloroisoquinoline, which can be synthesized following the procedure in WO 2003/099274 | B | 5N NaOH | 0.60 min (Cond.-MS-W1); 90%; LCMS: Anal. Calc. for [M + H]$^+$ C$_{10}$H$_7$ClNO$_2$: 208.02; found: 208.03. |
| Cap-157 | 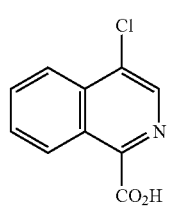<br>Prepared from 1,4-dichloroisoquinoline, which can be synthesized following the procedure in WO 2003/062241 | B |  | 1.49 min (Cond.-D1); 95%; LCMS: Anal. Calc. for [M + H]$^+$ C$_{10}$H$_{17}$ClNO: 208.02; found: 208.00. |

| Cap # | Cap | Method | Hydrolysis | Rt (LC-Cond.); % homogeneity index; MS data |
|---|---|---|---|---|
| Cap-158 | 5-chloroisoquinoline-1-carboxylic acid<br><br>Prepared from 1,5-dichloroisoquinoline, which can be synthesized following the procedure in WO 2003/099274 | B | 5N NaOH | 0.69 min (Cond.-MS-W1); 90%; LCMS: Anal. Calc. for [M + H]$^+$ C$_{10}$H$_7$ClNO$_2$: 208.02; found: 208.01. |
| Cap-159 | 5-fluoroisoquinoline-1-carboxylic acid<br><br>Prepared from 5-fluoro-1-chloroisoquinoline, which can be synthesized following the procedure in WO 2003/099274 | B | 5N NaOH | 0.41 min (Cond.-MS-W1); 90%; LCMS: Anal. Calc. for [M + H]$^+$ C$_{10}$H$_7$FNO$_2$: 192.05; found: 192.03. |
| Cap-160 | 6-fluoroisoquinoline-1-carboxylic acid<br><br>Prepared from 6-fluoro-1-chloroisoquinoline, which can be synthesized following the procedure in WO 2003/099274 | B | 5N NaOH | 0.30 min (Cond.-MS-W1); 90%; LCMS: Anal. Calc. for [M + H]$^+$ C$_{10}$H$_7$FNO$_2$: 192.05; found: 192.03. |
| Cap-161 | 4-(dimethylamino)quinoline-2-carboxylic acid<br><br>Prepared from 4-bromoquinoline-2-carboxylic acid and dimethylamine (DMSO, 100° C.) | — | — | 0.70 min (Cond. D1); 95%; LCMS: Anal. Calc. for [M + H]$^+$ C$_{12}$H$_{13}$N$_2$O$_2$: 217.10; found: 217.06. |
| Cap-162 | 7-methoxyquinoline-2-carboxylic acid<br><br>Prepared from m-anisidine following the procedure described in *J. Hetero. Chem.* 1993, 17 and *Heterocycles*, 2003, 60, 953. | — | — | 0.65 min (Cond.-M3); 95%; LCMS: Anal. Calc. for [M + H]$^+$ C$_{11}$H$_{10}$NO$_3$: 204.07; found: 203.94. |

Cap-163

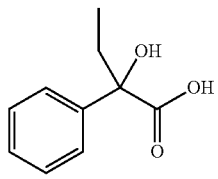

To a solution of 2-ketobutyric acid (1.0 g, 9.8 mmol) in diethylether (25 ml) was added phenylmagnesium bromide (22 ml, 1M in THF) dropwise. The reaction was stirred at ~25° C. under nitrogen for 17.5 h. The reaction was acidified with 1N HCl and the product was extracted with ethyl acetate (3×100 ml). The combined organic layer was washed with water followed by brine and dried over $MgSO_4$. After concentration in vacuo, a white solid was obtained. The solid was recrystallized from hexanes/ethyl acetate to afford Cap-163 as white needles (883.5 mg). $^1$H NMR (DMSO-$d_6$, δ=2.5 ppm, 500 MHz): 12.71 (br s, 1H), 7.54-7.52 (m, 2H), 7.34-7.31 (m, 2H), 7.26-7.23 (m, 1H), 5.52-5.39 (br s, 1H), 2.11 (m, 1H), 1.88 (m, 1H), 0.79 (app t, J=7.4 Hz, 3H).

Cap-164

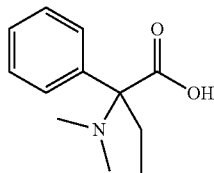

A mixture of 2-amino-2-phenylbutyric acid (1.5 g, 8.4 mmol), formaldehyde (14 mL, 37% in water), 1N HCl (10 mL) and 10% Pd/C (0.5 mg) in MeOH (40 mL) was exposed to $H_2$ at 50 psi in a Parr bottle for 42 h. The reaction was filtered over Celite and concentrated in vacuo, the residue was taken up in MeOH (36 mL) and the product was purified with a reverse phase HPLC (MeOH/$H_2$O/TFA) to afford the TFA salt of Cap-164 as a white solid (1.7 g). $^1$H NMR (DMSO-$d_6$, δ=2.5 ppm, 500 MHz) 7.54-7.47 (m, 5H), 2.63 (m, 1H), 2.55 (s, 6H), 2.31 (m, 1H), 0.95 (app t, J=7.3 Hz, 3H).

Cap-165

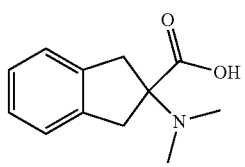

To a mixture of 2-amino-2-indanecarboxylic acid (258.6 mg, 1.46 mmol) and formic acid (0.6 ml, 15.9 mmol) in 1,2-dichloroethane (7 ml) was added formaldehyde (0.6 ml, 37% in water). The mixture was stirred at ~25° C. for 15 min then heated at 70° C. for 8 h. The volatile component was removed in vacuo, and the residue was dissolved in DMF (14 mL) and purified by a reverse phase HPLC (MeOH/$H_2$O/ TFA) to afford the TFA salt of Cap-165 as a viscous oil (120.2 mg). $^1$H NMR (DMSO-$d_6$, δ=2.5 ppm, 500 MHz): 7.29-7.21 (m, 4H), 3.61 (d, J=17.4 Hz, 2H), 3.50 (d, J=17.4 Hz, 2H), 2.75 (s, 6H). LC/MS: Anal. Calcd. for [M+H]$^+$ $C_{12}H_{16}NO_2$: 206.12. found: 206.07.

Cap-166a and -166b

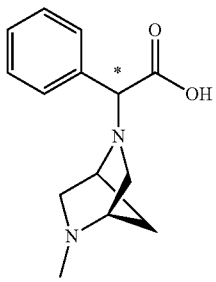

Cap-166a: Diastereomer-1
Cap-166b: Diastereomer-2

Caps-166a and -166b were prepared from (1S,4S)-(+)-2-methyl-2,5-diazabicyclo[2.2.1]heptane (2HBr) according to the method described for the synthesis of Cap-7a and Cap-7b, with the exception that the benzyl ester intermediate was separated using a semi-prep Chrialcel OJ column, 20×250 mm, 10 μm eluting with 85:15 heptane/ethanol mixture at 10 mL/min elution rate for 25 min. Cap-166b: $^1$H NMR (DMSO-$d_6$, δ=2.5 ppm, 500 MHz): 7.45 (d, J=7.3 Hz, 2H), 7.27-7.19 (m, 3H), 4.09 (s, 1H), 3.34 (app br s, 1H), 3.16 (app br s, 1H), 2.83 (d, J=10.1 Hz, 1H), 2.71 (m, 2H), 2.46 (m, 1H), 2.27 (s, 3H), 1.77 (d, J=9.8 Hz, 1H), 1.63 (d, J=9.8 Hz, 1H). LC/MS: Anal. Calcd. for [M+H]$^+$ $C_{14}H_{19}N_2O_2$: 247.14. found: 247.11.

Cap-167

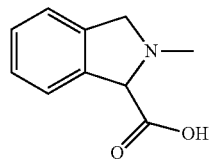

A solution of racemic Boc-1,3-dihydro-2H-isoindole carboxylic acid (1.0 g, 3.8 mmol) in 20% TFA/$CH_2Cl_2$ was stirred at ~25° C. for 4 h. All the volatile component was removed in vacuo. A mixture of the resultant crude material, formaldehyde (15 mL, 37% in water), 1N HCl (10 mL) and 10% Pd/C (10 mg) in MeOH was exposed to $H_2$ (40 PSI) in a Parr bottle for 23 h. The reaction mixture was filtered over Celite and concentrated in vacuo to afford Cap-167 as a yellow foam (873.5 mg). $^1$H NMR (DMSO-$d_6$, δ=2.5 ppm, 500 MHz) 7.59-7.38 (m, 4H), 5.59 (s, 1H), 4.84 (d, J=14 Hz, 1H), 4.50 (d, J=14.1 Hz, 1H), 3.07 (s, 3H). LC/MS: Anal. Calcd. for [M+H]⁺ $C_{10}H_{12}NO_2$: 178.09. found: 178.65.

Cap-168

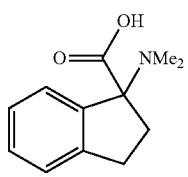

Racemic Cap-168 was prepared from racemic Boc-aminoindane-1-carboxylic acid according to the procedure described for the preparation of Cap-167. The crude material was employed as such.

Cap-169

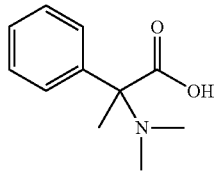

A mixture of 2-amino-2-phenylpropanoic acid hydrochloride (5.0 g, 2.5 mmol), formaldehyde (15 ml, 37% in water), 1N HCl (15 ml), and 10% Pd/C (1.32 g) in MeOH (60 mL) was placed in a Parr bottle and shaken under hydrogen (55 PSI) for 4 days. The reaction mixture was filtered over Celite and concentrated in vacuo. The residue was taken up in MeOH and purified by reverse phase prep-HPLC (MeOH/water/TFA) to afford the TFA salt of Cap-169 as a viscous semi-solid (2.1 g). ¹H NMR (CDCl₃, δ=7.26 ppm, 500 MHz): 7.58-7.52 (m, 2H), 7.39-7.33 (m, 3H), 2.86 (br s, 3H), 2.47 (br s, 3H), 1.93 (s, 3H). LC/MS: Anal. Calcd. for [M+H]⁺ $C_{11}H_{16}NO_2$: 194.12. found: 194.12.

Cap-170

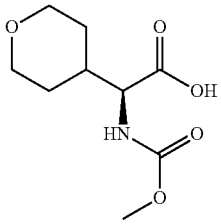

To (S)-2-amino-2-(tetrahydro-2H-pyran-4-yl)acetic acid (505 mg; 3.18 mmol; obtained from Astatech) in water (15 ml) was added sodium carbonate (673 mg; 6.35 mmol), and the resultant mixture was cooled to 0° C. and then methyl chloroformate (0.26 ml; 3.33 mmol) was added dropwise over 5 minutes. The reaction was allowed to stir for 18 hours while allowing the bath to thaw to ambient temperature. The reaction mixture was then partitioned between 1N HCl and ethyl acetate. The organic layer was removed and the aqueous layer was further extracted with 2 additional portions of ethyl acetate. The combined organic layers were washed with brine, dried over magnesium sulfate, filtered and concentrated in vacuo to afford Cap-170 a colorless residue. ¹H NMR (500 MHz, DMSO-d₆) δ ppm 12.65 (1H, br s), 7.44 (1H, d, J=8.24 Hz), 3.77-3.95 (3H, m), 3.54 (3H, s), 3.11-3.26 (2H, m), 1.82-1.95 (1H, m), 1.41-1.55 (2H, m), 1.21-1.39 (2H, m); LC/MS: Anal. Calcd. for [M+H]⁺ $C_9H_{16}NO_5$: 218.1. found 218.1.

Cap-171

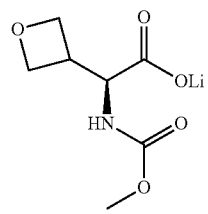

A solution of methyl 2-(benzyloxycarbonylamino)-2-(oxetan-3-ylidene)acetate (200 mg, 0.721 mmol; Il Farmaco (2001), 56, 609-613) in ethyl acetate (7 ml) and $CH_2Cl_2$ (4.00 ml) was degassed by bubbling nitrogen for 10 min. Dimethyl dicarbonate (0.116 ml, 1.082 mmol) and Pd/C (20 mg, 0.019 mmol) were then added, the reaction mixture was fitted with a hydrogen balloon and allowed to stir at ambient temperature overnight at which time TLC (95:5 $CH_2Cl_2$/MeOH: visualized with stain made from 1 g Ce(NH₄)₂SO₄, 6 g ammonium molybdate, 6 ml sulfuric acid, and 100 ml water) indicated complete conversion. The reaction was filtered through celite and concentrated. The residue was purified via Biotage® (load with dichloromethane on 25 samplet; elute on 25S column with dichloromethane for 3CV then 0 to 5% MeOH/dichloromethane over 250 ml then hold at 5% MeOH/dichloromethane for 250 ml; 9 ml fractions). Collected fractions containing desired material and concentrated to 120 mg (81%) of methyl 2-(methoxycarbonylamino)-2-(oxetan-3-yl)acetate as a colorless oil. ¹H NMR (500 MHz, CHLOROFORM-D) δ ppm 3.29-3.40 (m, J=6.71 Hz, 1H) 3.70 (s, 3H) 3.74 (s, 3H) 4.55 (t, J=6.41 Hz, 1H) 4.58-4.68 (m, 2H) 4.67-4.78 (m, 2H) 5.31 (br s, 1H). LC/MS: Anal. Calcd. for [M+H]⁺ $C_8H_{14}NO_5$: 204.2. found 204.0.

To methyl 2-(methoxycarbonylamino)-2-(oxetan-3-yl)acetate (50 mg, 0.246 mmol) in THF (2 mL) and water (0.5 mL) was added lithium hydroxide monohydrate (10.33 mg, 0.246 mmol). The resultant solution was allowed to stir overnite at ambient temperature. TLC (1:1 EA/Hex; Hanessian stain [1 g Ce(NH₄)₂SO₄, 6 g ammonium molybdate, 6 ml sulfuric acid, and 100 ml water]) indicated ~10% starting material remaining. Added an additional 3 mg LiOH and allowed to stir overnight at which time TLC showed no starting material remaining. Concentrated in vacuo and placed on high vac overnite providing 55 mg lithium 2-(methoxycarbonylamino)-2-(oxetan-3-yl)acetate as a colorless solid. ¹H NMR (500 MHz, MeOD) δ ppm 3.39-3.47 (m, 1H) 3.67 (s, 3H) 4.28 (d, J=7.93 Hz, 1H) 4.64 (t, J=6.26 Hz, 1H) 4.68 (t, J=7.02 Hz, 1H) 4.73 (d, J=7.63 Hz, 2H).

Cap-172

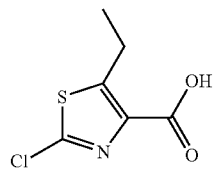

Cap-172, Step a

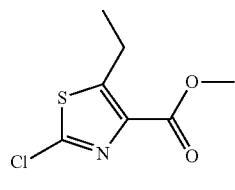

The following diazotization step was adapted from Barton, A.; Breukelman, S. P.; Kaye, P. T.; Meakins, G. D.; Morgan, D. J. *J. C. S. Perkin Trans I* 1982, 159-164: A solution of NaNO$_2$ (166 mg, 2.4 mmol) in water (0.6 mL) was added slowly to a stirred, cold (0° C.) solution of methyl 2-amino-5-ethyl-1,3-thiazole-4-carboxylate (186 mg, 1.0 mmol), CuSO$_4$.5H$_2$O (330 mg, 1.32 mmol), NaCl (260 mg, 4.45 mmol) and H$_2$SO$_4$ (5.5 mL) in water (7.5 mL). The mixture was stirred at 0° C. for 45 min and allowed to warm up to room temperature where it stirred further for 1 h before CuCl (118 mg) was added. This mixture was stirred further at room temperature for 16 h before it was diluted with brine and extracted with ether twice. The organic layers were combined, dried over MgSO$_4$ and concentrated to give methyl 2-chloro-5-ethylthiazole-4-carboxylate (i.e. Cap-172, step a) (175 mg, 85%) as an orange oil (80% pure) which was used directly in the next reaction. R$_f$=1.99 min (Cond.-MD1); LC/MS: Anal. Calcd. for [M+H]$^+$ C$_7$H$_9$ClNO$_2$S: 206.01. found: 206.05.

Cap-172

To a solution of methyl 2-chloro-5-ethylthiazole-4-carboxylate (175 mg) in THF/H$_2$O/MeOH (20 mL/3 mL/12 mL) was added LiOH (305 mg, 12.76 mmol). The mixture was stirred at room temperature overnight before it was concentrated down and neutralized with 1N HCl in ether (25 mL). The residue was extracted twice with ethyl acetate and the organic layers were combined, dried over MgSO$_4$ and evaporated to yield Cap-172 (60 mg, 74%) as a red solid which was used without further purification. $^1$H NMR (300 MHz, DMSO-d$_6$) δ ppm 13.03-13.42 (1H, m), 3.16 (2H, q, J=7.4 Hz), 1.23 (3H, t, J=7.5 Hz). R$_f$=1.78 min (Cond.-MD1); LC/MS: Anal. Calcd. for [M+H]$^+$ C$_6$H$_7$ClNO$_2$S: 191.99. found: 191.99.

Cap-173

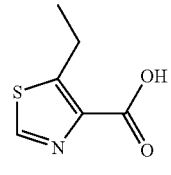

Cap-173, Step a

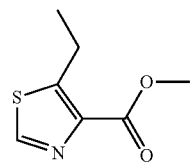

The following diazotization step was adapted from Barton, A.; Breukelman, S. P.; Kaye, P. T.; Meakins, G. D.; Morgan, D. J. *J. C. S. Perkin Trans I* 1982, 159-164: A solution of NaNO$_2$ (150 mg, 2.17 mmol) in water (1.0 mL) was added dropwise to a stirred, cold (0° C.) solution of methyl 2-amino-5-ethyl-1,3-thiazole-4-carboxylate (186 mg, 1.0 mmol) in 50% H$_3$PO$_2$ (3.2 mL). The mixture was stirred at 0° C. for 1 h and allowed to warm up to room temperature where it stirred further for 2 h. After recooling to 0° C., the mixture was treated slowly with a solution of NaOH (85 mg) in water (10 mL). The mixture was then diluted with saturated NaHCO$_3$ solution and extracted twice with ether. The organic layers were combined, dried over MgSO$_4$ and concentrated to give methyl 5-ethylthiazole-4-carboxylate (i.e. Cap-173, step a) (134 mg, 78%) as an orange oil (85% pure) which was used directly in the next reaction. R$_f$=1.58 min (Cond.-MD1); LC/MS: Anal. Calcd. for [M+H]$^+$ C$_2$H$_{10}$NO$_2$S: 172.05. found: 172.05.

Cap-173

To a solution of methyl 5-ethylthiazole-4-carboxylate (134 mg) in THF/H$_2$O/MeOH (18 mL/2.7 mL/11 mL) was added LiOH (281 mg, 11.74 mmol). The mixture was stirred at room temperature overnight before it was concentrated down and neutralized with 1N HCl in ether (25 mL). The residue was extracted twice with ethyl acetate and the organic layers were combined, dried over MgSO$_4$ and evaporated to yield Cap-173 (90 mg, 73%) as an orange solid which was used without further purification. $^1$H NMR (300 MHz, DMSO-d$_6$) δ ppm 12.74-13.04 (1H, m), 3.20 (2H, q, J=7.3 Hz), 1.25 (3H, t, J=7.5 Hz). $R_t$=1.27 min (Cond.-MD1); LC/MS: Anal. Calcd. for [M+H]$^+$ $C_6H_8NO_2S$: 158.03. found: 158.04.

Hz). $R_t$=0.39 min (Cond.-MD1); LC/MS: Anal. Calcd. for [M+H]$^+$ $C_8H_8NO_2$: 150.06. found: 150.07.

Cap-174

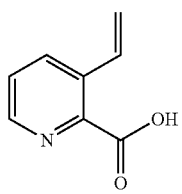

Cap-175

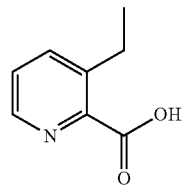

Cap-174, Step a

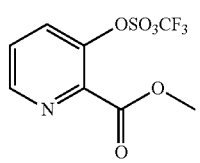

Cap-175, Step a

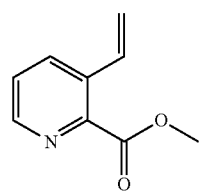

Triflic anhydride (5.0 g, 18.0 mmol) was added dropwise to a cold (0° C.) solution of methyl 3-hydroxypicolinate (2.5 g, 16.3 mmol) and TEA (2.5 mL, 18.0 mmol) in $CH_2Cl_2$ (80 mL). The mixture was stirred at 0° C. for 1 h before it was allowed to warm up to room temperature where it stirred for an additional 1 h. The mixture was then quenched with saturated $NaHCO_3$ solution (40 mL) and the organic layer was separated, washed with brine, dried over $MgSO_4$ and concentrated to give methyl 3-(trifluoromethylsulfonyloxy)picolinate (i.e. Cap-174, step a) (3.38 g, 73%) as a dark brown oil (>95% pure) which was used directly without further purification. $^1$H NMR (300 MHz, $CDCl_3$) δ ppm 8.72-8.79 (1H, m), 7.71 (1H, d, J=1.5 Hz), 7.58-7.65 (1H, m), 4.04 (3H, s). $R_t$=1.93 min (Cond.-MD1); LC/MS: Anal. Calcd. for [M+H]$^+$ $C_8H_7F_3NO_5S$: 286.00. found: 286.08.

Cap-174

To a solution of methyl 3-(trifluoromethylsulfonyloxy)picolinate (570 mg, 2.0 mmol) in DMF (20 mL) was added LiCl (254 mg, 6.0 mmol), tributyl(vinyl)stannane (761 mg, 2.4 mmol) and bis(triphenylphosphine)palladium dichloride (42 mg, 0.06 mmol). The mixture was heated at 100° C. overnight before a saturated solution of KF (20 mL) was added to the reaction mixture at room temperature. This mixture was stirred for 4 h before it was filtered through Celite and the pad of Celite was washed with ethyl acetate. The aqueous phase of the filtrate was then separated and concentrated down in vacuo. The residue was treated with 4N HCl in dioxanes (5 mL) and the resulting mixture was extracted with methanol, filtered and evaporated to afford Cap-174 (260 mg) as a green solid which was slightly contaminated with inorganic salts but was used without further purification. $^1$H NMR (300 MHz, DMSO-$d_6$) δ ppm 8.21 (1H, d, J=3.7 Hz), 7.81-7.90 (1H, m), 7.09 (1H, dd, J=7.7, 4.8 Hz), 6.98 (1H, dd, J=17.9, 11.3 Hz), 5.74 (1H, dd, J=17.9, 1.5 Hz), 5.20 (1H, d, J=11.0

To a solution of methyl 3-(trifluoromethylsulfonyloxy)picolinate (i.e. Cap 173, step a) (570 mg, 2.0 mmol), an intermediate in the preparation of Cap-174, in DMF (20 mL) was added LiCl (254 mg, 6.0 mmol), tributyl(vinyl)stannane (761 mg, 2.4 mmol) and bis(triphenylphosphine)palladium dichloride (42 mg, 0.06 mmol). The mixture was heated at 100° C. for 4 h before the solvent was removed in vacuo. The residue was taken up in acetonitrile (50 mL) and hexanes (50 mL) and the resulting mixture was washed twice with hexanes. The acetonitrile layer was then separated, filtered through Celite, and evaporated. Purification of the residue by flash chromatography on a Horizon instrument (gradient elution with 25% ethyl acetate in hexanes to 65% ethyl acetate in hexanes) afforded methyl 3-vinylpicolinate (i.e. Cap-175, step a) (130 mg, 40%) as a yellow oil. $^1$H NMR (300 MHz, $CDCl_3$) δ ppm 8.60 (1H, dd, J=4.6, 1.7 Hz), 7.94 (1H, d, J=7.7 Hz), 7.33-7.51 (2H, m), 5.72 (1H, d, J=17.2 Hz), 5.47 (1H, d, J=11.0 Hz), 3.99 (3H, s). $R_t$=1.29 min (Cond.-MD1); LC/MS: Anal. Calcd. for [M+H]$^+$ $C_9H_{10}NO_2$: 164.07. found: 164.06.

Cap-175, Step b

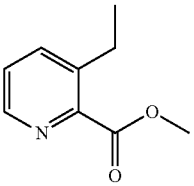

Palladium on carbon (10%, 25 mg) was added to a solution of methyl 3-vinylpicolinate (120 mg, 0.74 mmol) in ethanol (10 mL). The suspension was stirred at room temperature under an atmosphere of hydrogen for 1 h before it was filtered through Celite and the pad of Celite was washed with methanol. The filtrate was concentrated down to dryness to yield methyl 3-ethylpicolinate (i.e. Cap-175, step b) which was taken directly into the next reaction. $R_f$=1.15 min (Cond.-MD1); LC/MS: Anal. Calcd. for [M+H]$^+$ $C_9H_{12}NO_2$: 166.09. found: 166.09.

Cap-175

To a solution of methyl 3-ethylpicolinate in THF/H$_2$O/MeOH (5 mL/0.75 mL/3 mL) was added LiOH (35 mg, 1.47 mmol). The mixture was stirred at room temperature for 2 d before additional LiOH (80 mg) was added. After an additional 24 h at room temperature, the mixture was filtered and the solvent was removed in vacuo. The residue was then treated with 4N HCl in dioxanes (5 mL) and the resulting suspension was concentrated down to dryness to yield Cap-175 as a yellow solid which was used without further purification. $^1$H NMR (300 MHz, DMSO-$d_6$) δ ppm 8.47 (1H, dd, J=4.8, 1.5 Hz), 7.82-7.89 (1H, m), 7.53 (1H, dd, J=7.7, 4.8 Hz), 2.82 (2H, q, J=7.3 Hz), 1.17 (3H, t, J=7.5 Hz). $R_f$=0.36 min (Cond.-MD1); LC/MS: Anal. Calcd. for [M+H]$^+$ $C_8H_{10}NO_2$: 152.07. found: 152.10.

Cap-176

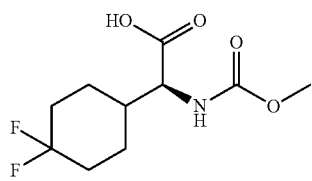 [SMILES: COC(=O)N[C@H](C(=O)O)C1CCC(F)(F)CC1]

Cap-176, Step a

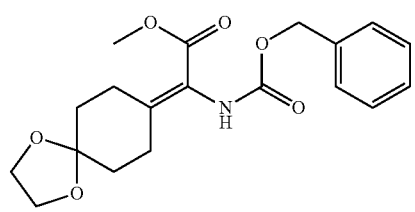 [SMILES: COC(=O)C(NC(=O)OCc1ccccc1)=C1CCC2(CC1)OCCO2]

A solution of 1,4-dioxaspiro[4.5]decan-8-one (15 g, 96 mmol) in EtOAc (150 mL) was added to a solution of methyl 2-(benzyloxycarbonylamino)-2-(dimethoxyphosphoryl)acetate (21.21 g, 64.0 mmol) in 1,1,3,3-tetramethylguanidine (10.45 mL, 83 mmol) and EtOAc (150 mL). The resulting solution was the stirred at ambient temperature for 72 h and then it was diluted with EtOAc (25 mL). The organic layer was washed with 1N HCl (75 mL), H2O (100 mL) and brine (100 mL), dried (MgSO$_4$), filtered and concentrated. The residue was purified via Biotage (5% to 25% EtOAc/Hexanes; 300 g column). The combined fractions containing the product were then concentrated under vacuum and the residue was re-crystallized from hexanes/EtOAc to give white crystals that corresponded to methyl 2-(benzyloxycarbonylamino)-2-(1,4-dioxaspiro[4.5]decan-8-ylidene)acetate (6.2 g) $^1$H NMR (400 MHz, CDCl$_3$-d) δ ppm 7.30-7.44 (5H, m), 6.02 (1H, br. s.), 5.15 (2H, s), 3.97 (4H, s), 3.76 (3H, br. s.), 2.84-2.92 (2H, m), 2.47 (2H, t, J=6.40 Hz), 1.74-1.83 (4H, m). LC (Cond. OL1): $R_f$=2.89 min. LC/MS: Anal. Calcd. For [M+Na]$^+$ $C_{19}H_{23}NNaO_6$: 745.21. found: 745.47.

Cap 176, Step b

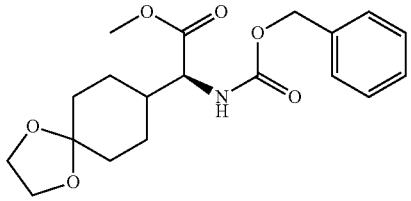 [SMILES: COC(=O)[C@@H](NC(=O)OCc1ccccc1)C1CCC2(CC1)OCCO2]

Ester Cap 176, step b was prepared from alkene Cap 176, step a according to the method of Burk, M. J.; Gross, M. F. and Martinez J. P. (*J. Am. Chem. Soc.,* 1995, 117, 9375-9376 and references therein): A 500 mL high-pressure bottle was charged with alkene Cap 176, step a (3.5 g, 9.68 mmol) in degassed MeOH (200 mL) under a blanket of N$_2$. The solution was then charged with (−)-1,2-Bis((2S,5S)-2,5-dimethylphospholano)ethane(cyclooctadiene)rhodium (I) tetrafluoroborate (0.108 g, 0.194 mmol) and the resulting mixture was flushed with N$_2$ (3×) and charged with H$_2$ (3×). The solution was shaken vigorously under 70 psi of H$_2$ at ambient temperature for 72 h. The solvent was removed under reduced pressure and the remaining residue was taken up in EtOAc. The brownish solution was then filtered through a plug of Silica Gel and eluted with EtOAc. The solvent was concentrated under vacuum to afford a clear oil corresponding to ester Cap 176, step b (3.4 g). $^1$H NMR (500 MHz, CDCl$_3$-d) δ ppm 7.28-7.43 (5H, m), 5.32 (1H, d, J=9.16 Hz), 5.06-5.16 (2H, m), 4.37 (1H, dd, J=9.00, 5.04 Hz), 3.92 (4H, t, J=3.05 Hz), 3.75 (3H, s), 1.64-1.92 (4 H, m), 1.37-1.60 (5H, m). LC (Cond. OL1): $R_f$=1.95 min. LC/MS: Anal. Calcd. For [M+H]$^+$ $C_{19}H_{26}NO_6$: 364.18. found: 364.27.

Cap 176, Step c

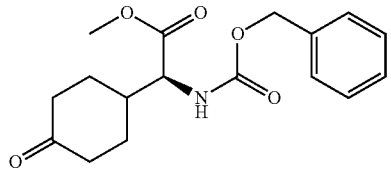 [SMILES: COC(=O)[C@@H](NC(=O)OCc1ccccc1)C1CCC(=O)CC1]

Ester Cap 176, step b (4.78 g, 13.15 mmol) was dissolved in THF (15 mL) followed by sequential addition of water (10 mL), glacial acetic acid (26.4 mL, 460 mmol) and dichloroacetic acid (5.44 mL, 65.8 mmol). The resulting mixture was stirred for 72 h at ambient temperature, and the reaction was quenched by slow addition of solid Na$_2$CO$_3$ with vigorous stirring until the release of gas was no longer visible. Crude product was extracted into 10% ethyl acetate-dichloromethane and the organic layers were combined, dried (MgSO$_4$) filtered and concentrated. The resulting residue was purified via Biotage (0 to 30% EtOAc/Hex; 25 g column) to afford ketone Cap 176, step c (3.86 g) as a clear oil. $^1$H NMR (400 MHz, CDCl$_3$-d) δ ppm 7.28-7.41 (5H, m), 5.55 (1H, d, J=8.28 Hz), 5.09 (2H, s), 4.46 (1H, dd, J=8.16, 5.14 Hz), 3.74 (3H, s), 2.18-2.46 (5H, m), 1.96-2.06 (1H, m), 1.90 (1H, ddd, J=12.99, 5.96, 2.89 Hz), 1.44-1.68 (2H, m, J=12.36, 12.36, 12.36, 12.36, 4.77 Hz). LC (Cond. OL1): $R_t$=1.66 min. LC/MS: Anal. Calcd. For [M+Na]+ $C_{17}H_{21}NNaO_5$: 342.13. found: 342.10.

Cap 176, Step d

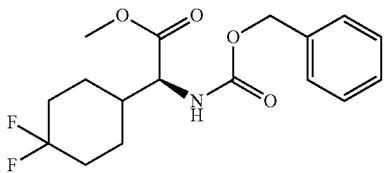 [SMILES: COC(=O)[C@@H](NC(=O)OCc1ccccc1)C1CCC(F)(F)CC1]

Deoxo-Fluor® (3.13 mL, 16.97 mmol) was added to a solution of ketone Cap 176, step c (2.71 g, 8.49 mmol) in $CH_2Cl_2$ (50 mL) followed by addition of a catalytic amount of EtOH (0.149 mL, 2.55 mmol). The resulting yellowish solution was stirred at rt overnight. The reaction was quenched by addition of sat. aq. $NaHCO_3$ (25 mL) and the mixture was extracted with EtOAc (3×75 mL)). The combined organic layers were dried ($MgSO_4$), filtered and dried to give a yellowish oil. The residue was purified via Biotage chromatography (2% to 15% EtOAc/Hex; 90 g column) and a white solid corresponding to the difluoro amino acid dilforide Cap 176, step d (1.5 g) was recovered. $^1H$ NMR (400 MHz, $CDCl_3$-d) δ ppm 7.29-7.46 (5H, m), 5.34 (1H, d, J=8.28 Hz), 5.12 (2H, s), 4.41 (1H, dd, J=8.66, 4.89 Hz), 3.77 (3H, s), 2.06-2.20 (2H, m), 1.83-1.98 (1H, m), 1.60-1.81 (4H, m), 1.38-1.55 (2H, m). $^{19}F$ NMR (376 MHz, $CDCl_3$-d) δ ppm −92.15 (1F, d, J=237.55 Hz), −102.44 (1F, d, J=235.82 Hz). LC (Cond. OL1): $R_t$=1.66 min. LC/MS: Anal. Calcd. For [2M+Na]+ $C_{34}H_{42}F_4N_2NaO_8$: 705.28. found: 705.18.

Cap 176, Step e

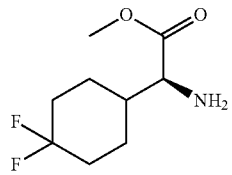

Difluoride Cap 176, step d (4 g, 11.72 mmol) was dissolved in MeOH (120 mL) and charged with Pd/C (1.247 g, 1.172 mmol). The suspension was flushed with $N_2$ (3×) and the reaction mixture was placed under 1 atm of $H_2$ (balloon). The mixture was stirred at ambient temperature for 48 h. The suspension was then filtered though a plug of Celite and concentrated under vacuum to give an oil that corresponded to amino acid Cap 176, step e (2.04 g) and that was used without further purification. $^1H$ NMR (400 MHz, DMSO-$d_6$) δ ppm 3.62 (3H, s), 3.20 (1H, d, J=5.77 Hz), 1.91-2.09 (2H, m), 1.50-1.88 (7H, m), 1.20-1.45 (2H, m). $^{19}F$ NMR (376 MHz, DMSO-$d_6$) δ ppm −89.39 (1F, d, J=232.35 Hz), −100.07 (1F, d, J=232.35 Hz). $^{13}C$ NMR (101 MHz, DMSO-$d_6$) δ ppm 175.51 (1C, s), 124.10 (1C, t, J=241.21, 238.90 Hz), 57.74 (1C, s), 51.39 (1C, s), 39.23 (1C, br. s.), 32.02-33.83 (2C, m), 25.36 (1C, d, J=10.02 Hz), 23.74 (1C, d, J=9.25 Hz). LC (Cond. OL2): $R_t$=0.95 min. LC/MS: Anal. Calcd. For [2M+H]+ $C_{18}H_{31}F_4N_2O_2$: 415.22. found: 415.40.

Cap 176, Step f

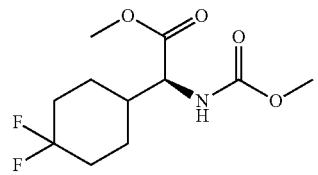 [SMILES: COC(=O)N[C@H](C(=O)OC)C1CCC(F)(F)CC1]

Methyl chloroformate (1.495 mL, 19.30 mmol) was added to a solution of amino acid Cap 176, step e (2 g, 9.65 mmol) and DIEA (6.74 mL, 38.6 mmol) in $CH_2Cl_2$ (100 mL). The resulting solution was stirred at rt for 3 h and volatiles were removed under reduced pressure. The residue was purified via Biotage (0% to 20% EtOAc/Hex; 90 g column). A clear oil that solidified upon standing under vacuum and corresponding to carbamate Cap-176, step f (2.22 g) was recovered. $^1H$ NMR (500 MHz, $CDCl_3$-d) δ ppm 5.27 (1H, d, J=8.55 Hz), 4.39 (1H, dd, J=8.85, 4.88 Hz), 3.77 (3H, s), 3.70 (3H, s), 2.07-2.20 (2H, m), 1.84-1.96 (1H, m), 1.64-1.82 (4H, m), 1.39-1.51 (2H, m). $^{19}F$ NMR (471 MHz, $CDCl_3$-d) δ ppm −92.55 (1F, d, J=237.13 Hz), −102.93 (1F, d, J=237.12 Hz). $^{13}C$ NMR (126 MHz, $CDCl_3$-d) δ ppm 171.97 (1C, s), 156.69 (1C, s), 119.77-125.59 (1C, m), 57.24 (1C, br. s.), 52.48 (1C, br. s.), 52.43 (1C, s), 39.15 (1C, s), 32.50-33.48 (2C, m), 25.30 (1C, d, J=9.60 Hz), 24.03 (1C, d, J=9.60 Hz). LC (Cond. OL1): $R_t$=1.49 min. LC/MS: Anal. Calcd. For [M+Na]+ $C_{11}H_{17}F_2NNaO_4$: 288.10. found: 288.03.

Cap-176

A solution of LiOH (0.379 g, 15.83 mmol) in Water (25 mL) was added to a solution of carbamate Cap-176, step f (2.1 g, 7.92 mmol) in THF (75 mL) and the resulting mixture was stirred at ambient temperature for 4 h. THF was removed under vacuum and the remaining aqueous phase was acidified with 1N HCl solution (2 mL) and then extracted with EtOAc (2×50 mL). The combined organic layers were dried ($MgSO_4$), filtered and concentrated to give a white foam corresponding to Cap-176 (1.92 g). $^1H$ NMR (400 MHz, DMSO-$d_6$) δ ppm 12.73 (1H, s), 7.50 (1H, d, J=8.78 Hz), 3.97 (1H, dd, J=8.53, 6.02 Hz), 3.54 (3H, s), 1.92-2.08 (2H, m), 1.57-1.90 (5H, m), 1.34-1.48 (1H, m), 1.27 (1H, qd, J=12.72, 3.26 Hz). $^{19}F$ NMR (376 MHz, DMSO-$d_6$) δ ppm −89.62 (1F, d, J=232.35 Hz), −99.93 (1F, d, J=232.35 Hz). LC (Cond. OL2): $R_t$=0.76 min. LC/MS: Anal. Calcd. For [M−H]+ $C_{10}H_{14}F_2NO_4$: 250.09. found: 250.10.

EXAMPLES

The present disclosure will now be described in connection with certain embodiments which are not intended to limit its scope. On the contrary, the present disclosure covers all alternatives, modifications, and equivalents as can be included within the scope of the claims. Thus, the following examples, which include specific embodiments, will illustrate one practice of the present disclosure, it being understood that the examples are for the purposes of illustration of certain embodiments and are presented to provide what is believed to be the most useful and readily understood description of its procedures and conceptual aspects.

Solution percentages express a weight to volume relationship, and solution ratios express a volume to volume relationship, unless stated otherwise. Nuclear magnetic resonance (NMR) spectra were recorded either on a Bruker 300, 400, or 500 MHz spectrometer; the chemical shifts (δ) are reported in parts per million.

Purity assessment and low resolution mass analysis were conducted on a Shimadzu LC system coupled with Waters Micromass ZQ MS system. It should be noted that retention times may vary slightly between machines. Unless noted otherwise, the LC conditions employed in determining the retention time ($R_t$) were:

Condition 1
Start % B=0
Final % B=100
Gradient time=3 min
Stop time=4 min
Flow Rate=4 mL/min
Wavelength=220 nm
Solvent A=0.1% TFA in 10% methanol/90% water
Solvent B=0.1% TFA in 90% methanol/10% water
Column=PHENOMENEX® 10u C18 3.0×50 mm
Condition 2
Start % B=0
Final % B=100
Gradient time=2 min
Stop time=3 min
Flow rate=4 mL/min
Wavelength=220 nm
Solvent A=10% MeOH/90% $H_2O$/0.1% TFA
Solvent B=90% MeOH/10% $H_2O$/0.1% TFA
Column 2=PHENOMENEX®-Luna 3.0×50 mm S10
Condition 2a
Start % B=0
Final % B=100
Gradient time=3 min
Stop time=4 min
Flow Rate=4 mL/min
Wavelength=220 nm
Solvent A=0.1% TFA in 10% methanol/90% water
Solvent B=0.1% TFA in 90% methanol/10% water
Column=PHENOMENEX®-Luna 3.0×50 mm S10
Condition 3
Start % B=0
Final % B=100
Gradient time=3 min
Stop time=4 min
Flow Rate=4 mL/min
Wavelength=220 nm
Solvent A=0.1% TFA in 10% methanol/90% water
Solvent B=0.1% TFA in 90% methanol/10% water
Column=PHENOMENEX®-Luna C18 10u 3.0×50 mm Condition 4
Start % B=0
Final % B=100
Gradient time=3 min
Stop time=4 min
Flow Rate=0.8 mL/min
Wavelength=220 nm
Solvent A=0.1% TFA in 10% methanol/90% water
Solvent B=0.1% TFA in 90% methanol/10% water
Column=PHENOMENEX®-Luna 2.0×50 mm, 3 μm
Oven Temp.=40° C.

Example QC-1

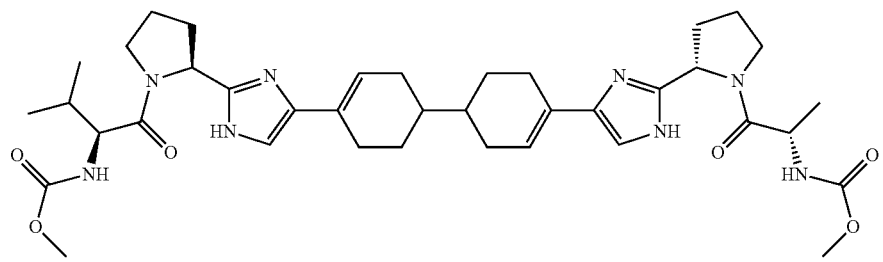 [SMILES: COC(=O)N[C@@H](C)C(=O)N1CCC[C@H]1c1nc(C2=CCC(C3CC=C(c4c[nH]c([C@@H]5CCCN5C(=O)[C@@H](NC(=O)OC)C(C)C)n4)CC3)CC2)c[nH]1]

Example QC-1a

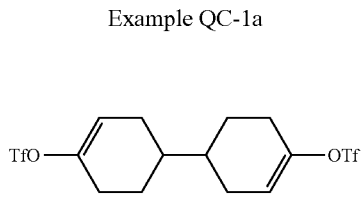

To a solution of bicyclohexanone (5.05 g, 26.0 mmol) and 2,6-diterbutyl phenol (11.75 g, 57.2 mmol) in 200 mL of dry dichloromethane was added triflic anhydride (9.10 mL, 54.6 mmol). The resulting solution was stirred at room temperature overnight. The solvent was removed under vacuum. The residue was taken up in hexanes and filtered. The filtrate was washed with 1 N HCl and brine. The organic layer was dried with potassium carbonate and concentrated. The crude product was purified by a flash chromatography (silica gel, 5% ethyl acetate/hexanes) to give Example QC-1a as a white solid (8.22 g, 69.0%, mixture of diastereomers). $^1$H NMR (500 MHz, $CDCl_3$) δ ppm 1.35-1.64 (m, 4H) 1.81-2.07 (m, 4H) 2.10-2.53 (m, 6H) 5.66-5.80 (m, 2H). LC/MS: Anal. Calcd. for $[M+H]^+$ $C_{14}H_{17}F_6O_6S_2$: 459.37. found (molecule did not ionize well in mass spec chamber).

Example QC-1b

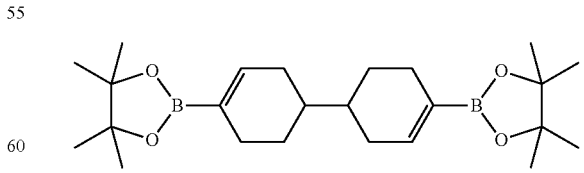

To a flask with bis(pinacolato)diboron (2.79 g, 11.0 mmol), potassium phenolate (1.98 g, 15.0 mmol), $PdCl_2(PPh_3)_2$ (0.21 g, 0.3 mmol) and triphenylphosphine (0.16 g, 0.6 mmol) was added 50 mL of dry toluene and (1a) (2.29 g, 5.0 mmol). The resulting mixture was stirred at 50° C. for 3 h. The reaction was quenched with water and extracted with toluene. The organic layers were combined, washed with brine, dried with MgSO$_4$ and concentrated. The crude product was purified by flash chromatography (silica gel, 5-80% ethyl acetate/hexanes) to give Example QC-1b as a white solid (1.14 g, 55%, mixture of diastereomers). $^1$H NMR (500 MHz, CDCl$_3$) δ ppm 1.10-1.19 (m, 2H) 1.24 (s, 24H) 1.31-1.43 (m, 2H) 1.73-1.90 (m, 4H) 1.97-2.29 (m, 6H) 6.52-6.58 (m, 2H).

Example QC-1c

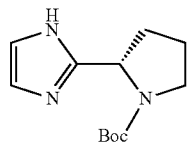 [SMILES: CC(C)(C)OC(=O)N1CCC[C@H]1c1ncc[nH]1]

Glyoxal (11 mL of 40% in water) was added drop-wise over 11 min to a methanol (32 mL) solution of ammonium hydroxide (32 mL) and (S)-Boc-prolinal (8.564 g, 42.98 mmol) and stirred at ambient temperature for 19 h. The volatile component was removed in vacuo and the residue was purified by a flash chromatography (silica gel, ethyl acetate) followed by a recrystallization (ethyl acetate, room temperature) to afford imidazole Example QC-1c as a white fluffy solid (4.43 g). $^1$H NMR (DMSO-D$_6$, δ=2.50, 400 MHz): 11.68/11.59 (br s, 1H), 6.94 (s, 1H), 6.76 (s, 1H), 4.76 (m, 1H), 3.48 (m, 1H), 3.35-3.29 (m, 1H), 2.23-1.73 (m, 4H), 1.39/1.15 (two s, 9H). LC (Cond. 2): RT=0.87 min; >95% homogeneity index. LC/MS: Anal. Calcd. for [M+H]$^+$ C$_{12}$H$_{20}$N$_3$O$_2$ 238.16. found 238.22.

Imidazole Example QC-1c had an ee of 98.9% when analyzed under chiral HPLC condition noted below:
Column: Chiralpak AD, 10 um, 4.6×50 mm
Solvent: 1.7% ethanol/heptane (isocratic)
Flow rate: 1 ml/min
Wavelength: either 220 or 256 nm
Relative retention time: 3.25 min (R), 5.78 min (S)

Example QC-1d

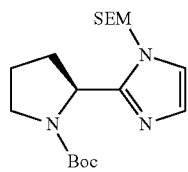 [SMILES: CC(C)(C)OC(=O)N1CCC[C@H]1c1nccn1COCC[Si](C)(C)C]

To a solution of Example QC-1c (4.98 g, 21.0 mmol) in 35 mL of dry dimethylformamide was added sodium hydride (0.88 g of 60% in mineral oil, 22.0 mmol). The resulting mixture was stirred at room temperature for 40 min. 2-(trimethylsilyl)ethoxymethyl chloride (3.75 mL, 21.0 mmol) was then added dropwise over 5 min. The resulting solution was stirred at room temperature for 2 h. The reaction was quenched with water, and extracted with ethyl acetate. The organic layers were combined, washed with brine, dried with MgSO$_4$ and concentrated. The crude product was purified by flash chromatography (silica gel, 35-50% ethyl acetate/hexanes) to give Example QC-1d as a colorless oil (6.30 g, 81.6%). $^1$H NMR (500 MHz, CDCl$_3$) δ ppm −0.03 (s, 9H) 0.76-0.99 (m, 2H) 1.20/1.38 (rotomers, s/s, 9H) 1.76-2.50 (m, 4H) 3.37-3.77 (m, 4H) 4.80-5.03 (m, 1H) 5.07-5.16 (m, Hz, 1H) 5.40/5.78 (rotomers, d/d, J=10.68/10.99 Hz, 1H) 6.85 (s, 1H) 6.96 (s, 1H). LC/MS: Anal. Calcd. for C$_{18}$H$_{34}$N$_3$O$_3$Si [M+H]$^+$ 368.24. found 368.43.

Example QC-1e

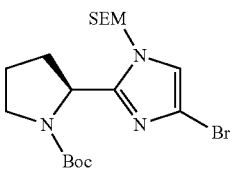 [SMILES: CC(C)(C)OC(=O)N1CCC[C@H]1c1nc(Br)cn1COCC[Si](C)(C)C]

To a solution of Example QC-1d (2.00 g, 5.45 mmol) in 30 mL of dry acetonitrile at 0° C. was added N-bromosuccinimide (0.97 g, 5.45 mmol) in 30 mL of dry acetonitrile dropwise over 10 min. The resulting solution was stirred at 0° C. for 2 h. The solvent was removed under vacuum. The residue was taken up in dichloromethane and washed with water. The aqueous layer was re-extracted with dichloromethane. The organic layers were combined, dried with MgSO$_4$ and concentrated. The crude product was purified by flash chromatography (silica gel, 15-40% ethyl acetate/hexanes) to give Example QC-1e as a light yellow oil (1.66, 68.3%). $^1$H NMR (500 MHz, CDCl$_3$) δ ppm −0.02 (s, 9H) 0.79-1.00 (m, 2H) 1.21/1.39 (rotomers, s/s, 9H) 1.81-2.08 (m, 2H) 2.10-2.41 (m, 2H) 3.36-3.74 (m, 4H) 4.85/4.99 (rotomers, m/m, 1H) 5.26 (m, 1H) 5.39/5.75 (rotomers, d/d, J=11.29/11.60 Hz, 1H) 6.93/6.95 (rotomers, s/s, 1H). LC/MS: Anal. Calcd. for C$_{18}$H$_{33}$$^{79}$BrN$_3$O$_3$Si [M]$^+$ 446.15. found 446.39.

Example QC-1f

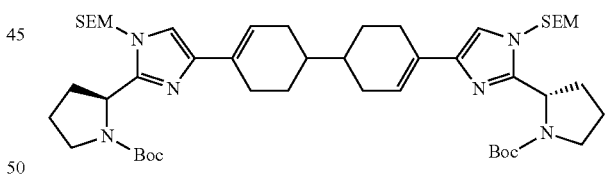

To a solution of Example QC-1b (456 mg, 1.1 mmol), Example QC-1e (982 mg, 2.2 mmol), sodium bicarbonate (554 mg, 6.6 mmol) in 21 mL of dimethylformamide and 7 mL of water was added Pd(PPh$_3$)$_4$ (127 mg, 0.11 mmol). The resulting solution was refluxed at 85° C. overnight. The solvent was removed under vacuum. The residue was taken up in 20% methanol/chloroform and washed with water. The organic layer was washed with brine, dried with MgSO$_4$ and concentrated. The crude product was purified by reserve phase HPLC system (methanol/water/TFA) to give Example QC-1f as a white solid (560 mg, 57%, mixture of diastereomers). $^1$H NMR (500 MHz, CDCl$_3$) δ ppm −0.02 (s, 18H) 0.74-1.03 (m, 4H) 1.19 (s, 9H) 1.38 (s, 9H) 1.43-1.59 (m, 2H) 1.76-2.54 (m, 20H) 3.32-3.58 (m, 6H) 3.58-3.77 (m, 2H) 4.81 (s, 1H) 4.97 (s, 1H) 5.07-5.21 (m, 2H) 5.21-5.32 (m, 1H) 5.60

(t, J=11.29 Hz, 1H) 5.71-5.96 (m, 2H) 6.79 (s, 2H). LC/MS: Anal. Calcd. for $C_{48}H_{81}N_6O_6Si_2$ [M+H]$^+$ 893.58. found 893.42.

Example QC-1 g

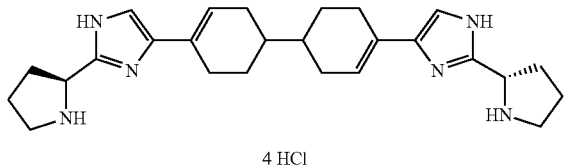 [SMILES: C1=C(c2c[nH]c([C@@H]3CCCN3)n2)CCC(C2CC=C(c3c[nH]c([C@@H]4CCCN4)n3)CC2)C1]

4 HCl

To a solution of Example QC-1f (164 mg, 0.18 mmol) in 2 mL of dichloromethane was added HCl (4 N in 1,4-dioxane, 2 mL). The resulting solution was stirred at room temperature overnight. The solvent was removed under vacuum. The residue was dissolved in minimal methanol and triturated with diethyl ether. The resulting solid was collected by filtration and washed with diethyl ether to give the HCl salt of Example QC-1 g as a light yellow solid (88.7 mg, 85.2%. mixture of diastereomers). LC/MS: Anal. Calcd. for $C_{26}H_{37}N_6$ [M+H]$^+$ 433.31. found 433.56.

Example QC-1

To a solution of Example QC-1 g (43.0 mg, 0.074 mmol) and (S)-2-(methoxycarbonylamino)-3-methylbutanoic acid (Cap-51) (26.0 mg, 0.148 mmol) in 2 mL of dry dimethylformamide was added diisopropylethylamine (78 µL, 0.446 mmol). The resulting mixture was stirred at room temperature for 5 min. HATU (59 mg, 0.156 mmol) was then added. The solution was stirred at room temperature for 2 h. The solvent was removed under vacuum. The crude product was purified by reverse phase HPLC (methanol/water/TFA). The like fractions were combined, neutralized with saturated NaHCO$_3$ aqueous solution, and extracted with EtOAc. The organic layers were dried with MgSO$_4$, and concentrated to give Example QC-1 (free base, mixture of diastereomers) as a white solid (29.5 mg, 53.4%). LC/MS: RT.=2.36 minutes (Cond. 1); LC/MS: Anal. Calcd. for $C_{40}H_{58}N_8O_6$ [M+H]$^+$ 747.46. found 747.72; HRMS: Anal. Calcd. for $C_{40}H_{58}N_8O_6$ [M+H]$^+$ 747.4558. found 747.4587.

Examples QC-2 to QC-5

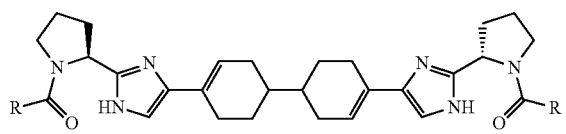

Examples QC-2 to QC-5 were prepared as free base diasteromeric mixtures by substituting the respective acids for Cap-51 and using the same method described for Example QC-1.

| Example | 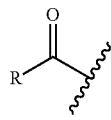 R | RT (LC-Cond); % homogeneity index; MS data |
|---|---|---|
| QC-2 | 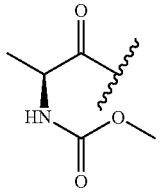 | RT = 2.08 minutes (Cond. 1); LC/MS: Anal. Calcd. for $C_{36}H_{50}N_8O_6$ [M + H]$^+$ 691.39; found 691.58; HRMS: Anal. Calcd. for $C_{36}H_{50}N_8O_6$ [M + H]$^+$ 691.3932; found 691.3965 |
| QC-3 | 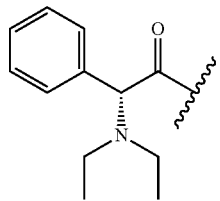 [SMILES: *C(=O)[C@@H](c1ccccc1)N(CC)CC] | RT = 2.10 minutes (Cond. 1); LC/MS: Anal. Calcd. for $C_{50}H_{66}N_8O_2$ [M + H]$^+$ 811.54; found 811.63; HRMS: Anal. Calcd. for $C_{50}H_{66}N_8O_2$ [M + H]$^+$ 811.5387; found 811.5426 |
| QC-4 | 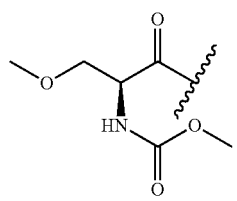 | RT = 1.54 minutes (Cond. 2); LC/MS: Anal. Calcd. for $C_{38}H_{54}N_8O_8$ [M + H]$^+$ 751.41; found 751.34; HRMS: Anal. Calcd. for $C_{38}H_{54}N_8O_8$ [M + H]$^+$ 751.4143; found 751.4175 |
| QC-5 |  | RT = 1.61 minutes (Cond. 3); LC/MS: Anal. Calcd. for $Q_{40}H_{58}N_8O_8$ [M + H]$^+$ 779.45; found 779.26 |

Example QC-6

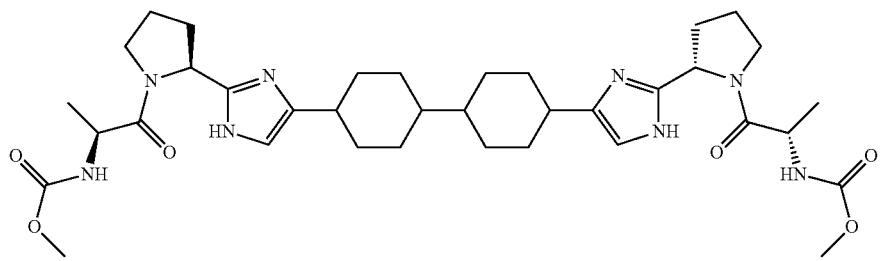 [SMILES: COC(=O)N[C@@H](C)C(=O)N1CCC[C@H]1c1nc(C2CCC(C3CCC(c4c[nH]c([C@@H]5CCCN5C(=O)[C@H](C)NC(=O)OC)n4)CC3)CC2)c[nH]1]

Example QC-6a

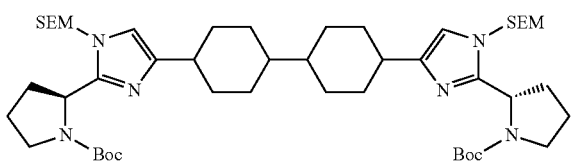 [SMILES: CC(C)(C)OC(=O)N1CCC[C@H]1c1nc(C2CCC(C3CCC(c4cn(COCC[Si](C)(C)C)c([C@@H]5CCCN5C(=O)OC(C)(C)C)n4)CC3)CC2)cn1COCC[Si](C)(C)C]

To a solution of Example QC-1 f (554 mg, 0.62 mmol) in 25 mL of methanol in a hydrogenation flask was added palladium (10% on carbon) (125 mg) under nitrogen. The flask was then mixed on the Parr Shaker at 40 atm overnight. After the reaction was complete, the mixture was filtered and the solvent was removed under vacuum to give Example QC-6a as a colorless glassy diastereomeric mixture (506 mg, 90.9%). LC/MS: Anal. Calcd. for $C_{48}H_{85}N_6O_6Si_2$ $[M+H]^+$ 897.61. found 897.25.

Example QC-6b

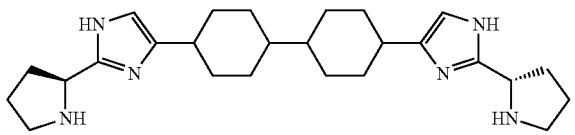 [SMILES: c1[nH]c([C@@H]2CCCN2)nc1C1CCC(C2CCC(c3c[nH]c([C@@H]4CCCN4)n3)CC2)CC1]

To a solution of Example QC-6a (506 mg, 0.56 mmol) in 10 mL of dichloromethane was added 4N HCl in dioxane (5 mL). The resulting solution was then stirred at room temperature overnight. The solvent was removed under vacuum.

The residue was dissolved in minimal methanol and triturated with diethyl ether. The resulting solid was collected by filtration and washed with diethyl ether to give the HCl salt diastereomeric mixture of Example QC-6b as a light brown solid (300 mg, 92%). LC/MS: Anal. Calcd. for $C_{26}H_{41}N_6$ $[M+H]^+$ 437.34. found 437.41.

Example QC-6

Example QC-6 was synthesized as free base from Example QC-6b and Cap-52 according to the procedure described for the synthesis of Example QC-1. LC/MS: RT=2.09 minutes (Cond. 1); LC/MS: Anal. Calcd. for $C_{36}H_{54}N_8O_6$ $[M+H]^+$ 695.42. found 695.70; LC/MS: Anal. Calcd. for $C_{36}H_{54}N_8O_6$ $[M+H]^+$ 695.4245. found 695.4275.

Examples QC-7 and QC-8

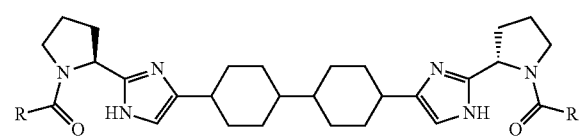

Examples QC-7 to QC-8 were prepared as free base diastereomeric mixtures by substituting the respective acids for Cap-52 using the same method described for Example QC-6.

| Example | 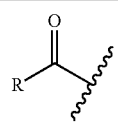 | RT (LC-Cond); % homogeneity index; MS data |
|---|---|---|
| QC-7 | 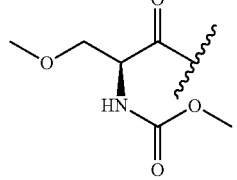 | RT = 2.09 minutes (Cond. 1); LC/MS: Anal. Calcd. for $C_{38}H_{58}N_8O_8$ $[M + H]^+$ 755.45; found 755.73; HRMS: Anal. Calcd. for $C_{38}H_{58}N_8O_8$ $[M + H]^+$ 755.4456; found 755.4488 |
| QC-8 | 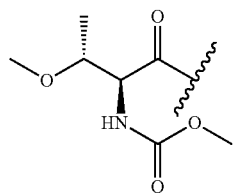 | RT = 1.64 minutes (Cond. 3); LC/MS: Anal. Calcd. for $C_{40}H_{62}N_8O_8$ $[M + H]^+$ 783.48; found 783.29; HRMS: Anal. Calcd. for $C_{40}H_{62}N_8O_8$ $[M + H]^+$ 783.4769; found 783.4807 |

Example QC-9

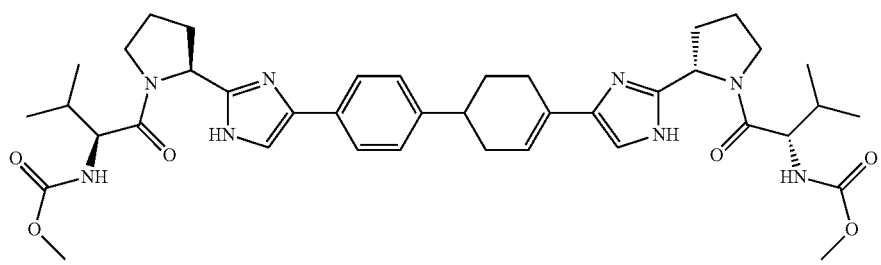 [SMILES: COC(=O)N[C@H](C(=O)N1CCC[C@H]1c1nc(C2=CCC(c3ccc(-c4c[nH]c([C@@H]5CCCN5C(=O)[C@@H](NC(=O)OC)C(C)C)n4)cc3)CC2)c[nH]1)C(C)C]

Example QC-9a

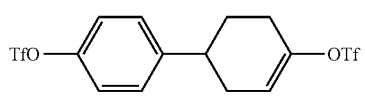

Example QC-9a was synthesized as a diastereomeric mixture from 4-(4-hydroxyphenyl)cyclohexanone according to the procedure described for the synthesis of Example QC-1a. $^1$H NMR (500 MHz, CDCl$_3$) δ ppm 1.89-1.99 (m, 1H) 2.04-2.12 (m, 1H) 2.25-2.61 (m, 4H) 2.85-2.95 (m, 1H) 5.83-5.87 (m, 1H) 7.20-7.24 (m, 2H) 7.26-7.31 (m, 2H). LC/MS: Anal. Calcd. for [M+H]$^+$ C$_{14}$H$_{12}$F$_6$O$_6$S$_2$: 453.99. found (molecule did not ionize well in mass spec chamber).

Example QC-9b

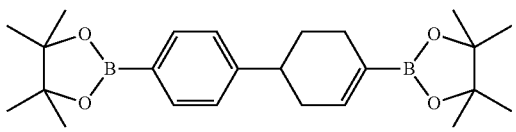

Example QC-9b was synthesized as a diastereomeric mixture from Example QC-9a according to the procedure described for the synthesis of Example QC-1b. $^1$H NMR (500 MHz, CDCl$_3$) δ ppm 1.27 (s, 12H) 1.32 (s, 12H) 1.62-1.75 (m, 1H) 1.88-1.98 (m, 1H) 2.14-2.46 (m, 4H) 2.73-2.85 (m, 1H) 6.60-6.67 (m, J=3.05 Hz, 1H) 7.22 (d, J=8.24 Hz, 2H) 7.74 (d, J=7.93 Hz, 2H). LC/MS: Anal. Calcd. for [M+H]$^+$ C$_{24}$H$_{36}$B$_2$O$_4$: 410.28. found (molecule did not ionize well in mass spec chamber).

Example QC-9c

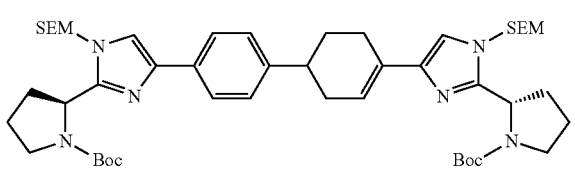

Example QC-9c was synthesized as a diastereomeric mixture from Example QC-1e and Example QC-9b according to the procedure described for the synthesis of Example QC-1f. $^1$H NMR (500 MHz, CDCl$_3$) δ ppm −0.01 (s, 18H) 0.82-1.00 (m, 4H) 1.24 (s, 9H) 1.39 (s, 9H) 1.72-2.68 (m, 14H) 2.73-2.96 (m, 1H) 3.29-3.81 (m, 8H) 4.81-5.05 (m, 2H) 5.06-5.23 (m, 2H) 5.31-5.43 (m, 1H) 5.76-5.90 (m, 1H) 6.48-6.67 (m, 1H) 6.74 (s, 1H) 7.10 (s, 1H) 7.22 (d, J=6.71 Hz, 2H) 7.67 (d, J=7.63 Hz, 2H); LC/MS: Anal. Calcd. for C$_{48}$H$_{77}$N$_6$O$_6$Si$_2$ [M+H]$^+$ 889.55. found 889.83.

Example QC-9d

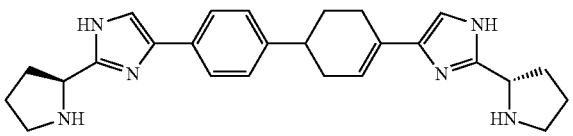

Example QC-9d was synthesized from Example QC-9c according to the procedure described for the synthesis of Example QC-1 g. LC/MS: Anal. Calcd. for C$_{26}$H$_{33}$N$_6$ [M+H]$^+$ 429.28. found 429.31.

Example QC-9

Example QC-9 was synthesized as a free base diastereomeric mixture from Example QC-9d and Cap-51 according to the procedure described for the synthesis of Example QC-1. LC/MS: RT=2.20 minutes (Cond. 1); LC/MS: Anal. Calcd. for C$_{40}$H$_{54}$N$_8$O$_6$ [M+H]$^+$ 743.42. found 743.31

Examples QC-10 to QC-12

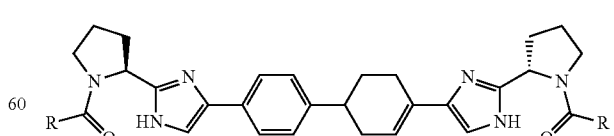

Examples QC-10 to QC-12 were prepared as free base diastereomeric mixtures by substituting the respective acids for Cap-51 using the same method described for Example QC-9.

| Example | 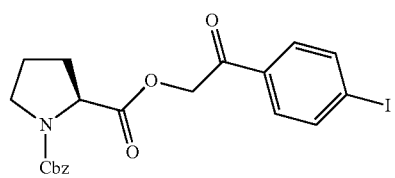 | RT (LC-Cond); % homogeneity index; MS data |
|---------|---|---|
| QC-10 | | RT = 1.94 minutes (Cond. 1); LC/MS: Anal. Calcd. for $C_{36}H_{46}N_8O_6$ [M + H]$^+$ 687.36; found 687.13. |
| QC-11 | | RT = 1.98 minutes (Cond. 1); LC/MS: Anal. Calcd. for $C_{38}H_{50}N_8O_8$ [M + H]$^+$ 747.38; found 747.46. |
| QC-12 | | RT = 2.09 minutes (Cond. 1); LC/MS: Anal. Calcd. for $C_{40}H_{54}N_8O_8$ [M + H]$^+$ 775.41; found 775.33. |

Example QC-13

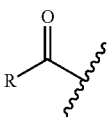

Example QC-13a

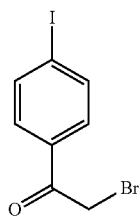

To a solution of 4-iodophenyl ethanone (14.76 g, 60.0 mmol) in 150 mL of dichloromethane was added bromine (9.5 g, 59.5 mmol) dropwise. The resulting solution was stirred at room temperature overnight. The solvent was removed under vacuum. The crude product was recrystallized with dichloromethane/hexanes to give Example QC-13a (11.8 g, 60.5%) as a grey solid. $^1$H NMR (500 MHz, CDCl$_3$) δ ppm 4.38 (s, 2H) 7.68 (d, J=8.55 Hz, 2H) 7.86 (d, J=8.85 Hz, 2H); LC/MS: Anal. Calcd. for $C_8H_7^{71}$BrIO [M+H]$^+$ 325.86. found 325.11.

Example QC-13b

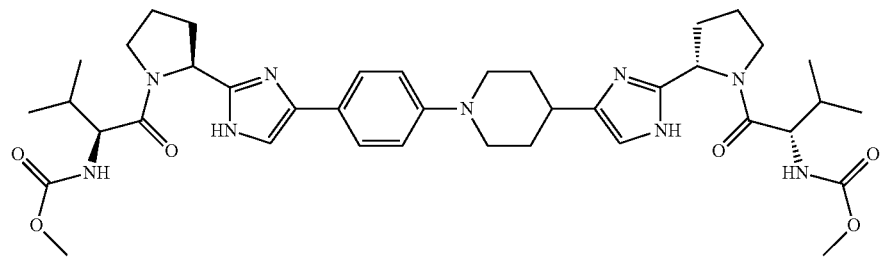 [SMILES: COC(=O)N[C@H](C(=O)N1CCC[C@H]1c1nc(-c2ccc(N3CCC(c4c[nH]c([C@@H]5CCCN5C(=O)[C@@H](NC(=O)OC)C(C)C)n4)CC3)cc2)c[nH]1)C(C)C]

To a solution of (S)-1-(benzyloxycarbonyl)pyrrolidine-2-carboxylic acid (6.5 g, 26.1 mmol) in 150 mL of ethyl acetate was added triethylamine (4.0 mL, 28.7 mmol) and Example QC-13a (8.5 g, 26.1 mmol) at 0° C. The resulting mixture was stirred at room temperature overnight. The reaction mixture was filtered. The filtrate was washed with saturated sodium bicarbonate aqueous solution, and brine. The organic layer was dried with MgSO$_4$ and concentrated. The crude product was purified by a flash chromatography (silica gel, 10-40% ethyl acetate/hexanes) to give the product as a white solid Example QC-13b (15.3 g, 85.4%). $^1$H NMR (500 MHz, CDCl$_3$) δ ppm 1.87-2.01 (m, 1H) 2.01-2.16 (m, 1H) 2.22-2.42 (m, 2H) 3.44-3.58 (m, 1H) 3.59-3.71 (m, 1H) 4.45-4.58 (m, 1H) 5.04-5.50 (m, 4H) 7.27-7.38 (m, 5H) 7.53 (d, J=8.24 Hz, 1H) 7.59 (d, J=8.24 Hz, 1H) 7.85 (dd, J=8.39, 3.81 Hz, 2H). LC/MS: Anal. Calcd. for $C_{21}H_{21}INO_5$ [M+H]$^+$ 494.05. found 494.32.

Example QC-13c

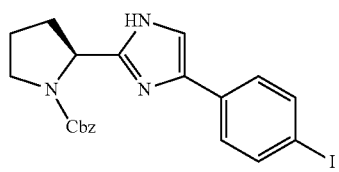 [SMILES: O=C(OCc1ccccc1)N1CCC[C@H]1c1nc(-c2ccc(I)cc2)c[nH]1]

A solution of Example QC-13b (15.3 g, 31 mmol) and ammonium acetate (18.0 g, 233 mmol) in 250 mL of xylene was stirred at 110° C. overnight. The reaction mixture was washed with brine, dried with MgSO$_4$ and concentrated. The crude product was purified by flash chromatography (silica gel, 25%-65% ethyl acetate/hexanes) to give the product as a yellow solid Example QC-13c (14.1 g, 96.1%). $^1$H NMR (300 MHz, CDCl$_3$) δ ppm 1.88-2.03 (m, 1H) 2.08-2.33 (m, 2H) 2.82-3.16 (m, 1H) 3.33-3.67 (m, 2H) 4.87-5.31 (m, 3H) 7.20 (s, 1H) 7.27-7.41 (m, 5H) 7.42-7.73 (m, 4H) 10.38/10.76 (s/s, 1H). LC/MS: Anal. Calcd. for C$_{21}$H$_{21}$IN$_3$O$_2$ [M+H]$^+$ 474.07. found 474.20.

Example QC-13d

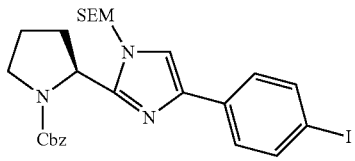 [SMILES: C[Si](C)(C)CCOCn1cc(-c2ccc(I)cc2)nc1[C@@H]1CCCN1C(=O)OCc1ccccc1]

To a solution of Example QC-13c (7.6 g, 16.06 mmol) in 30 mL of dimethylformamide was added sodium hydride (0.706 g, 17.66 mmol). The resulting mixture was stirred at room temperature for 40 min. 2-(Trimethylsilyl)ethoxymethyl chloride (2.84 ml, 16.06 mmol) was then added dropwise over 5 min. After stirred at room temperature for 2 h, the reaction was quenched with water and extracted with ethyl acetate. The combined organic layers were washed with brine, dried with MgSO$_4$ and concentrated. The crude product was purified by a flash chromatography (silica gel, 25%-50% ethyl acetate/hexanes) to give Example QC-13d (8.5 g, 88%) as an yellow oil [Note: the exact SEM-regiochemical make up of the product was not determined] $^1$H NMR (500 MHz, CDCl$_3$) δ ppm −0.02/−0.05 (rotomers, s/s, 9H) 0.73-0.99 (m, 2H) 1.87-2.02 (m, 1H) 2.09-2.34 (m, 2H) 2.34-2.48/2.50-2.68 (rotomers, m/m, 1H) 3.26-3.44 (m, 1H) 3.45-3.84 (m, 3H) 4.59/4.85 (rotomers, d/d, J=11.29 Hz/12.21 Hz, 1H) 4.89-5.13 (m, 3H) 5.16/5.90 (rotomers, d/d, J=10.99 Hz/10.99 Hz, 1H) 6.94-7.04 (m, 1H) 7.13-7.37 (m, 5H) 7.50 (d, J=8.55 Hz, 2H) 7.61-7.71 (m, 2H). Anal. Calcd. for C$_{27}$H$_{35}$IN$_3$O$_3$Si [M+H]$^+$ 604.15. found 604.44.

Example QC-13e

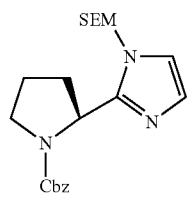 [SMILES: C[Si](C)(C)CCOCn1ccnc1[C@@H]1CCCN1C(=O)OCc1ccccc1]

To a solution of Example QC-1d (8.5 g, 23.13 mmol) in 150 mL of methanol was added 9 mL of 4 M HCl in dioxane. After stirring at room temperature overnight, the reaction solution was concentrated under vacuum to give a yellow oil. The yellow oil was placed under vacuum overnight to give (S)-4-iodo-2-(pyrrolidin-2-yl)-1-((2-(trimethylsilyl)ethoxy)methyl)-1H-imidazole HCl salt as a yellow solid.

To a mixture of (S)-2-(pyrrolidin-2-yl)-1-((2-(trimethylsilyl)ethoxy)methyl)-1H-imidazole HCl salt (7.03 g, 23.13 mmol) in sodium hydroxide aqueous solution (25.4 mL, 50.9 mmol) at 0° C. was added benzyl chloroformate (3.63 mL, 25.4 mmol) and sodium hydroxide aqueous solution (2M, 12.72 mL, 25.4 mmol) dropwise at the same time over 1 h. After stirring at 0° C. for 1 additional hour, the reaction mixture was extracted with ethyl acetate. The combined organic layers was dried with MgSO$_4$ and concentrated. The crude product was purified by a flash chromatography (silica gel, 25%-65% ethyl acetate/hexanes) to give Example QC-13e (8.8 g, 21.9 mmol, 95%). $^1$H NMR (500 MHz, CDCl$_3$) δ ppm −0.07/−0.03 (rotomers, s/s, 9H) 0.69-0.97 (m, 2H) 1.84-2.00 (m, 1H) 2.05-2.50 (m, 3H) 3.23-3.38 (m, 1H) 3.42-3.85 (m, 3H) 4.52/4.87 (rotomers, d/d, J=11.29 Hz, 1H) 4.89-5.14 (m, 3H) 5.13/5.85 (rotomers, d/d, J=10.99 Hz, 1H) 6.70/6.87 (rotomers, s/s, 1H) 6.94-6.99 (m, 1H) 6.99-7.05 (m, 1H) 7.25-7.33 (m, 4H). LC/MS: Anal. Calcd. for C$_{21}$H$_{32}$N$_3$O$_3$Si [M+H]$^+$ 402.22. found 402.26.

Example QC-13f

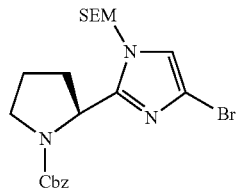 [SMILES: C[Si](C)(C)CCOCn1cc(Br)nc1[C@@H]1CCCN1C(=O)OCc1ccccc1]

To a solution of Example QC-13e (8.8 g, 21.91 mmol) in 100 mL of acetonitrile at 0° C. was added NBS (3.90 g, 21.91 mmol) in 60 mL of acetonitrile dropwise over 10 min. After stirring at 0° C. for 2 h, the solvent was removed under vacuum. The residue was dissolved in dichloromethane and washed with water. The organic layer was dried with MgSO$_4$ and concentrated. The crude product was purified by a flash chromatography (silica gel, 20%-30% ethyl acetate/hexanes) to give Example QC-13f (7.5 g, 15.61 mmol, 71.2%) as a yellow oil. $^1$H NMR (500 MHz, Chloroform-D) δ ppm −0.06/−0.02 (rotomers, s/s, 9H) 0.67-1.00 (m, 2H) 1.85-1.99 (m, 1H) 2.03-2.16 (m, 1H) 2.16-2.43 (m, 2H) 3.36 (t, J=8.24 Hz, 1H) 3.48-3.79 (m, 3H) 4.68/4.82 (rotomers, d/d, J=11.60 Hz, 1H) 4.85-5.15 (m, 3H) 5.27/5.81 (rotomers, d/d, J=11.29 Hz, 1H) 6.93/6.94 (s/s, 1H) 6.95-7.02 (m, 1H) 7.25-7.36 (m, 4H). LC/MS: Anal. Calcd. for C$_{21}$H$_{30}$$^{79}$BrN$_3$O$_3$Si [M]$^+$ 479.12. found 479.26.

Example QC-13g

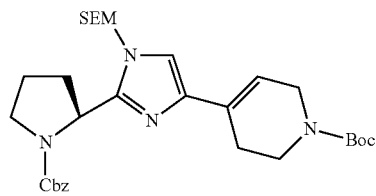 [SMILES: CC(C)(C)OC(=O)N1CC=C(c2cn(COCC[Si](C)(C)C)c([C@@H]3CCCN3C(=O)OCc3ccccc3)n2)CC1]

To a mixture of Example QC-13f (4.08 g, 8.49 mmol), tert-butyl 4-(4,4,5,5-tetramethyl-1,3,2-dioxaborolan-2-yl)-5,6-dihydropyridine-1(2H)-carboxylate (2.63 g, 8.49 mmol), and sodium bicarbonate (2.140 g, 25.5 mmol) in DME (180 ml) and water (60.0 ml) was added Tetrakis(triphenylphosphine)palladium (0) (0.491 g, 0.425 mmol). The resulting mixture was stirred at 85° C. overnight. The solvent was removed under vacuum. The aqueous mixture was extracted with 20% methanol/chloroform. The organic layer was washed with water, brine, dried with MgSO₄ and concentrated. The crude product was purified by a flash chromatography (silica gel, 25%-50% ethyl acetate/hexanes) to give Example QC-13g (3.8 g, 6.52 mmol, 76.8%) as a yellow oil. ¹H NMR (500 MHz, CDCl₃) δ ppm –0.06/–0.04 (rotomers, s/s, 9H) 0.69-0.97 (m, 2H) 1.45/1.47 (rotomers, s/s, 9H) 1.85-1.99 (m, 1H) 2.05-2.28 (m, 2H) 2.29-2.63 (m, 3H) 3.20-3.80 (m, 6H) 4.05 (s, 2H) 4.51/4.85 (rotomers, d/d, J=11.29 Hz, 1H) 4.81-5.13 (m, 3H) 5.11/5.86 (rotomers, d/d, J=10.99 Hz, 1H) 6.37 (s, 1H) 6.57/6.76 (rotomers, s/s, 1H) 7.01 (d, J=5.49 Hz, 1H) 7.19-7.37 (m, 4H). LC/MS: Anal. Calcd. for C₃₁H₄₇N₄O₅Si [M+H]⁺ 583.33. found 583.65.

Example QC-13h

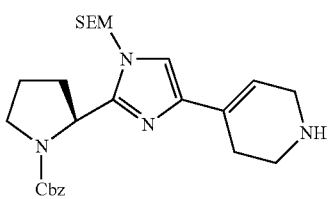 [SMILES: C[Si](C)(C)CCOCn1cc(C2=CCNCC2)nc1[C@@H]1CCCN1C(=O)OCc1ccccc1]

To a solution Example QC-13g (3.8 g, 6.52 mmol) in 40 mL of methanol was added HCl (4N in dioxane, 10 ml, 40.00 mmol). The solution was stirred at room temperature overnight. The solvent was removed under vacuum. To the residue was added saturated sodium bicarbonate. The mixture was extracted with ethyl acetate. The combined organic layers were washed with brine, dried with MgSO₄ and concentrated. The crude product was purified by flash chromatography (silica gel, 5% methanol/dichloromethane) to give Example QC-13h (1.90 g, 3.94 mmol, 60.4%) as a yellow solid. ¹H NMR (500 MHz, Chloroform-D) δ ppm –0.06/–0.02 (rotomers, s/s, 9H) 0.69-1.05 (m, 2H) 1.78-2.00 (m, 1H) 2.01-2.52 (m, 3H) 2.63 (s, 2H) 3.23-3.76 (m, 6H) 3.81 (s, 2H) 4.45-5.87 (m, 5H) 6.28 (s, 1H) 6.65/6.84 (rotomers, s/s, 1H) 6.93-7.09 (m, 1H) 7.17-7.42 (m, 4H). LC/MS: Anal. Calcd. for C₂₆H₃₉N₄O₃Si [M+H]⁺ 483.28. found 483.55.

Example QC-13i

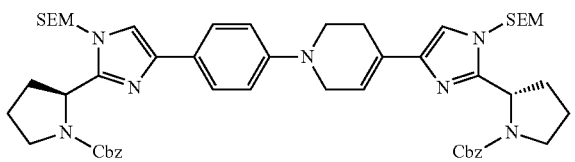 [SMILES: C[Si](C)(C)CCOCn1cc(C2=CCN(c3ccc(-c4cn(COCC[Si](C)(C)C)c([C@@H]5CCCN5C(=O)OCc5ccccc5)n4)cc3)CC2)nc1[C@@H]1CCCN1C(=O)OCc1ccccc1]

A mixture of Example QC-13d (3.19 g, 5.28 mmol), Example QC-13h (1.7 g, 3.52 mmol), copper(I) iodide (0.134 g, 0.704 mmol), L-proline (0.162 g, 1.409 mmol) and potassium carbonate (0.973 g, 7.04 mmol) in DMSO (30 ml) was bubbled with nitrogen for 10 min. The mixture was then stirred at 90° C. overnight. Water was added into the reaction. The mixture was extracted with ethyl acetate. The combined organic layers were washed with brine, dried with MgSO₄ and concentrated. The crude product was purified by flash chromatography (silica gel, 10%-40% ethyl acetate/hexanes then 40%-75% ethyl acetate/hexanes) to give Example QC-13i (1.30 g, 38.6%) as a yellow oil. [Note: the exact SEM-regiochemical make up of the product was not determined] ¹H NMR (300 MHz, CDCl₃) δ ppm –0.19-0.10 (m, 18H) 0.65-1.06 (m, 4H) 1.69-2.01 (m, 2H) 2.07-2.75 (m, 8H) 3.22-3.99 (m, 12H) 4.60 (t, J=10.61 Hz, 1H) 4.77-5.29 (m, 9H) 5.72 (d, J=10.61 Hz, 0.5H) 5.80-5.97 (m, 1H) 6.06 (s, 0.5H) 6.84-7.11 (m, 5H) 7.17-7.24 (m, 2H) 7.26-7.39 (m, 6H) 7.62-7.73 (m, 2H); LC (Cond. 1): RT=3.28 min; LC/MS: Anal. Calcd. for C₅₃H₇₂N₇O₆Si₂ [M+H]⁺ 958.51. found 958.84.

Example QC-13j

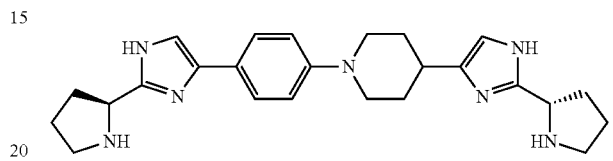

A mixture of Example QC-13i (600 mg, 0.626 mmol) and palladium on carbon (666 mg, 0.626 mmol) in methanol (10 ml) and ethyl acetate (10.00 mL) in a hydrogenation flask and was placed under hydrogen (50 atm.) for 16 h. The catalyst was filtered. To the filtrate was added 6 mL of 4 N HCl in 1,4-dioxane, and the resulting solution was stirred at room temperature overnight. The solvent was removed under vacuum. The residue was triturated with diethyl ether. The resulting solid was collected by filtration and washed with diethyl ether to give the HCl salt of Example QC-13j (232 mg, 86%) as a brown oil-like solid. ¹H NMR (500 MHz, DMSO-D₆) δ ppm 1.79-2.05 (m, 6H) 2.12-2.23 (m, 2H) 2.29-2.48 (m, 8H) 2.80-2.96 (m, 2H) 3.29-3.52 (m, 3H) 4.96-5.10 (m, 2H) 6.93/7.10 (s/s, 2H) 7.20-7.49 (m, 4H); LC (Cond. 2): RT=0.69 min; LC/MS: Anal. Calcd. for C₂₅H₃₄N₇ [M+H]⁺ 432.29. found 432.30.

Example QC-13

Example QC-13 was synthesized from Example QC-14j and Cap-51 according to the procedure described for the synthesis of Example QC-1, with the exception that the final purified material was not neutralized and Example QC13 was obtained as TFA salt. LC/MS: RT=1.95 min. (Cond. 1); LC/MS: Anal. Calcd. for C₃₉H₅₆N₉O₆ [M+H]⁺ 746.44. found 746.97.

Examples QC-14 and QC-15

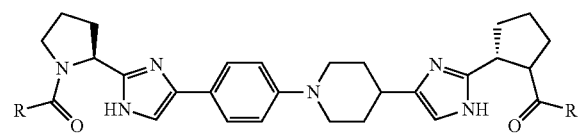

Examples QC-14 to QC-15 were prepared as TFA salts by substituting the respective acids for Cap-51 using the same method described for Example QC-13.

| Example | R (structure) | RT (LC-Cond); % homogeneity index; MS data |
|---|---|---|
| QC-14 | | RT = 1.64 minutes (Cond. 1); LC/MS: Anal. Calcd. for $C_{37}H_{52}N_9O_8$ [M + H]$^+$ 750.39; found 750.92; |
| QC-15 | | RT = 1.93 minutes (Cond. 1); LC/MS: Anal. Calcd. for $C_{41}H_{60}N_9O_6$ [M + H]$^+$ 774.47; found 774.76; |

Example QC-16 and QC-17

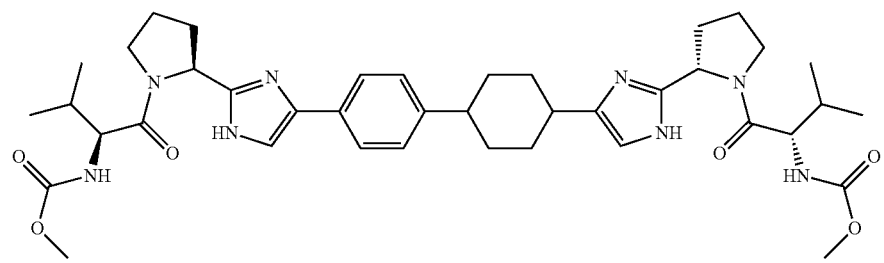

Example QC-16a

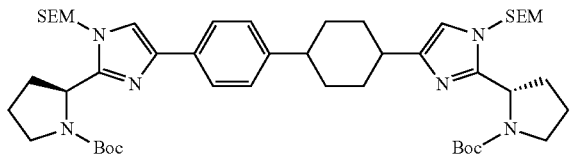

To a solution of Example QC-9c (260 mg, 0.3 mmol) in 10 mL of methanol was added palladium (10% on carbon) (100 mg) under nitrogen. The flask was then vacuumed and flushed with $N_2$ for 3 times. After being vacuumed again, the mixture was hydrogenated under $H_2$ balloon overnight. After the reaction was complete, the mixture was filtered and the solvent was removed under vacuum to give Example QC-16a as a greasy solid diastereomeric mixture. LC/MS: RT=3.28 minutes (Cond. 1); LC/MS: Anal. Calcd. for $C_{48}H_{87}N_6O_6Si_2$ [M+H]$^+$ 891.56. found 891.64.

Example QC-16b

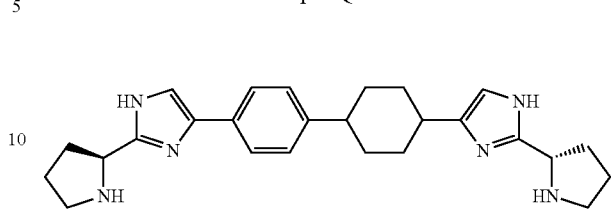

Example QC-16b was synthesized as a diastereomeic mixture from Example QC-16a according to the procedure described for the synthesis of Example QC-1g. LC/MS: RT=1.53 minutes and 1.64 minutes (Cond. 1); LC/MS: Anal. Calcd. for $C_{26}H_{35}N_6$ [M+H]$^+$ 431.29. found 431.25 and 431.26.

Example QC-16 and QC-17

Example QC-16 and QC-17 were synthesized as free bases from Example QC-13b and Cap-51 according to the procedure described for the synthesis of Example QC-1. The crude residue was purified by reverse phase HPLC (Acetonitrile/Water/NH$_4$OAc) to give two diastereomers QC-16 and QC-17. QC-16: $^1$HNMR (300 MHz, DMSO-D$_6$) δ ppm 0.73-0.93 (m, 12H), 1.45-2.30 (m, 18H), 2.40-2.65 (m, overlap with DMSO solvent peak), 3.15-3.45 (m, overlap with water peak), 3.52 (s, 6H), 3.75 (m, 3H), 4.01 (m, 2H), 5.03 (m, 2H), 7.00-7.70 (m, 6H), 11.23 (d, 1H), 11.66 (br, 1H); LC/MS: RT=2.20 minutes (Cond. 1); LC/MS: Anal. Calcd. for $C_{40}H_{56}N_8O_6$ [M+H]$^+$ 745.44. found 745.31; QC-17: $^1$H NMR (500 MHz, DMSO-D$_6$) δ ppm 0.75-0.93 (m, 12H), 1.30-1.62 (m, 4H), 1.75-2.22 (m, 14H), 2.40-2.65 (m, overlap with DMSO solvent peak), 3.15-3.45 (m, overlap with water peak), 3.53 (s, 6H), 3.78 (m, 3H), 4.04 (m, 2H), 5.03 (m, 2H), 7.10-7.70 (m, 6H), 11.25 (d, 1H), 11.68 (br, 1H); LC/MS: RT=2.20 minutes (Cond. 1); LC/MS: Anal. Calcd. for $C_{40}H_{56}N_8O_6$ [M+H]$^+$ 745.44. found 745.37.

Example M-1

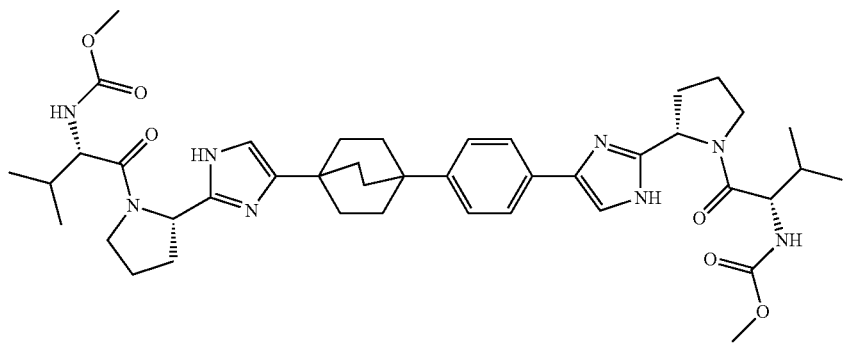 [SMILES: COC(=O)N[C@H](C(=O)N1CCC[C@H]1c1nc(-c2ccc(C34CCC(c5c[nH]c([C@@H]6CCCN6C(=O)[C@@H](NC(=O)OC)C(C)C)n5)(CC3)CC4)cc2)c[nH]1)C(C)C]

Example M-1a

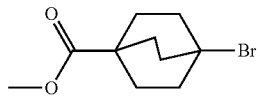

A dichloromethane (13 mL) solution of bromine (2.25 g, 14.1 mmol) was added drop-wise over 10 min to a heterogeneous refluxing mixture of 4-(methoxycarbonyl)bicycle[2.2.2]octane-1-carboxylic acid (2.02 g, 9.52 mmol) and mercuric oxide (3.5 g, 16.16 mmol) in dichloromethane (40 mL), and heating was continued for 3.3 h. After the reaction mixture was allowed to cool to room temperature, it was filtered and the resulting light orange filtrate was treated with MgSO$_4$ and filtered again. The volatile component of the filtrate was removed in vacuo, and the resulting residue was purified with a BIOTAGE® (5-10% ethyl acetate/hexanes) to afford Example M-1a as a white solid (1.37 g). $^1$H NMR (DMSO-d$_6$, δ=2.50, 400 MHz): 3.56 (s, 3H), 2.22-2.18 (m, 6H), 1.91-1.87 (m, 6H). LC (Cond. 2): RT=1.79 min. LC/MS: Anal. Calcd. for [M+H]$^+$ C$_{10}$H$_{16}$BrO$_2$: 247.03. found 247.33.

Example M-1b

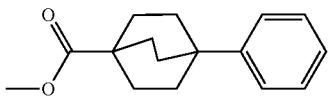 [SMILES: COC(=O)C12CCC(c3ccccc3)(CC1)CC2]

A benzene (65 mL) solution of Example M-1a (3.758 g, 15.21 mmol) was added drop-wise to a cooled (~−12° C.) mixture of benzene (200 mL) and aluminum trichloride (8.93 g, 67 mmol) over 15 min. The heterogeneous mixture was stirred for 1 h while allowing the cooling bath to thaw gradually to ~3° C., and then the cooling bath was removed and stirring was continued for ~14 h. The reaction mixture was then heated for ~4 hr, and after the mixture was allowed to cool to ambient condition and most of the volatile component was removed in vacuo. The residue was taken up dichloromethane (100 mL), poured into 150 mL of ice-water, and the phases were separated. The aqueous phase was washed with dichloromethane (50 mL), and the combined organic phase was washed with saturated sodium bicarbonate, dried (MgSO$_4$) and evaporated in vacuo. A silica gel mesh was prepared from the resulting crude material and submitted to flash chromatography (3-4.5% ethyl acetate/hexanes) to afford Example M-1b as an off-white solid (2.739 g). $^1$H NMR (DMSO-d$_6$, δ=2.50, 400 MHz): 7.34-7.26 (m, 4H), 7.18-7.13 (m, 1H), 3.59 (s, 3H), 1.86-1.76 (m, 12H). LC (Cond. 2): RT=2.04 min. LC/MS: Anal. Calcd. for [M+H]$^+$ C$_{16}$H$_{21}$O$_2$: 245.15. found 245.24.

Example M-1c

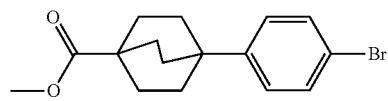

A chloroform (16 mL) solution of bromine (2.07 g, 12.95 mmol) was added drop-wise, via an addition funnel, over 13 min to a vigorously stirred mixture of Example M-1b (3.01 g, 12.33 mmol) and silver trifluoroacetate (3.15 g, 14.26 mmol) in chloroform (45 mL). After stirring for 105 min, the precipitate was filtered and washed with chloroform, and the filtrate was evaporated in vacuo. The resultant crude material was purified with flash chromatography (sample was loaded as a silica gel mesh; 4-6% ethyl acetate/hexanes) to afford Example M-1c as a white solid (3.495 g). $^1$H NMR (DMSO-d$_6$, δ=2.50, 400 MHz): 7.46 (d, J=8.5, 2H), 7.28 (d, J=8.8, 2H), 3.59 (s, 3H), 1.82-1.76 (m, 12H). LC (Cond. 2): RT=2.16 min. LC/MS: Anal. Calcd. for [M+H]$^+$ C$_{16}$H$_{20}$BrO$_2$: 323.06. found 323.18.

Example M-1d

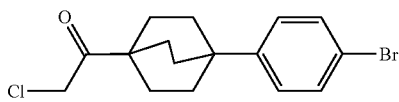

Butyl lithium (1.6 M/hexanes) (19.5 mL, 31.2 mmol) was added drop-wise over 15 min to a cooled (ice-water) tetrahydrofuran (10 mL) solution of i-Pr$_2$NH (4.5 mL, 31.6 mmol) and stirred for 25 min. The resultant LDA solution was added drop-wise over 15 min to a cooled (−78° C.) tetrahydrofuran (30 mL) solution of Example M-1c (2.48 g, 7.68 mmol) and chloroiodomethane (5.57 g, 31.6 mmol), and stirred for 130 min. A tetrahydrofuran (30 mL) solution of acetic acid (12 mL) was added drop-wise over 10 min to the above reaction mixture, and 20 min later the cooling bath was removed and stirring was continued for 30 min. Then the volatile component was removed in vacuo, and the residue was taken up in ethyl acetate (100 mL) and washed with saturated sodium bicarbonate solution (20 ml, 4×) and sodium thiosulfate solution (3.3 g in 30 mL water), dried (MgSO$_4$) and evaporated in vacuo. A silica gel mesh was prepared from the resulting crude material and submitted to flash chromatography (30-50% dichloromethane/hexanes) to afford Example M-1d as an off-white solid (2.02 g). $^1$H NMR (DMSO-d$_6$, δ=2.50, 400 MHz): 7.46 (d, J=8.6, 2H), 7.29 (d, J=8.6, 2H), 4.78 (s, 2H), 1.82-1.76 (m, 12H). HRMS: Anal. Calcd. for [M] C$_{16}$H$_{18}$BrClO: 340.0230. found 340.0234.

Example M-1e

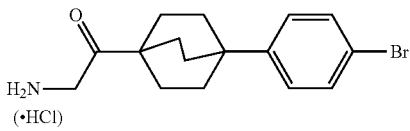
(•HCl)

Diformylimide sodium salt (0.7187 g, 7.18 mmol) and potassium iodide (0.148 g, 0.892 mmol) were added to a tetrahydrofuran (12.5 mL) solution of Example M-1d (1.01 g, 2.96 mmol), and the heterogeneous mixture was sonicated for a few minutes and then stirred at ambient condition for ~23 h. The reaction mixture was filtered, the filtered solid was washed with dichloromethane, and the filtrate was evaporated in vacuo. The resulting crude solid was transferred to a 350 mL pressure tube containing methanol (40 mL), water (20 mL) and concentrated HCl (2.5 mL), and the heterogeneous mixture was heated at 60° C. for 23 h. Removal of the volatile component in vacuo afforded Example M-1e as a light yellow solid (1.078 g), which was used in the next step without purification. $^1$H NMR (DMSO-d$_6$, δ=2.50, 400 MHz): 8.01 (br s, ~3H), 7.48 (d, J=8.6, 2H), 7.30 (d, J=8.6, 2H), 4.06 (s, 2H), 1.80 (app s, 12H). LC (Cond. 2): RT=1.58 min. LC/MS: Anal. Calcd. for [M+H]$^+$ C$_{16}$H$_{21}$BrNO: 322.08. found 322.21.

Example M-1f

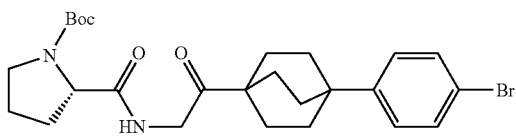 [SMILES: CC(C)(C)OC(=O)N1CCC[C@H]1C(=O)NCC(=O)C12CCC(c3ccc(Br)cc3)(CC1)CC2]

i-Pr$_2$EtN (1.02 mL, 2.5 mmol) was added drop-wise over a few minutes to a mixture of Example M-1e (0.84 g, 2.35 mmol), Boc-L-Proline (0.657 g, 3.05 mmol) and HATU (1.07 g, 2.82 mmol) in dimethylformamide (15 mL), and the reaction mixture was stirred for 50 min. The volatile component was removed in vacuo, and the residue was taken up in dichloromethane (80 mL) and washed with water (25 mL, 2×) and saturated sodium bicarbonate (25 mL, 2×). The organic layer was dried (MgSO$_4$) and evaporated in vacuo. The resultant crude material was submitted to a BIOTAGE® purification (100 g silica gel; 40-70% ethyl acetate/hexanes) to afford Example M-1f as a white dense solid (938 mg); a slightly impure sample of Example M-1f was also retrieved (118 mg). $^1$H NMR (DMSO-d$_6$, δ=2.50, 400 MHz): 7.92-7.85 (m, 1H), 7.47 (d, J=8.8, 2H), 7.29 (d, J=8.8, 2H), 4.16-4.01 (m, 3H), 3.40-3.24 (m, 2H; partially overlapped with water signal), 2.15-2.00 (m, 1H), 1.89-1.70 (m, 15H), 1.39/1.33 (two overlapped s, 9H). LC (Cond. 2): RT=2.10 min. LC/MS: Anal. Calcd. for [M+H]$^+$ C$_{26}$H$_{36}$BrN$_2$O$_4$: 519.19. found 519.18.

Example M-1g

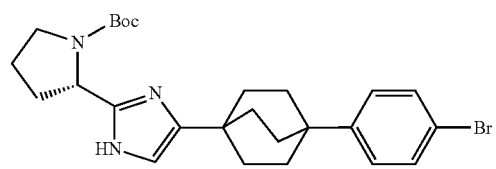 [SMILES: CC(C)(C)OC(=O)N1CCC[C@H]1c1nc(C23CCC(c4ccc(Br)cc4)(CC2)CC3)c[nH]1]

A mixture of Example M-1f (1.044 g, 2.01 mmol) and ammonium acetate (1.260 g, 16.35 mmol) in xylenes (12 mL) was heated with a microwave at 140° C. for 2 h. An additional ammonium acetate (240 mg, 3.11 mmol) was added and the mixture heated similarly for 30 min. Then the volatile component was removed in vacuo, and the residue was treated with dichloromethane (80 mL), water (20 mL) and saturated sodium bicarbonate solution (4 mL), and vigorously stirred and the phases were separated. The organic layer was dried (MgSO$_4$) and evaporated in vacuo. The crude material was purified with a BIOTAGE® (60-100% ethyl acetate/hexanes) to retrieve Example M-1g as a white foam (716 mg). $^1$H NMR (MeOH-d$_4$, δ=3.29, 400 MHz): 7.39 (d, J=8.6, 2H), 7.26 (d, J=8.8, 2H), 6.57/6.54 (overlapping br s, 1H), 4.78-4.72 (m, 1H), 3.66-3.57 (m, 1H), 3.48-3.41 (m, 1H), 2.32-1.86 (overlap of br m & app s, 16H), 1.43 (app s, 2.61H), 1.20 (s, 6.39H). LC (Cond. 2): RT=1.80 min. LC/MS: Anal. Calcd. for [M+H]$^+$ C$_{26}$H$_{35}$BrN$_3$O$_2$: 500.19. found 500.11.

Example M-1h

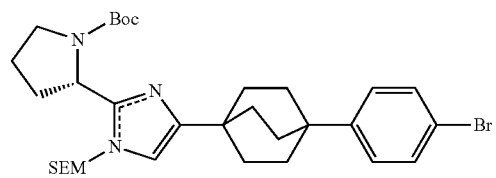

Sodium hydride (60%; 57 mg, 1.43 mmol) was added in one batch to a dimethylformamide (6 mL) solution of the imidazole Example M-1g (503 mg, 1.005 mmol), and the mixture was stirred for 70 min. Then, SEM-Cl (0.21 mL, 1.187 mmol) was added drop-wise over 30 sec to the above reaction mixture, and the heterogeneous mixture was stirred for 4.3 h. The volatile component was removed in vacuo, and the residue was partitioned between dichloromethane and water. The organic layer was dried (MgSO$_4$) and evaporated in vacuo. The resulting crude material was purified with a BIOTAGE® (20-35% ethyl acetate/hexanes) to afford Example M-1h as a white foam (417 mg). $^1$H NMR (DMSO-d$_6$, δ=2.50, 400 MHz): 7.46 (d, J=8.6, 2H), 7.31 (d, J=8.8, 2H), 6.78/6.75 (two overlapping s, 1H), 5.54 (br d, J=10.5, 0.32H), 5.28 (br d, J=11.1, 0.68H), 5.17 (app br d, J=10.8, 1H), 4.88 (br m, 0.32H), 4.78 (br m, 0.68H), 3.5-3.3 (m, 4H), 2.28-1.73 (overlap of br m & app s, 16H), 1.35 (s, 2.9H), 1.11

(s, 6.1H), 0.89-0.75 (m, 2H), −0.04 (s, 9H). LC/MS (Cond. 2): Anal. Calcd. for [M+H]⁺ $C_{32}H_{49}BrN_3O_3Si$: 630.27. found 630.33.

Example M-1i

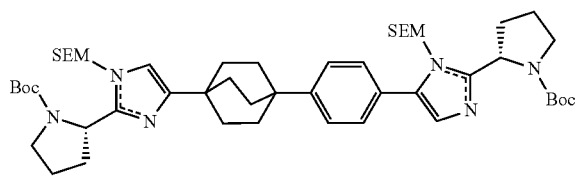

Palladium(II) acetate (15.7 mg, 0.070 mmol) was added in one batch to a 75 mL pressure tube containing Example M-1h (539 mg, 0.855 mmol), Example QC-1d (409.3 mg, 1.14 mmol), triphenylphosphine (35.5 mg, 0.135 mmol) and potassium carbonate (132 mg, 0.958 mmol) in dioxane (8 mL), and the reaction mixture was flushed with nitrogen for 5 min and heated with 120° C. oil bath for 16 h. After it was allowed to cool to ambient condition, the mixture was filtered and the filtrate was rotervaped. The resulting crude material was purified with a combination of BIOTAGE® (100 g silica gel; 40-80% ethyl acetate/hexanes) and a reverse phase HPLC (water/methanol/TFA). The combined HPLC fractions was neutralized with excess NH₃/methanol, rotervaped, and the resulting material was partitioned between dichloromethane (50 mL), water (30 mL) and satd. sodium bicarbonate solution (1 mL). The organic phase was dried (MgSO₄) and evaporated in vacuo to afford Example M-1i as a white foam (352 mg). The exact SEM regiochemical make up was not determined as it was inconsequential for the current purpose. ¹H NMR (DMSO-D₆, δ=2.50, 400 MHz): 7.45-7.35 (m, 4H), 6.93/6.91 (overlapping s, 1H), 6.79/6.76 (overlapping s, 1H), 5.56-5.52 (m, 0.7H), 5.37-5.16 (m, 3.3H), 5.05-4.78 (m, 2H), 3.56-3.33 (m, 8H), 2.29-1.76 (m, 20H), 1.37 (s, 6.53), 1.13/1.12 (overlapping s, 11.47H), 0.90-0.76 (m, 4H), −0.03/−0.06/−0.07 (overlapping s, 18H). LC/MS (Cond. 2): Anal. Calcd. for [M-SEM+H]⁺ $C_{44}H_{44}N_6O_5Si$: 786.49. found 787.50.

Example M-1j

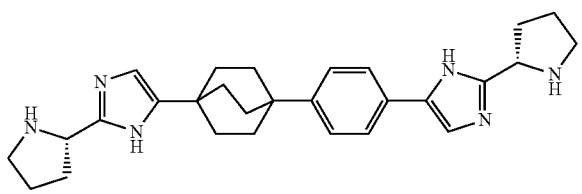 [SMILES: c1cc(C23CCC(c4cnc([C@@H]5CCCN5)[nH]4)(CC2)CC3)ccc1-c1cnc([C@@H]2CCCN2)[nH]1]

A mixture of water (2 mL) and concentrated HCl (1 mL) was added to a mixture of HCl/dioxanes (4.0 N, 7 mL) and Example M-1i (348 mg, 0.379 mmol), and the resultant solution was stirred at ambient condition until LC/MS analysis indicated completion of reaction (~48 h). The volatile component was removed in vacuo to afford Example M-1j (0.4HCl) as an off-white solid, weighing 244.6 mg (~16 mg above the theoretical yield). The sample contained unidentified impurities, and was used in the next step with out purification. LC (Cond. 2): RT=0.86 min. LC/MS: Anal. Calcd. for [M+H]⁺ $C_{28}H_{37}N_6$: 457.31. found 457.36.

Example M1

HATU (106.2 mg, 0.279 mmol) was added to a dimethylformamide (2 mL) solution of Example M-1j (4HCl salt) (78 mg, 0.129 mmol), (S)-2-(methoxycarbonylamino)-3-methylbutanoic acid (57.7 mg, 0.329 mmol) and i-Pr₂EtN (0.15 mL, 0.859 mmol), and the reaction mixture was stirred for 30 min. The volatile component was removed in vacuo, and the crude material was first passed through MCX (2 g; methanol wash; 2.0 M ammonia/methanol elution) and then submitted to a reverse phase HPLC purification (water/methanol/TFA) to afford a hygroscopic material. The purified material was free-based (MCX; methanol wash; 2.0 M ammonia/methanol elution) and dried in vacuo to afford Example M-1 as an off-white foam (43 mg). ¹H NMR (DMSO-D₆, δ=2.50, 400 MHz): 12.16-11.18 (collections of s, ~2H), 7.65-6.37 (m, 8H), 5.30-4.99 (m, 2H), 4.06-3.99 (m, 2H), 3.83-3.65 & 3.55-3.49 (m, 4H), 3.525/3.53/3.41 (three s, 6H), 2.18-1.75 (m, 22H), 0.89-0.81 (m, 12H). LC (Cond. 2): RT=1.33 min. LC/MS: Anal. Calcd. for [M+H]⁺ $C_{42}H_{59}H_8O_6$: 771.46. found 771.47.

Examples M-2 and M-3

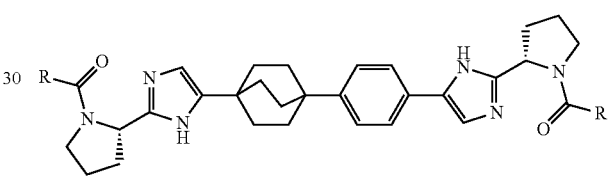

Examples M2 and M3 were prepared as TFA salts from Example M-1j and appropriate acids by employing the procedure described for the synthesis of Example M-1, with the exception that an additional purification was conducted with a second reverse phase HPLC system (water/acetonitrile/TFA) and that the final purified material was not free-based.

| Example | R group | RT (LC-Cond.); % homogeneity index; MS data |
|---|---|---|
| M-2 | methoxycarbonyl-alanine | 1.13 min (Cond. 2); >95%; LC/MS: Anal. Calcd. for [M + H]⁺ $C_{38}H_{51}N_8O_6$: 715.39; found 715.45 |
| M-3 | methoxycarbonyl-phenylalanine | 1.36 min (Cond. 2); >95%; LC/MS: Anal. Calcd. for [M + H]⁺ $C_{48}H_{55}N_8O_6$: 839.42; found 839.32 |

Example M-4

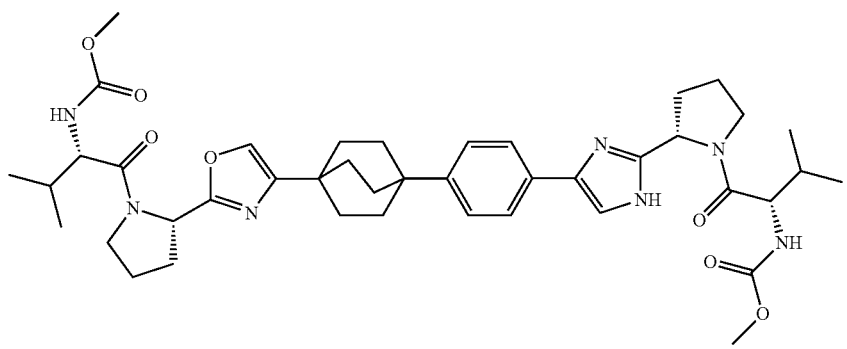 [SMILES: COC(=O)N[C@H](C(=O)N1CCC[C@H]1c1nc(-c2ccc(C34CCC(c5coc([C@@H]6CCCN6C(=O)[C@@H](NC(=O)OC)C(C)C)n5)(CC3)CC4)cc2)c[nH]1)C(C)C]

Example M-4-a

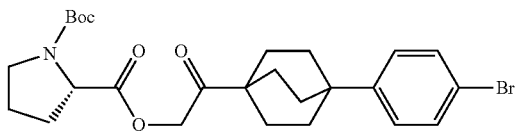 [SMILES: CC(C)(C)OC(=O)N1CCC[C@H]1C(=O)OCC(=O)C12CCC(c3ccc(Br)cc3)(CC1)CC2]

Hunig's base (500 µL, 2.87 mmol) was added drop-wise over ~1 min to a acetonitrile (5 mL)/dichloromethane (5 mL) semi-solution of (S)-1-(tert-butoxycarbonyl)pyrrolidine-2-carboxylic acid (645 mg, 3.00 mmol), Example M-1d (405 mg, 1.185 mmol) and potassium iodide (60.5 mg, 0.364 mmol), and the reaction mixture was stirred at ambient condition for ~18 h. The volatile component was removed in vacuo and the residue was partitioned between dichloromethane and water, dried (MgSO$_4$) and evaporated in vacuo. The resulting crude material was submitted to a BIOTAGE® purification (15-30% ethyl acetate/hexanes) to afford Example M-4-a as a white foam (559 mg). $^1$H NMR (DMSO-D$_6$, δ=2.50, 400 MHz): 7.47 (d, J=8.5, 2H), 7.29 (d, J=8.8, 2H), 5.13-4.91 (m, 2H), 4.29-4.23 (m, 1H), 3.39-3.26 (m, 2H), 2.30-2.16 (m, 1H), 2.11-2.03 (m, 1H), 1.89-1.73 (m, 14H), 1.39 (s, 3.59H), 1.34 (s, 5.41H). LC (Cond. 2): RT=2.20 min. LC/MS: Anal. Calcd. for [M-Boc+H]$^+$ C$_{21}$H$_{27}$BrNO$_3$: 420.12. found 420.13.

Example M-4-b

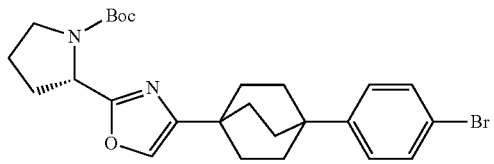 [SMILES: CC(C)(C)OC(=O)N1CCC[C@H]1c1nc(C23CCC(c4ccc(Br)cc4)(CC2)CC3)co1]

Ammonium acetate (825 mg, 10.70 mmol) was added into a toluene (10 mL) solution of Example M-4-a (556 mg, 1.068 mmol), and the mixture was heated under a Dean-Stark set up with a ~120° C. oil bath for ~5.7 h. After it was allowed to cool to ambient condition, the volatile component was removed in vacuo, and the residue was carefully partitioned between dichloromethane (50 mL) and 50% saturated sodium bicarbonate solution (20 mL). The organic layer was dried (MgSO$_4$), and evaporated in vacuo. The resulting crude material was purified with a BIOTAGE® (0-20% ethyl acetate/dichloromethane) to afford Example M-4-b (430 mg) as a dense solid, and Example M-1g (12 mg) as a white film. Example M-4-b: $^1$H NMR (DMSO-D$_6$, δ=2.50, 400 MHz): 7.67/7.63 (overlapped s, 1H), 7.47 (d, J=8.5, 2H), 7.31 (d, J=8.8, 2H), 4.85-4.73 (m, 1H), 3.48-3.42 (m, 1H), 3.38-3.32 (m, 1H), 2.29-2.15 (m, 1H), 1.95-1.75 (15H), 1.38 (s, 2.21H), 1.18 (s, 6.79H). LC (Cond. 2): RT=2.28 min. LC/MS: Anal. Calcd. for [M+H]$^+$ C$_{26}$H$_{34}$BrN$_2$O$_3$: 501.18. found 501.15.

Example M-4-c

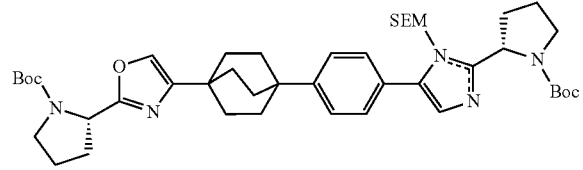

Palladium (II) acetate (11.1 mg, 0.049 mmol) was added in one batch to a 75 mL pressure tube containing Example M-4-b (412 mg, 0.822 mmol), Example QC-1d (323 mg, 0.879 mmol), triphenylphosphine (25.1 mg, 0.096 mmol) and potassium carbonate (139 mg, 1.004 mmol) in dioxane (7 mL), and the reaction mixture was flushed with nitrogen for a few minutes and heated with 122° C. oil bath for ~17 h. After it was allowed to cool to ambient condition, the mixture was filtered, and the filtrate was rotervaped. The resulting crude material was purified with a combination of BIOTAGE® (100 g silica gel; 40-100% ethyl acetate/hexanes) and reverse phase HPLC (water/methanol/TFA). The combined HPLC fraction was neutralized with excess ammonia/methanol, concentrated in vacuo, and the resulting material was partitioned between dichloromethane (50 mL) and dilute aqueous sodium bicarbonate solution (~6%, 32 mL). The organic phase was dried (MgSO$_4$) and evaporated in vacuo to afford the coupled product Example M-4-c as a white foam (162 mg). The exact regioisomeric make up of the SEM protecting group was not determined as it is inconsequential for the current purpose. $^1$H NMR (DMSO-D$_6$, δ=2.50, 400 MHz): 7.67/7.64 (overlapped s, 1H), 7.45-7.35 (m, 4H), 6.93/6.91 (overlapped s, 1H), 5.54-4.74 (m, 4H), 3.57-3.33 (m, 6H), 2.29-1.77 (m, 20H), 1.38/1.37 (overlapped s, 5.85H), 1.19/1.13 (overlapped s, 12.15H), 0.83-0.76 (2H), −0.06/−0.07

(overlapped s, 9H). LC (Cond. 2): RT=2.09 min. LC/MS: Anal. Calcd. for [M+H]+ C44H66N5O6Si: 788.48. found 788.54.

Example M-4-d

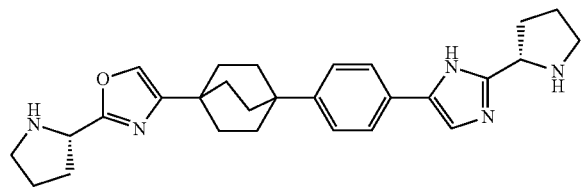 [SMILES: c1cc(C23CCC(c4coc([C@@H]5CCCN5)n4)(CC2)CC3)ccc1-c1cnc([C@@H]2CCCN2)[nH]1]

HCl (6 mL of 4.0 N HCl/dioxane) was added to Example M-4-c (158.1 mg, 0.201 mmol) and the mixture was stirred at ambient condition for 15 h, resulting in a formation of a heavy suspension. An aqueous HCl solution (1 mL of a solution prepared from 2 mL water and 1 mL concentrated HCl) was added to the above mixture and stirring was continued for 23.5 h. Removal of the volatile component in vacuo afforded the HCl salt of Example M-4-d, containing unidentified impurity, as off-white fluffy solid (118 mg). LC (Cond. 2): RT=1.06 min. LC/MS: Anal. Calcd. for [M+H]+ C28H36N5O: 458.29. found 458.32.

Example M-4

Example M-4 (TFA salt) was prepared from Example M-4-d according to the procedure described for the synthesis of Example M-1. $^1$H NMR (DMSO-D6, δ=2.50, 400 MHz): 14.50 (app br s, 2H), 8.02 (s, 1H), 7.67 (d, J=8.3, 2H), 7.63 (s, 1H), 7.52 (d, J=8.6, 2H), 7.35 (d, J=8.3, 2H), 5.13-5.09 (m, 1H), 5.03 (dd, J=3.9, 1H), 4.12-4.08 (m, 1H), 4.06-4.02 (m, 1H), 3.89-3.70 (m, 4H), 3.54/3.52 (overlapping s, 6H), 2.43-2.36 (m, 1H), 2.23-1.77 (m, 21H), 0.91-0.76 (12H). [Note: a minor component presumed to be a rotamer appears to be present and its chemical shift was not included]. LC (Cond. 2): RT=1.68 min. LC/MS: Anal. Calcd. for [M+H]+ C42H58N7O7: 772.44. found 772.51.

Example M-5

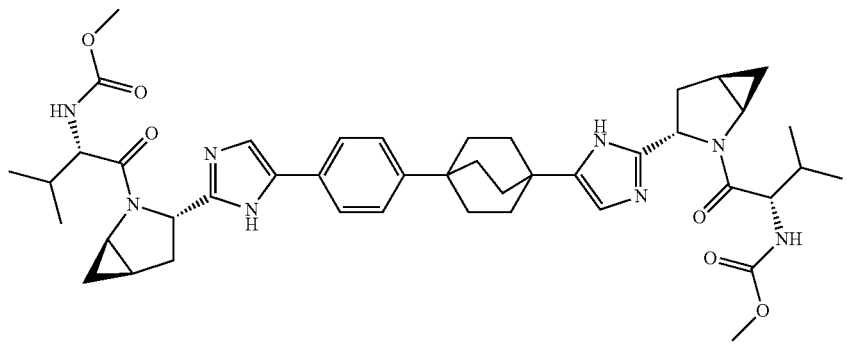 [SMILES: COC(=O)N[C@H](C(=O)N1[C@@H]2C[C@@H]2C[C@H]1c1ncc(-c2ccc(C34CCC(c5cnc([C@@H]6C[C@H]7C[C@H]7N6C(=O)[C@@H](NC(=O)OC)C(C)C)[nH]5)(CC3)CC4)cc2)[nH]1)C(C)C]

Example M-5a

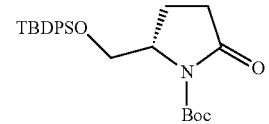

To a solution of (S)-5-(hydroxymethyl)pyrrolidin-2-one (10 g, 87 mmol) in dichloromethane (50 mL) was added tert-butylchlorodiphenylsilane (25.6 g, 93 mmol), triethylamine (12.1 mL, 87 mmol) and DMAP (1.06 g, 8.7 mmol). The mixture was stirred at room temperature until the starting pyrrolidinone was completely consumed, and then it was diluted with dichloromethane (50 mL) and washed with water (50 mL). The organic layer was dried (Na2SO4), filtered, and evaporated in vacuo, and the crude material was submitted to flash chromatography (silica gel; 30 to 100% of ethyl acetate/hexanes) to afford the silyl ether as a colorless oil (22.7 g, 74% yield). $^1$H NMR (400 MHz, DMSO-d6, δ=2.5 ppm) 7.69 (br s, 1H), 7.64-7.61 (m, 4H), 7.50-7.42 (m, 6H), 3.67-3.62 (m, 1H), 3.58-3.51 (m, 2H), 2.24-2.04 (m, 3H), 1.87-1.81 (m, 1H), 1.00 (s, 9H).

Di-tert-butyl dicarbonate (38.5 g, 177 mmol) was added in portions as a solid over 10 min to a dichloromethane (200 mL) solution of the silyl ether prepared above (31.2 g, 88.3 mmol), triethylamine (8.93 g, 88 mmol), and DMAP (1.08 g, 8.83 mmol) and stirred for 18 h at 24° C. Most of the volatile material was removed in vacuo and the crude material taken up in 20% ethyl acetate/hexanes and applied to a 2 L funnel containing 1.3 L of silica gel and then eluted with 3 L of 20% ethyl acetate/hexane and 2 L of 50% ethyl acetate). Upon concentration of the desired fractions in a rotary evaporator, a white slurry of solid formed which was filtered, washed with hexanes and dried in vacuo to afford carbamate Example M-5a as a white solid (32.65 g, 82% yield). $^1$H NMR (400 MHz, DMSO-d6, δ=2.5 ppm) 7.61-7.59 (m, 2H), 7.56-7.54 (m, 2H), 7.50-7.38 (m, 6H), 4.18 (m, 1H), 3.90 (dd, J=10.4, 3.6, 1H), 3.68 (dd, J=10.4, 2.1, 1H), 2.68-2.58 (m, 1H), 2.40-2.33 (m, 1H), 2.22-2.12 (m, 1H), 2.01-1.96 (m, 1H), 1.35 (s, 9H), 0.97 (s, 9H). LC (Cond. 2): RT=2.18 min. LC/MS: Anal. Calcd. for [M+Na]⁺ C₂₆H₃₅NNaO₄Si: 476.22. found 476.14.

Example M-5b

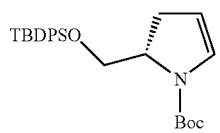

A three-necked flask equipped with a thermometer and a nitrogen inlet was charged with Example M-5a (10.05 g, 22.16 mmol) and toluene (36 mL), and lowered into −55° C. cooling bath. When the internal temperature of the mixture reached −50° C., lithium triethylborohydride (23 mL of 1.0 M/tetrahydrofuran, 23 mmol) was added dropwise over 30 min and the mixture stirred for 35 min while maintaining the internal temperature between −50° C. and −45° C. Hunig's base (16.5 mL, 94 mmol) was added dropwise over 10 min. Then, DMAP (34 mg, 0.278 mmol) was added in one batch, followed by the addition of trifluoroacetic anhydride (3.6 mL, 25.5 mmol) over 15 min, while maintaining the internal temperature between −50° C. and −45° C. The cooling bath was removed 10 min later, and the reaction mixture was stirred for 14 h while allowing it to rise to ambient temperature. It was diluted with toluene (15 mL), cooled with an ice-water bath, and treated slowly with water (55 mL) over 5 min. The phases were separated and the organic layer washed with water (50 mL, 2×) and concentrated in vacuo. The crude material was purified by flash chromatography (silica gel; 5% ethyl acetate/hexanes) to afford Example M-5b as a colorless viscous oil (7.947 g, 82% yield). ¹H NMR (400 MHz, DMSO-d₆, δ=2.5 ppm) 7.62-7.58 (m, 4H), 7.49-7.40 (m, 6H), 6.47 (br s, 1H), 5.07/5.01 (overlapping br d, 1H), 4.18 (br s, 1H), 3.89 (br s, 0.49H), 3.69 (br s, 1.51H), 2.90-2.58 (br m, 2H), 1.40/1.26 (overlapping br s, 9H), 0.98 (s, 9H). LC (Cond. 2): RT=2.41 min. LC/MS: Anal. Calcd. for [M+Na]⁺ C₂₆H₃₅NNaO₃Si: 460.23. found 460.19.

Examples M-5c-1 and M-5c-2

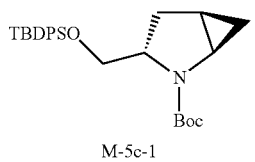

M-5c-1

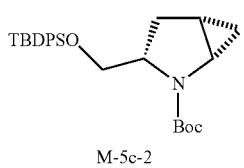

M-5c-2

Diethylzinc (19 mL of ~1.1 M in toluene, 20.9 mmol) was added dropwise over 15 min to a cooled (−30° C.) toluene (27 mL) solution of dihydropyrrole Example M-5b (3.94 g, 9.0 mmol). Chloroiodomethane (stabilized over copper; 3.0 mL, 41.2 mmol) was added dropwise over 10 min, and stirred while maintaining the bath temperature at −25° C. for 1 h and between −25° C. and −21° C. for 18.5 h. The reaction mixture was opened to the air and quenched by the slow addition of 50% saturated sodium bicarbonate solution (40 mL), and then removed from the cooling bath and stirred at ambient temperature for 20 min. It was filtered through a filter paper and the white cake was washed with 50 mL of toluene. The organic phase of the filtrate was separated and washed with water (40 mL, 2×), dried (MgSO₄) and concentrated in vacuo. The crude material was purified using a BIOTAGE® system (350 g silica gel; sample was loaded with 7% ethyl acetate/hexanes; eluted with 7-20% ethyl acetate/hexanes) to afford Examples M-5c-1/5c-2 as a colorless viscous oil, mainly as the trans isomer (3.691 g, 90.7%). [Note: the exact trans/cis ratio was not determined at this stage]. ¹H NMR (DMSO-d₆, δ=2.50, 400 MHz) of Example M-5c-1: 7.62-7.60 (m, 4H), 7.49-7.40 (m, 6H), 3.76 (br m, 1H), 3.67 (br m, 2H), 3.11-3.07 (m, 1H), 2.23 (br m, 1H), 2.03 (br m, 1H), 1.56-1.50 (m, 1H), 1.33 (br s, 9H), 1.00 (s, 9H), 0.80-0.75 (m, 1H), 0.30 (br m, 1H). LC (Cond. 2): RT=2.39 min. LC/MS: Anal. Calcd. for [M+Na]⁺ C₂₇H₃₇NNaO₃Si: 474.24. found 474.14.

Examples M-5d-1 and M-5d-2

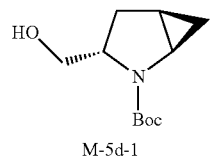 [SMILES: CC(C)(C)OC(=O)N1[C@H](CO)C[C@H]2C[C@H]21]

M-5d-1

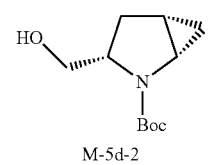 [SMILES: CC(C)(C)OC(=O)N1[C@H](CO)C[C@@H]2C[C@@H]21]

M-5d-2

TBAF (7.27 mL of 1.0 M in THF, 7.27 mmol) was added dropwise over 5 min to a THF (30 mL) solution of Examples M-5c-1/−5c-2 (3.13 g, 6.93 mmol) and the mixture was stirred at ambient condition for 4.75 hours. After it was treated with saturated NH₄Cl solution (5 mL), most of the volatile component was removed in vacuo and the residue was partitioned between CH₂Cl₂ (70 mL) and 50% saturated NH₄Cl solution (30 mL). The aqueous phase was extracted with CH₂Cl₂ (30 mL), and the combined organic phase was dried (MgSO₄), filtered, concentrated in vacuo, and then exposed to high vacuum overnight. The resulting crude material was purified with a BIOTAGE® (40-50% EtOAc/hexanes) to afford Examples M-5d-1/5d-2 as colorless oil, mainly as the trans isomer, contaminated with traces of lower R_f impurities (1.39 g, ~94%). [Note: the exact trans/cis ratio was not been determined at this stage]. ¹H NMR (DMSO-d₆, δ=2.50, 400 MHz) of Example M-5d-1: 4.70 (app t, J=5.7, 1H), 3.62-3.56 (m, 1H), 3.49-3.44 (m, 1H), 3.33-3.27 (m, 1H), 3.08-3.04 (m, 1H), 2.07 (br m, 1H), 1.93-1.87 (m, 1H), 1.51-144 (m, 1H), 1.40 (s, 9H), 0.76-0.71 (m, 1H), 0.26 (br m, 1H).

Example M-5e

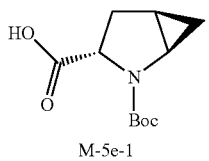 [SMILES: CC(C)(C)OC(=O)N1[C@@H]2C[C@@H]2C[C@H]1C(=O)O]

M-5e-1

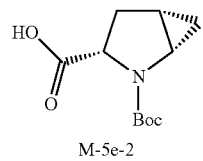 [SMILES: CC(C)(C)OC(=O)N1[C@H](C(=O)O)C[C@@H]2C[C@@H]21]

M-5e-2

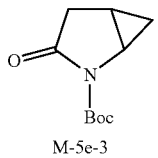 [SMILES: CC(C)(C)OC(=O)N1C(=O)CC2CC21]

M-5e-3

A semi-solution of NaIO$_4$ (6.46 g, 30.2 mmol) in H$_2$O (31 mL) was added to a solution of Examples M-5d-1/-5d-2 (2.15 g, 10.08 mmol) in CH$_3$CN (20 mL) and CCl$_4$ (20 mL). R$^u$Cl$_3$ (0.044 g, 0.212 mmol) was added immediately and the heterogeneous reaction mixture was vigorously stirred for 75 minutes. The reaction mixture was diluted H$_2$O (60 mL) and extracted with CH$_2$Cl$_2$ (50 mL, 3×). The combined organic phase was treated with 1 mL CH$_3$OH, allowed to stand for about 5 min, and then filtered through a pad of diatomaceous earth (CELITE®). The CELITE® was washed with CH$_2$Cl$_2$ (50 mL), and the filtrate was rotervaped to afford a light charcoal-colored solid. $^1$H NMR of the crude material indicated a 1.00:0.04:0.18 mole ratio among trans acid M-5e-1: presumed cis acid M-5e-2:side product M-5e-3. The crude material was dissolved in EtOAc (~10 mL) with heating, and allowed to stand at ambient condition with seeding. About 15 minutes into the cooling phase, a rapid crystal formation was observed. About 1 hour later, hexanes (~6 mL) was added and the mixture was refrigerated overnight (it did not appear that additional compound has precipitated out). The mixture was filtered and washed with ice/water cooled hexanes/EtOAc (2:1 ratio; 20 mL) and dried under high vacuum to afford the first crop of Example M-5e-1 (off-white crystals, 1.222 g). The mother liquor was rotervaped, and the residue was dissolved in ~3 ml of EtOAc (with heating), allowed to stand at ambient condition for 1 hour, and then 3 mL hexanes was added and stored in a refrigerator for ~15 hr. A second crop of Example M-5e-1 (grey crystals, 0.133 g) was retrieved similarly. $^1$H NMR (400 MHz, DMSO-d$_6$, δ=2.5 ppm) 12.46 (s, 1H), 3.88 (app br s, 1H), 3.27 (app br s, 1H; overlapped with water signal), 2.28 (br m, 1H), 2.07 (app br s, 1H), 1.56 (app s, 1H), 1.40/1.34 (two overlapped s, 9H), 0.71 (m, 1H), 0.45 (m, 1H). $^{13}$C-NMR (100.6 MHz, DMSO-d$_6$, δ=39.21 ppm) 172.96, 172.60, 154.45, 153.68, 78.74, 59.88, 59.58, 36.91, 31.97, 31.17, 27.77, 27.52, 14.86, 14.53, 13.69. MP (dec.) for the first crop: 147.5-149.5° C. LC/MS: [M+Na]$^+$=250.22. Anal. Calcd. For C$_{11}$H$_{17}$NO$_4$: C, 58.13; H, 7.54; N, 6.16. Found (for first crop): C, 58.24; H, 7.84; N, 6.07. Optical rotation (10 mg/mL in CHCl$_3$): [α]$_D$=−216 and −212 for the first and second crop, respectively.

Example M-5f

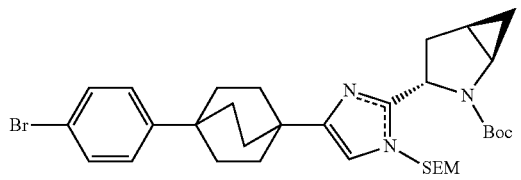

Example M-5f was prepared in three steps from Example M-5e-1 according to the procedure outlined for the preparation of Example M-1 h from (S)-Boc-proline. [Note: the SEM-regiochemical make up was not determined] $^1$H NMR (400 MHz, DMSO-d$_6$, δ=2.5 ppm) 7.46 (d, J=8.6, 2H), 7.31 (d, J=8.8, 2H), 6.76 (s, 1H), 5.27 (app br s, 1H), 5.14 (d, J=10.9, 1H), 4.60 (app br s, 1H), 3.50-3.37 (m, 3H), 2.24 (m, 2H), 1.80 (app s, 12H), 1.61 (br m, 1H), 1.12 (br s, 9H), 0.89-0.73 (m, 2H), 0.70 (br m, 1H), 0.56 (br m, 1H), −0.04 (s, 9H). LC/MS (Cond. 2): RT=2.05 min. LC/MS: Anal. Calcd. for [M+H]$^+$ C$_{33}$H$_{49}$$^{79}$BrN$_3$O$_3$Si: 642.27. found 642.25.

Example M-5g

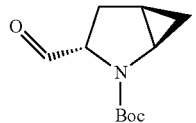 [SMILES: CC(C)(C)OC(=O)N1[C@H](C=O)C[C@H]2C[C@H]21]

Dimethylsulfoxide (1 mL, 14.09 mmol) was added dropwise over 6 min to a cooled (−78° C.) dichloromethane (14 mL) solution of oxalyl chloride (0.62 mL, 7.08 mmol), and stirred for 23 min. A dichloromethane (11 mL) solution of Example M-5d (1.0 g, 4.69 mmol; trans/cis ratio=~25/1) was added dropwise to the above mixture over 8 min, and stirring of the heterogeneous mixture was continued at similar temperature for 80 min. Triethylamine (2.5 mL, 17.94 mmol) was added and the reaction was stirred at −78° C. for 3 hr, then at 0° C. for 1 hr and then the bath was removed and stirring continued for 10 min. The reaction mixture was diluted with dichloromethane (25 mL) and washed with water (15 mL, 2×), dried (MgSO$_4$) and evaporated in vacuo to afford Example M-5g as a light brown oil (1.07 g). The trans/cis stereochemical makeup of the product was not determined, and it was used in the next step without purification.

Example M-5h

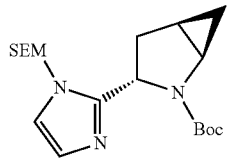 [SMILES: CC(C)(C)OC(=O)N1[C@@H]2C[C@@H]2C[C@H]1c1nccn1COCC[Si](C)(C)C]

Example M-5h was prepared in two steps from Example M-5g according to the procedure outlined for the preparation of Example QC-1d from (S)-Boc-prolinal. $^1$H NMR (400 MHz, DMSO-d$_6$, δ=2.5 ppm) 7.14 (app s, 1H), 6.81 (d, J=0.8, 1H), 5.57-5.31 (app br s, 1H), 5.22 (d, J=5.22, 1H), 4.73 (app br s, 1H), 3.47-3.27 (br m, 3H), 2.24 (app br s, 2H), 1.63 (app br s, 1H), 1.45-1.02 (app br m, 9H), 0.89-0.69 (m, 3H), 0.55 (m, 1H), −0.04 (s, 9H). LC/MS (Cond. 2): RT=1.60 min. LC/MS: Anal. Calcd. for [M+H]$^+$ C$_{19}$H$_{34}$N$_3$O$_3$Si: 380.24. found 380.21.

Example M-5i

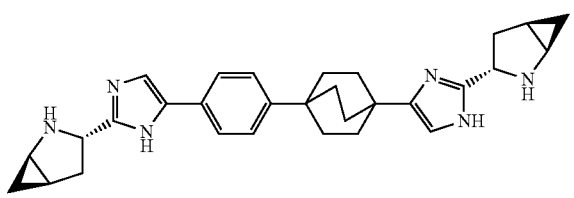 [SMILES: c1cc(C23CCC(c4c[nH]c([C@@H]5C[C@H]6C[C@H]6N5)n4)(CC2)CC3)ccc1-c1cnc([C@@H]2C[C@H]3C[C@H]3N2)[nH]1]

Example M-5i (TFA salt) was prepared in two steps starting from Example M-5f and Example M-5h according to the procedure described for the preparation of Example M-1j from Example M-1h and Example QC-1d, with the exception that the crude material was purified with a reverse phase HPLC (methanol/water/TFA) and then free-based with MCX (6g; MeOH wash; 2.0 M NH$_3$/MeOH elution). Example M-5i was retrieved as an off-white foam (162 mg). $^1$H NMR (400 MHz, DMSO-d$_6$, δ=2.5 ppm) 11.75 (app br s, ~1H; only one of the imidazole NH was observed), 7.61 (d, J=8.3, 2H), 7.33 (app br s, 1H), 7.29 (d, J=8.5, 2H), 6.50 (s, 1H), 3.97 (dd, J=9.8, 7.3, 1H), 3.88 (dd, J=10.0, 7.2, 1H), 2.83-2.77 (m, 2H), 2.14-2.03 (m, 2H), 1.94-1.76 (m, 14H), 1.44-1.36 (m, 2H), 0.67-0.64 (m, 1H), 0.63-0.60 (m, 1H), 0.34-0.27 (m, 2H). LC/MS (Cond. 2): RT=0.94 min. LC/MS: Anal. Calcd. for [M+H]$^+$ C$_{30}$H$_{37}$N$_6$: 481.31. found 481.27.

Example M-5

Example M-5 (TFA salt) was prepared from Example M-5i according to the procedure outlined in Example M-1. $^1$H NMR (400 MHz, DMSO-d$_6$, δ=2.5 ppm): 14.13/13.98 (two br s, 2H), 7.99 (br s, 1H), 7.69 (d, J=8.3, 2H), 7.51 (d, J=8.3, 2H), 7.30 (s, 1H), 7.25/7.23 (two overlapping d, J=8.5/9.4, 1.82H), 6.99-6.93 (br m, 0.18H), 4.98 (m, 1H), 4.90 (m, 1H), 4.40 (m, 1.77H), 4.33-4.27 (br m, 0.23H), 3.72 (br m, 2H), 3.54 (s, 3H), 3.53 (s, 3H), 2.38-2.07 (m, 4H), 1.96-1.83 (m, 14H), 0.98-0.72 (m, 16H), (Note: the signal of 2H appears to have overlapped with that of the solvent signal). LC/MS (Cond. 2): RT=1.35 min. LC/MS: Anal. Calcd. for [M+H]$^+$ C$_{44}$H$_{59}$N$_8$O$_6$: 795.46. found 795.44.

Examples M-6 and M-7

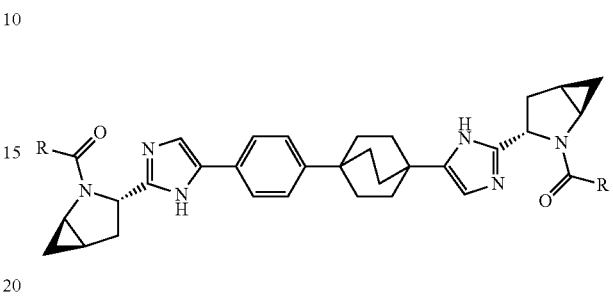

Examples M-6 and M-7 were prepared as TFA salts from Example M-5i and appropriate acids by employing the procedure described for the synthesis of Example M-5, with the exception that an additional purification was conducted with a second reverse phase HPLC system (water/acetonitrile/TFA) for Example M-7.

| Example | R | RT (LC-Cond.); % homogeneity index; MS data |
|---|---|---|
| M-6 | ![structure] | 1.20 min (Cond. 2); >98%; LC/MS: Anal. Calcd. for [M + H]$^+$ C$_{42}$H$_{55}$N$_8$O$_6$: 767.42; found 767.47 |
| M-7 | ![structure] | 1.93 min (Cond. 2a); >95%; LC/MS: Anal. Calcd. for [M + H]$^+$ C$_{50}$H$_{55}$N$_8$O$_6$: 863.42; found 863.41 |

Example M-8

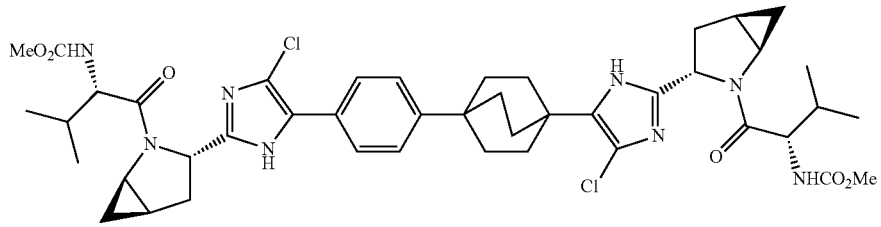

The TFA salt of Example 5 (41 mg) was free based with MCX column (MeOH wash; 2 N NH3/MeOH), and the resultant colorless glassy oil (29 mg) was dissolved in DMF (2 mL), treated with NCS (10.7 mg, 0.080 mmol) and heated at 50° C. for 15 hr. The reaction mixture was allowed to cool to ambient condition, diluted with MeOH and submitted to reverse phase HPLC purification (XTERRA 30×100 mm S5; water/MeOH/TFA) to afford the TFA salt of Example 8 as a white foam (27.4 mg). $^1$H NMR (400 MHz, DMSO-$d_6$, δ=2.5 ppm) 7.61 (d, J=8.6, 2H), 7.46 (d, J=8.5, 2H), 7.15 (app t, 2H), 4.98-4.92 (m, 2H), 4.43-4.38 (m, 2H), 3.62-3.55 (an overlap of 'm' & 's', 8H), 2.35-2.21 (m, 4H), 2.10-1.80 (m, 16H), 1.04-0.86 (m, 14H), 0.71 (m, 2H). LC/MS (Cond. 4): RT=3.97 min. LC/MS: Anal. Calcd. for [M+H]$^+$ $C_{44}H_{58}Cl_2N_8O_6$: 863.28. found 863.40.

BIOLOGICAL ACTIVITY

An HCV Replicon assay was utilized in the present disclosure, and was prepared, conducted and validated as described in commonly owned PCT/US2006/022197 and in O'Boyle et. al. *Antimicrob Agents Chemother.* 2005 April; 49(4):1346-53. Assay methods incorporating luciferase reporters have also been used as described (Apath.com).

HCV-neo replicon cells and replicon cells containing mutations in the NS5A region were used to test the currently described family of compounds. The compounds were determined to have more than 10-fold less inhibitory activity on cells containing mutations than wild-type cells. Thus, the compounds of the present disclosure can be effective in inhibiting the function of the HCV NS5A protein and are understood to be as effective in combinations as previously described in application PCT/US2006/022197 and commonly owned WO/04014852. Further, the compounds of the present disclosure can be effective against the HCV 1b genotype. It should also be understood that the compounds of the present disclosure can inhibit multiple genotypes of HCV. Table 2 shows the $EC_{50}$ (Effective 50% inhibitory concentration) values of representative compounds of the present disclosure against the HCV 1b genotype. In one embodiment, compounds of the present disclosure are inhibitory versus 1a, 1b, 2a, 2b, 3a, 4a, and 5a genotypes. $EC_{50}$ values against HCV 1b are as follows: A (1-10 μM); B (100-999 nM); C (4.57-99 nM); D (2 nM-4.57 nM).

The compounds of the present disclosure may inhibit HCV by mechanisms in addition to or other than NS5A inhibition. In one embodiment the compounds of the present disclosure inhibit HCV replicon and in another embodiment the compounds of the present disclosure inhibit NS5A.

TABLE 2

| Example | 1b $EC_{50}$ (in nM or range) | Range | Name |
| --- | --- | --- | --- |
| QC-1 | | D | methyl ((1S)-1-(((2S)-2-(4-(4'-(2-((2S)-1-((2S)-2-((methoxycarbonyl)amino)-3-methylbutanoyl)-2-pyrrolidinyl)-1H-imidazol-4-yl)-1,1'-bi(3-cyclohexen-1-yl)-4-yl)-1H-imidazol-2-yl)-1-pyrrolidinyl)carbonyl)-2-methylpropyl)carbamate |
| QC-2 | | C | methyl ((1S)-2-((2S)-2-(4-(4'-(2-((2S)-1-(N-(methoxycarbonyl)-L-alanyl)-2-pyrrolidinyl)-1H-imidazol-4-yl)-1,1'-bi(3-cyclohexen-1-yl)-4-yl)-1H-imidazol-2-yl)-1-pyrrolidinyl)-1-methyl-2-oxoethyl)carbamate |
| QC-3 | | D | (1R,1'R)-2,2'-(1,1'-bi(3-cyclohexen-1-yl)-4,4'-diylbis(1H-imidazole-4,2-diyl(2S)-2,1-pyrrolidinediyl))bis(N,N-diethyl-2-oxo-1-phenylethanamine) |
| QC-4 | | C | methyl ((1S)-2-((2S)-2-(4-(4'-(2-((2S)-1-(N-(methoxycarbonyl)-O-methyl-L-seryl)-2-pyrrolidinyl)-1H-imidazol-4-yl)-1,1'-bi(3-cyclohexen-1-yl)-4-yl)-1H-imidazol-2-yl)-1-pyrrolidinyl)-1-(methoxymethyl)-2-oxoethyl)carbamate |
| QC-5 | | D | methyl ((1S,2R)-2-methoxy-1-(((2S)-2-(4-(4'-(2-((2S)-1-(N-(methoxycarbonyl)-O-methyl-L-threonyl)-2-pyrrolidinyl)-1H-imidazol-4-yl)-1,1'-bi(3-cyclohexen-1-yl)-4-yl)-1H-imidazol-2-yl)-1-pyrrolidinyl)carbonyl)propyl)carbamate |
| QC-6 | | B | methyl ((1S)-2-((2S)-2-(4-(4'-(2-((2S)-1-(N-(methoxycarbonyl)-L-alanyl)-2-pyrrolidinyl)-1H-imidazol-4-yl)-1,1'-bi(cyclohexyl)-4-yl)-1H-imidazol-2-yl)-1-pyrrolidinyl)-1-methyl-2-oxoethyl)carbamate |
| QC-7 | 17.11 | A | methyl ((1S)-2-((2S)-2-(4-(4'-(2-((2S)-1-(N-(methoxycarbonyl)-O-methyl-L-seryl)-2-pyrrolidinyl)-1H-imidazol-4-yl)-1,1'-bi(cyclohexyl)-4-yl)-1H-imidazol-2-yl)-1-pyrrolidinyl)-1-(methoxymethyl)-2-oxoethyl)carbamate |
| QC-8 | 2.40 | B | methyl ((1S,2R)-2-methoxy-1-(((2S)-2-(4-(4'-(2-((2S)-1-(N-(methoxycarbonyl)-O-methyl-L-threonyl)-2-pyrrolidinyl)-1H-imidazol-4-yl)-1,1'-bi(cyclohexyl)-4-yl)-1H-imidazol-2-yl)-1-pyrrolidinyl)carbonyl)propyl)carbamate |
| QC-9 | 0.011 | D | methyl ((1S)-1-(((2S)-2-(4-(4-(4-(2-((2S)-1-((2S)-2-((methoxycarbonyl)amino)-3-methylbutanoyl)-2-pyrrolidinyl)-1H-imidazol-4-yl)phenyl)-1-cyclohexen-1-yl)-1H-imidazol-2-yl)-1- |

TABLE 2-continued

| Example | 1b EC$_{50}$ (in nM or range) | Range | Name |
|---|---|---|---|
| QC-10 | | C | pyrrolidinyl)carbonyl)-2-methylpropyl)carbamate<br>methyl ((1S)-2-((2S)-2-(4-(4-(4-(2-((2S)-1-(N-(methoxycarbonyl)-1-alanyl)-2-pyrrolidinyl)-1H-imidazol-4-yl)-3-cyclohexen-1-yl)phenyl)-1H-imidazol-2-yl)-1-pyrrolidinyl)-1-methyl-2-oxoethyl)carbamate |
| QC-11 | | C | methyl ((1S)-2-((2S)-2-(4-(4-(4-(2-((2S)-1-(N-(methoxycarbonyl)-O-methyl-L-seryl)-2-pyrrolidinyl)-1H-imidazol-4-yl)-3-cyclohexen-1-yl)phenyl)-1H-imidazol-2-yl)-1-pyrrolidinyl)-1-(methoxymethyl)-2-oxoethyl)carbamate |
| QC-12 | | C | methyl ((1S,2R)-2-methoxy-1-(((2S)-2-(4-(4-(4-(2-((2S)-1-(N-(methoxycarbonyl)-O-methyl-L-threonyl)-2-pyrrolidinyl)-1H-imidazol-4-yl)-3-cyclohexen-1-yl)phenyl)-1H-imidazol-2-yl)-1-pyrrolidinyl)carbonyl)propyl)carbamate |
| QC-13 | | C | methyl ((1S)-1-(((2S)-2-(4-(1-(4-(2-((2S)-1-((2S)-2-((methoxycarbonyl)amino)-3-methylbutanoyl)-2-pyrrolidinyl)-1H-imidazol-4-yl)phenyl)-4-piperidinyl)-1H-imidazol-2-yl)-1-pyrrolidinyl)carbonyl)-2-methylpropyl)carbamate |
| QC-14 | | B | methyl ((1S)-2-((2S)-2-(4-(4-(4-(2-((2S)-1-(N-(methoxycarbonyl)-O-methyl-L-seryl)-2-pyrrolidinyl)-1H-imidazol-4-yl)-1-piperidinyl)phenyl)-1H-imidazol-2-yl)-1-pyrrolidinyl)-1-(methoxymethyl)-2-oxoethyl)carbamate |
| QC-15 | | C | methyl ((1S)-1-(((2S)-2-(4-(1-(4-(2-((2S)-1-((2S)-2-((methoxycarbonyl)amino)-3,3-dimethylbutanoyl)-2-pyrrolidinyl)-1H-imidazol-4-yl)phenyl)-4-piperidinyl)-1H-imidazol-2-yl)-1-pyrrolidinyl)carbonyl)-2,2-dimethylpropyl)carbamate |
| QC-16 | | D | methyl ((1S)-1-(((2S)-2-(4-(4-(4-(2-((2S)-1-((2S)-2-((methoxycarbonyl)amino)-3-methylbutanoyl)pyrrolidin-2-yl)-1H-imidazol-4-yl)phenyl)cyclohexyl)-1H-imidazol-2-yl)pyrrolidin-1-yl)carbonyl)-2-methylpropyl)carbamate (Isomer 1) |
| QC-17 | | D | methyl ((1S)-1-(((2S)-2-(4-(4-(4-(2-((2S)-1-((2S)-2-((methoxycarbonyl)amino)-3-methylbutanoyl)pyrrolidin-2-yl)-1H-imidazol-4-yl)phenyl)cyclohexyl)-1H-imidazol-2-yl)pyrrolidin-1-yl)carbonyl)-2-methylpropyl)carbamate (isomer II) |
| M-1 | 0.009 | D | methyl ((1S)-1-(((2S)-2-(4-(4-(4-(2-((2S)-1-((2S)-2-((methoxycarbonyl)amino)-3-methylbutanoyl)-2-pyrrolidinyl)-1H-imidazol-4-yl)phenyl)bicyclo[2.2.2]oct-1-yl)-1H-imidazol-2-yl)-1-pyrrolidinyl)carbonyl)-2-methylpropyl)carbamate |
| M-2 | | C | methyl ((1S)-2-((2S)-2-(4-(4-(4-(2-((2S)-1-(N-(methoxycarbonyl)-L-alanyl)-2-pyrrolidinyl)-1H-imidazol-4-yl)bicyclo[2.2.2]oct-1-yl)phenyl)-1H-imidazol-2-yl)-1-pyrrolidinyl)-1-methyl-2-oxoethyl)carbamate |
| M-3 | | D | methyl ((1R)-2-((2S)-2-(4-(4-(4-(2-((2S)-1-((2R)-2-((methoxycarbonyl)amino)-2-phenylacetyl)-2-pyrrolidinyl)-1H-imidazol-4-yl)bicyclo[2.2.2]oct-1-yl)phenyl)-1H-imidazol-2-yl)-1-pyrrolidinyl)-2-oxo-1-phenylethyl)carbamate |
| M-4 | | A | methyl ((1S)-1-(((2S)-2-(4-(4-(4-(2-((2S)-1-((2S)-2-((methoxycarbonyl)amino)-3-methylbutanoyl)-2-pyrrolidinyl)-1H-imidazol-4-yl)phenyl)bicyclo[2.2.2]oct-1-yl)-1,3-oxazol-2-yl)-1-pyrrolidinyl)carbonyl)-2-methylpropyl)carbamate |
| M-5 | | D | methyl ((1S)-1-(((1R,3S,5R)-3-(5-(4-(4-(2-((1R,3S,5R)-2-((2S)-2-((methoxycarbonyl)amino)-3-methylbutanoyl)-2-azabicyclo[3.1.0]hex-3-yl)-1H-imidazol-5-yl)bicyclo[2.2.2]oct-1-yl)phenyl)-1H-imidazol-2-yl)-2-azabicyclo[3.1.0]hex-2-yl)carbonyl)-2-methylpropyl)carbamate |
| M-6 | | D | methyl ((1S)-1-(((1R,3S,5R)-3-(5-(4-(2-((1R,3S,5R)-2-((2S)-2-((methoxycarbonyl)amino)butanoyl)-2-azabicyclo[3.1.0]hex-3-yl)-1H-imidazol-5-yl)bicyclo[2.2.2]oct-1-yl)phenyl)-1H-imidazol-2-yl)-2-azabicyclo[3.1.0]hex-2-yl)carbonyl)propyl)carbamate |
| M-7 | | D | methyl ((1R)-2-((1R,3S,5R)-3-(5-(4-(2-((1R,3S,5R)-2-((2R)-2-((methoxycarbonyl)amino)-2-phenylacetyl)-2-azabicyclo[3.1.0]hex-3-yl)-1H-imidazol-5-yl)bicyclo[2.2.2]oct-1-yl)phenyl)-1H-imidazol-2-yl)-2-azabicyclo[3.1.0]hex-2-yl)-2-oxo-1-phenylethyl)carbamate |
| M-8 | | D | methyl ((1S)-1-(((1R,3S,5R)-3-(4-chloro-5-(4-(4-(4-chloro-2-((1R,3S,5R)-2-((2S)-2-((methoxycarbonyl)amino)-3-methylbutanoyl)-2-azabicyclo[3.1.0]hex-3-yl)-1H-imidazol-5-yl)bicyclo[2.2.2]oct-1-yl)phenyl)-1H-imidazol-2-yl)-2-azabicyclo[3.1.0]hex-2-yl)carbonyl)-2-methylpropyl)carbamate |

The compounds of the present disclosure may inhibit HCV by mechanisms in addition to or other than NS5A inhibition. In one embodiment the compounds of the present disclosure inhibit HCV replicon and in another embodiment the compounds of the present disclosure inhibit NS5A.

It will be evident to one skilled in the art that the present disclosure is not limited to the foregoing illustrative examples, and that it can be embodied in other specific forms without departing from the essential attributes thereof. It is therefore desired that the examples be considered in all respects as illustrative and not restrictive, reference being made to the appended claims, rather than to the foregoing examples, and all changes which come within the meaning and range of equivalency of the claims are therefore intended to be embraced therein.

What is claimed is:

1. A compound of Formula (I):

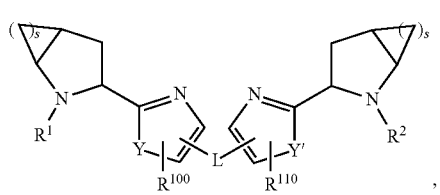

or a pharmaceutically acceptable salt thereof, wherein:
s is 0 or 1;
L is -$L^1$-$L^2$-, wherein $L^1$ and $L^2$ are independently selected from:

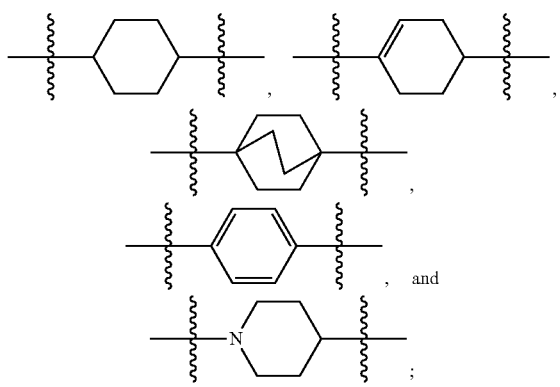

provided that at least one of $L^1$ and $L^2$ is other than

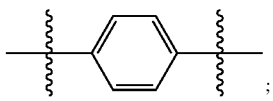

Y and Y' are independently oxygen (O) or NH;
$R^1$ is hydrogen or —C(O)$R^x$;
$R^2$ is hydrogen or —C(O)$R^y$;
$R^x$ and $R^y$ are independently selected from cycloalkyl, heteroaryl, heterocyclyl, alkoxy, and alkyl substituted with one or more substituents independently selected from aryl, alkenyl, cycloalkyl, heterocyclyl, heteroaryl, —O$R^3$,
—C(O)O$R^4$, —N$R^a R^b$, and —C(O)N$R^c R^d$,
wherein aryl and heteroaryl may optionally be substituted with one or more substituents independently selected from alkyl, haloalkyl, arylalkyl, heterocyclyl, heterocyclylalkyl, halogen, cyano, nitro, —C(O)O$R^4$, O$R^5$, —N$R^a R^b$, (N$R^a R^b$)alkyl, and (MeO)(HO)P(O)O—, and
wherein cycloalkyl and heterocyclyl may optionally be fused onto an aromatic ring and may optionally be substituted with one or more substituents independently selected from alkyl, hydroxyl, halogen, aryl, —N$R^a R^b$, oxo, and —C(O)O$R^4$;
$R^3$ is hydrogen, alkyl, or arylalkyl;
$R^4$ is alkyl or arylalkyl;
$R^5$ is hydrogen, alkyl, or arylalkyl;

$R^a$ and $R^b$ are independently selected from hydrogen, alkyl, cycloalkyl, arylalkyl, heteroaryl, —C(O)$R^6$, —C(O)O$R^7$, —C(O)N$R^c R^d$, and (N$R^c R^d$)alkyl, or alternatively, $R^a$ and $R^b$, together with the nitrogen atom to which they are attached, form a five- or six-membered ring or bridged bicyclic ring structure, wherein said five- or six-membered ring or bridged bicyclic ring structure optionally may contain one or two additional heteroatoms independently selected from nitrogen, oxygen, and sulfur and may contain one, two, or three substituents independently selected from $C_1$ to $C_6$ alkyl, $C_1$ to $C_4$ haloalkyl, aryl, hydroxyl, $C_1$ to $C_6$ alkoxy, $C_1$ to $C_4$ haloalkoxy, and halogen;
$R^6$ is alkyl;
$R^7$ is alkyl, arylalkyl, cycloalkyl, or haloalkyl;
$R^{100}$ and $R^{110}$ are independently selected from hydrogen, alkyl, cyanoalkyl, and halo;
$R^c$ and $R^d$ are independently selected from hydrogen, alkyl, arylalkyl, and cycloalkyl.

2. The compound according to claim 1, or a pharmaceutically acceptable salt thereof, wherein L is selected from:

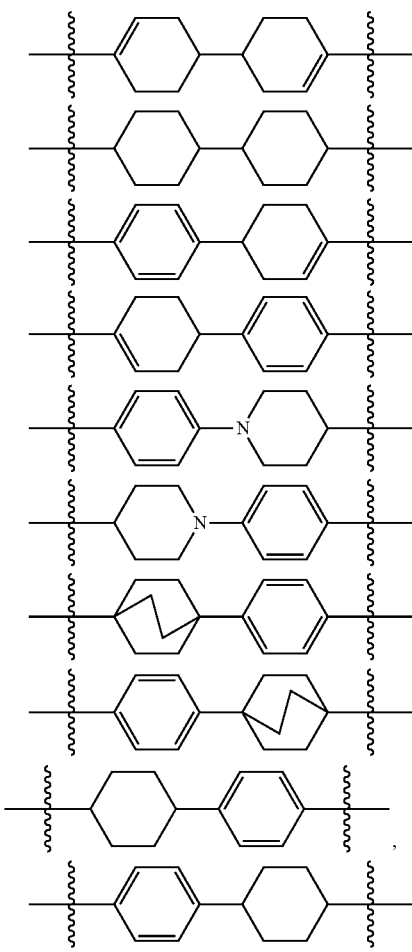

3. The compound according to claim 1, or a pharmaceutically acceptable salt thereof, wherein Y and Y' are each NH.

4. The compound according to claim 1, or a pharmaceutically acceptable salt thereof, wherein Y is oxygen (O), and Y' is NH.

5. The compound of claim 1, or a pharmaceutically acceptable salt thereof, wherein:

$R^1$ is —C(O)$R^x$;

$R^2$ is —C(O)$R^y$;

$R^x$ and $R^y$ are independently alkyl substituted by at least one —N$R^aR^b$, characterized by Formula (A):

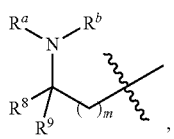

(A)

wherein:

m is 0 or 1;

$R^8$ is hydrogen or alkyl;

$R^9$ is selected from hydrogen, cycloalkyl, aryl, heteroaryl, heterocyclyl, and alkyl optionally substituted with a substituent selected from aryl, alkenyl, cycloalkyl, heterocyclyl, heteroaryl, heterobicyclyl, —O$R^3$, —C(O)O$R^4$, —N$R^aR^b$, and —C(O)N$R^cR^d$, wherein aryl and heteroaryl may optionally be substituted with one or more substituents independently selected from alkyl, haloalkyl, arylalkyl, heterocyclyl, heterocyclylalkyl, halogen, cyano, nitro, —C(O)O$R^4$, O$R^5$, —N$R^aR^b$, (N$R^aR^b$)alkyl, and (MeO)(HO)P(O)O—, and wherein cycloalkyl and heterocyclyl may optionally be fused onto an aromatic ring and may optionally be substituted with one or more substituents independently selected from alkyl, hydroxyl, halogen, aryl, —N$R^aR^b$, oxo, and —C(O)O$R^4$;

$R^{100}$ and $R^{110}$ are independently selected from hydrogen and halo; and $R^3$, $R^4$, $R^5$, $R^a$, $R^b$, $R^c$, and $R^d$ are defined as in claim 1.

6. The compound of claim 5, or a pharmaceutically acceptable salt thereof, wherein:

m is 0;

$R^8$ is hydrogen or $C_1$ to $C_4$ alkyl;

$R^9$ is selected from hydrogen, $C_1$ to $C_6$ alkyl optionally substituted with —O$R^{12}$, $C_3$ to $C_6$ cycloalkyl, allyl, —CH$_2$C(O)N$R^cR^d$, (N$R^cR^d$)alkyl,

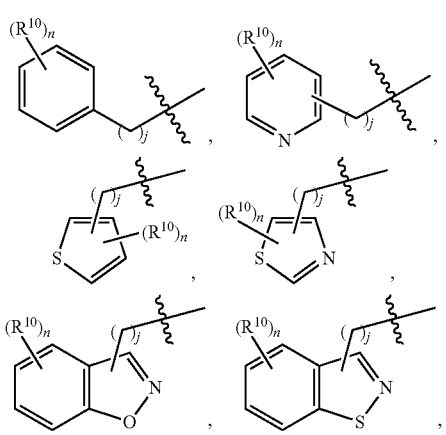

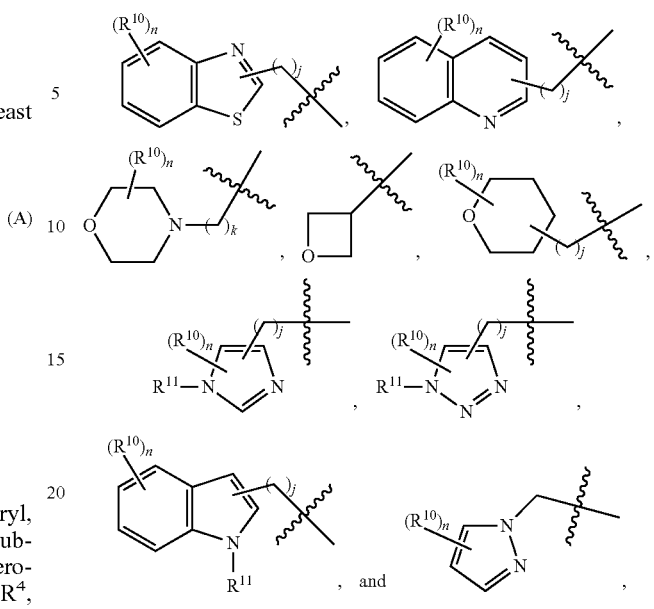

, and wherein j is 0 or 1;

k is 1, 2, or 3;

n is 0 or an integer selected from 1 through 4;

each $R^{10}$ is independently hydrogen, $C_1$ to $C_4$ alkyl, $C_1$ to $C_4$ haloalkyl, halogen, nitro, —OBn, or (MeO)(OH)P(O)O—;

$R^{11}$ is hydrogen, $C_1$ to $C_4$ alkyl, or benzyl;

$R^{12}$ is hydrogen, $C_1$ to $C_4$ alkyl, or benzyl;

$R^a$ is hydrogen or $C_1$ to $C_4$ alkyl;

$R^b$ is $C_1$ to $C_4$ alkyl, $C_3$ to $C_6$ cycloalkyl, benzyl, 3-pyridyl, pyrimidin-5-yl, acetyl, —C(O)O$R^7$, or —C(O)N$R^cR^d$;

$R^7$ is $C_1$ to $C_4$ alkyl or $C_1$ to $C_4$ haloalkyl;

$R^c$ is hydrogen or $C_1$ to $C_4$ alkyl; and $R^d$ is hydrogen, $C_1$ to $C_4$ alkyl, or $C_3$ to $C_6$ cycloalkyl.

7. The compound of claim 5, or a pharmaceutically acceptable salt thereof, wherein:

m is 0;

$R^8$ is hydrogen;

$R^9$ is phenyl optionally substituted with one up to five substituents independently selected from $C_1$ to $C_6$ alkyl, $C_1$ to $C_4$ haloalkyl, halogen, $C_1$ to $C_6$ alkoxy, hydroxyl, cyano, and nitro; and N$R^aR^b$ is a heterocyclyl or heterobicyclyl group selected from:

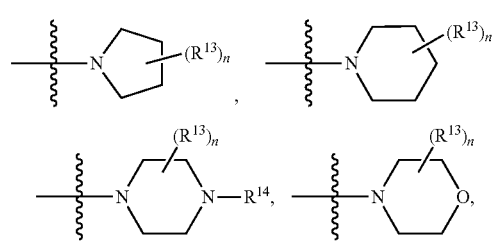

[Structures shown]

, and

[Structures shown]

, wherein n is 0, 1, or 2;

each $R^{13}$ is independently selected from $C_1$ to $C_6$ alkyl, phenyl, trifluoromethyl, halogen, hydroxyl, methoxy, and oxo; and $R^{14}$ is $C_1$ to $C_6$ alkyl, phenyl, benzyl, or $C(O)OR^{15}$ group, wherein $R^{15}$ is $C_1$ to $C_4$ alkyl, phenyl, or benzyl.

8. The compound of claim 5, or a pharmaceutically acceptable salt thereof, wherein:

m is 1;

$R^8$ is hydrogen;

$R^9$ is $C_1$ to $C_6$ alkyl, arylalkyl, or heteroarylalkyl;

$R^a$ is hydrogen; and $R^b$ is —C(O)OR$^4$, wherein $R^4$ is $C_1$ to $C_6$ alkyl.

9. The compound of claim 1, or a pharmaceutically acceptable salt thereof, wherein:

$R^1$ is —C(O)R$^x$;

$R^2$ is —C(O)R$^y$; and $R^x$ and $R^y$ are heteroaryl or heterocyclyl independently selected from:

[Structures shown]

wherein n is 0 or an integer selected from 1 through 4;

each $R^{13}$ is independently selected from hydrogen, $C_1$ to $C_6$ alkyl, $C_1$ to $C_4$ haloalkyl, phenyl, benzyl, $C_1$ to $C_6$ alkoxy, $C_1$ to $C_4$ haloalkoxy, heterocyclyl, halogen, $NR^cR^d$, hydroxyl, cyano, and oxo, where $R^c$ and $R^d$ are independently hydrogen or $C_1$ to $C_4$ alkyl; and $R^{14}$ is hydrogen (H), $C_1$ to $C_6$ alkyl, benzyl, or —C(O)OR$^4$, wherein $R^4$ is $C_1$ to $C_6$ alkyl.

10. The compound of claim 1, or a pharmaceutically acceptable salt thereof, wherein:

$R^1$ is hydrogen or —C(O)R$^x$;

$R^2$ is hydrogen or —C(O)R$^y$;

$R^x$ and $R^y$ are cycloalkyl independently selected from:

[Structures shown]

and wherein j is 0, 1, 2, or 3;

k is 0, 1, or 2;

n is 0 or an integer selected from 1 though 4;

each $R^{13}$ is independently selected from hydrogen, $C_1$ to $C_6$ alkyl, $C_1$ to $C_4$ haloalkyl, $C_1$ to $C_6$ alkoxy, halogen, hydroxyl, cyano, and nitro; and $R^a$ and $R^b$ are independently hydrogen, $C_1$ to $C_6$ alkyl, or $C(O)OR^4$, wherein $R^4$ is $C_1$ to $C_6$ alkyl.

11. The compound of claim 1, or a pharmaceutically acceptable salt thereof, wherein:

$R^1$ is —C(O)R$^x$;

$R^2$ is —C(O)R$^y$;

$R^x$ and $R^y$ are independently arylalkyl, wherein aryl part of said arylalkyl may optionally be substituted with ($NR^aR^b$)alkyl; and $R^a$ and $R^b$ are independently hydrogen, $C_1$ to $C_6$ alkyl, or benzyl, or alternatively, $R^a$ and $R^b$, together with the nitrogen atom to which they are attached, form a five- or six-membered ring selected from

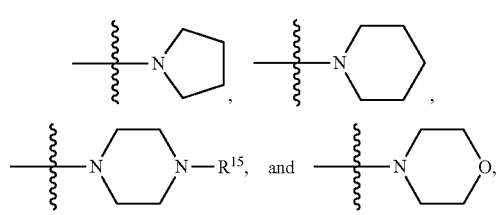

wherein R[15] is hydrogen, $C_1$ to $C_6$ alkyl, or benzyl.

12. The compound of claim 1, or a pharmaceutically acceptable salt thereof, wherein:

$R^1$ is —C(O)R[x];

$R^2$ is —C(O)R[y]; and

R[x] and R[y] are the same and are selected from the group consisting of:

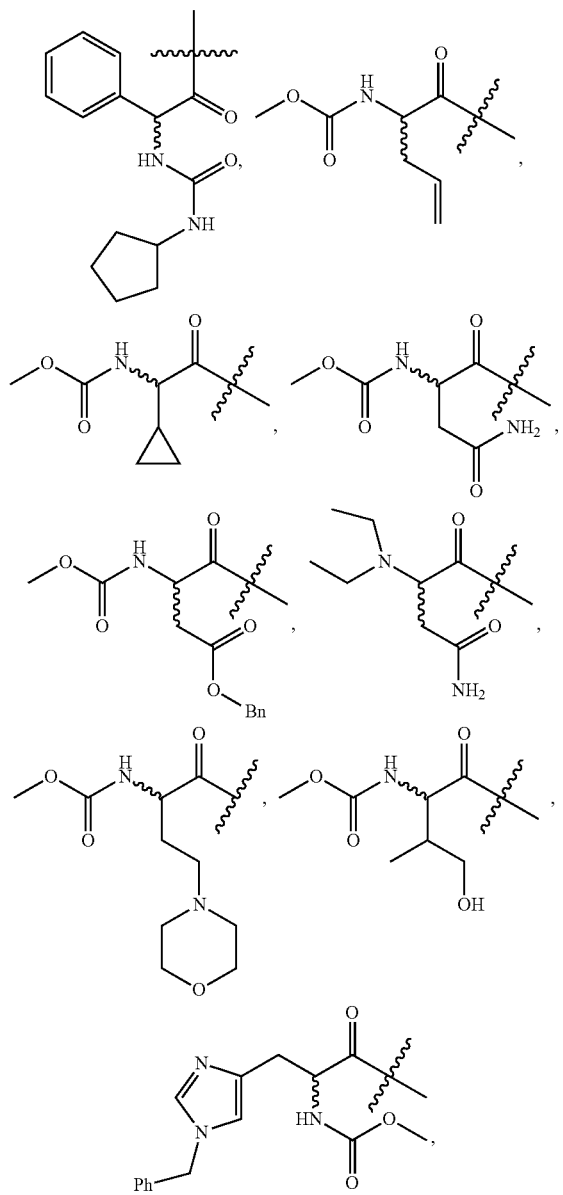

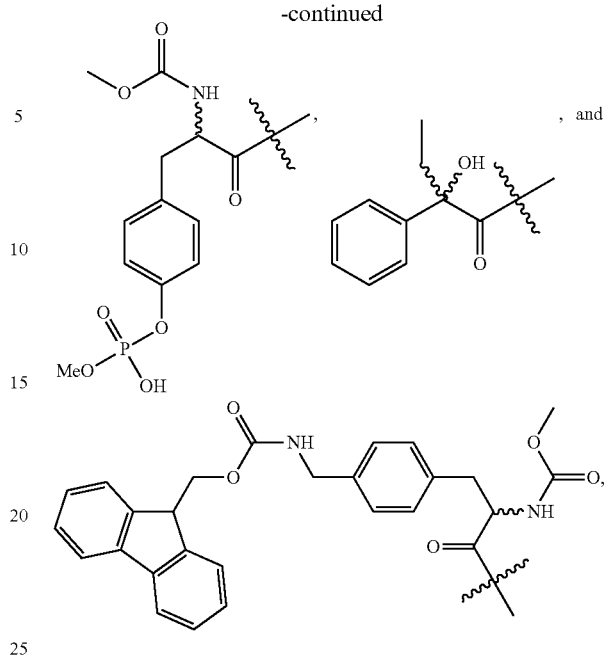

wherein a squiggle bond (~~) in the structure indicates that a stereogenic center to which the bond is attached can take either (R)- or (S)-configuration so long as chemical bonding principles are not violated.

13. The compound of claim 1, or a pharmaceutically acceptable salt thereof, wherein:

$R^1$ is —C(O)R[x];

$R^2$ is —C(O)R[y]; and

R[x] and R[y] are both t-butoxy.

14. The compound of claim 1, or a pharmaceutically acceptable salt thereof, wherein $R^1$ and $R^2$ are both hydrogen.

15. A compound of Formula (II):

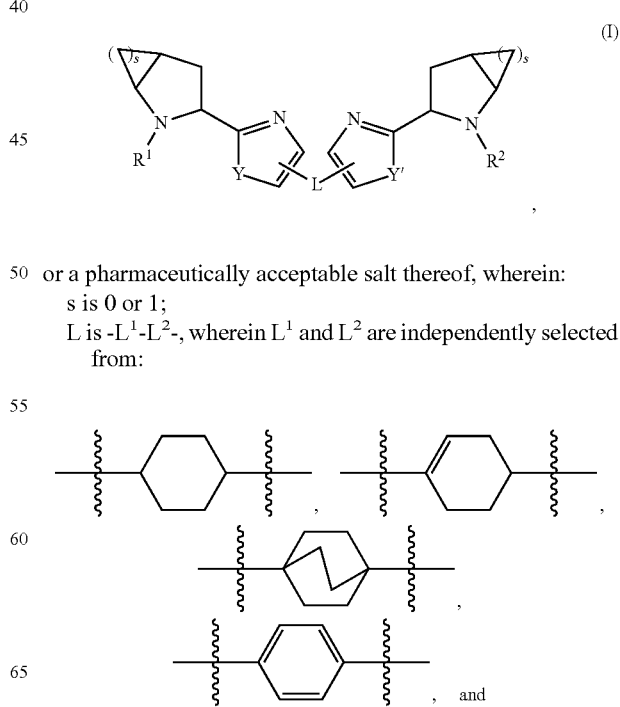

or a pharmaceutically acceptable salt thereof, wherein:

s is 0 or 1;

L is -L[1]-L[2]-, wherein L[1] and L[2] are independently selected from:

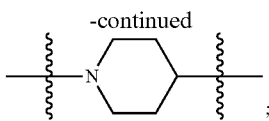

provided that at least one of $L^1$ and $L^2$ is other than

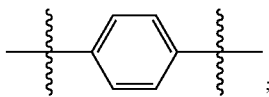 [SMILES: *c1ccc(*)cc1]

Y and Y' are independently oxygen (O) or NH;
$R^1$ is hydrogen or —C(O)$R^x$;
$R^2$ is hydrogen or —C(O)$R^y$;
$R^x$ and $R^y$ are independently selected from cycloalkyl, heteroaryl, heterocyclyl, alkoxy, and alkyl substituted with one or more substituents independently selected from aryl, alkenyl, cycloalkyl, heterocyclyl, heteroaryl, —O$R^3$, —C(O)O$R^4$, —N$R^a R^b$, and —C(O)N$R^c R^d$,
wherein aryl and heteroaryl may optionally be substituted with one or more substituents independently selected from alkyl, haloalkyl, arylalkyl, heterocyclyl, heterocyclylalkyl, halogen, cyano, nitro, —C(O)O$R^4$, O$R^5$, —N$R^a R^b$, (N$R^a R^b$)alkyl, and (MeO)(HO)P(O)O—, and
wherein cycloalkyl and heterocyclyl may optionally be fused onto an aromatic ring and may optionally be substituted with one or more substituents independently selected from alkyl, hydroxyl, halogen, aryl, —N$R^a R^b$, oxo, and —C(O)O$R^4$;
$R^3$ is hydrogen, alkyl, or arylalkyl;
$R^4$ is alkyl or arylalkyl;
$R^5$ is hydrogen, alkyl, or arylalkyl;
$R^a$ and $R^b$ are independently selected from hydrogen, alkyl, cycloalkyl, arylalkyl, heteroaryl, —C(O)$R^6$, —C(O)O$R^7$, —C(O)N$R^c R^d$, and (N$R^c R^d$)alkyl, or alternatively, $R^a$ and $R^b$, together with the nitrogen atom to which they are attached, form a five- or six-membered ring or bridged bicyclic ring structure, wherein said five- or six-membered ring or bridged bicyclic ring structure optionally may contain one or two additional heteroatoms independently selected from nitrogen, oxygen, and sulfur and may contain one, two, or three substituents independently selected from $C_1$ to $C_6$ alkyl, $C_1$ to $C_4$ haloalkyl, aryl, hydroxyl, $C_1$ to $C_6$ alkoxy, $C_1$ to $C_4$ haloalkoxy, and halogen;
$R^6$ is alkyl;
$R^7$ is alkyl, arylalkyl, or haloalkyl; and
$R^c$ and $R^d$ are independently selected from hydrogen, alkyl, arylalkyl, and cycloalkyl.

16. A compound, or a pharmaceutically acceptable salt thereof, selected from the group consisting of:
methyl((1S)-1-(((2S)-2-(4-(4'-(2-((2S)-1-((2S)-2-((methoxycarbonyl)amino)-3-methylbutanoyl)-2-pyrrolidinyl)-1H-imidazol-4-yl)-1,1'-bi(3-cyclohexen-1-yl)-4-yl)-1H-imidazol-2-yl)-1-pyrrolidinyl)carbonyl)-2-methylpropyl)carbamate;
methyl((1S)-2-((2S)-2-(4-(4'-(2-((2S)-1-(N-(methoxycarbonyl)-L-alanyl)-2-pyrrolidinyl)-1H-imidazol-4-yl)-1,1'-bi(3-cyclohexen-1-yl)-4-yl)-1H-imidazol-2-yl)-1-pyrrolidinyl)-1-methyl-2-oxoethyl)carbamate;
(1'R)-2,2'-(1,1'-bi(3-cyclohexen-1-yl)-4,4'-diylbis(1H-imidazole-4,2-diyl(2S)-2,1-pyrrolidinediyl))bis(N,N-diethyl-2-oxo-1-phenylethanamine);
methyl((1S)-2-((2S)-2-(4-(4'-(2-((2S)-1-(N-(methoxycarbonyl)-O-methyl-L-seryl)-2-pyrrolidinyl)-1H-imidazol-4-yl)-1,1'-bi(3-cyclohexen-1-yl)-4-yl)-1H-imidazol-2-yl)-1-pyrrolidinyl)-1-(methoxymethyl)-2-oxoethyl)carbamate;
methyl((1S,2R)-2-methoxy-1-(((2S)-2-(4-(4'-(2-((2S)-1-(N-(methoxycarbonyl)-O-methyl-L-threonyl)-2-pyrrolidinyl)-1H-imidazol-4-yl)-1,1'-bi(3-cyclohexen-1-yl)-4-yl)-1H-imidazol-2-yl)-1-pyrrolidinyl)carbonyl)propyl)carbamate;
methyl((1S)-2-((2S)-2-(4-(4'-(2-((2S)-1-(N-(methoxycarbonyl)-L-alanyl)-2-pyrrolidinyl)-1H-imidazol-4-yl)-1,1'-bi(cyclohexyl)-4-yl)-1H-imidazol-2-yl)-1-pyrrolidinyl)-1-methyl-2-oxoethyl)carbamate;
methyl((1S)-2-((2S)-2-(4-(4'-(2-((2S)-1-(N-(methoxycarbonyl)-O-methyl-L-seryl)-2-pyrrolidinyl)-1H-imidazol-4-yl)-1,1'-bi(cyclohexyl)-4-yl)-1H-imidazol-2-yl)-1-pyrrolidinyl)-1-(methoxymethyl)-2-oxoethyl)carbamate;
methyl((1S,2R)-2-methoxy-1-(((2S)-2-(4-(4'-(2-((2S)-1-(N-(methoxycarbonyl)-O-methyl-L-threonyl)-2-pyrrolidinyl)-1H-imidazol-4-yl)-1,1'-bi(cyclohexyl)-4-yl)-1H-imidazol-2-yl)-1-pyrrolidinyl)carbonyl)propyl)carbamate;
methyl((1S)-1-(((2S)-2-(4-(4-(4-(2-((2S)-1-((2S)-2-((methoxycarbonyl)amino)-3-methylbutanoyl)-2-pyrrolidinyl)-1H-imidazol-4-yl)phenyl)-1-cyclohexen-1-yl)-1H-imidazol-2-yl)-1-pyrrolidinyl)carbonyl)-2-methylpropyl)carbamate;
methyl((1S)-2-((2S)-2-(4-(4-(4-(2-((2S)-1-(N-(methoxycarbonyl)-L-alanyl)-2-pyrrolidinyl)-1H-imidazol-4-yl)-3-cyclohexen-1-yl)phenyl)-1H-imidazol-2-yl)-1-pyrrolidinyl)-1-methyl-2-oxoethyl)carbamate;
methyl((1S)-2-((2S)-2-(4-(4-(4-(2-((2S)-1-(N-(methoxycarbonyl)-O-methyl-L-seryl)-2-pyrrolidinyl)-1H-imidazol-4-yl)-3-cyclohexen-1-yl)phenyl)-1H-imidazol-2-yl)-1-pyrrolidinyl)-1-(methoxymethyl)-2-oxoethyl)carbamate;
methyl((1S,2R)-2-methoxy-1-(((2S)-2-(4-(4-(4-(2-((2S)-1-(N-(methoxycarbonyl)-O-methyl-L-threonyl)-2-pyrrolidinyl)-1H-imidazol-4-yl)-3-cyclohexen-1-yl)phenyl)-1H-imidazol-2-yl)-1-pyrrolidinyl)carbonyl)propyl)carbamate;
methyl((1S)-1-(((2S)-2-(4-(1-(4-(2-((2S)-1-((2S)-2-((methoxycarbonyl)amino)-3-methylbutanoyl)-2-pyrrolidinyl)-1H-imidazol-4-yl)phenyl)-4-piperidinyl)-1H-imidazol-2-yl)-1-pyrrolidinyl)carbonyl)-2-methylpropyl)carbamate;
methyl((1S)-2-((2S)-2-(4-(4-(4-(2-((2S)-1-(N-(methoxycarbonyl)-O-methyl-L-seryl)-2-pyrrolidinyl)-1H-imidazol-4-yl)-1-piperidinyl)phenyl)-1H-imidazol-2-yl)-1-pyrrolidinyl)-1-(methoxymethyl)-2-oxoethyl)carbamate;
methyl((1S)-1-(((2S)-2-(4-(1-(4-(2-((2S)-1-((2S)-2-((methoxycarbonyl)amino)-3,3-dimethylbutanoyl)-2-pyrrolidinyl)-1H-imidazol-4-yl)phenyl)-4-piperidinyl)-1H-imidazol-2-yl)-1-pyrrolidinyl)carbonyl)-2,2-dimethylpropyl)carbamate;
methyl((1S)-1-(((2S)-2-(4-(4-(4-(2-((2S)-1-((2S)-2-((methoxycarbonyl)amino)-3-methylbutanoyl)-2-pyrrolidinyl)-1H-imidazol-4-yl)phenyl)bicyclo[2.2.2]oct-1-yl)-1H-imidazol-2-yl)-1-pyrrolidinyl)carbonyl)-2-methylpropyl)carbamate;
methyl((1S)-2-((2S)-2-(4-(4-(4-(2-((2S)-1-(N-(methoxycarbonyl)-L-alanyl)-2-pyrrolidinyl)-1H-imidazol-4-yl)bicyclo[2.2.2]oct-1-yl)phenyl)-1H-imidazol-2-yl)-1-pyrrolidinyl)-1-methyl-2-oxoethyl)carbamate;

methyl((1R)-2-((2S)-2-(4-(4-(4-(2-((2S)-1-((2R)-2-((methoxycarbonyl)amino)-2-phenylacetyl)-2-pyrrolidinyl)-1H-imidazol-4-yl)bicyclo[2.2.2]oct-1-yl)phenyl)-1H-imidazol-2-yl)-1-pyrrolidinyl)-2-oxo-1-phenylethyl)carbamate;

methyl((1S)-1-(((2S)-2-(4-(4-(4-(2-((2S)-1-((2S)-2-((methoxycarbonyl)amino)-3-methylbutanoyl)-2-pyrrolidinyl)-1H-imidazol-4-yl)phenyl)bicyclo[2.2.2]oct-1-yl)-1,3-oxazol-2-yl)-1-pyrrolidinyl)carbonyl)-2-methylpropyl)carbamate;

methyl((1S)-1-(((1R,3S,5R)-3-(5-(4-(4-(2-((1R,3S,5R)-2-((2S)-2-((methoxycarbonyl)amino)-3-methylbutanoyl)-2-azabicyclo[3.1.0]hex-3-yl)-1H-imidazol-5-yl)bicyclo[2.2.2]oct-1-yl)phenyl)-1H-imidazol-2-yl)-2-azabicyclo[3.1.0]hex-2-yl)carbonyl)-2-methylpropyl)carbamate;

methyl((1S)-1-(((1R,3S,5R)-3-(5-(4-(4-(2-((1R,3S,5R)-2-((2S)-2-((methoxycarbonyl)amino)butanoyl)-2-azabicyclo[3.1.0]hex-3-yl)-1H-imidazol-5-yl)bicyclo[2.2.2]oct-1-yl)phenyl)-1H-imidazol-2-yl)-2-azabicyclo[3.1.0]hex-2-yl)carbonyl)propyl)carbamate;

methyl((1R)-2-((1R,3S,5R)-3-(5-(4-(4-(2-(1R,3S,5R)-2-((2R)-2-((methoxycarbonyl)amino)-2-phenylacetyl)-2-azabicyclo[3.1.0]hex-3-yl)-1H-imidazol-5-yl)bicyclo[2.2.2]oct-1-yl)phenyl)-1H-imidazol-2-yl)-2-azabicyclo[3.1.0]hex-2-yl)-2-oxo-1-phenylethyl)carbamate;

methyl((1S)-1-(((2S)-2-(4-(4-(4-(2-((2S)-1-((2S)-2-((methoxycarbonyl)amino)-3-methylbutanoyl)pyrrolidin-2-yl)-1H-imidazol-4-yl)phenyl)cyclohexyl)-1H-imidazol-2-yl)pyrrolidin-1-yl)carbonyl)-2-methylpropyl)carbamate;

methyl((1S)-1-(((1R,3S,5R)-3-(4-chloro-5-(4-(4-(4-chloro-2-((1R,3S,5R)-2-((2S)-2-((methoxycarbonyl)amino)-3-methylbutanoyl)-2-azabicyclo[3.1.0]hex-3-yl)-1H-imidazol-5-yl)bicyclo[2.2.2]oct-1-yl)phenyl)-1H-imidazol-2-yl)-2-azabicyclo[3.1.0]hex-2-yl)carbonyl)-2-methylpropyl)carbamate; and corresponding stereoisomers thereof.

17. A compound which is

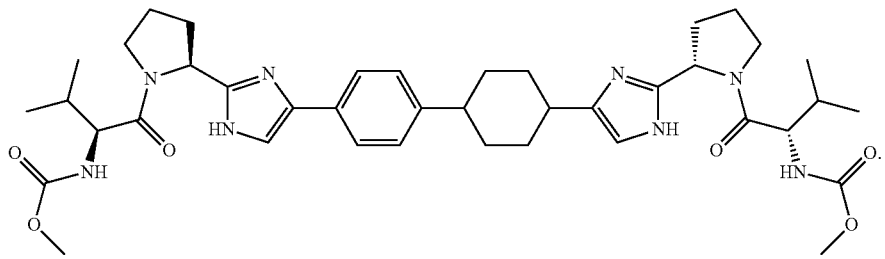 [SMILES: COC(=O)N[C@H](C(=O)N1CCC[C@H]1c1nc(-c2ccc(C3CCC(c4c[nH]c([C@@H]5CCCN5C(=O)[C@@H](NC(=O)OC)C(C)C)n4)CC3)cc2)c[nH]1)C(C)C]

18. A compound which is

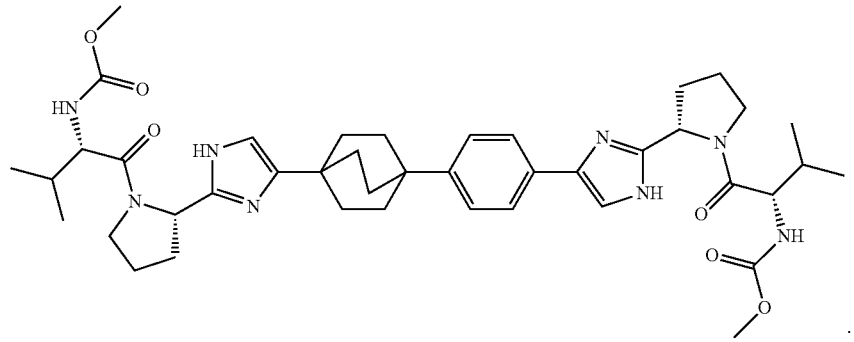 [SMILES: COC(=O)N[C@H](C(=O)N1CCC[C@H]1c1nc(-c2ccc(C34CCC(c5c[nH]c([C@@H]6CCCN6C(=O)[C@@H](NC(=O)OC)C(C)C)n5)(CC3)CC4)cc2)c[nH]1)C(C)C]

19. A composition comprising a compound of claim 1, or a pharmaceutically acceptable salt thereof, and a pharmaceutically acceptable carrier.

20. A method of treating an HCV infection in a patient, comprising administering to the patient a therapeutically effective amount of a compound of claim 1, or a pharmaceutically acceptable salt thereof.

* * * * *